US012398204B2

(12) United States Patent
Peters

(10) Patent No.: US 12,398,204 B2
(45) Date of Patent: Aug. 26, 2025

(54) METHOD OF TREATING AN OCULAR CONDITION BY ADMINISTERING MULTISPECIFIC ANTIBODIES THAT ACTIVATES TIE2 AND BINDS A RECEPTOR TYROSINE KINASE AGONIST

(71) Applicant: EyePoint Pharmaceuticals, Inc., Watertown, MA (US)

(72) Inventor: Kevin Peters, Cincinnati, OH (US)

(*) Notice: Subject to any disclaimer, the term of this patent is extended or adjusted under 35 U.S.C. 154(b) by 0 days.

(21) Appl. No.: 18/528,957

(22) Filed: Dec. 5, 2023

(65) Prior Publication Data

US 2024/0174740 A1 May 30, 2024

Related U.S. Application Data

(63) Continuation of application No. 17/117,993, filed on Dec. 10, 2020, now Pat. No. 11,873,334, which is a continuation of application No. 16/579,078, filed on Sep. 23, 2019, now Pat. No. 10,894,824.

(60) Provisional application No. 62/832,461, filed on Apr. 11, 2019, provisional application No. 62/735,331, filed on Sep. 24, 2018.

(51) Int. Cl.
*C07K 16/22* (2006.01)
*A61K 9/00* (2006.01)
*C07K 16/40* (2006.01)

(52) U.S. Cl.
CPC .............. *C07K 16/22* (2013.01); *C07K 16/40* (2013.01); *A61K 9/0019* (2013.01); *A61K 9/0048* (2013.01); *C07K 2317/31* (2013.01); *C07K 2317/35* (2013.01); *C07K 2317/51* (2013.01); *C07K 2317/92* (2013.01)

(58) Field of Classification Search
CPC .... C07K 16/22; C07K 16/40; C07K 2317/31; C07K 2317/35; C07K 2317/51; C07K 2317/64; C07K 2317/76; C07K 2317/92; C07K 16/2896; A61K 9/0019; A61K 9/0048; A61K 2039/505
See application file for complete search history.

(56) References Cited

U.S. PATENT DOCUMENTS 4,179,337 A 12/1979 Davis et al.
4,301,144 A 11/1981 Iwasaki et al.
4,496,689 A 1/1985 Mitra
4,640,835 A 2/1987 Shimizu et al.
4,670,417 A 6/1987 Iwasaki et al.
4,791,192 A 12/1988 Nakagawa et al.
5,625,825 A 4/1997 Rostoker et al.
6,133,426 A 10/2000 Gonzalez et al.
6,407,213 B1 6/2002 Carter et al.
7,226,755 B1 6/2007 Peters et al.
7,374,758 B2 5/2008 Papadopoulos et al.
7,758,859 B2 7/2010 Fuh et al.
7,973,142 B2 7/2011 Rotello et al.
8,258,268 B2 9/2012 Wu et al.
8,268,314 B2 9/2012 Baehner et al.
8,349,322 B2 1/2013 Borras et al.
8,524,235 B2 9/2013 Rotello et al.
8,901,076 B2 12/2014 Binz et al.
8,999,325 B2 4/2015 Peters et al.
9,174,950 B2 11/2015 Shalwitz et al.
9,403,789 B2 8/2016 Eissenstat et al.
9,458,211 B1 10/2016 Bakker et al.
RE46,592 E 10/2017 Gray et al.
9,795,594 B2 10/2017 Gray et al.
9,926,367 B2 3/2018 Rotello et al.
9,968,674 B2 5/2018 Ioffe et al.
10,035,850 B2 7/2018 Gekkieva et al.
10,150,811 B2 12/2018 Peters et al.
10,220,048 B2 3/2019 Peters et al.
10,253,094 B2 4/2019 Peters et al.
10,276,202 B1 4/2019 Jubert et al.
10,329,357 B2 6/2019 Peters et al.
10,463,650 B2 11/2019 Gray et al.
10,464,992 B2 11/2019 Furfine et al.
10,597,452 B2 3/2020 Peters et al.
10,604,569 B2 3/2020 Peters et al.
10,646,542 B2 5/2020 Binz et al.
10,815,300 B2 10/2020 Peters
10,894,824 B2 1/2021 Peters
10,973,916 B2 4/2021 Yang et al.
11,136,389 B2 10/2021 Peters et al.
11,136,986 B2 10/2021 Peters
11,180,551 B2 11/2021 Peters et al.
11,814,425 B2 11/2023 Rotello et al.
(Continued)

FOREIGN PATENT DOCUMENTS

CN 101802002 A 8/2010
CN 102753577 A 10/2012
(Continued)

OTHER PUBLICATIONS

Attwood. Genomics. The Babel of bioinformatics. Science. Oct. 20, 2000;290(5491):471-3.
(Continued)

*Primary Examiner* — Robert S Landsman

(74) *Attorney, Agent, or Firm* — Sterne, Kessler, Goldstein & Fox P.L.L.C.

(57) ABSTRACT

The disclosure provides compositions comprising multi-specific compounds, including a compound that targets a phosphatase and a receptor tyrosine kinase agonist. Also provided are methods for the treatment of conditions associated with angiogenesis, comprising administering a multi-specific compound that targets a phosphatase and a receptor tyrosine kinase agonist.

19 Claims, 29 Drawing Sheets

Specification includes a Sequence Listing.

(56) References Cited

U.S. PATENT DOCUMENTS

| | | | |
|---|---|---|---|
| 11,873,334 | B2 | 1/2024 | Peters |
| 12,043,664 | B2 | 7/2024 | Peters et al. |
| 12,145,986 | B2 | 11/2024 | Peters et al. |
| 2003/0158083 | A1 | 8/2003 | Peters |
| 2003/0215899 | A1 | 11/2003 | Meng et al. |
| 2004/0077065 | A1 | 4/2004 | Evdokimov et al. |
| 2004/0254197 | A1 | 12/2004 | Tasaka et al. |
| 2005/0059639 | A1 | 3/2005 | Wei |
| 2007/0134234 | A1 | 6/2007 | Smith et al. |
| 2007/0154482 | A1 | 7/2007 | Sukhatme et al. |
| 2007/0299116 | A1 | 12/2007 | Gray et al. |
| 2008/0004267 | A1 | 1/2008 | Gray et al. |
| 2008/0108631 | A1 | 5/2008 | Gray et al. |
| 2009/0022715 | A1 | 1/2009 | Rotello et al. |
| 2009/0227639 | A1 | 9/2009 | Gray et al. |
| 2009/0246206 | A1 | 10/2009 | Nielsen et al. |
| 2010/0030487 | A1 | 2/2010 | Evdokimov et al. |
| 2010/0069448 | A1 | 3/2010 | Gray et al. |
| 2010/0111894 | A1 | 5/2010 | Benny-Ratsaby et al. |
| 2010/0256147 | A1 | 10/2010 | Hangauer |
| 2011/0212951 | A1 | 9/2011 | Gray et al. |
| 2011/0268656 | A1 | 11/2011 | Ho et al. |
| 2011/0268694 | A1 | 11/2011 | Shalwitz et al. |
| 2011/0274699 | A1 | 11/2011 | Rotello et al. |
| 2012/0077853 | A1 | 3/2012 | Gray et al. |
| 2012/0077975 | A1 | 3/2012 | Gray et al. |
| 2012/0128625 | A1 | 5/2012 | Shalwitz et al. |
| 2012/0129847 | A1 | 5/2012 | Peters et al. |
| 2012/0237442 | A1 | 9/2012 | Rossi et al. |
| 2013/0023543 | A1 | 1/2013 | Gray et al. |
| 2013/0095105 | A1 | 4/2013 | Peters et al. |
| 2013/0096140 | A1 | 4/2013 | Gray et al. |
| 2013/0324558 | A1 | 12/2013 | Gray et al. |
| 2014/0179693 | A1 | 6/2014 | Shalwitz et al. |
| 2014/0221666 | A1 | 8/2014 | Gray et al. |
| 2014/0242026 | A1 | 8/2014 | Shalwitz et al. |
| 2014/0249100 | A1 | 9/2014 | Shalwitz et al. |
| 2014/0275103 | A1 | 9/2014 | Peters et al. |
| 2015/0065781 | A1 | 3/2015 | Bais et al. |
| 2015/0210656 | A1 | 7/2015 | Gray et al. |
| 2015/0297675 | A1 | 10/2015 | Osborne |
| 2016/0008327 | A1 | 1/2016 | Shalwitz et al. |
| 2016/0030393 | A1 | 2/2016 | Breslin et al. |
| 2016/0038467 | A1 | 2/2016 | Peters |
| 2016/0075797 | A1 | 3/2016 | Weaver et al. |
| 2016/0082129 | A1 | 3/2016 | Peters |
| 2016/0130337 | A1 | 5/2016 | Gekkieva et al. |
| 2016/0251421 | A1 | 9/2016 | Brown et al. |
| 2016/0333090 | A1 | 11/2016 | Horlick et al. |
| 2016/0340420 | A1 | 11/2016 | Zhang et al. |
| 2017/0096479 | A1 | 4/2017 | Koenig et al. |
| 2017/0260265 | A1 | 9/2017 | Duerr et al. |
| 2017/0275353 | A1 | 9/2017 | Sheng et al. |
| 2017/0298019 | A1 | 10/2017 | Gardner et al. |
| 2017/0319602 | A1 | 11/2017 | Peters et al. |
| 2017/0349649 | A1 | 12/2017 | Rotello et al. |
| 2018/0009890 | A1 | 1/2018 | Peters et al. |
| 2018/0022741 | A1 | 1/2018 | Peters et al. |
| 2018/0022804 | A1 | 1/2018 | Peters et al. |
| 2018/0037579 | A1 | 2/2018 | Peters et al. |
| 2018/0044432 | A1 | 2/2018 | Peters et al. |
| 2018/0092883 | A1 | 4/2018 | Peters et al. |
| 2018/0207233 | A1 | 7/2018 | Rudolf et al. |
| 2018/0221346 | A1 | 8/2018 | Gray et al. |
| 2018/0237429 | A1 | 8/2018 | Peters et al. |
| 2018/0237430 | A1 | 8/2018 | Peters et al. |
| 2018/0251457 | A1 | 9/2018 | Peters et al. |
| 2018/0353614 | A1 | 12/2018 | Peters |
| 2019/0023773 | A1 | 1/2019 | Rotello et al. |
| 2019/0046609 | A1 | 2/2019 | Yancopoulos |
| 2019/0076405 | A1 | 3/2019 | Shalwitz |
| 2019/0077862 | A1 | 3/2019 | Peters et al. |
| 2019/0077863 | A1 | 3/2019 | Peters et al. |
| 2019/0218282 | A1 | 7/2019 | Dengl et al. |
| 2019/0256889 | A1 | 8/2019 | Quaggin |
| 2019/0290725 | A1 | 9/2019 | Vitti et al. |
| 2019/0343918 | A1 | 11/2019 | Graham et al. |
| 2019/0381008 | A1 | 12/2019 | Zeitz et al. |
| 2020/0087412 | A1 | 3/2020 | Fang et al. |
| 2020/0115455 | A1 | 4/2020 | Bedi et al. |
| 2020/0140547 | A1 | 5/2020 | Bedi et al. |
| 2020/0231703 | A1 | 7/2020 | Peters et al. |
| 2021/0095017 | A1 | 4/2021 | Peters et al. |
| 2021/0171618 | A1 | 6/2021 | Peters |
| 2023/0134885 | A1 | 5/2023 | Peters et al. |

FOREIGN PATENT DOCUMENTS

| | | | |
|---|---|---|---|
| CN | 107602702 | A | 1/2018 |
| EP | 2592073 | B1 | 8/2017 |
| EP | 2846836 | B1 | 8/2019 |
| EP | 3628324 | A1 | 4/2020 |
| WO | WO 9312227 | A1 | 6/1993 |
| WO | WO 9631598 | A1 | 10/1996 |
| WO | WO-9845331 | A3 | 12/1998 |
| WO | WO 0224782 | A1 | 3/2002 |
| WO | WO 2007033216 | A2 | 3/2007 |
| WO | WO 2007087457 | A2 | 8/2007 |
| WO | WO-2007116360 | A2 | 10/2007 |
| WO | WO-2008132568 | A2 | 11/2008 |
| WO | WO 2009006112 | A1 | 1/2009 |
| WO | WO 2009055343 | A2 | 4/2009 |
| WO | WO 2009136352 | A1 | 11/2009 |
| WO | WO-2010040508 | A1 | 4/2010 |
| WO | WO-2010060748 | A1 | 6/2010 |
| WO | WO-2011135067 | A1 | 11/2011 |
| WO | WO-2013056233 | A1 | 4/2013 |
| WO | WO-2013056240 | A1 | 4/2013 |
| WO | WO 2011087066 | A1 | 5/2013 |
| WO | WO-2015109898 | A1 | 7/2015 |
| WO | WO 2016049183 | A1 | 3/2016 |
| WO | WO-2016115092 | A1 | 7/2016 |
| WO | WO-2016122996 | A1 | 8/2016 |
| WO | WO-2017035430 | A2 | 3/2017 |
| WO | WO-2018017714 | A1 | 1/2018 |
| WO | WO-2018067646 | A1 | 4/2018 |
| WO | WO-2018229034 | A1 | 12/2018 |
| WO | WO-2019168947 | A1 | 9/2019 |
| WO | WO-2019175727 | A1 | 9/2019 |
| WO | WO-2019222547 | A1 | 11/2019 |
| WO | WO 2020068653 | A1 | 2/2020 |

OTHER PUBLICATIONS

Campbell. Chapter 1: General properties and applications of monoclonal antibodies. Monoclonal Antibody Technology. Elsevier Science Publishers, The Netherlands, (pp. 1-32) (1984).

Clarke, JM et al., Targeted inhibition of VEGF Receptor-2: An update on Ramucirumab, Expert Opin Biol. Ther. Aug. 2013 ; 13(8): 1187-1196. doi:10.1517/14712598.2013.810717.

Colman et al., Effects of amino acid sequence changes on antibody-antigen interactions, Research in Immunology, 1994; 145(1):33-36.

Crescioli, Silvia et al., IgG4 Characteristics and Functions in Cancer Immunity, Curr Allerty Asthma Rep (2016) 16:7.

Goel, et al. Effects of vascular-endothelial protein tyrosine phosphatase inhibition on breast cancer vasculature and metastatic progression. J Natl Cancer Inst. Aug. 21, 2013; 105(16):1188-201. doi: 10.1093/jnci/djt164. Epub Jul. 30, 2013.

Golay, et al. Mechanism of action of therapeutic monoclonal antibodies: promises and pitfalls of in vitro and in vivo assays. Arch Biochem Biophys. Oct. 15, 2012;526(2):146-53. doi: 10.1016/j.abb.2012.02.011. Epub Feb. 25, 2012.

Houghten, et al. New Approaches to Immunization, Vaccines 86, Cold Spring Harbor Laboratory, p. 21-25, 1986.

International Search Report and Written Opinion dated Feb. 5, 2020, for PCT/US19/52405.

International Union of Basic and Clinical Pharmacology (IUPHAR) /British Pharmacological Society (BPS) Guide to Pharmacology Database: Ligand ID: 8371, International Non-proprietary Name: abicipar pegol, Synonyms: AGN-150998| MP0122;

(56) References Cited

OTHER PUBLICATIONS

Specialist databases: IMGT/mAb-DB 477, GtoPdb PubChem SID: 252166583; Link https://www.guidetopharmacology.org/GRAC/LigandDisplayForward?tab=summary&ligandId=8371, printed Jun. 15, 2020.
International Union of Basic and Clinical Pharmacology (IUPHAR) /British Pharmacological Society (BPS) Guideto Pharmacology Database: Ligand ID: 8371, International Non-proprietary Name: abicipar pegol, Biological activity: Peptide Sequence; https://www.guidetopharmacology.org/GRAC/LigandDisplayForward?tab=structure&ligandId=8371printed6/15/20 (MV R329387).
International Union of Basic and Clinical Pharmacology (IUPHAR)/British Pharmacological Society (BPS) Guideto Pharmacology Database: Ligand ID: 8371, International Non-proprietary Name: abiciparpegol, Target: VEGFA, printed Jun. 15, 2020:https://www.guidetopharmacology.org/GRAC/LigandDisplayForward?tab=biology&ligandId=8371.
International Union of Basic andClinical Pharmacology (IUPHAR) /British Pharmacological Society (BPS)Guideto Pharmacology Database: Ligand ID: 8371, Intl Non-proprietary Name: abicipar pegol, Clinical Data; Summary of Clinical Use, and Mechanism of Action andPharmacodynamic Effects; Link:Jun. 15, 2020: https://www.guidetopharmacology.org/GRAC/LigandDisplayForward?tab=biology&ligandId=8371, Printed Jun. 15, 2020.
IUPHAR/BPS Guide to Pharmacology database for Ligand ID: 8371, Name: abicipar pegol, available at https://www.guidetopharmacology.org/GRAC/LigandDisplayForward?tab=summary&ligandId=8371 , 5 pages, Printed Nov. 21, 2019.
Kienast, Y. et al., Ang-2-VEGF-A CrossMab, a Novel Bispecific Human IgG1 Antibody Blocking VEGF-A and Ang-2 Functions Simultaneously, Mediates Potent antitumor, Antiangiogenic, and Antimetastic Efficascy, Clinical Cancer Resarch, Oct. 4, 2013, vol. 19 No. 24, pp. 6730-6740; Abstract p. 6730, col. 2, Paragraph 2, Supplementary Figure 1; DOI 10.1158/1078-0432.CCR-13-0081.
Nguyen, et al. Vascular endothelial growth factor is a critical stimulus for diabetic macular edema. Am J Ophthalmol. Dec. 2006;142(6):961-9. Epub Aug. 2, 2006.
Owens, et al. The genetic engineering of monoclonal antibodies. J Immunol Methods. Feb. 10, 1994;168(2):149-65.
Paul. Fundamental Immunology. Chapter 8 Immunogenicty and antigen structure., 3d ed., p. 242, 1993.
Rudikoff et al. Single amino acid substitution altering antigen-binding specificity. PNAS USA 79:1979-1983 (1982).
Shen, et al. Targeting VE-PTP activates TIE2 and stabilizes the ocular vasculature. J Clin Invest. Oct. 2014;124(10):4564-76.
Silva, Raquel Lima et al., Tyrosine blocking collagen IV-derived peptide suppresses ocular neovascularization and vascular leakage, Sci Transl Med. Jan. 18, 2017; 9(373). doi:10.1126/scitranslmed.aai8030.
Simeon, Rudo et al., In vitro-engineered non-antibody protein therapeutics, Protein Cell 218, 9(1);3-14.
Skolnick, et al. From genes to protein structure and function: novel applications of computational approaches in the genomic era. Trends Biotechnol. Jan. 2000;18(1):34-9.
Tam, Susan H. et al., Functional Biophysical, and Structural Characterization of Human IgG1 and Ig4Fc Variants with Ablated Immune Functionality, Antibodies 2017, 6 12: doi:10.3390/antib6030012.
Trieu, Michelle et al., Vasculotide, an Angiopoietin-1, Mimetic, Restores Microcirculatory Perfusion and Microvascular Leakage and Decreases Fluid Resuscitation Requirements in Hemorrhagic Shock, Anesthesiology, V. 128, No. 2, p. 361, Feb. 2018.
Van Der Flier, et al. Antibody neutralization of vascular endothelial growth factor (VEGF) fails to attenuate vascular permeability and brain edema in experimental pneumococcal meningitis. J Neuroimmunol. Mar. 2005;160(1-2):170-7.
Wang, Qin, et al., Novel VEGF Decoy Receptor Fusion Protein Conbercept Targeting Multiple VEGR Isoforms Provide Remarkable Anti-Angiogenesis Effect in Viv, Aug. 2013: PLOS One, vol. 8, Issue 8.
Wang, Xinhua et al., IgG engineering to modulate antibody effector functions, Genetech,Protein Cell 2018; 9(1:)63-73; DOI 10.107/sAcceptd Jun. 19, 2017.
Witte, et al. Monoclonal antibodies targeting the VEGF receptor-2 (FIk1/KDR) as an anti-angiogenic therapeutic strategy. Cancer Metastasis Rev. Jun. 1998;17(2):155-61.
Wu et al. Humanization of a murine monoclonal antibody by simultaneous optimization of framework and CDR residues. J.Mol. Biol. 294:151-162 (1999).
Yang, Jihong et al., Comparison of Binding Characteristics and In Vitro Activities of Three Inhibitors of Vascular Endothelial Grow Factor A, Molecular Pharmaceutics, 2014, American Chemical Society, 3421-3430.
Yu et al., Interaction between Bevacizumab and Murine VEGF-A: A Reassessment, Investigative Ophthalmology & Visual Science, 2008, vol. 49 (2), pp. 522-527.
Amarasinghe, K.K.D., et al., "Design and synthesis of potent, non-peptidic inhibitors of HPTPß," Bioorganic & Medicinal Chemistry Letters, 16:4252-4256, Elsevier, Netherlands (2006).
Baumer, S., et al., "Vascular endothelial cell-specific phosphotyrosine phosphatase (VEPTP) activity is required for blood vessel development," Blood 107(12):4754-4762, The American Society of Hematology, United States (Jun. 2006).
Bosse, R. and Vestweber D., "Only simultaneous blocking of the L- and P-selectin completely inhibits neutrophil C migration into mouse peritoneum", Eur. J. Immunol. 24:3019-3024, VCH Verlagsgesellschaft mbH, Germany (1994).
Broermann, A., et al., "Dissociation of VE-PTP from VE-cadherin is required for leukocyte extravasation and for VEGF-induced vascular permeability in vivo," J Exp Med. 208(12):2393-401, The Rockefeller University Press, United States (Nov. 2011).
Campbell,A.M., "Monoclonal Antibody Technology," Chapter 1, pp. 1-32, Elsevier, Inc., Netherlands (1984).
Campochiaro, P.A., et al., "Enhanced Benefit in Diabetic Macular Edema from AKB-9778 Tie2 Activation Combined with Vascular Endothelial Growth Factor Suppression. Ophthalmology," 123(8):1-9, Elsevier, Inc., Netherlands (Aug. 2016).
Clackson, T., et al., "Making antibody fragments using phage display libraries," Nature. 352(6336):624-628, Nature Research, United Kingdom (Aug. 1991).
Doukas, J., et al., "Topical administration of a multi-targeted kinase inhibitor suppresses choroidal neovascularization and retinal edema," J Cell Physiol. 216(1):29-37, Author Manuscript, John Wiley & Sons, Inc., United States (Jul. 2008).
Edwards, B.M., et al., "The remarkable flexibility of the human antibody repertoire; isolation of over one thousand different antibodies to a single protein, BLyS," J Mol Biol 334(1):103-18, Elsevier, Netherlands (Nov. 2003).
Elias, L. and Hunt, W.C., "A literature analysis of prognostic factors for response and quality of response of patients with renal cell carcinoma to interleukin-2-based therapy," Oncology 61(2):91-101, S. Karger AG, Basel (2001).
Frye, M., et al., "Interfering with VE-PTP stabilizes endothelial junctions in vivo via Tie-2 in the absence ofVE-cadherin," JEM 212(13):2267-2287, The Rockefeller University Press, United States (Dec. 2015).
Fukuhara, S. and Mochizuki, N., "Vascular endothelial cells and adjoining cells for their mutual adhesion/interaction for stabilization and angiogenesis," Seikagaku. The Journal of Japanese Biochemical Society 82(4):290-301, Japanese Biochemical Society, Japan (Apr. 2010).
Fukuhara, S., et al., "Differential function of Tie2 at cell-cell contacts and cell-substratum contacts regulated by angiopoietin-1," Nat Cell Biol. 10(5):513-526, Nature Publishing Group, Germany (May 2008).
Gallagher, D.C., et al., "Angiopoietin 2 is a Potential Mediator of High-Dose Interleutkin 2-Induced Vascular Leak," Clin Cancer Res 13(7):2115-2120, American Association for Cancer Research, United States (Apr. 2007).
Gotsch, U., et al., "VE-cadherin antibody accelerates neutrophil recruitment in vivo," J Cell Sci. 110:583-588, The Company of Biologists Limited, Great Britain (Mar. 1997).

(56) References Cited

OTHER PUBLICATIONS

Gozes, Y., et al., "Anthrax Lethal Toxin Induces Ketotifen-Sensitive Intradermal Vascular Leakage in Certain Inbred Mice," Infect Immun. 74(2):1266-1272, The American Society for Microbiology, United States (Feb. 2006).
Gurnik, S., et al., "Angiopoietin-2-induced blood-brain barrier compromise and increased stroke size are rescued by VE-PTP-dependent restoration of Tie2 signaling," Acta Neuropathol 131(5):753-773, Springer, Germany (May 2016).
Hayashi, M., et al., VE-PTP regulates VEGFR2 activity in stalk cells to establish endothelial cell polarity and lumen formation. Nat Commun. 4:1672, Macmillan Publishing Limited, United Kingdom (2013).
Hudson, P.J. and Souriau, C., "Engineered antibodies," Nat Med. 9(1):129-34, Nature Publishing Group, Germany (Jan. 2003).
Imamura, T., et al., "Induction of vascular leakage through release of bradykinin and a novel kin in by cysteine proteinases from *Staphylococcus aureus*," J Exp Med. 201(10):1669-1676, The Rockefeller University Press, United States (May 2005).
International Search Report and Written Opinion for International Application No. PCT/US2012/060263, U.S. Patent and Trademark Office, Alexandria, VA, mailed on Dec. 6, 2012, 7 pages.
International Search Report and Written Opinion for International Application No. PCT/US2012/060273, U.S. Patent and Trademark Office, Alexandria, VA, mailed on Dec. 24, 2012, 9 pages.
International Search Report and Written Opinion for International Application No. PCT/US2017/042855, U.S. Patent and Trademark Office, Alexandria, VA, mailed on Dec. 26, 2017, 21 pages.
Jubala, C.M., et al., "CD20 expression in normal canine B cells and in canine non-Hodgkin Lymphoma," Vet Pathol. 42(4):468-476, SAGE Publications, New York (Jul. 2005).
Kipriyanov, S.M. and Le Gall, F., "Generation and production of engineered antibodies," Mol Biotechnol. 26(1):39-60, Humana Press, Inc., Springer Science+Business Media, Germany (Jan. 2004).
Lloyd, C., et al., "Modelling the human immune response: performance of a 1011 human antibody repertoire against a broad panel of therapeutically relevant antigens," Protein Engineering, Design & Selection 22:159-168, Oxford University Press, United Kingdom (Mar. 2009).
Lo, B.K.C., "Antibody humanization by CDR grafting," Ch.7 in Methods in Mol Biol., Antibody Engineering: Methods and Protocols 248:135-59, Totowa, New Jersey (2004).
Lucentis prescribing information, p. 1-28, Genentech, Inc. (2018).
Luo, G., et al., "Molecular mechanism underlying the action of a novel fusion inhibitor of influenza A virus," J Virol. 71(5):4062-4070, American Society for Microbiology, United States (May 1997).
Marneros, A., et al., "Endogenous endostatin inhibits choroidal neovascularization," FASEB J. 21(14):3809-3818, Federation of American Societies for Experimental Biology, United States (Dec. 2007).
Medicago AB phosphate-buffer saline specification sheet, p. 1-2, www.medicago.se (2010).
Mellberg, S., et al., "Transcriptional profiling reveals a critical role for tyrosine phosphatase VEPTP in regulation of VEGFR2 activity and endothelial cell morphogenesis," FASEB J. 23(5):1490-1502, Federation of American Societies for Experimental Biology, United States (May 2009).
Miles, A.A. and Miles, E.M., "Vascular reactions to histamine, histamine-liberator and leukotaxine in the skin of guinea-pigs," J Physiol. 118(2):228-257, Wiley-Blackwell on behalf of The Physiological Society, United States (Oct. 1952).
Morrissey, C., et al., "Differential expression of angiogenesis associated genes in prostate cancer bone, liver and lymph node metastases," Clin Exp Metastasis. 25(4):377-388, Springer Science+ Business Media B.V., Germany (2008).
Muyldermans, S., "Single domain camel antibodies: current status," Reviews in Molecular Biotechnology 74(4):277-302, Elsevier, Netherlands (Jun. 2001).
Nishimura, E., "Current status and feature of diabetic retinopathy drug therapy," Journal of the Showa Medical Association 70(1):45-51, Showa Medical Association, Japan (Feb. 2010).
Notice of Allowance dated Jan. 15, 2020, in U.S. Appl. No. 16/180,850, Peters, K., filed Nov. 5, 2018, 9 pages.
Notice of Allowance mailed Jan. 30, 2015, in U.S. Appl. No. 13/652,154, Peters, K., filed Oct. 15, 2012, 8 pages.
Notice of Allowance mailed Nov. 30, 2018, in U.S. Appl. No. 15/654,289, Peters, K., filed Jul. 19, 2017, 7 pages.
Notice of Allowance mailed Sep. 26, 2018, in U.S. Appl. No. 15/438,218, Peters, K., filed Feb. 21, 2017, 8 pages.
Nottebaum, A.F., et al. VE-PTP maintains the endothelial barrier via plakoglobin and becomes dissociated from VE-cadherin by leukocytes and by VEGF, J Exp Med. 205(12):2929-2945, The Rockefeller University Press, United States (Nov. 2008).
Office Action mailed Apr. 17, 2015, in U.S. Appl. No. 13/652,203, Peters, K., et al., filed Oct. 15, 2012, 12 pages.
Office Action mailed Apr. 7, 2014, in U.S. Appl. No. 13/652,154, Peters, K., et al., filed Oct. 15, 2012, 25 pages.
Office Action mailed Aug. 22, 2016 in U.S. Appl. No. 13/652,203, Peters, K., et al., filed Oct. 15, 2012, 15 pages.
Office Action mailed Aug. 3, 2018, in U.S. Appl. No. 15/438,218, Peters, K., et al., filed Feb. 21, 2017, 8 pages.
Office Action mailed Aug. 30, 2019, in U.S. Appl. No. 16/180,850, Peters, K., et al., filed Nov. 5, 2018, 11 pages.
Office Action mailed Aug. 30, 2019, in U.S. Appl. No. 16/180,854, Peters, K., et al., filed Nov. 5, 2018, 11 pages.
Office Action mailed Jan. 4, 2016, in United States U.S. Appl. No. 13/652,203, Peters, K., et al., filed Oct. 15, 2012, 17 pages.
Office Action mailed Jul. 6, 2018, in U.S. Appl. No. 15/654,289, Peters, K., et al., filed Jul. 19, 2017, 8 pages.
Office Action mailed Jul. 9, 2018, in U.S. Appl. No. 15/463,340, Peters, K., et al., filed Mar. 20, 2017, 14 pages.
Office Action mailed Mar. 1, 2018, in U.S. Appl. No. 15/438,218, Peters, K., et al., filed Feb. 21, 2017, 10 pages.
Office Action mailed May 15, 2014, in U.S. Appl. No. 13/652,203, Peters, K., et al., filed Oct. 15, 2012, 12 pages.
Office Action mailed Sep. 11, 2013, in U.S. Appl. No. 13/652,203, Peters, K., et al., filed Oct. 15, 2012, 10 pages.
Office Action mailed Sep. 22, 2016, in U.S. Appl. No. 14/627,463, Peters, K., et al., filed Feb. 20, 2015, 24 pages.
Office Action mailed Sep. 5, 2013, in U.S. Appl. No. 13/652,154, Peters, K., et al., filed Oct. 15, 2012, 23 pages.
Oliner, J., et al., "Suppression of angiogenesis and tumor growth by selective inhibition of angiopoietin-2," Cancer Cell. 6(5):507-516, Cell Press, United States (Nov. 2004).
Park, Y-H., et al., "Effect of sorafenib on experimental choroidal neovascularization in the rat," Clin Experiment Ophthalmol. 38(7):718-726, Royal Australian and New Zealand College of Ophthalmologists, Australia (Oct. 2010).
Praidou, A., et al., "Angiogenic growth factors and their inhibitors in diabetic retinopathy," Curr Diabetes Rev. 6(5):304-312, Bentham Science Publishers Ltd., United Arab Emirates (Sep. 2010).
Riemer, A.B., et al., Matching of trastuzumab (Herceptin) epitope mimics onto the surface of Her-2/neu—a new method of epitope definition. Mol Immunol. 42(9):1121-1124, Elsevier, Netherlands (May 2005).
Saharinen, P., et al., "Angiopoietins assemble distinct Tie2 signalling complexes in endothelial cell-cell and cell-matrix contacts," Nat Cell Biol. 10(5):527-537, Supplementary Information, Nature Publishing Group, Germany (May 2008).
Schindelholz, B, et al., "Regulation of CNS and motor axon guidance in *Drosophila* by the receptor tyrosine phosphatase DPTP52F," Development, 128: 4371-4382, The Company of Biologists Limited, Great Britain (2001).
Shen J, et al., "In Vivo Immunostaining Demonstrates Macrophages Associate with Growing and Regressing Vessels," Invest. Ophthalmol. Vis. Sci., 48(9):4335-4341, Association for Research in Vision and Ophthalmology, United States (2007).
Sidwell, R.W., et al. "Utilization of pulse oximetry for the study of the inhibitory effects of antiviral agents on influenza virus in mice," Antimicrob Agents Chemother. 36(2):473-476, American Society for Microbiology, United States (Feb. 1992).

(56) References Cited

OTHER PUBLICATIONS

Smith, L. E. H., et al., "Oxygen-induced retinopathy in the mouse," Invest Ophthalmol Vis Sci. 35(1):101-111, Association for Research in Vision and Ophthalmology (Jan. 1994).
Sone, H., et al., "Effects of intraocular or systemic administration of neutralizing antibody against vascular endothelial growth factor on the murine experimental model of retinopathy," Life Sci. 65(24):2573-2580, Elsevier, Netherlands (1999).
Stancovski, I., et al., "Mechanistic aspects of the opposing effects of monoclonal antibodies to the ERBB2 receptor on tumor growth," Proc Natl Acad Sci U SA. 88(19):8691-8695, United States National Academy of Sciences, United States (Oct. 1991).
Supplementary European Search Report and Search Opinion for EP Application No. EP 12840220.3, Munich, Germany, mailed on May 11, 2015, 7 pages.
Supplementary European Search Report and Search Opinion for EP Application No. EP 12840725.1, Munich, Germany, mailed on May 12, 2015.
Tobe, T., et al., "Targeted Disruption of the FGF2 Gene Does Not Prevent Choroidal Neovascularization in a Murine Model," Am. J. Pathol., 153(5):1641-1646, American Society to Investigative Pathology (1998).
Varughese, M., et al., "Internalization of a Bacillus anthracis protective antigen-c-Myc fusion protein mediated by cell surface anti-c-Myc antibodies," Mol Med. 4(2):87-95, Springer Nature, Germany (Feb. 1998).
Yacyshyn, O.K., et al., "Tyrosine phosphatase beta regulates angiopoietin-Tie2 signaling in human endothelial cells," Angiogenesis 12(1):25-33 Springer Science+Business Media B.V., Germany (2009).
Office Action mailed Sep. 16, 2022, in U.S. Appl. No. 16/784,970, Rotello, R.J., et al., filed Feb. 7, 2020, 18 pages.
Office Action mailed Nov. 29, 2022, in U.S. Appl. No. 16/751,824, Peters, K., et al., filed Jan. 24, 2020, 21 pages.
Office Action mailed Dec. 14, 2022, in U.S. Appl. No. 17/027,034, Peters, K., et al., filed Sep. 21, 2020, 11 pages.
Saharinen, P., et al., "Therapeutic targeting of the angiopoietin-TIE pathway," Nat Rev Drug Discov 16(9):635-661, Nature Portfolio, Germany (Sep. 2017).
Souma, T., et al., "Context-dependent functions of angiopoietin 2 are determined by the endothelial phosphatase VEPTP," Proc Natl Acad Sci USA 115(6):1298-1303, National Academy of Sciences, United States (Feb. 2018).
U.S. Appl. No. 18/443,782, filed Feb. 16, 2024, Inventors: Kevin Peters et al., Applicant: EyePoint Pharmaceuticals, Inc.
Campochiaro, P., et al., "Targeting Tie2 for Treatment of Diabetic Retinopathy and Diabetic Macular Edema," Current Diabetes Reports 16(12):126, Springer Nature, United States (Dec. 2016).
Kim, J., et al., "Impaired angiopoietin/Tie2 signaling compromises Schlemm's canal integrity and induces glaucoma," The Journal of Clinical Investigation 127(10):3877-3896, American Society for Clinical Investigation, United States (Oct. 2017).
Takagi, H., et al., "Potential role of the angiopoietin/tie2 system in ischemia-induced retinal neovascularization," Investigative Ophthalmology & Visual Science 44(1):393-402, Association for Research in Vision and Ophthalmology, United States (Jan. 2003).
Campochiaro, P., et al., "Treatment of Diabetic Macular Edema with an Inhibitor of Vascular Endothelial-Protein Tyrosine Phosphatase That Activates Tie2," Ophthalmology 122(3):545-554, Elsevier, United States (Mar. 2015).
Brigell, M., et al., "A Phase 1b/2a Open-Label, Multiple-Ascending Dose Cohort Study to Assess the Safety, Tolerability, Pilot Efficacy, Pharmacokinetics and Pharmacodynamic Effects of 28-Day Repeat Subcutaneous Doses of AKB-9778 in Subjects with Diabetic Macular Edema," Investigative Ophthalmology & Visual Science (ARVO Annual Meeting Abstract) 55(13): 1757, 1 page, Association for Research in Vision and Ophthalmology, United States (Apr. 2014).
Shen, J., et al., "Blockade of Vascular Endothelial Protein Tyrosine Phosphatase: A Novel Approach to Stabilizing the Retinal Vasculature," Investigative Ophthalmology & Visual Science.
(ARVO Annual Meeting Abstract) 54(15): 6094, 1 page, Association for Research in Vision and Ophthalmology, United States (Jun. 2013).

METHOD OF TREATING AN OCULAR CONDITION BY ADMINISTERING MULTISPECIFIC ANTIBODIES THAT ACTIVATES TIE2 AND BINDS A RECEPTOR TYROSINE KINASE AGONIST

CROSS REFERENCE TO RELATED APPLICATIONS

This application is a continuation of U.S. application Ser. No. 17/117,993, filed Dec. 10, 2020, now U.S. Pat. No. 11,873,334, which is a continuation of U.S. application Ser. No. 16/579,078, filed Sep. 23, 2019, now U.S. Pat. No. 10,894,824, which claims the benefit of U.S. Provisional Application No. 62/832,461, filed Apr. 11, 2019, and U.S. Provisional Application No. 62/735,331, filed Sep. 24, 2018, each of which is incorporated herein by reference in its entirety.

REFERENCE TO A SEQUENCE LISTING SUBMITTED ELECTRONICALLY VIA EFS-WEB

The content of the electronically submitted sequence listing (Name: 4986_0210005_Seqlisting_ST26, Size: 345,321 bytes; and Date of Creation: Dec. 1, 2023) is herein incorporated by reference in its entirety.

BACKGROUND

Individual compounds with the ability to modulate distinct targets can be combined to generate multispecific compounds. Such multispecific compounds can have advantages over the parent compounds administered individually. These advantages can include, for example, a simpler dosing regimen, longer half-life within a subject, or the ability to bind targets in close proximity.

INCORPORATION BY REFERENCE

Each patent, publication, and non-patent literature cited in the application is hereby incorporated by reference in its entirety as if each was incorporated by reference individually.

SUMMARY

In some embodiments, the disclosure provides a compound comprising: (a) a first domain, wherein the first domain modulates a phosphatase, wherein the phosphatase modulates Tie2; and (b) a second domain that specifically binds a receptor tyrosine kinase agonist.

In some embodiments, the disclosure provides a method of treating a condition in a subject in need thereof, the method comprising administering to the subject a therapeutically-effective amount of a compound disclosed herein.

BRIEF DESCRIPTION OF THE FIGURES

FIG. 21A provides a western blot. FIG. 21B provides quantification of Tie2 activation. FIG. 21C provides quantification of VEGFR2 phosphorylation.

FIG. 22A provides a western blot. FIG. 22B provides quantification of Tie2 activation. FIG. 22C provides quantification of VEGFR2 phosphorylation.

FIG. 23A provides quantification of Tie2 activation. FIG. 23B provides quantification of VEGFR2 phosphorylation.

FIG. 24A provides quantification of Tie2 activation. FIG. 24B provides quantification of VEGFR2 phosphorylation.

FIG. 25A provides quantification of Tie2 activation. FIG. 25B provides quantification of VEGFR2 phosphorylation.

FIG. 26A provides quantification of Tie2 activation. FIG. 26B provides quantification of VEGFR2 phosphorylation.

FIG. 27A provides quantification of Tie2 activation. FIG. 27B provides quantification of VEGFR2 phosphorylation.

DETAILED DESCRIPTION

Figure 1:
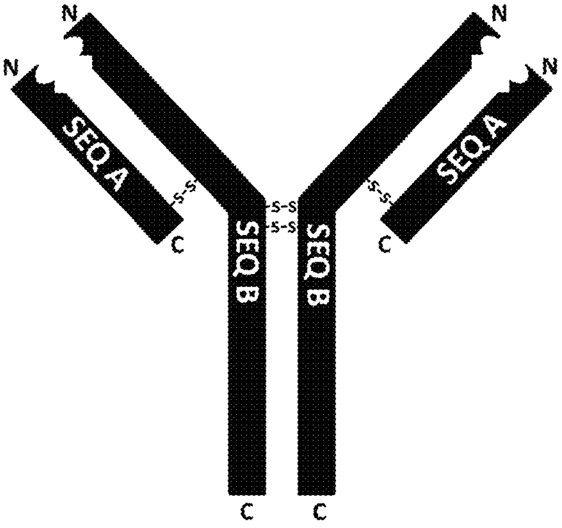
FIG. 1: Schematic of the basic four chain antibody unit. Light chain sequences are represented by "SEQ A". Heavy chain sequences are represented by "SEQ B". N and C denote N- and C-termini, respectively. —S—S— denotes disulfide bonds.

The present disclosure provides compositions and methods for modulating phosphatases and kinases, for example, receptor tyrosine kinases. Compositions and methods are provided for modulating Tie2, for example, to promote Tie2 phosphorylation, signaling, and/or activation. In some embodiments, the disclosure provides compositions and methods for targeting a phosphatase that modulates Tie2 signaling. In some embodiments, the phosphatase that modulates Tie2 signaling is human protein tyrosine phosphatase-beta (HPTP-0).

Compositions and methods are provided for modulating receptor tyrosine kinases, for example, to reduce receptor tyrosine kinase phosphorylation, signaling, and/or activation. In some embodiments, the disclosure provides compositions and methods for targeting a receptor tyrosine kinase agonist, e.g. vascular endothelial growth factor (VEGF). In some embodiments, the disclosure provides compositions and methods for targeting a receptor tyrosine kinase, e.g. a VEGF receptor.

In some embodiments, the present disclosure provides compositions and methods for targeting human protein tyrosine phosphatase-beta (HPTP-β) or vascular endothelial protein tyrosine phosphatase (VE-PTP or VEPTP), and vascular endothelial growth factor (VEGF). In some embodiments, the present disclosure provides multispecific compounds, agents, antibodies, fragments, or derivatives thereof that target HPTP-β (VE-PTP) and VEGF.

The agents disclosed herein can be used for the treatment of disorders that are characterized by, for example, vascular instability, angiogenesis, neovascularization, vascular leakage, and/or edema. The agents disclosed herein can be used for the treatment of, for example, vascular disorders, ocular disorders, cancers, renal disorders, and complications of diabetes.

HPTP-β/VE-PTP, Tie2, and Vascular Stability

HPTP-β is a member of the receptor-like family of the protein tyrosine phosphatases (PTPases). HPTP-β is a transmembrane protein found primarily in vascular endothelial cells that displays structural and functional similarity to cell adhesion molecules. Orthologues of HPTP-0 are found in various species including, for example, zebrafish, chicken, dog, mouse, marmoset, and monkey. The orthologues are generally referred to as vascular endothelial protein tyrosine phosphatase (VE-PTP). HPTP-β (VE-PTP) can influence vascular stability through effects on Tie2-mediated signaling.

Tie2 (tyrosine kinase with immunoglobulin and epidermal growth factor homology domains 2) is a membrane receptor tyrosine kinase expressed primarily in vascular endothelial cells. Upstream factors can regulate Tie2 phosphorylation, influencing downstream signaling and vascular stabilization. Non-limiting examples of such factors include angiopoietin 1 (Ang1/Angpt1), angiopoietin 2 (Ang2/Angpt2), and HPTP-β (VE-PTP).

Ang1 is an agonist of Tie2. Binding of Ang1 to Tie2 promotes receptor phosphorylation and downstream signaling to induce vascular stabilization through highly organized angiogenesis, tightening of endothelial cell junctions, enhancement of endothelial viability, reduction of endothelial inflammation, and improvement of endothelial function.

Ang2 acts in a context-dependent antagonist or agonist of Tie2. During angiogenesis, Ang2 acts as a negative regulator of Ang1-Tie2 signaling.

HPTP-β (VE-PTP) is a phosphatase that can modulate Tie2 signaling. HPTP-β (VE-PTP) can dephosphorylate the Tie2 receptor. Under physiological conditions, HPTP-β (VE-PTP) regulates the duration of Tie2 phosphorylation. Inhibition of HPTP-β (VE-PTP), therefore, can result in increased Tie2 phosphorylation, increased Tie2-mediated signaling, and enhanced vascular stability. Inhibitors of HPTP-β (VE-PTP) are Tie2 activators. For example, a compound, inhibitor, antibody, antibody fragment, variant, or derivative thereof that binds HPTP-β (VE-PTP) can promote Tie2 phosphorylation, thereby activating Tie2 downstream signaling, and promoting vascular stability.

By the process described above, HPTP-β (VE-PTP) activity can contribute to, for example, disorders that are characterized by vascular instability, angiogenesis, neovascularization, vascular leakage, and/or edema. For example, HPTP-β (VE-PTP) activity can contribute to vascular disorders, ocular disorders, cancers, renal disorders, complications of diabetes, and other disorders. Inhibition of HPTP-β (VE-PTP) activity can reduce such disorders.

VEGF and Vascular Stability

Vascular endothelial growth factors (VEGFs) are primarily found in endothelial cells, and are implicated in pathological neovascularization in a number of diseases. The VEGFs are members of the cystine-knot growth factor superfamily, the PDGF family, and the VEGF family. The VEGFs can act as pro-angiogenic factors. The VEGF family consists of VEGF-A, VEGF-B, VEGF-C, VEGF-D and placental growth factor (PGF). Nine VEGF-A isoforms exist: $VEGF_{121}$, $VEGF_{145}$, $VEGF_{148}$, $VEGF_{162}$, $VEGF_{16}s$, $VEGF_{165b}$, $VEGF_{183}$, $VEGF_{189}$, and $VEGF_{206}$.

VEGF is a hypoxia-regulated gene, and VEGF levels are increased in hypoxic or ischemic conditions. VEGF is an agonist of VEGF receptors (VEGFRs). VEGFRs are receptor tyrosine kinases; binding of VEGF to a VEGFR can result in phosphorylation of the receptor, and subsequently of downstream signal transducers. VEGFR-mediated signaling can result in aberrant vasculogenesis, angiogenesis, and permeabilization of blood vessels, contributing to pathologic vascular instability. Thus, inhibition of VEGF can result in decreased VEGFR-mediated signaling and enhanced vascular stability. For example, an inhibitor, antibody, antibody fragment, variant, or derivative thereof that binds VEGF can reduce VEGFR ligation, thereby reducing VEGFR-mediated signaling, and promoting vascular stability. Non-limiting examples of agents that bind VEGF include aflibercept (Eylea®), a recombinant protein comprising the VEGF-binding portions of human VEGF receptors 1 and 2 fused to the Fc portion of human IgG1; brolucizumab, a humanized single-chain antibody fragment (scFv); RTH258, a humanized single-chain antibody fragment (scFv); ranibizumab (Lucentis®), a humanized monoclonal antibody fragment (Fab); bevacizumab (Avastin®), a humanized monoclonal antibody; conbercept, a recombinant fusion protein comprising extracellular domains from VEGF receptors 1 and 2 fused to the Fc portion of human IgG1; Abicipar, a designed ankyrin repeat protein (DARPin); MP0112, a DARPin; MP0250, a DARPin; CT-322, an adnectin; and PRS-050, an anticalin.

By the process described above, VEGF can contribute to, for example, disorders that are characterized by vascular instability, angiogenesis, neovascularization, vascular leakage, and/or edema. For example, VEGF can contribute to vascular disorders, ocular disorders, cancers, renal disorders, complications of diabetes, and other disorders. For example, ischemia in the eye can lead to increased VEGF production, resulting in vascular leakage and pathological neovascularization in the retina. Inhibition of VEGFR-mediated signaling can reduce such disorders.

Receptor Tyrosine Kinases (RTKs) and Receptor Tyrosine Kinase Agonists

Receptor tyrosine kinases (RTKs) are cell surface receptors that participate in the regulation of cell growth, differentiation, and survival. Binding of an agonist to a RTK can cause neighboring RTKs to associate with each other, forming dimers. Dimerization can cause cross-phosphorylation—each RTK in the dimer phosphorylates multiple tyrosine residues on the other RTK. Once cross-phosphorylated, the cytoplasmic tails of the RTKs can initiate signal transduction pathways, for example, by serving as docking platforms for various intracellular proteins. RTK signaling can lead to changes of gene transcription and expression in a cell.

Non-limiting examples of RTKs include AATK, AATYK, AATYK1, AATYK2, ACH, ALK, ARK, AXL, BDB, BDB1, BEK, BFGFR, BREK, Brt, CAK, CCK4, CD115, CD117, CD135, CD136, CD140a, CD140b, CD167, CD202b, CD220, CD221, CD246, CD309, CD331, CD332, CD333, CD334, CDHF12, CDHR16, CDw136, CEK, CEK2, CEK3, c-Eyk, CFD1, C-FMS, C-Kit, cprk, c-ros-1, CSF1R, CSFR, D3S3195, DDR1, DDR2, DFNB97, DKFZp761P1010, Dtk, ECT1, EDDR1, EGFR, EphA10, EphA1-8. EphB1, EphB2, EphB3, EphB4, EphB6, ErbB2, ErbB3, ErbB4, Etk-2, FGFR1, FGFR2. FGFR3. FGFR4, FLG, FLK1, FLK2, FLT, FLT1, FLT2, FLT3, FLT4, FMS, GAS9, H2, H3, H4, H5, HGFR, HSCR1, IGF1R, IGFIR, IGFR, INSR, INSRR, IRR, JKT5A, JTK11, JTK12, JTK13, JTK14, JTK2, JTK4, JTK5, JWS, KAL2, KDR, KGFR, KIAA0641, KIAA1079, KIAA1883, KIT, KPI2, K-SAM, LMR1, LMR2, LMR3, LMTK1, LMTK2, LMTK3, LTK, MCF3, MEN2A, MEN2B, Mer, MERTK, MET, MGC18216, MST1R, MTC, MTC1, MTRK1, MuSK, NEP, NOK, N-SAM, NTRK2, NTRK3, NTRK4, NTRKR1, NTRKR2, PBT, PCL, PDGFR, PDGFR1, PDGFR2, PDGFRA, PDGFR-alpha, PDGFRB, PDGFR-beta, PPP1R100, PPP1R101, PPP1R77, PTC, PTK3A, PTK7, PTK8, RCCP2, Rek, RET, RET51, RON, ROR1, ROR2, ROS, ROS1, RP38, RSE, RTK6, RYK, Ryk, RYK1, SCFR, Sky, STK, STYK1, SuRTK106, TEK, TIE1, TIE2, Tif, TK14, TK25, TKT, TRK, TrkA, TrkB, TrkC, TYK1, TYKLM3, TYRO10, Tyro12, Tyro3, Tyro7, UFO, VEGFR, VEGFR1, VEGFR2, VEGFR3, VMCM, and VMCM1.

Non-limiting examples of RTK agonists include VEGF, Ang1, Ang2, BDNF, EGF, FGF, HGF, IGF, insulin, MSP, NGF, NT-3, and PDGF.

Antibodies and Antigen-Binding Compounds.

The basic four chain antibody unit comprises two identical heavy chain (H) polypeptide sequences and two identical light chain (L) polypeptide sequences. Each of the heavy chains can comprise one N-terminal variable ($V_H$) region and three or four C-terminal constant ($C_H1$, $C_H2$, $C_H3$, and $C_H4$) regions. Each of the light chains can comprise one N-terminal variable ($V_L$) region and one C-terminal constant ($C_L$) region. The light chain variable region is aligned with the heavy chain variable region and the light chain constant region is aligned with heavy chain constant region $C_{H1}$. The pairing of a heavy chain variable region and light chain variable region together forms a single antigen-binding site. Each light chain is linked to a heavy chain by one covalent disulfide bond. The two heavy chains are linked to each other by one or more disulfide bonds depending on the heavy chain isotype. Each heavy and light chain also comprises regularly-spaced intrachain disulfide bridges. The C-terminal constant regions of the heavy chains comprise the Fc region of the antibody, which mediate effector functions, for example, through interactions with Fc receptors or complement proteins. FIG. 1 provides a simple representative schematic basic four chain antibody unit; light chain sequences are represented by "SEQ A". Heavy chain sequences are represented by "SEQ B", —S—S— denotes disulfide bonds, N and C denote N- and C-termini, respectively.

The light chain can be designated kappa or lambda based on the amino acid sequence of the constant region. The heavy chain can be designated alpha, delta, epsilon, gamma, or mu based on the amino acid sequence of the constant region. Antibodies are categorized into five immunoglobulin classes, or isotypes, based on the heavy chain. IgA comprises alpha heavy chains, IgD comprises delta heavy chains, IgE comprises epsilon heavy chains, IgG comprises gamma heavy chains, and IgM comprises mu heavy chains. Antibodies of the IgG, IgD, and IgE classes comprise monomers of the four chain unit described above (two heavy and two light chains), while the IgM and IgA classes can comprise multimers of the four chain unit. The alpha and gamma classes are further divided into subclasses on the basis of differences in the sequence and function of the heavy chain constant region. Subclasses of IgA and IgG expressed by humans include IgG1, IgG2, IgG3, IgG4, IgA1 and IgA2.

The constant regions are minimally involved in antigen binding. Rather, the constant regions can mediate various effector functions. Different IgG isotypes or subclasses can be associated with different effector functions or therapeutic characteristics, for example, because of interactions with different Fc receptors and/or complement proteins. Antibodies comprising Fc regions that engage activating Fc receptors can, for example, participate in antibody-dependent cell-mediated cytotoxicity (ADCC), antibody-dependent cellular phagocytosis (ADCP), complement-dependent cytotoxicity (CDC), induction of signaling through immunoreceptor tyrosine-based activation motifs (ITAMs), and induction of cytokine secretion. Antibodies comprising Fc regions that engage inhibitory Fc receptors can, for example, induce signaling through immunoreceptor tyrosine-based inhibitory motifs (ITIMs).

Different antibody subclasses comprise different abilities to elicit immune effector functions. For example, IgG1 and IgG3 can effectively recruit complement to activate CDC, IgG2 elicits minimal ADCC. IgG4 has a lesser ability to trigger immune effector functions. Modifications to the constant regions can also affect antibody characteristics, for example, enhancement or reduction of Fc receptor ligation, enhancement or reduction of ADCC, enhancement or reduction of ADCP, enhancement or reduction of CDC, enhancement or reduction of signaling through ITAMs, enhancement or reduction of cytokine induction, enhancement or reduction of signaling through ITIMs, enhancement or reduction of half-life, or enhancement or reduction of coengagement of antigen with Fc receptors. Modifications can include, for example, amino acid mutations, altering post-translational modifications (e.g., glycosylation), combining domains from different isotypes or subclasses, or a combination thereof.

A compound or antibody of the disclosure can comprise constant regions or Fc regions that are selected or modified to provide suitable antibody characteristics, for example, suitable characteristics for treating a disease or condition as disclosed herein. In some embodiments, IgG1 can be used, for example, to promote immune activation effector functions (e.g., ADCC, ADCP, CDC, ITAM signaling, cytokine induction, or a combination thereof for the treatment of a cancer). In some embodiments, IgG4 can be used, for example, in cases where antagonistic properties of the antibody in the absence of immune effector functions are desirable (e.g., for treatment of ocular disorders).

Non-limiting examples of antibody modifications and their effects are provided in TABLE 1.

TABLE 1

| Effect | Isotype | Mutation(s)/modification(s) |
|---|---|---|
| Enhanced ADCC | IgG1 | F243L/R292P/Y300L/V305I/P396L |
| Enhanced ADCC | IgG1 | S239D/I332E |
| Enhanced ADCC | IgG1 | S239D/I332E/A330L |
| Enhanced ADCC | IgG1 | S298A/E333A/K334A |
| Enhanced ADCC | IgG1 | In one heavy chain: L234Y/L235Q/G236W/S239M/H268D/D270E/S298A<br>In the opposing heavy chain: D270E/K326D/A330M/K334E |
| Enhanced ADCP | IgG1 | G236A/S239D/I332E |
| Enhanced CDC | IgG1 | K326W/E333S |
| Enhanced CDC | IgG1 | S267E/H268F/S324T |
| Enhanced CDC | IgG1, IgG3 | Combination of domains from IgG1/IgG3 |
| Enhanced CDC | IgG1 | E345R/E430G/S440Y |
| Loss of glycosylation, reduced effector functions | IgG1 | N297A or N297Q or N297G |
| Reduced effector functions | IgG1, IgG4 | L235E |
| Reduced effector functions | IgG1 | L234A/L235A |
| Reduced effector functions | IgG4 | F234A/L235A |
| Reduced effector functions | IgG4 | F234A/L235A/G237A/P238S |
| Reduced effector functions | IgG4 | F234A/L235A/ΔG236/G237A/P238S |
| Reduced effector functions | IgG2, IgG4 | Combination of domains from IgG2/IgG4 |
| Reduced effector functions | IgG2 | H268Q/V309L/A330S/P331S |
| Reduced effector functions | IgG2 | V234A/G237A/P238S/H268A/V309L/A330S/P331S |
| Reduced effector functions | IgG1 | L234A/L235A/G237A/P238S/H268A/A330S/P331S |
| Increased half-life | IgG1 | M252Y/S254T/T256E |
| Increased half-life | IgG1 | M428L/N434S |
| Increased antigen/Fc receptor coengagement | IgG1 | S267E/L328F |

TABLE 1-continued

| Effect | Isotype | Mutation(s)/modification(s) |
|---|---|---|
| Altered antigen/Fc receptor coengagement | IgG1 | N325S/L328F |
| Reduced Fab arm exchange | IgG4 | S228P |

The variable (V) regions mediate antigen binding and define the specificity of a particular antibody for an antigen. The variable region comprises relatively invariant sequences called framework regions, and hypervariable regions, which differ considerably in sequence among antibodies of different binding specificities. The variable region of each antibody heavy or light chain comprises four framework regions separated by three hypervariable regions. The variable regions of heavy and light chains fold in a manner that brings the hypervariable regions together in close proximity to create an antigen binding site. The four framework regions largely adopt an β-sheet configuration, while the three hypervariable regions form loops connecting, and in some cases forming part of, the β-sheet structure.

Within hypervariable regions are amino acid residues that primarily determine the binding specificity of the antibody. Sequences comprising these residues are known as complementarity determining regions (CDRs). One antigen binding site of an antibody comprises six CDRs, three in the hypervariable regions of the light chain, and three in the hypervariable regions of the heavy chain. The CDRs in the light chain are designated L1, L2, and L3, while the CDRs in the heavy chain are designated H1, H2, and H3. CDRs can also be designated LCDR1, LCDR2, LCDR3, HCDR1, HCDR2, and HCDR3, respectively. The contribution of each CDR to antigen binding varies among antibodies. CDRs can vary in length. For example, CDRs are often 5 to 14 residues in length, but CDRs as short as 0 residues or as long as 25 residues or longer exist.

Several methods are used to predict or designate CDR sequences. These methods can use different numbering systems, for example, because sequence insertions and deletions are numbered differently.

The Kabat method was developed by aligning a limited number of antibody sequences and determining the positions of the most variable residues. Based on the alignment, a numbering scheme was introduced for residues in the variable regions. This numbering scheme can be used to determine the positions marking the beginning and the end of each CDR. One iteration of the Kabat numbering system identifies CDRs in the light chain variable region using the following residue positions: LCDR1 around residues 24-34; LCDR2 around residues 50-56; and LCDR3 around residues 89-97. One iteration of the Kabat numbering system identifies CDRs in the heavy chain variable region using the following residue positions: HCDR1 around residues 31-35; HCDR2 around residues 50-65; and HCDR3 around residues 95-102.

The Chothia method was developed based on analysis of three dimensional antibody structures. The analysis determined that hypervariable loops adopt a restricted set of conformations based on the presence of certain residues at key positions in CDRs and flanking framework regions. This method uses a similar numbering scheme as the Kabat method, but numbers insertions and deletions differently. One iteration of the Chothia numbering system identifies CDRs in the light chain variable region using the following residue positions: LCDR1 around residues 24-34; LCDR2 around residues 50-56; and LCDR3 around residues 89-97.

One iteration of the Chothia numbering system identifies CDRs in the heavy chain variable region using the following residue positions: HCDR1 around residues 26-34; HCDR2 around residues 52-56; and HCDR3 around residues 95-102.

The IMGT method (International ImMunoGeneTics database) was developed by integrating existing definitions of framework regions and CDRs, structural data, and data from alignment of antibody variable region sequences. This integration led to the identification of conserved residues in the framework regions that can be used as reference points for identifying CDRs. Examples of conserved residues in variable regions include cysteine at approximately residue 23 (in framework region 1), tryptophan at approximately residue 41 (in framework region 2), a hydrophobic amino acid at approximately residue 89 (in framework region 3), cysteine at approximately residue 104 (in framework region 3), and phenylalanine or tryptophan at approximately residue 118 (in framework region 4). CDRs can be identified in a sequence encoding an antibody variable region of interest by using a computational alignment-based algorithm.

The IMGT method of numbering consistently assigns the same numbers to the conserved amino acids, but the lengths of CDRs and framework regions are permitted to vary. Therefore, IMGT numbering of residues is not necessarily sequential. The length of CDRs identified by the IMGT method can vary. For example, LCDR1 or HCDR1 can be about 5 to about 12 amino acids, LCDR2 or HCDR2 can be about 0 to about 10 amino acids, and LCDR3 or HCDR3 can be about 5 to about 91 amino acids.

The Paratome method was developed based on multiple structural alignments of available antibody-antigen complexes. The structural positions that bind antigen were found to be similar among the examined antibodies, and antibody sequences from the data set were annotated with Antigen Binding Regions (ABRs, similar to CDRs). ABRs in a query sequence can be identified using a computational tool, which first aligns the query sequence against antibodies with solved antibody-antigen structures, then infers the positions of ABRs based on the alignment. Antibodies with solved structures can also have ABRs identified using a structural, rather than sequence-based, alignment method.

A subset of residues within CDRs contacts an antigen. These residues that contact antigen can be referred to as specificity-determining residues (SDRs). However, residues other than SDRs can contribute to binding activity by helping to maintain the conformation of the binding site. The number of SDRs in an antibody can vary based on the size and type of antigen that is recognized, for example, between 0-14 SDRs can be found within a CDR. SDRs can be enriched in some residues, such as tyrosine, serine, tryptophan, and asparagine.

A monoclonal antibody can be obtained from a population of substantially-homogeneous antibodies, i.e., the individual antibodies comprising the population are identical except for possible naturally-occurring mutations that can be present in minor amounts. In contrast to polyclonal antibody preparations, which include different antibodies directed against different epitopes, each monoclonal antibody is directed against a single epitope.

A compound herein can be a monoclonal antibody, for example, a chimeric antibody wherein a portion of the heavy and/or light chain is identical to or homologous to a corresponding sequence in an antibody derived from a particular species or belonging to a particular antibody class or subclass, while the remainder of the chain(s) is identical or homologous to a corresponding sequence in an antibody derived from another species or belonging to another antibody class or subclass, or an antigen-binding fragment of such an antibody.

An antibody fragment or antigen-binding fragment can comprise a portion of an antibody, for example, the antigen-binding or variable region of the intact antibody. Non-limiting examples of antibody fragments include Fab, Fab', $F(ab')_2$, dimers and trimers of Fab conjugates, Fv, scFv, minibodies, dia-, tria-, and tetrabodies, and linear antibodies. Fab and Fab' are antigen-binding fragments that can comprise the $V_H$ and $C_H1$ domains of the heavy chain linked to the $V_L$ and CL domains of the light chain via a disulfide bond. A $F(ab')_2$ can comprise two Fab or Fab' that are joined by disulfide bonds. A Fv can comprise the $V_H$ and $V_L$ domains held together by non-covalent interactions. A scFv (single-chain variable fragment) is a fusion protein that can comprise the $V_H$ and $V_L$ domains connected by a peptide linker. Manipulation of the orientation of the $V_H$ and $V_L$ domains and the linker length can be used to create different forms of molecules that can be monomeric, dimeric (diabody), trimeric (triabody), or tetrameric (tetrabody). Minibodies are scFv-$C_H3$fusion proteins that assemble into bivalent dimers.

Non-limiting examples of epitopes include amino acids, sugars, lipids, phosphoryl, and sulfonyl groups. An epitope can have specific three-dimensional structural characteristics, and/or specific charge characteristics. Epitopes can be conformational or linear.

For human administration, monoclonal antibodies generated from non-human species can be further optimized by a humanization process to reduce the likelihood of immunogenicity while preserving target specificity. Humanization processes involve the incorporation of human DNA to the genetic sequence of the genes that produce the isolated antibodies. The recombinant DNA is cloned and expressed in cells for large-scale production of the newly humanized antibodies.

An example of a humanized antibody is a modified chimeric antibody. A chimeric antibody can be generated as described above. The chimeric antibody is further mutated outside of the CDRs to substitute non-human sequences in the variable regions with the homologous human sequences. Another example of a humanized antibody is a CDR-grafted antibody, in which non-human CDR sequences are introduced into the human heavy and light chain variable sequences of a human antibody scaffold to replace the corresponding human CDR sequences.

A humanized antibody can be produced in mammalian cells, bioreactors, or transgenic animals, such as mouse, chicken, sheep, goat, pig, or marmoset. The transgenic animal can have a substantial portion of the human antibody-producing genome inserted into the genome of the animal.

In addition to antibodies and antibody fragments, other antigen-binding compounds can also bind target molecules. Non-limiting examples of non-antibody-derived antigen-binding compounds include ankyrin proteins, ankyrin repeat proteins, designed ankyrin repeat proteins (DARPins), affibodies, avimers, adnectins, anticalins, Fynomers, Kunitz domains, knottins, (3-hairpin mimetics, and receptors and derivatives thereof, e.g. VEGF receptors, or the VEGF-binding portions of human VEGF receptors 1 and 2.

Designed ankyrin repeat proteins (DARPins) can be protein scaffolds based on ankyrin repeat proteins. A DARPin can comprise one or more ankyrin repeats that comprise a shared sequence and/or structural motif. The individual ankyrin repeats can comprise a shared sequence and/or structural motif despite comprising mutations, substitutions, additions and/or deletions when compared to one other. A DARPin can comprise, for example, about 1, 2, 3, 4, 5, 6, 7, 8, 9, or 10 ankyrin repeats, or more. A DARPin can comprise an N-terminal capping repeat, one or more internal ankyrin repeats, and a C-terminal capping repeat. Each ankyrin repeat can comprise framework residues and protein-interaction residues. The framework residues can contribute to structure or folding topology, for example, the structure of an ankyrin repeat or interaction with a neighboring ankyrin repeat. Protein-interaction residues can contribute to binding of a target molecule, for example, via direct interaction with the target molecule, or by stabilizing directly-interacting residues in a conformation that allows binding.

Compounds, antibodies, fragments or derivatives thereof, or other compounds that bind target molecules in this disclosure can bind to targets with a $K_D$ of, for example, less than about 500 nM, less than about 300 nM, less than about 200 nM, less than about 100 nM, less than about 90 nM, less than about 80 nM, less than about 70 nM, less than about 60 nM, less than about 50 nM, less than about 40 nM, less than about 30 nM, less than about 20 nM, less than about 10 nM, less than about 5 nM, less than about 4 nM, less than about 3 nM, less than about 2 nM, less than about 1 nM, less than about 900 pM, less than about 800 pM, less than about 700 pM, less than about 600 pM, less than about 500 pM, less than about 400 pM, less than about 300 pM, less than about 200 pM, less than about 100 pM, less than about 90 pM, less than about 80 pM, less than about 70 pM, less than about 60 pM, less than about 50 pM, less than about 40 pM, less than about 30 pM, less than about 20 pM, less than about 10 pM, less than about 9 pM, less than about 8 pM, less than about 7 pM, less than about 6 pM, less than about 5 pM, less than about 4 pM, less than about 3 pM, less than about 2 pM, less than about 1 pM, less than about 900 fM, less than about 800 fM, less than about 700 fM, less than about 600 fM, less than about 500 fM, less than about 400 fM, less than about 300 fM, less than about 200 fM, less than about 100 fM, less than about 90 fM, less than about 80 fM, less than about 70 fM, less than about 60 fM, less than about 50 fM, less than about 40 fM, less than about 30 fM, less than about 20 fM, or less than about 10 fM.

In some embodiments, a compound, antibody, fragment or derivatives thereof, or other compound that a bind target molecule in this disclosure can bind to the target with a $K_D$ of, for example, about 10 fM to about 500 nM, about 30 fM to about 500 nM, about 30 fM to about 400 nM, about 30 fM to about 300 nM, about 30 fM to about 200 nM, about 30 fM to about 100 nM, about 30 fM to about 90 nM, about 30 fM to about 80 nM, about 30 fM to about 70 nM, about 30 fM to about 60 nM, about 30 fM to about 50 nM, about 30 fM to about 40 nM, about 30 fM to about 30 nM, about 30 fM to about 20 nM, about 30 fM to about 10 nM, about 30 fM to about 9 nM, about 30 fM to about 8 nM, about 30 fM to about 7 nM, about 30 fM to about 6 nM, about 30 fM to about 5 nM, about 30 fM to about 4 nM, about 30 fM to about 3 nM, about 30 fM to about 2 nM, about 30 fM to about 1 nM, about 30 fM to about 900 pM, about 30 fM to about 800 pM, about 30 fM to about 700 pM, about 30 fM to about 600 pM, about 30 fM to about 500 pM, about 30 fM to about 400 pM, about 30 fM to about 300 pM, about 30 fM to about 200 pM, about 30 fM to about 100 pM, about 30 fM to about 90 pM, about 30 fM to about 80 pM, about 30 fM to about 70 pM, about 30 fM to about 60 pM, about 30 fM to about 50 pM, about 30 fM to about 40 pM, about 30 fM to about 30 pM, about 30 fM to about 20 pM, about 30 fM to about 10 pM, about 30 fM to about 1 pM, about 30 fM to about 900 fM, about 30 fM to about 800 fM, about 30 fM to about 700 fM, about 30 fM to about 600 fM, about 30 fM to about 500 fM, about 30 fM to about 400 fM, about 30 fM to about 300 fM, about 30 fM to about 200 fM, about 30 fM to about 100 fM, about 30 fM to about 500 nM, about 30 fM to about 400 nM, about 30 fM to about 300 nM, about 30 fM to about 200 nM, about 30 fM to about 100 nM, about 30 fM to about 90 nM, about 30 fM to about 80 nM, about 30 fM to about 70 nM, about 30 fM to about 60 nM, about 30 fM to about 50 nM, about 30 fM to about 40 nM, about 30 fM to about 30 nM, about 30 fM to about 20 nM, about 30 fM to about 10 nM, about 30 fM to about 9 nM, about 30 fM to about 8 nM, about 30 fM to about 7 nM, about 30 fM to about 6 nM, about 30 fM to about 5 nM, about 30 fM to about 4 nM, about 30 fM to about 3 nM, about 30 fM to about 2 nM, about 30 fM to about 1 nM, about 30 fM to about 900 pM, about 30 fM to about 800 pM, about 30 fM to about 700 pM, about 30 fM to about 600 pM, about 30 fM to about 500 pM, about 30 fM to about 400 pM, about 30 fM to about 300 pM, about 30 fM to about 200 pM, about 30 fM to about 100 pM, about 30 fM to about 90 pM, about 30 fM to about 80 pM, about 30 fM to about 70 pM, about 30 fM to about 60 pM, about 30 fM to about 50 pM, about 30 fM to about 40 pM, about 30 fM to about 30 pM, about 30 fM to about 20 pM, about 30 fM to about 10 pM, about 1 pM to about 500 nM, about 1 pM to about 400 nM, about 1 pM to about 300 nM, about 1 pM to about 200 nM, about 1 pM to about 100 nM, about 1 pM to about 90 nM, about 1 pM to about 80 nM, about 1 pM to about 70 nM, about 1 pM to about 60 nM, about 1 pM to about 50 nM, about 1 pM to about 40 nM, about 1 pM to about 30 nM, about 1 pM to about 20 nM, about 1 pM to about 10 nM, about 1 pM to about 9 nM, about 1 pM to about 8 nM, about 1 pM to about 7 nM, about 1 pM to about 6 nM, about 1 pM to about 5 nM, about 1 pM to about 4 nM, about 1 pM to about 3 nM, about 1 pM to about 2 nM, about 1 pM to about 1 nM, about 1 pM to about 900 pM, about 1 pM to about 800 pM, about 1 pM to about 700 pM, about 1 pM to about 600 pM, about 1 pM to about 500 pM, about 1 pM to about 400 pM, about 1 pM to about 300 pM, about 1 pM to about 200 pM, about 1 pM to about 100 pM, about 1 pM to about 90 pM, about 1 pM to about 80 pM, about 1 pM to about 70 pM, about 1 pM to about 60 pM, about 1 pM to about 50 pM, about 1 pM to about 40 pM, about 1 pM to about 30 pM, about 1 pM to about 20 pM, about 1 pM to about 10 pM, about 100 pM to about 500 nM, about 100 pM to about 400 nM, about 100 pM to about 300 nM, about 100 pM to about 200 nM, about 100 pM to about 100 nM, about 100 pM to about 90 nM, about 100 pM to about 80 nM, about 100 pM to about 70 nM, about 100 pM to about 60 nM, about 100 pM to about 50 nM, about 100 pM to about 40 nM, about 100 pM to about 30 nM, about 100 pM to about 20 nM, about 100 pM to about 10 nM, about 100 pM to about 9 nM, about 100 pM to about 8 nM, about 100 pM to about 7 nM, about 100 pM to about 6 nM, about 100 pM to about 5 nM, about 100 pM to about 4 nM, about 100 pM to about 3 nM, about 100 pM to about 2 nM, about 100 pM to about 1 nM, about 100 pM to about 900 pM, about 100 pM to about 800 pM, about 100 pM to about 700 pM, about 100 pM to about 600 pM, about 100 pM to about 500 pM, about 100 pM to about 400 pM, about 100 pM to about 300 pM, or about 100 pM to about 200 pM.

In some embodiments, a compound, antibody, fragment or derivatives thereof, or other compound of the disclosure can bind HPTP-β (VE-PTP) with a $K_D$ of about 500 fM to about 500 pM. In some embodiments, a compound, antibody, fragment or derivatives thereof, or other compound of the disclosure can bind HPTP-β (VE-PTP) with a $K_D$ of about 1 pM to about 500 pM. In some embodiments, a compound, antibody, fragment or derivatives thereof, or other compound of the disclosure can bind HPTP-β (VE-PTP) with a $K_D$ of about 60 pM to about 500 pM. In some embodiments, a compound, antibody, fragment or derivatives thereof, or other compound of the disclosure can bind HPTP-β (VE-PTP) with a $K_D$ of about 100 pM to about 500 pM. In some embodiments, a compound, antibody, fragment or derivatives thereof, or other compound of the disclosure can bind HPTP-β (VE-PTP) with a $K_D$ of about 1 pM to about 300 pM. In some embodiments, a compound, antibody, fragment or derivatives thereof, or other compound of the disclosure can bind HPTP-β (VE-PTP) with a $K_D$ of about 1 pM to about 200 pM. In some embodiments, a compound, antibody, fragment or derivatives thereof, or other compound of the disclosure can bind HPTP-β (VE-PTP) with a $K_D$ of about 1 pM to about 120 pM. In some embodiments, a compound, antibody, fragment or derivatives thereof, or other compound of the disclosure can bind HPTP-β (VE-PTP) with a $K_D$ of about 1 pM to about 70 pM.

In some embodiments, a compound, antibody, fragment or derivatives thereof, or other compound of the disclosure can bind VEGF with a $K_D$ of about 30 fM to about 900 pM. In some embodiments, a compound, antibody, fragment or derivatives thereof, or other compound of the disclosure can bind VEGF with a $K_D$ of about 30 fM to about 600 pM. In some embodiments, a compound, antibody, fragment or derivatives thereof, or other compound of the disclosure can bind VEGF with a $K_D$ of about 30 fM to about 200 pM. In some embodiments, a compound, antibody, fragment or derivatives thereof, or other compound of the disclosure can bind VEGF with a $K_D$ of about 30 fM to about 30 pM. In some embodiments, a compound, antibody, fragment or derivatives thereof, or other compound of the disclosure can bind VEGF with a $K_D$ of about 30 fM to about 40 pM. In some embodiments, a compound, antibody, fragment or derivatives thereof, or other compound of the disclosure can bind VEGF with a $K_D$ of about 30 fM to about 1 pM. In some embodiments, a compound, antibody, fragment or derivatives thereof, or other compound of the disclosure can bind VEGF with a $K_D$ of about 30 fM to about 200 fM. In some embodiments, a compound, antibody, fragment or derivatives thereof, or other compound of the disclosure can bind VEGF with a $K_D$ of about 1 pM to about 900 pM. In some embodiments, a compound, antibody, fragment or derivatives thereof, or other compound of the disclosure can bind VEGF with a $K_D$ of about 1 pM to about 600 pM. In some embodiments, a compound, antibody, fragment or derivatives thereof, or other compound of the disclosure can bind VEGF with a $K_D$ of about 1 pM to about 200 pM. In some embodiments, a compound, antibody, fragment or derivatives thereof, or other compound of the disclosure can bind VEGF with a $K_D$ of about 1 pM to about 30 pM. In some embodiments, a compound, antibody, fragment or derivatives thereof, or other compound of the disclosure can bind VEGF with a $K_D$ of about 1 pM to about 40 pM.

In some embodiments, a compound, antibody, fragment or derivatives thereof, or other compound of the disclosure can bind VEGF with a $K_D$ of about 30 fM to about 2 pM. In some embodiments, a compound, antibody, fragment or derivatives thereof, or other compound of the disclosure can bind VEGF with a $K_D$ of about 35 fM to about 200 fM. In some embodiments, a compound, antibody, fragment or derivatives thereof, or other compound of the disclosure can bind VEGF with a $K_D$ of about 100 fM to about 2 pM.

In some embodiments, a compound, antibody, fragment or derivatives thereof, or other compound of the disclosure can bind VEGF with a $K_D$ of about 20 pM to about 1 nM. In some embodiments, a compound, antibody, fragment or derivatives thereof, or other compound of the disclosure can bind VEGF with a $K_D$ of about 20 pM to about 800 pM. In some embodiments, a compound, antibody, fragment or derivatives thereof, or other compound of the disclosure can bind VEGF with a $K_D$ of about 20 pM to about 350 pM.

In some embodiments, a compound, antibody, fragment or derivatives thereof, or other compound of the disclosure can bind VEGF with a $K_D$ of about 30 fM to about 700 pM.

In some embodiments, a compound, antibody, fragment or derivatives thereof, or other compound of the disclosure can bind VEGF with a $K_D$ of about 40 fM to about 520 pM. In some embodiments, a compound, antibody, fragment or derivatives thereof, or other compound of the disclosure can bind VEGF with a $K_D$ of about 40 fM to about 110 pM.

Polyvalent, Multispecific Compounds

Antigen-binding compounds can be combined to generate polyvalent and/or multispecific compounds. Such polyvalent and/or multispecific compounds can have advantages over the parent compounds administered individually. These advantages can include, for example, a simpler dosing regimen, longer half-life within a subject, and the ability to bind target antigens in close proximity.

Multispecific antibodies can be produced by a number of methods. In one method, monospecific antibodies or derivatives thereof can be chemically coupled, for example, via chemical coupling of two IgG antibody units into a conjugate.

In another method, cloning techniques can be used to append additional antigen binding domain(s) to a conventional IgG antibody or derivative thereof. An additional antigen-binding domain can be, for example, a single variable domain (sVD), a single-chain variable fragment (scFv), a single-chain Fab, a peptide, an ankyrin protein, an ankyrin repeat protein, a designed ankyrin repeat protein (DARPin), an affibody, an avimer, an adnectin, an anticalin, a Fynomer, a Kunitz domain, a knottin, a β-hairpin mimetic, a tetrameric polyethylene oxide clustered peptide, a peptide derived from one or more receptors (e.g. VEGF receptors, or the VEGF-binding portions of human VEGF receptors 1 and 2), or a derivative thereof.

The additional antigen-binding domain (e.g., sVD, scFv, single-chain Fab, peptide, ankyrin protein, ankyrin repeat protein, DARPin, affibody, avimer, adnectin, anticalin, Fynomer, Kunitz domain, knottin, β-hairpin mimetic, tetrameric polyethylene oxide clustered peptide, or peptide derived from one or more receptors) can be appended to the N or C-terminus of the light chain and/or heavy chain of the IgG or Fab, for example, via a peptide linker. In some embodiments, a scFv can be appended to the C-termini of the heavy chains of an IgG to provide a tetravalent bispecific antibody. A scFv can be appended to the C-termini of the light chains of an IgG to provide a tetravalent bispecific antibody. A scFv can be appended to the C-termini of the light chains and the C-termini of the heavy chains of an IgG, to provide a hexavalent bispecific antibody. In some embodiments, a DARPin can be appended to the C-termini of the heavy chains of an IgG to provide a tetravalent bispecific antibody. A DARPin can be appended to the C-termini of the light chains of an IgG to provide a tetravalent bispecific antibody. A DARPin can be appended to the C-termini of the light chains and the C-termini of the heavy chains of an IgG, to provide a hexavalent bispecific antibody. Additional examples of multispecific antibodies produced by cloning techniques include: (i) DVD-Ig™ (dual variable domain immunoglobulin, tandem linkage of the second $V_H$ and $V_L$ to the N-termini of HC and LC, respectively), (ii) Tandemab (tandem linkage of 2 $V_H$-$C_H1$ in combination of common LC), (iii) DNL (natural association of 2 antibodies or antibody fragments anchored with DDD (dimerization and docking domain) from PKA (protein kinase A) and AD (anchoring domain) from A-kinase anchor protein (AKAP), respectively), (iv) LUZ-Y (leucine zipper tethered at the C-termini of HC and later proteolytically removed), (v) 2-in-1-IgG (same LC and HC capable of dual recognition), and (vi) $mAb^2$ (engineered loops in $C_H3$ domain of IgG to obtain second specificity).

Another class of multispecific antibodies can be characterized by structures with variable domains or scFvs as the building blocks. Non-limiting examples of such multispecific antibodies include two $V_H$ domains joined in tandem, diabodies (heterodimers containing 2 polypeptide chains encoding $V_LA$-$V_HB$ and $V_HA$-$V_LB$ in the order of $V_H$-$V_L$ or $V_L$-$V_H$ with a linker of 5 amino acids), dsDbs (interchain disulfide bond between $V_L$ and $V_H$ of the same antibody), DARTs (dual-affinity re-targeting, interchain disulfide bond between 2 $V_L$), scDbs (single chain Diabody), tandAbs (Diabody dimer via flexible linkers in between), and 2 scFvs connected in tandem by an adjustable linker.

Another class of multispecific antibodies can contain different antigen binding fragments, while retaining the basic IgG structure. Such antibodies can comprise, for example, two distinct heavy chains and/or two distinct light chains. Various techniques can be used to promote pairing of desirable light and heavy chain combinations, rather than random chain associations. Non-limiting examples of such techniques include use of a common light chain, orthogonal Fab interface (complementary mutations introduced at LC and HC interface in one Fab and no change to the other Fab), CrossMab (wherein one Fab $V_H$ or $C_H1$ domain(s) can be switched with the partner $V_L$ or $C_L$ domain(s), with the other Fab untouched), and replacing the Fab with a single chain antigen-binding domain. Further examples include engineering strategies that can introduce mutations into the $C_H3$ domains to promote heterodimerization based on steric or electrostatic complementarity. The "knobs in holes" approach can involve creating a "knob" by replacing threonine at position 366 with a bulky tryptophan residue on one heavy chain, and making a corresponding "hole" by triple mutations (T366S, L368A and Y407V) on the partner heavy chain. Another approach can involve creating alternating human IgG and IgA fragments in $C_H3$ to provide the so-called SEEDbody (Strand-Exchange Engineered Domain) to guide heavy chain heterodimerization.

Non-limiting schematics of multispecific antibodies are provided in FIGS. 2-15.

Figure 2:
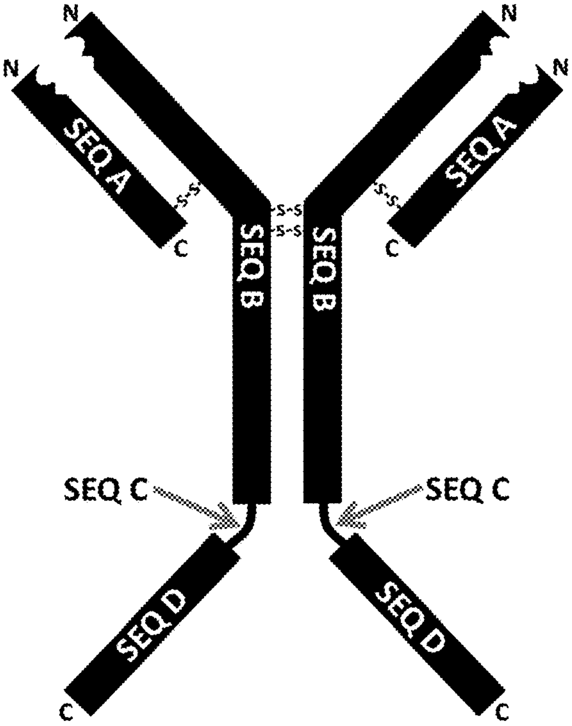
FIG. 2: Schematic of a tetravalent, bispecific antibody with sequences appended to the heavy chain C-termini. Light chain sequences of the IgG isotype antibody unit are represented by "SEQ A". Heavy chain sequences of the IgG isotype antibody unit are represented by "SEQ B". Linker sequences are represented by "SEQ C". Appended antigen binding domain sequences are represented by "SEQ D". N and C denote N- and C-termini, respectively. —S—S— denotes disulfide bonds.

FIG. 2 provides a schematic of a tetravalent, bispecific antibody with sequences appended to the heavy chain C-termini. Light chain sequences of the IgG isotype antibody unit are represented by "SEQ A". Heavy chain sequences of the IgG isotype antibody unit are represented by "SEQ B". Linker sequences are represented by "SEQ C". Appended antigen binding domain sequences are represented by "SEQ D". N and C denote N- and C-termini, respectively. —S—S— denotes disulfide bonds.

Figure 3:
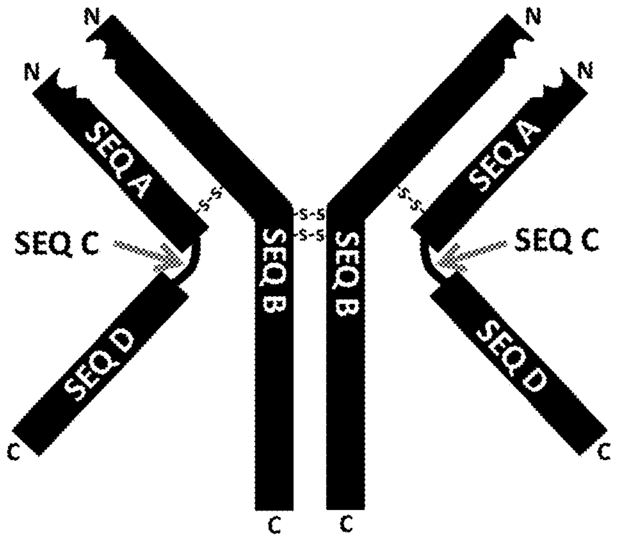
FIG. 3: Schematic of a tetravalent, bispecific antibody with sequences appended to the light chain C-termini. Light chain sequences of the IgG isotype antibody unit are represented by "SEQ A". Heavy chain sequences of the IgG isotype antibody unit are represented by "SEQ B". Linker sequences are represented by "SEQ C". Appended antigen binding domain sequences are represented by "SEQ D". N and C denote N- and C-termini, respectively. —S—S— denotes disulfide bonds.

FIG. 3 provides a schematic of a tetravalent, bispecific antibody with sequences appended to the light chain C-termini. Light chain sequences of the IgG isotype antibody unit are represented by "SEQ A". Heavy chain sequences of the IgG isotype antibody unit are represented by "SEQ B". Linker sequences are represented by "SEQ C". Appended antigen binding domain sequences are represented by "SEQ D". N and C denote N- and C-termini, respectively. —S—S— denotes disulfide bonds.

Figure 4:
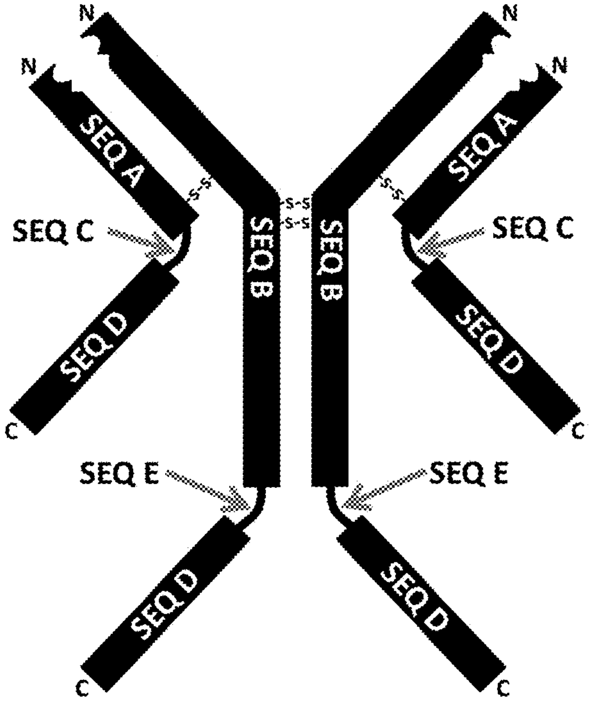
FIG. 4: Schematic of a hexavalent, bispecific antibody with sequences appended to the heavy chain and light chain C-termini. Light chain sequences of the IgG isotype antibody unit are represented by "SEQ A". Heavy chain sequences of the IgG isotype antibody unit are represented by "SEQ B". Linker sequences are represented by "SEQ C" and "SEQ E". Appended antigen binding domain sequences are represented by "SEQ D". N and C denote N- and C-termini, respectively. —S—S— denotes disulfide bonds.

FIG. 4 provides a schematic of a hexavalent, bispecific antibody with sequences appended to the heavy chain and light chain C-termini. Light chain sequences of the IgG isotype antibody unit are represented by "SEQ A". Heavy chain sequences of the IgG isotype antibody unit are represented by "SEQ B". Linker sequences are represented by "SEQ C" and "SEQ E". Appended antigen binding domain sequences are represented by "SEQ D". N and C denote N- and C-termini, respectively. —S—S— denotes disulfide bonds.

Figure 5:
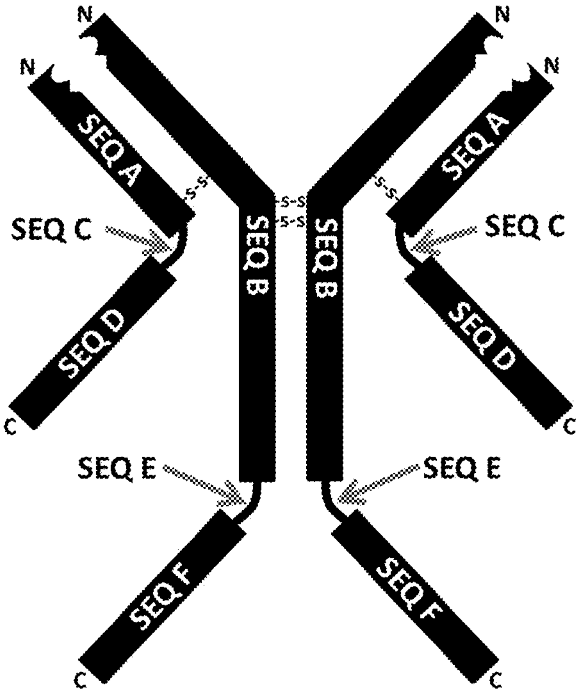
FIG. 5: Schematic of a hexavalent, trispecific antibody with sequences appended to the heavy chain and light chain C-termini. Light chain sequences of the IgG isotype antibody unit are represented by "SEQ A". Heavy chain sequences of the IgG isotype antibody unit are represented by "SEQ B". Linker sequences are represented by "SEQ C" and "SEQ E". Appended antigen binding domain sequences are represented by "SEQ D" and "SEQ F". N and C denote N- and C-termini, respectively. —S—S— denotes disulfide bonds.

FIG. 5 provides a schematic of a hexavalent, trispecific antibody with sequences appended to the heavy chain and light chain C-termini. Light chain sequences of the IgG isotype antibody unit are represented by "SEQ A". Heavy chain sequences of the IgG isotype antibody unit are represented by "SEQ B". Linker sequences are represented by "SEQ C" and "SEQ E". Appended antigen binding domain sequences are represented by "SEQ D" and "SEQ F". N and C denote N- and C-termini, respectively. —S—S— denotes disulfide bonds.

Figure 6:
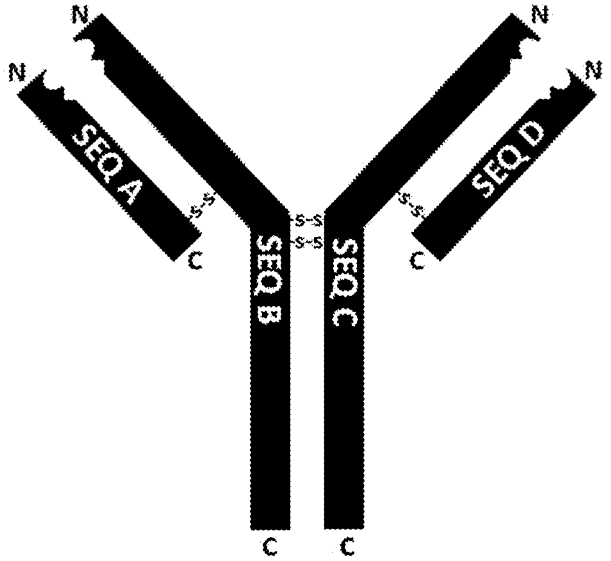
FIG. 6: Schematic of a bivalent, bispecific antibody with two different heavy chain sequences and two different light chain sequences. Light chain sequences are represented by "SEQ A" and "SEQ D". Heavy chain sequences are represented by "SEQ B" and "SEQ C". N and C denote N- and C-termini, respectively. —S—S— denotes disulfide bonds.

FIG. 6 provides a schematic of a bivalent, bispecific antibody with two different heavy chain sequences and two different light chain sequences. Light chain sequences are represented by "SEQ A" and "SEQ D". Heavy chain sequences are represented by "SEQ B" and "SEQ C". N and C denote N- and C-termini, respectively. —S—S— denotes disulfide bonds.

Figure 7:
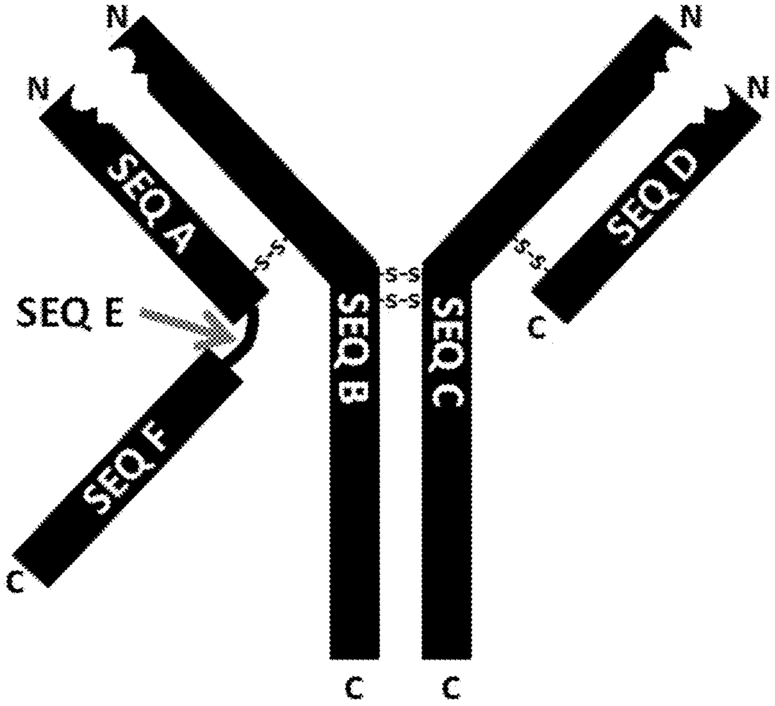
FIG. 7: Schematic of a trivalent, trispecific antibody with two different heavy chain sequences, two different light chain sequences, and a sequence appended to the C-terminus of one light chain. Light chain sequences of the IgG isotype antibody unit are represented by "SEQ A" and "SEQ D". Heavy chain sequences of the IgG isotype antibody unit are represented by "SEQ B" and "SEQ C". A linker sequence is represented by "SEQ E". An appended antigen binding domain sequence is represented by "SEQ F". N and C denote N- and C-termini, respectively. —S—S— denotes disulfide bonds.

FIG. 7 provides a schematic of a trivalent, trispecific antibody with two different heavy chain sequences, two different light chain sequences, and a sequence appended to the C-terminus of one light chain. Light chain sequences of the IgG isotype antibody unit are represented by "SEQ A" and "SEQ D". Heavy chain sequences of the IgG isotype antibody unit are represented by "SEQ B" and "SEQ C". A linker sequence is represented by "SEQ E". An appended antigen binding domain sequence is represented by "SEQ F". N and C denote N- and C-termini, respectively. —S—S— denotes disulfide bonds.

Figure 8:
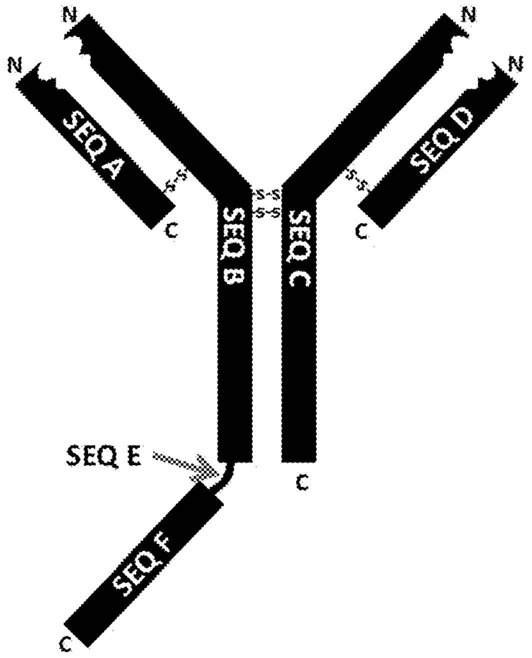
FIG. 8: Schematic of a trivalent, trispecific antibody with two different heavy chain sequences, two different light chain sequences, and a sequence appended to the C-terminus of one heavy chain. Light chain sequences of the IgG isotype antibody unit are represented by "SEQ A" and "SEQ D". Heavy chain sequences of the IgG isotype antibody unit are represented by "SEQ B" and "SEQ C". A linker sequence is represented by "SEQ E". An appended antigen binding domain sequence is represented by "SEQ F". N and C denote N- and C-termini, respectively. —S—S— denotes disulfide bonds.

FIG. 8 provides a schematic of a trivalent, trispecific antibody with two different heavy chain sequences, two different light chain sequences, and a sequence appended to the C-terminus of one heavy chain. Light chain sequences of the IgG isotype antibody unit are represented by "SEQ A" and "SEQ D". Heavy chain sequences of the IgG isotype antibody unit are represented by "SEQ B" and "SEQ C". A linker sequence is represented by "SEQ E". An appended antigen binding domain sequence is represented by "SEQ F". N and C denote N- and C-termini, respectively. —S—S— denotes disulfide bonds.

Figure 9:
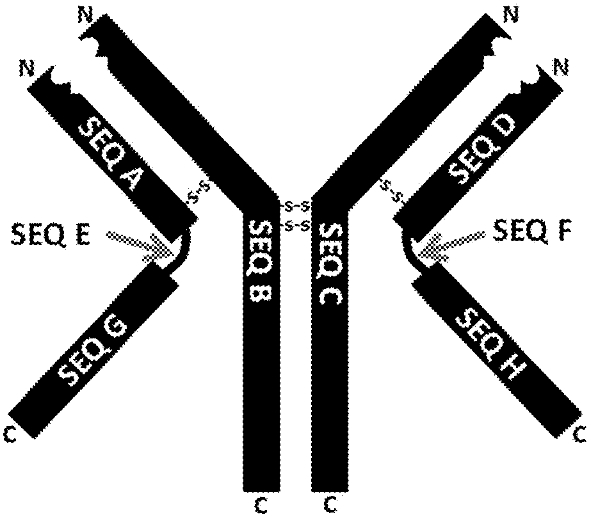
FIG. 9: Schematic of a tetravalent antibody with two different heavy chain sequences, two different light chain sequences, and sequences appended to both light chain C-termini. Light chain sequences of the IgG isotype antibody unit are represented by "SEQ A" and "SEQ D". Heavy chain sequences of the IgG isotype antibody unit are represented by "SEQ B" and "SEQ C". Linker sequences are represented by "SEQ E" and "SEQ F". Appended antigen binding domain sequences are represented by "SEQ G" and "SEQ H". N and C denote N- and C-termini, respectively. —S—S— denotes disulfide bonds.

FIG. 9 provides a schematic of a tetravalent antibody with two different heavy chain sequences, two different light chain sequences, and sequences appended to both light chain C-termini. Light chain sequences of the IgG isotype antibody unit are represented by "SEQ A" and "SEQ D". Heavy chain sequences of the IgG isotype antibody unit are represented by "SEQ B" and "SEQ C". Linker sequences are represented by "SEQ E" and "SEQ F". Appended antigen binding domain sequences are represented by "SEQ G" and "SEQ H". N and C denote N- and C-termini, respectively. —S—S— denotes disulfide bonds.

Figure 10:
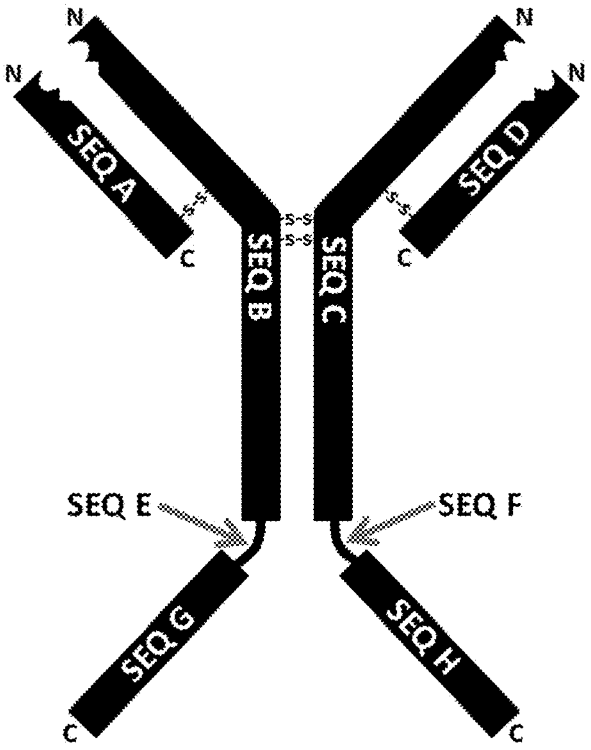
FIG. 10: Schematic of a tetravalent antibody with two different heavy chain sequences, two different light chain sequences, and sequences appended to both heavy chain C-termini. Light chain sequences of the IgG isotype antibody unit are represented by "SEQ A" and "SEQ D". Heavy chain sequences of the IgG isotype antibody unit are represented by "SEQ B" and "SEQ C". Linker sequences are represented by "SEQ E" and "SEQ F". Appended antigen binding domain sequences are represented by "SEQ G" and "SEQ H". N and C denote N- and C-termini, respectively. —S—S— denotes disulfide bonds.

FIG. 10 provides a schematic of a tetravalent antibody with two different heavy chain sequences, two different light chain sequences, and sequences appended to both heavy chain C-termini. Light chain sequences of the IgG isotype antibody unit are represented by "SEQ A" and "SEQ D". Heavy chain sequences of the IgG isotype antibody unit are represented by "SEQ B" and "SEQ C". Linker sequences are represented by "SEQ E" and "SEQ F". Appended antigen binding domain sequences are represented by "SEQ G" and "SEQ H". N and C denote N- and C-termini, respectively. —S—S— denotes disulfide bonds.

Figure 11:
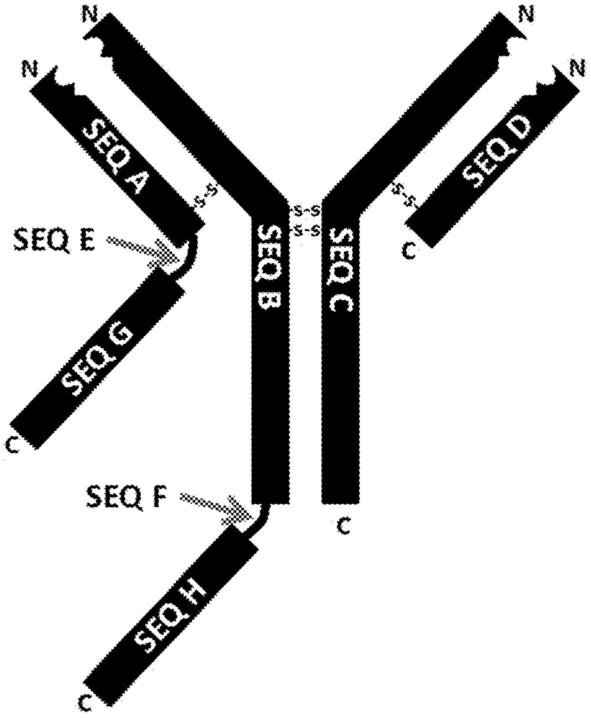
FIG. 11: Schematic of a tetravalent antibody with two different heavy chain sequences, two different light chain sequences, and sequences appended to one heavy chain C-terminus and one light chain C-terminus in cis. Light chain sequences of the IgG isotype antibody unit are represented by "SEQ A" and "SEQ D". Heavy chain sequences of the IgG isotype antibody unit are represented by "SEQ B" and "SEQ C". Linker sequences are represented by "SEQ E" and "SEQ F". Appended antigen binding domain sequences are represented by "SEQ G" and "SEQ H". N and C denote N- and C-termini, respectively. —S—S— denotes disulfide bonds.

FIG. 11 provides a schematic of a tetravalent antibody with two different heavy chain sequences, two different light chain sequences, and sequences appended to one heavy chain C-terminus and one light chain C-terminus in cis. Light chain sequences of the IgG isotype antibody unit are represented by "SEQ A" and "SEQ D". Heavy chain sequences of the IgG isotype antibody unit are represented by "SEQ B" and "SEQ C". Linker sequences are represented by "SEQ E" and "SEQ F". Appended antigen binding domain sequences are represented by "SEQ G" and "SEQ H". N and C denote N- and C-termini, respectively. —S—S— denotes disulfide bonds.

Figure 12:
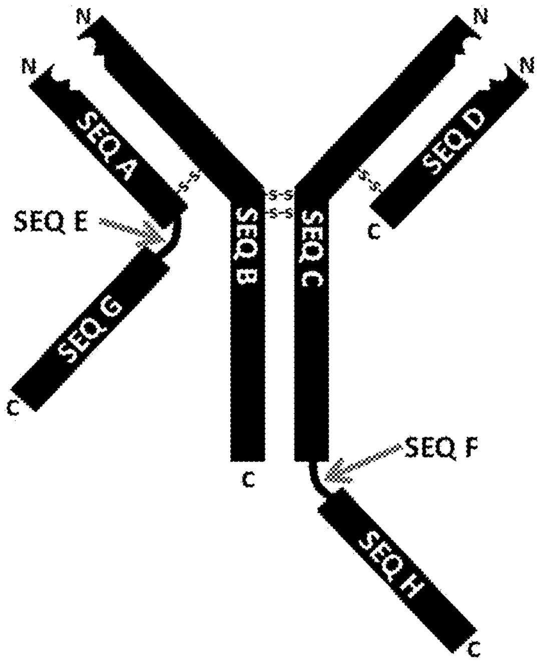
FIG. 12: Schematic of a tetravalent antibody with two different heavy chain sequences, two different light chain sequences, and sequences appended to one heavy chain C-terminus and one light chain C-terminus in trans. Light chain sequences of the IgG isotype antibody unit are represented by "SEQ A" and "SEQ D". Heavy chain sequences of the IgG isotype antibody unit are represented by "SEQ B" and "SEQ C". Linker sequences are represented by "SEQ E" and "SEQ F". Appended antigen binding domain sequences are represented by "SEQ G" and "SEQ H". N and C denote N- and C-termini, respectively. —S—S— denotes disulfide bonds.

FIG. 12 provides a schematic of a tetravalent antibody with two different heavy chain sequences, two different light chain sequences, and sequences appended to one heavy chain C-terminus and one light chain C-terminus in trans. Light chain sequences of the IgG isotype antibody unit are represented by "SEQ A" and "SEQ D". Heavy chain sequences of the IgG isotype antibody unit are represented by "SEQ B" and "SEQ C". Linker sequences are represented by "SEQ E" and "SEQ F". Appended antigen binding domain sequences are represented by "SEQ G" and "SEQ H". N and C denote N- and C-termini, respectively. —S—S— denotes disulfide bonds.

Figure 13:
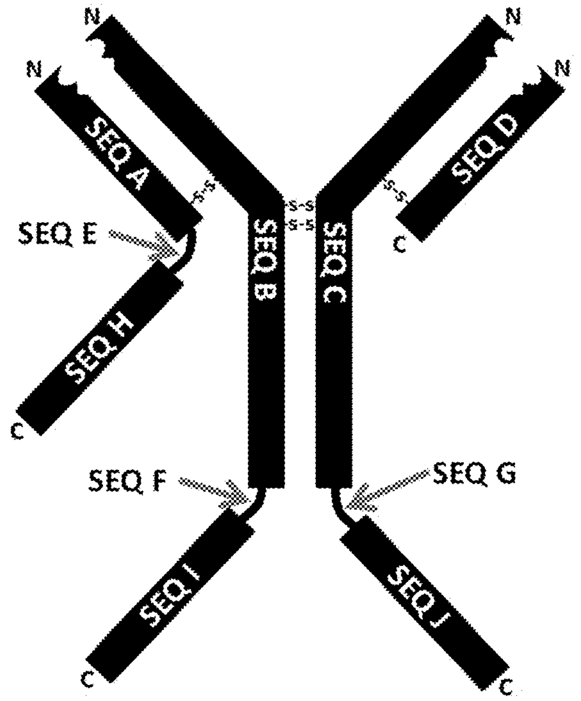
FIG. 13: Schematic of a pentavalent antibody with two different heavy chain sequences, two different light chain sequences, and sequences appended to both heavy chain C-termini and one light chain C-terminus. Light chain sequences of the IgG isotype antibody unit are represented by "SEQ A" and "SEQ D". Heavy chain sequences of the IgG isotype antibody unit are represented by "SEQ B" and "SEQ C". Linker sequences are represented by "SEQ E", "SEQ F", and "SEQ G". Appended antigen binding domain sequences are represented by "SEQ H", "SEQ I", and "SEQ J". N and C denote N- and C-termini, respectively. —S—S— denotes disulfide bonds.

FIG. 13 provides a schematic of a pentavalent antibody with two different heavy chain sequences, two different light chain sequences, and sequences appended to both heavy chain C-termini and one light chain C-terminus. Light chain sequences of the IgG isotype antibody unit are represented by "SEQ A" and "SEQ D". Heavy chain sequences of the IgG isotype antibody unit are represented by "SEQ B" and "SEQ C". Linker sequences are represented by "SEQ E", "SEQ F", and "SEQ G". Appended antigen binding domain sequences are represented by "SEQ H", "SEQ I", and "SEQ J". N and C denote N- and C-termini, respectively. —S—S— denotes disulfide bonds.

Figure 14:
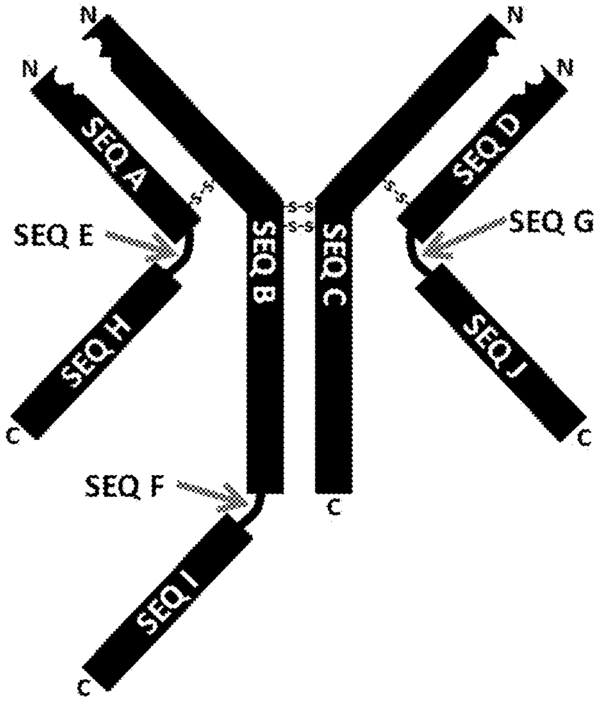
FIG. 14: Schematic of a pentavalent antibody with two different heavy chain sequences, two different light chain sequences, and sequences appended to one heavy chain C-terminus and both light chain C-termini. Light chain sequences of the IgG isotype antibody unit are represented by "SEQ A" and "SEQ D". Heavy chain sequences of the IgG isotype antibody unit are represented by "SEQ B" and "SEQ C". Linker sequences are represented by "SEQ E", "SEQ F", and "SEQ G". Appended antigen binding domain sequences are represented by "SEQ H", "SEQ I", and "SEQ J". N and C denote N- and C-termini, respectively. —S—S— denotes disulfide bonds.

FIG. 14 provides a schematic of a pentavalent antibody with two different heavy chain sequences, two different light chain sequences, and sequences appended to one heavy chain C-terminus and both light chain C-termini. Light chain sequences of the IgG isotype antibody unit are represented by "SEQ A" and "SEQ D". Heavy chain sequences of the IgG isotype antibody unit are represented by "SEQ B" and "SEQ C". Linker sequences are represented by "SEQ E", "SEQ F", and "SEQ G". Appended antigen binding domain sequences are represented by "SEQ H", "SEQ I", and "SEQ J". N and C denote N- and C-termini, respectively. —S—S— denotes disulfide bonds.

Figure 15:
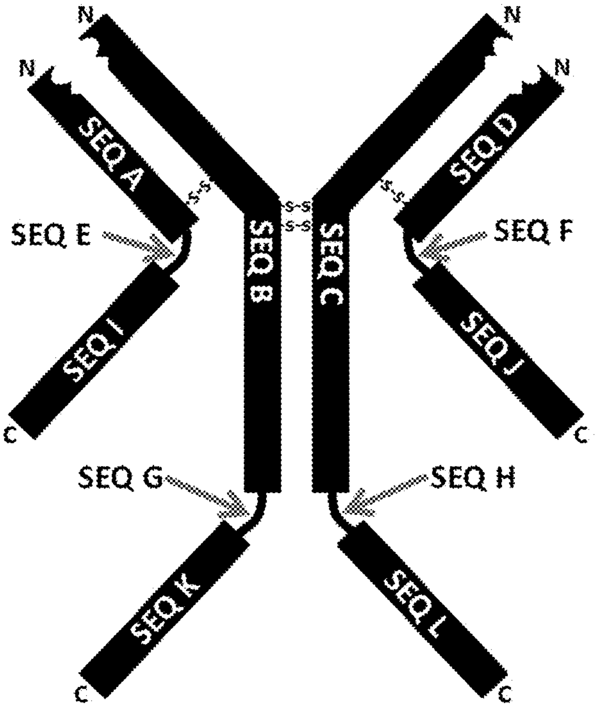
FIG. 15: Schematic of a hexavalent antibody with two different heavy chain sequences, two different light chain sequences, and sequences appended to the heavy chain and light chain C-termini. Light chain sequences of the IgG isotype antibody unit are represented by "SEQ A" and "SEQ D". Heavy chain sequences of the IgG isotype antibody unit are represented by "SEQ B" and "SEQ C". Linker sequences are represented by "SEQ E", "SEQ F", "SEQ G", and "SEQ H". Appended antigen binding domain sequences are represented by "SEQ I", "SEQ J", "SEQ K" and "SEQ L". N and C denote N- and C-termini, respectively. —S—S— denotes disulfide bonds.

FIG. 15 provides a schematic of a hexavalent antibody with two different heavy chain sequences, two different light chain sequences, and sequences appended to the heavy chain and light chain C-termini. Light chain sequences of the IgG isotype antibody unit are represented by "SEQ A" and "SEQ D". Heavy chain sequences of the IgG isotype antibody unit are represented by "SEQ B" and "SEQ C". Linker sequences are represented by "SEQ E", "SEQ F", "SEQ G", and "SEQ H". Appended antigen binding domain sequences are represented by "SEQ I", "SEQ J", "SEQ K", and "SEQ L". N and C denote N- and C-termini, respectively. —S—S— denotes disulfide bonds.

Antigen-binding compounds specific for, for example, HPTP-β (VE-PTP), can be combined with antigen-binding compounds specific for, for example, a RTK agonist, to provide a polyvalent multispecific compound that can bind both HPTP-β (VE-PTP) and the RTK agonist. For example, an antigen binding compound specific for HPTP-β (VE-PTP) can be combined with an antigen-binding compound specific for VEGF, Ang1, Ang2, BDNF, EGF, FGF, HGF, IGF, insulin, MSP, NGF, NT-3, PDGF, or any combination thereof, to provide a polyvalent multispecific compound that can bind both HPTP-β (VE-PTP) and a RTK agonist.

Antigen-binding compounds specific for, for example, HPTP-β (VE-PTP), can be combined with antigen-binding compounds specific for, for example, VEGF, to provide a polyvalent multispecific compound that can bind both HPTP-β (VE-PTP) and VEGF. Compounds that bind both HPTP-β (VE-PTP) and VEGF can inhibit HPTP-β (VE-PTP), activate Tie2, inhibit VEGF binding to VEGFRs, and inhibit VEGFR signaling.

Sequences derived from aflibercept, a recombinant protein comprising the VEGF-binding portions of human VEGF receptors 1 and 2, can be combined with antigen-binding compounds specific for HPTP-β (VE-PTP). For example, sequences derived from aflibercept can be fused to the C-termini of the heavy chains of a HPTP-β (VE-PTP)-specific antibody, to provide a tetravalent, bispecific antibody (FIG. 2). Sequences derived from aflibercept can be fused to the C-termini of the light chains of a HPTP-β (VE-PTP)-specific antibody, to provide a tetravalent, bispecific antibody (FIG. 3). Sequences derived from aflibercept can be fused to the C-termini of the light chains and heavy chains of a HPTP-β (VE-PTP)-specific antibody, to provide a hexavalent, bispecific antibody (FIG. 4).

Sequences derived from brolucizumab, a humanized single-chain antibody fragment (scFv) inhibitor of VEGF that binds to the receptor binding site of VEGF, can be combined with antigen-binding compounds specific for HPTP-β (VE-PTP). For example, sequences from brolucizumab can be fused to the C-termini of the heavy chains of a HPTP-β (VE-PTP)-specific antibody, to provide a tetravalent, bispecific antibody (FIG. 2). Sequences derived from brolucizumab can be fused to the C-termini of the light chains of a HPTP-β (VE-PTP)-specific antibody, to provide a tetravalent, bispecific antibody (FIG. 3). Sequences derived from brolucizumab can be fused to the C-termini of the light chains and heavy chains of a HPTP-β (VE-PTP)-specific antibody, to provide a hexavalent, bispecific antibody (FIG. 4).

Sequences derived from ranibizumab, a humanized monoclonal antibody fragment (Fab) that binds to and inhibits the activity of VEGF, can be combined with antigen-binding compounds specific for HPTP-β (VE-PTP). For example, the sequences from ranibizumab can be cloned into an scFv, and the ranibizumab-derived scFv can be fused to can be fused to the C-termini of the heavy chains of a HPTP-β (VE-PTP)-specific antibody, to provide a tetravalent, bispecific antibody (FIG. 2). The ranibizumab-derived scFv can be fused to the C-termini of the light chains of a HPTP-β (VE-PTP)-specific antibody, to provide a tetravalent, bispecific antibody (FIG. 3). The ranibizumab-derived scFv can be fused to the C-termini of the light chains and heavy chains of a HPTP-β (VE-PTP)-specific antibody, to provide a hexavalent, bispecific antibody (FIG. 4).

Sequences derived from bevacizumab, a humanized monoclonal antibody that that binds to and inhibits activity of VEGF, can be combined with antigen-binding compounds specific for HPTP-β (VE-PTP). For example, the sequences from bevacizumab can be cloned into an scFv, and the bevacizumab-derived scFv can be fused to can be fused to the C-termini of the heavy chains of a HPTP-β (VE-PTP)-specific antibody, to provide a tetravalent, bispecific antibody (FIG. 2). The bevacizumab-derived scFv can be fused to the C-termini of the light chains of a HPTP-β (VE-PTP)-specific antibody, to provide a tetravalent, bispecific antibody (FIG. 3). The bevacizumab-derived scFv can be fused to the C-termini of the light chains and heavy chains of a HPTP-β (VE-PTP)-specific antibody, to provide a hexavalent, bispecific antibody (FIG. 4).

Sequences derived from conbercept, a recombinant protein comprising the VEGF-binding portions of VEGF receptors 1 and 2, can be combined with antigen-binding compounds specific for HPTP-β (VE-PTP). For example, sequences derived from conbercept can be fused to the C-termini of the heavy chains of a HPTP-β (VE-PTP)-specific antibody, to provide a tetravalent, bispecific antibody (FIG. 2). Sequences derived from conbercept can be fused to the C-termini of the light chains of a HPTP-β (VE-PTP)-specific antibody, to provide a tetravalent, bispecific antibody (FIG. 3). Sequences derived from conbercept can be fused to the C-termini of the light chains and heavy chains of a HPTP-β (VE-PTP)-specific antibody, to provide a hexavalent, bispecific antibody (FIG. 4).

Sequences derived from abicipar, a VEGF-binding DARPin, can be combined with antigen-binding compounds specific for HPTP-β (VE-PTP). For example, sequences derived from abicipar can be fused to the C-termini of the heavy chains of a HPTP-β (VE-PTP)-specific antibody, to provide a tetravalent, bispecific antibody (FIG. 2). Sequences derived from abicipar can be fused to the C-termini of the light chains of a HPTP-β (VE-PTP)-specific antibody, to provide a tetravalent, bispecific antibody (FIG. 3). Sequences derived from abicipar can be fused to the C-termini of the light chains and heavy chains of a HPTP-β (VE-PTP)-specific antibody, to provide a hexavalent, bispecific antibody (FIG. 4).

Antigen-binding compounds specific for HPTP-β (VE-PTP) can be combined with DARPins or amino acid sequences therefrom, for example, amino acid sequences comprising any one of SEQ ID NOS: 158-217. Amino acid sequences comprising any one of SEQ ID NOS: 158-217 can be fused to the C-termini of the heavy chains of a HPTP-β (VE-PTP)-specific antibody, to provide a tetravalent, bispecific antibody (FIG. 2). Amino acid sequences comprising any one of SEQ ID NOS: 158-217 can be fused to the C-termini of the light chains of a HPTP-β (VE-PTP)-specific antibody, to provide a tetravalent, bispecific antibody (FIG. 3). Amino acid sequences comprising any one of SEQ ID NOS: 158-217 can be fused to the C-termini of the light chains and heavy chains of a HPTP-β (VE-PTP)-specific antibody, to provide a hexavalent, bispecific antibody (FIG. 4).

Multiple VEGF-specific compounds can be combined with an antigen-binding compound specific for HPTP-β (VE-PTP). For example, one binding domain, (e.g. aflibercept-derived sequences) can be fused to the C-termini of the heavy chains of an anti-HPTP-β (VE-PTP) antibody, and another binding domain (e.g. brolucizumab-derived sequences) be fused to the C-termini of the light chains of the HPTP-β (VE-PTP)-specific antibody, to provide a hexavalent, trispecific antibody (FIG. 5).

If different heavy chains are used in the basic four chain IgG antibody unit (e.g., using the "knobs in holes" approach), antibodies can be generated that are bivalent, trivalent, tetravalent, pentavalent, or hexavalent, and that are monospecific, bispecific, trispecific, tetraspecific, pentaspecific, or hexaspecific.

In one non-limiting example, one arm of the antibody unit can contain CDRs specific for HPTP-β (VE-PTP), while the other arm of the antibody unit can contain CDRs specific for VEGF (FIG. 6).

In one non-limiting example, both antigen binding fragments of the basic antibody unit can be HPTP-β (VE-PTP)-specific, and a binding domain specific for VEGF (e.g. aflibercept-derived sequence, brolucizumab-derived sequence, ranibizumab-derived sequence, or a bevacizumab-derived sequence) can be fused to one light chain, to provide a trivalent bispecific antibody (FIG. 7).

In one non-limiting example, both antigen binding fragments of the basic antibody unit can be HPTP-β (VE-PTP)-specific, and a binding domain specific for VEGF (e.g. aflibercept-derived sequence, brolucizumab-derived sequence, ranibizumab-derived sequence, or a bevacizumab-derived sequence) can be fused to one heavy chain, to provide a trivalent bispecific antibody (FIG. 8).

In one non-limiting example, both antigen binding fragments of the basic antibody unit can be HPTP-β (VE-PTP)-specific, and a binding domain specific for VEGF (e.g. aflibercept-derived sequence, brolucizumab-derived sequence, ranibizumab-derived sequence, or a bevacizumab-derived sequence) can be fused to one light chain, and a second, different binding domain specific for VEGF can be fused to the other light chain, to provide a tetravalent trispecific antibody (FIG. 9).

In one non-limiting example, both antigen binding fragments of the basic antibody unit can be HPTP-β (VE-PTP)-specific, a binding domain specific for VEGF (e.g. aflibercept-derived sequence, brolucizumab-derived sequence, ranibizumab-derived sequence, or a bevacizumab-derived sequence) can be fused to one heavy chain, and a second, different binding domain specific for VEGF can be fused to the other heavy chain, to provide a tetravalent trispecific antibody (FIG. 10).

In one non-limiting example, both antigen binding fragments of the basic antibody unit can be HPTP-β (VE-PTP)-specific, and a binding domain specific for VEGF (e.g. aflibercept-derived sequence, brolucizumab-derived sequence, ranibizumab-derived sequence, or a bevacizumab-derived sequence) can be fused to one heavy chain, and a second, different binding domain specific for VEGF can be fused to one light chain in cis, to provide a tetravalent trispecific antibody (FIG. 11).

In one non-limiting example, both antigen binding fragments of the basic antibody unit can be HPTP-β (VE-PTP)-specific, a binding domain specific for VEGF (e.g. aflibercept-derived sequence, brolucizumab-derived sequence, ranibizumab-derived sequence, or a bevacizumab-derived sequence) can be fused to one heavy chain, and a second, different binding domain specific for VEGF can be fused to one light chain in trans, to provide a tetravalent trispecific antibody (FIG. 12).

In one non-limiting example, both antigen binding fragments of the basic antibody unit can be HPTP-β (VE-PTP)-specific, a binding domain specific for VEGF (e.g. aflibercept-derived sequence, brolucizumab-derived sequence, ranibizumab-derived sequence, or a bevacizumab-derived sequence) can be fused to one heavy chain, a second, different binding domain specific for VEGF can be fused to a second heavy chain, and a third, different binding domain specific for VEGF can be fused to one light chain, to provide a pentavalent tetraspecific antibody (FIG. 13).

In one non-limiting example, both antigen binding fragments of the basic antibody unit can be HPTP-β (VE-PTP)-specific, a binding domain specific for VEGF (e.g. aflibercept-derived sequence, brolucizumab-derived sequence, ranibizumab-derived sequence, or a bevacizumab-derived sequence) can be fused to one heavy chain, a second, different binding domain specific for VEGF can be fused to a one light chain, and a third, different binding domain specific for VEGF can be fused to the other light chain, to provide a pentavalent tetraspecific antibody (FIG. 14).

In one non-limiting example, both antigen binding fragments of the basic antibody unit can be HPTP-β (VE-PTP)-specific, a binding domain specific for VEGF (e.g. aflibercept-derived sequence, brolucizumab-derived sequence, ranibizumab-derived sequence, or a bevacizumab-derived sequence) can be fused to one heavy chain, a second, different binding domain specific for VEGF can be fused to the other heavy chain, a third, different binding domain specific for VEGF can be fused to one light chain, and a fourth binding domain specific for VEGF can be fused to the other light chain, to provide a hexavalent pentaspecific antibody (FIG. 15).

In one non-limiting example, both antigen binding fragments of the basic antibody unit can be HPTP-β (VE-PTP)-specific, one binding domain, (e.g. an aflibercept-derived sequence) can be fused to the C-terminus of one heavy chain, and second binding domain (e.g. a brolucizumab-derived sequence) be fused to the C-terminus of the other heavy chain, to provide a tetravalent, trispecific antibody (FIG. 10). In one non-limiting example, both antigen binding fragments of the basic antibody unit can be HPTP-β (VE-PTP)-specific, an aflibercept-derived sequence can be fused to the C-terminus of one light chain, and a brolucizumab-derived sequence be fused to the C-terminus of another light chain, to provide a tetravalent, trispecific antibody (FIG. 9). In one non-limiting example, both antigen binding fragments of the basic antibody unit can be HPTP-β (VE-PTP)-specific, an aflibercept-derived sequence can be fused to the C-terminus of one heavy chain, and a brolucizumab-derived sequence be fused to the C-terminus of one light chain, to provide a tetravalent, trispecific antibody (FIG. 11, FIG. 12). In one non-limiting example, both antigen binding fragments of the basic antibody unit can be HPTP-β (VE-PTP)-specific, an aflibercept-derived sequence can be fused to the C-terminus of one heavy chain, a brolucizumab-derived sequence can be fused to the C-terminus of another heavy chain, and ranibizumab-derived sequences can be fused to the C-termini of both light chains, to provide a hexavalent, tetraspecific antibody (FIG. 15). In one non-limiting example, both antigen binding fragments of the basic antibody unit can be HPTP-β (VE-PTP)-specific, an aflibercept-derived sequence can be fused to the C-terminus of one heavy chain, a brolucizumab-derived sequence can be fused to the C-terminus of another heavy chain, a ranibizumab-derived sequence can be fused to the C-terminus of one light chain, and a bevacizumab-derived sequence can be fused to the C-terminus of another light chain, to provide a hexavalent, pentaspecific antibody (FIG. 15).

Antigen-binding compounds specific for, for example, HPTP-β (VE-PTP), can be combined with other amino acid sequences to provide polyvalent multispecific compounds that, for example, enhance Tie2 activation, enhance Tie2 phosphorylation, enhance Tie2 signaling, reduce VEGFR activation, reduce VEGFR phosphorylation, reduce VEGFR signaling, or a combination thereof.

Antigen-binding compounds specific for HPTP-β (VE-PTP) can be combined with collagen IV-derived biomimetic peptides, for example, amino acid sequences comprising SEQ ID NO: 152 or SEQ ID NO: 153. Amino acid sequences comprising SEQ ID NO: 152 or SEQ ID NO: 153 can be fused to the C-termini of the heavy chains of a HPTP-β (VE-PTP)-specific antibody, to provide a tetravalent, bispecific antibody (FIG. 2). Amino acid sequences comprising SEQ ID NO: 152 or SEQ ID NO: 153 can be fused to the C-termini of the light chains of a HPTP-β (VE-PTP)-specific antibody, to provide a tetravalent, bispecific antibody (FIG. 3). Amino acid sequences comprising SEQ ID NO: 152 or SEQ ID NO: 153 the C-termini of the light chains and heavy chains of a HPTP-β (VE-PTP)-specific antibody, to provide a hexavalent, bispecific antibody (FIG. 4).

Antigen-binding compounds specific for HPTP-β (VE-PTP) can be combined with Ang1 mimetics, for example, vasculotide. Sequences derived from vasculotide can be fused to the C-termini of the heavy chains of a HPTP-β (VE-PTP)-specific antibody, to provide a tetravalent, bispecific antibody (FIG. 2). Sequences derived from vasculotide can be fused to the C-termini of the light chains of a HPTP-β (VE-PTP)-specific antibody, to provide a tetravalent, bispecific antibody (FIG. 3). Sequences derived from vasculotide can be fused to the C-termini of the light chains and heavy chains of a HPTP-β (VE-PTP)-specific antibody, to provide a hexavalent, bispecific antibody (FIG. 4).

Antigen-binding compounds specific for, for example, HPTP-β (VE-PTP), can be combined with antigen-binding compounds specific for, for example, a RTK, to provide a polyvalent multispecific compound that can bind both HPTP-β (VE-PTP) and the RTK. For example, an antigen binding compound specific for HPTP-β (VE-PTP) can be combined with an antigen-binding compound specific for VEGFR (e.g. VEGFR2), to provide a polyvalent multispecific compound that can bind both HPTP-β (VE-PTP) and VEGFR.

Compounds that bind both HPTP-β (VE-PTP) and VEGFR can inhibit HPTP-β (VE-PTP), activate Tie2, inhibit VEGF binding to VEGFR, and inhibit VEGFR signaling.

Sequences derived from ramucirumab, a humanized monoclonal antibody that binds an extracellular domain of VEGFR2 and inhibits VEGFR2 signaling, can be combined with antigen-binding compounds specific for HPTP-β (VE-PTP). For example, the sequences from ramucirumab can be cloned into an scFv, and the ramucirumab-derived scFv can be fused to can be fused to the C-termini of the heavy chains of a HPTP-β (VE-PTP)-specific antibody, to provide a tetravalent, bispecific antibody (FIG. 2). The ramucirumab-derived scFv can be fused to the C-termini of the light chains of a HPTP-β (VE-PTP)-specific antibody, to provide a tetravalent, bispecific antibody (FIG. 3). The ramucirumab-derived scFv can be fused to the C-termini of the light chains and heavy chains of a HPTP-β (VE-PTP)-specific antibody, to provide a hexavalent, bispecific antibody (FIG. 4).

Multiple compounds that enhance Tie2 activation, enhance Tie2 phosphorylation, enhance Tie2 signaling, reduce VEGFR activation, reduce VEGFR phosphorylation, reduce VEGFR signaling, or a combination thereof, can be combined with an antigen-binding compound specific for HPTP-β (VE-PTP). For example, one binding domain, (e.g. brolucizumab-derived sequences) can be fused to the C-termini of the heavy chains of an anti-HPTP-β (VE-PTP) antibody, and another binding domain (e.g. vasculotide-derived sequences) be fused to the C-termini of the light chains of the HPTP-β (VE-PTP)-specific antibody, to provide a hexavalent, trispecific antibody (FIG. 5).

Compounds, antibodies, or derivatives thereof disclosed herein can have 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 domains or more. Each domain can modulate, bind, antagonize, inhibit or activate any targets disclosed herein, for example, a phosphatase, a phosphatase that modulates Tie2 signaling, a protein tyrosine phosphatase, a receptor-like protein tyrosine phosphatase, a Tie2 modulator, HPTP-β (VE-PTP), an extracellular domain of HPTP-β (VE-PTP), the first FN3 repeat of an extracellular domain of HPTP-β (VE-PTP), a kinase, a tyrosine kinase, a receptor tyrosine kinase, a receptor tyrosine kinase activator, a receptor tyrosine kinase agonist, a growth factor, a growth factor receptor activator, a growth factor receptor agonist, a cysteine-knot growth factor superfamily member, a pro-angiogenic factor, a PDGF family member, a VEGF receptor, a VEGF receptor agonist, a VEGF family member, a VEGF, VEGF-A, VEGF-B, VEGF-C, VEGF-D, PGF, $VEGF_{121}$, $VEGF_{145}$, $VEGF_{148}$, $VEGF_{162}$, $VEGF_{165}$, $VEGF_{165b}$, $VEGF_{183}$, $VEGF_{189}$ or $VEGF_{206}$.

Inhibitors, Activators, Modulators, and Binding Agents

A HPTP-β (VE-PTP) inhibitor, modulator, or binding agent of the disclosure can include a compound, a recombinant protein, an antibody, antigen-binding fragment, variant, or derivative thereof, a Tie2-peptomimetic, a tetrameric polyethylene oxide clustered peptide, a collagen IV-biomimetic peptide, a DARPin or derivative thereof, an affinibody, an avimer, an adnectin, an anticalin, a Fynomer, a Kunitz domain, a knottin, a β-hairpin mimetic, or a peptide derived from one or more receptors, either alone or in combination with another amino acid sequence or multiple other amino acid sequences. The inhibitor, modulator, or binding agent can undergo modifications, for example, enzymatic cleavage or posttranslational modifications.

In some embodiments, a HPTP-β (VE-PTP) inhibitor, modulator, or binding agent of the disclosure can inhibit HPTP-β (VE-PTP) by interfering with the interaction of HPTP-β (VE-PTP) and Tie2. In some embodiments, a HPTP-β (VE-PTP) inhibitor, modulator, or binding agent of the disclosure can inhibit HPTP-β (VE-PTP) by stabilizing HPTP-β (VE-PTP) in an inactive conformation. In some embodiments, a HPTP-β (VE-PTP) inhibitor, modulator, or binding agent of the disclosure can inhibit HPTP-β (VE-PTP) by promoting internalization of HPTP-β (VE-PTP) (e.g., promoting endocytosis and degradation of HPTP-β (VE-PTP)). In some embodiments, a HPTP-β (VE-PTP) inhibitor, modulator, or binding agent of the disclosure can inhibit HPTP-β (VE-PTP) by blocking binding of a ligand that activates HPTP-β (VE-PTP). In some embodiments, a HPTP-β (VE-PTP) inhibitor, modulator, or binding agent of the disclosure can inhibit HPTP-β (VE-PTP) by modulating oligomerization of HPTP-β (VE-PTP).

In some embodiments, a HPTP-β (VE-PTP) inhibitor, modulator, or binding agent of the disclosure can bind to a dominant-negative isoform of HPTP-β (VE-PTP). A dominant-negative isoform can correspond to a form of HPTP-β (VE-PTP) deficient in phosphatase activity that can compete with endogenous HPTP-β (VE-PTP).

A HPTP-β (VE-PTP) inhibitor, modulator, or binding agent of the disclosure can comprise a plurality of HPTP-β (VE-PTP) binding sites. In some embodiments, a HPTP-β (VE-PTP) inhibitor, modulator, or binding agent can bind to two HPTP-β (VE-PTP) molecules simultaneously, thereby bringing the two HPTP-β (VE-PTP) molecules into close proximity. In some embodiments, a HPTP-β (VE-PTP) inhibitor, modulator, or binding agent can bind to three HPTP-β (VE-PTP) molecules simultaneously, thereby bringing the three HPTP-β (VE-PTP) molecules into close proximity. In some embodiments, a HPTP-β (VE-PTP) inhibitor, modulator, or binding agent can bind to four HPTP-β (VE-PTP) molecules simultaneously, thereby bringing the four HPTP-β (VE-PTP) molecules into close proximity.

A HPTP-β (VE-PTP) inhibitor, modulator, or binding agent of the disclosure can be covalently or non-covalently conjugated to another moiety or vehicle. A moiety or vehicle can, for example, provide binding specificity for an additional target, inhibit degradation, increase half-life, increase absorption, reduce toxicity, reduce immunogenicity, and/or increase biological activity of the inhibitor, modulator, or binding agent. Non-limiting examples of the moiety to which the inhibitor, modulator, or binding agent can be conjugated include a Fc domain of an immunoglobulin, a peptide, a lipid, a carbohydrate, a dendrimer, an oligosaccharide, a cholesterol group such as a steroid, and a polymer such as a polyethylene glycol (PEG), a polylysine, or a dextran.

A compound of the present disclosure can be used for targeting HPTP-β (VE-PTP) to restore Tie2 activity. A HPTP-β (VE-PTP) inhibitor, modulator, or binding agent can thus be a Tie2 activator. In some embodiments, a compound of the present disclosure can initiate or inhibit a signaling cascade downstream of HPTP-β (VE-PTP) or Tie2, for example, Akt/PI3-K signaling, Rac1 signaling, MAPK/Ras signaling, or NF-κB signaling.

Inhibition of HPTP-β (VE-PTP) can lead to vascular stabilization, which can be beneficial for the treatment of, for example, disorders that are characterized by vascular instability, angiogenesis, neovascularization, vascular leakage, and/or edema. For example, inhibition of HPTP-β (VE-PTP) can be beneficial for the treatment of vascular disorders, ocular disorders, cancers, renal disorders, complications of diabetes, and other disorders. In some embodiments, a HPTP-β (VE-PTP) inhibitor, modulator, or binding agent of the disclosure can be used to treat, for example, diabetic retinopathy, non-proliferative diabetic retinopathy (NPDR), glaucoma, intraocular pressure, ocular edema, ocular hemorrhage, ocular hypertension, ocular inflammation, ocular neovascularization, ocular vascular leak, retinal perfusion, or retinopathy.

A Tie2 activator, modulator, or binding agent of the disclosure can include, for example, a compound, a recombinant protein, a peptide, an antibody, an antigen-binding fragment, variant, or derivative thereof, an angiopoietin 1 recombinant protein, an Ang1 mimetic, a Tie2 agonist, a HPTP-β (VE-PTP) phosphatase inhibitor, a Tie2-peptomimetic, a tetrameric polyethylene oxide clustered peptide, a collagen IV-biomimetic peptide, a DARPin or derivative thereof, an affinibody, an avimer, an adnectin, an anticalin, a Fynomer, a Kunitz domain, a knottin, a β-hairpin mimetic, or a peptide derived from one or more receptors, either alone or in combination with another amino acid sequence or multiple other amino acid sequences. The activator, modulator, or binding agent can undergo modifications, for example, enzymatic cleavage or posttranslational modifications.

A Tie2 activator, modulator, or binding agent of the disclosure can be covalently or non-covalently conjugated to another moiety or vehicle. A moiety or vehicle can, for example, provide binding specificity for an additional target, inhibit degradation, increase half-life, increase absorption, reduce toxicity, reduce immunogenicity, and/or increase biological activity of the activator, modulator, or binding agent. Non-limiting examples of the moiety to which the activator, modulator, or binding agent can be conjugated include a Fc domain of an immunoglobulin, a peptide, a lipid, a carbohydrate, a dendrimer, an oligosaccharide, a cholesterol group such as a steroid, and a polymer such as a polyethylene glycol (PEG), a polylysine, or a dextran.

In some embodiments, a compound of the present disclosure can initiate or inhibit a signaling cascade downstream of Tie2, for example, Akt/PI3-K signaling, Rac1 signaling, MAPK/Ras signaling, or NF-κB signaling.

The activation of Tie2 can lead to vascular stabilization, which can be beneficial for the treatment of, for example, disorders that are characterized by vascular instability, angiogenesis, neovascularization, vascular leakage, and/or edema. For example, activation of Tie2 can be beneficial for the treatment of ocular disorders, cancers, renal disorders, complications of diabetes, and other disorders. In some embodiments, a Tie2 activator, modulator, or binding agent of the disclosure can be used to treat diabetic retinopathy, non-proliferative diabetic retinopathy (NPDR), glaucoma, intraocular pressure, ocular edema, ocular hemorrhage, ocular hypertension, ocular inflammation, ocular neovascularization, ocular vascular leak, retinal perfusion, or retinopathy.

A VEGF inhibitor, modulator, or binding agent of the disclosure can include a compound, a recombinant protein, a peptide, an antibody, antigen-binding fragment, variant, or derivative thereof, a DARPin or derivative thereof, an affinibody, an avimer, an adnectin, an anticalin, a Fynomer, a Kunitz domain, a knottin, a β-hairpin mimetic, a tetrameric polyethylene oxide clustered peptide, a collagen IV-biomimetic peptide, or a peptide derived from one or more receptors (e.g. VEGF receptors, or the VEGF-binding portions of human VEGF receptors 1 and 2), either alone or in combination with another amino acid sequence or multiple other amino acid sequences. The inhibitor, modulator, or binding agent can undergo modifications, for example, enzymatic cleavage or posttranslational modifications.

A VEGF inhibitor, modulator, or binding agent of the disclosure can comprise a plurality of VEGF binding sites. In some embodiments, a VEGF inhibitor, modulator, or binding agent can bind to two VEGF molecules simultaneously, thereby bringing the two VEGF molecules into close proximity. In some embodiments, a VEGF inhibitor, modulator, or binding agent can bind to three VEGF molecules simultaneously, thereby bringing the three VEGF molecules into close proximity. In some embodiments, a VEGF inhibitor, modulator, or binding agent can bind to four VEGF molecules simultaneously, thereby bringing the four VEGF molecules into close proximity.

A VEGF inhibitor, modulator, or binding agent of the disclosure can be covalently or non-covalently conjugated to another moiety or vehicle. A moiety or vehicle can, for example, provide binding specificity for an additional target, inhibit degradation, increase half-life, increase absorption, reduce toxicity, reduce immunogenicity, and/or increase biological activity of the inhibitor, modulator, or binding agent. Non-limiting examples of the moiety to which the inhibitor, modulator, or binding agent can be conjugated include a Fc domain of an immunoglobulin, a peptide, a lipid, a carbohydrate, a dendrimer, an oligosaccharide, a cholesterol group such as a steroid, and a polymer such as a polyethylene glycol (PEG), a polylysine, or a dextran.

A VEGFR inhibitor, modulator, or binding agent of the disclosure can include a compound, a recombinant protein, an antibody, an antigen-binding fragment, variant, or derivative thereof, a tetrameric polyethylene oxide clustered peptide, a collagen IV-biomimetic peptide, a DARPin or derivative thereof, an affinibody, an avimer, an adnectin, an anticalin, a Fynomer, a Kunitz domain, a knottin, a β-hairpin mimetic, or a peptide derived from one or more receptors, either alone or in combination with another amino acid sequence or multiple other amino acid sequences. The inhibitor, modulator, or binding agent can undergo modifications, for example, enzymatic cleavage or posttranslational modifications.

A VEGFR inhibitor, modulator, or binding agent of the disclosure can comprise a plurality of VEGFR binding sites. In some embodiments, a VEGFR inhibitor, modulator, or binding agent can bind to two VEGFR molecules simultaneously, thereby bringing the two VEGFR molecules into close proximity. In some embodiments, a VEGFR inhibitor, modulator, or binding agent can bind to three VEGFR molecules simultaneously, thereby bringing the three VEGFR molecules into close proximity. In some embodiments, a VEGFR inhibitor, modulator, or binding agent can bind to four VEGFR molecules simultaneously, thereby bringing the four VEGFR molecules into close proximity.

A VEGFR inhibitor, modulator, or binding agent of the disclosure can be covalently or non-covalently conjugated to another moiety or vehicle. A moiety or vehicle can, for example, provide binding specificity for an additional target, inhibit degradation, increase half-life, increase absorption, reduce toxicity, reduce immunogenicity, and/or increase biological activity of the inhibitor, modulator, or binding agent. Non-limiting examples of the moiety to which the inhibitor, modulator, or binding agent can be conjugated include a Fc domain of an immunoglobulin, a peptide, a lipid, a carbohydrate, a dendrimer, an oligosaccharide, a cholesterol group such as a steroid, and a polymer such as a polyethylene glycol (PEG), a polylysine, or a dextran.

In some embodiments, a VEGFR inhibitor, modulator, or binding agent of the disclosure can inhibit VEGFR by stabilizing VEGFR in an inactive conformation. In some embodiments, a VEGFR inhibitor, modulator, or binding agent of the disclosure can inhibit VEGFR by promoting internalization of VEGFR (e.g., promoting endocytosis and degradation of VEGFR). In some embodiments, a VEGFR inhibitor, modulator, or binding agent of the disclosure can inhibit VEGFR by blocking binding of a ligand that activates VEGFR (e.g., blocking VEGF ligation of VEGFR). In some embodiments, a VEGFR inhibitor, modulator, or binding agent of the disclosure can inhibit VEGFR by modulating oligomerization of VEGFR (e.g., preventing or reducing the likelihood of dimerization or oligomerization of VEGFR).

A compound of the present disclosure can be used for interfering with the interaction of VEGF and VEGFR, thereby reducing VEGFR phosphorylation and downstream signaling. In some embodiments, inhibition of VEGF can reduce aberrant vasculogenesis, angiogenesis, or blood vessel permeabilization, thereby reducing pathologic vascular instability. In some embodiments, inhibition of VEGF can be beneficial for the treatment of disorders that are characterized by vascular instability, angiogenesis, neovascularization, vascular leakage, and/or edema. For example, inhibition of VEGF can be beneficial for the treatment of vascular disorders, ocular disorders, cancers, renal disorders, complications of diabetes, and other disorders. In some embodiments, a VEGF inhibitor, modulator, or binding agent of the disclosure can be used to treat diabetic retinopathy, non-proliferative diabetic retinopathy (NPDR), glaucoma, intraocular pressure, ocular edema, ocular hemorrhage, ocular hypertension, ocular inflammation, ocular neovascularization, ocular vascular leak, retinal perfusion, or retinopathy. In some embodiments, inhibition of VEGF can reduce cancer.

Methods

The promotion of Tie2-signaling and inhibition of VEGFR signaling can lead to vascular stabilization, which can be beneficial for the treatment of a condition with a vascular component. A compound disclosed herein can be used to treat, for example, a disease characterized by changes in the vasculature, a disease characterized by decreased Tie2 activation, or a disease characterized by involvement of VEGF in pathogenesis, whether progressive or non-progressive, acute or chronic.

In some embodiments, a compound disclosed herein can be used to treat an ocular disorder. A compound disclosed herein can be used to treat, for example, age-related macular degeneration (dry form), age-related macular degeneration (wet form), atopic keratitis, Bests disease, blepharitis, blurry vision, choroidal neovascularization, chronic retinal detachment, chronic uveitis/vitritis, choroiditis, conjunctivitis, contact lens overwear, corneal graft neovascularization, corneal graft rejection, corneal neovascularization, cystoid macular edema, diabetic macular edema, double vision, diabetic retinopathy, diseases associated with rubeosis (neovascularization of the angle), diseases caused by abnormal proliferation of fibrovascular or fibrous tissue including all forms of proliferative vitreoretinopathy, Eales disease, elevated intraocular pressure, epidemic keratoconjunctivitis, floaters, glaucoma, hard yellow exudates within 500 µm of the center of the fovea with adjacent retinal thickening, hyperviscosity syndromes, infections causing choroiditis, infections causing retinitis, iris neovascularization, ischemic retinopathy, loss of contrast, macular telangectasia, mariginal keratolysis, multifocal choroiditis, myopia, neovascular glaucoma, non-proliferative diabetic retinopathy (NPDR), ocular edema, ocular hemorrhage, ocular histoplasmosis, ocular hypertension, ocular inflammation, ocular ischemia, ocular neovascularization, ocular trauma, ocular vascular leak, optic pits, papilloedema, pars planitis, phylectenulosis, polypoidal choroidal vasculopathy, post-laser complications, proliferative diabetic retinopathy, pterygium keratitis sicca, radial keratotomy, retinal angiomatous proliferation, retinal degeneration, retinal edema (including macular edema), retinal neovascularization, retinal perfusion, retinal thickening within 1 disc diameter of the center of the fovea, retinal thickening within 500 µm of the center of the fovea, retinal vein occlusion (central or branch), retinitis, retinitis pigmentosa, retinopathy, retinopathy of prematurity, scleritis, Stargarts disease, superior limbic keratitis, surgery induced edema, surgery induced neovascularization, Terrien's marginal degeneration, trachoma, trauma, uveitis, vasculitis (e.g. central retinal vein occlusion), or other ophthalmic diseases wherein the eye disease or disorder is associated with ocular neovascularization, vascular leakage, or retinal edema, or a combination thereof.

In some embodiments, a compound disclosed herein can be used to treat a complication of diabetes (e.g., a comorbidity of diabetes). A compound disclosed herein can be used to treat, for example, Acute glomerulonephritis, Acute myocardial infarction, Amputation, Amyotrophy, Aneurysm, Angina pectoris, Aortic aneurysm, Aortic dissection, Atherosclerosis, Atherosclerotic cardiovascular disease, Atrial fibrillation, Autonomic neuropathy, Blindness, Cardiovascular complications of diabetes, Cerebrovascular complications of diabetes, Charcot's arthropathy, Chronic glomerulonephritis, Chronic renal failure, Claudication, Clinically significant macular edema, Coronary artery disease, Cranial nerve palsy, Cystoid macular degeneration, Cystoid macular edema, Diabetic cardiomyopathy, Diabetic cheiroarthropathy, Diabetic coma, Diabetic encephalopathy, Diabetic foot wound, Diabetic hyperglycemia, Diabetic hyperlipidemia, Diabetic hyperosmolar syndrome, Diabetic hypoglycemia, Diabetic ketoacidosis, Diabetic myonecrosis, Diabetic nephropathy, Diabetic neuropathy, Diabetic ophthalmologic disease, Diabetic peripheral vascular disease, Diabetic retinopathy, Diffuse idiopathic skeletal hyperostosis, Dupuytren's contracture, Embolism, End-stage renal disease, Erectile dysfunction, Forestier disease, Gangrene, Gas gangrene, Gastroparesis/diarrhea, Heart failure, Hyperglycemic crisis, Hypertension, Ischemic heart disease, Ketoacidosis, Lipohypertrophy, Metabolic complications of diabetes, Mononeuropathy, Myocardial infarction, Nephritis, Nephropathy, Nephrosis, Nephrotic syndrome, Neurogenic bladder, Neuropathic arthropathy, Neuropathy, Orthostatic hypotension, Osteoarthritis, Osteoporosis, Periodontal disease, Peripheral vascular disease, Polyneuropathy, Proliferative retinopathy, Renal failure, Renal insufficiency, Restrictive lung disease, Retinal detachment, Retinal edema, Retinopathy, Stroke, Thrombosis, Transient ischemic attack, Ulceration, Ventricular fibrillation, Vitreous hemorrhage, or a combination thereof.

In some embodiments, a compound disclosed herein can be used to treat a renal disorder. A compound disclosed herein can be used to treat, for example, Acute kidney injury, Acute proliferative glomerulonephritis, Adenine phosphoribosyltransferase deficiency, Alport syndrome, Analgesic nephropathy, Autosomal dominant polycystic kidney disease, Autosomal recessive polycystic kidney disease, Balkan endemic nephropathy, Benign nephrosclerosis, Bright's disease, Cardiorenal syndrome, CFHR5 nephropathy, Chronic kidney disease, Chronic kidney disease-mineral and bone disorder, Congenital nephrotic syndrome, Conorenal syndrome, Contrast-induced nephropathy, Cystic kidney disease, Dents disease, Diabetic nephropathy, Diffuse proliferative nephritis, Distal renal tubular acidosis, Diuresis, EAST syndrome, End Stage Renal Disease, Epithelial-mesenchymal transition, Epstein syndrome, Fanconi syndrome, Fechtner syndrome, Focal proliferative nephritis, Focal segmental glomerulosclerosis, Fraley syndrome, Galloway Mowat syndrome, Gitelman syndrome, Glomerulocystic kidney disease, Glomerulopathy, Goodpasture syndrome, High anion gap metabolic acidosis, HIV-associated nephropathy, Horseshoe kidney, Hydronephrosis, Hypertensive kidney disease, IgA nephropathy, Interstitial nephritis, Juvenile nephronophthisis, Kidney cancer, Kidney disease, Kidney stone disease, Lightwood-Albright syndrome, Lupus nephritis, Malarial nephropathy, Medullary cystic kidney disease, Medullary sponge kidney, Membranous glomerulonephritis, Mesoamerican nephropathy, Milk-alkali syndrome, Minimal mesangial glomerulonephritis, Multicystic dysplastic kidney, Nephritis, Nephrocalcinosis, Nephrogenic diabetes insipidus, Nephromegaly, Nephroptosis, Nephrosis, Nephrotic syndrome, Nutcracker syndrome, Papillorenal syndrome, Phosphate nephropathy, Polycystic kidney disease, Primary hyperoxaluria, Proximal renal tubular acidosis, Pyelonephritis, Pyonephrosis, Rapidly progressive glomerulonephritis, Renal agenesis, Renal angina, Renal artery stenosis, Renal cyst, Renal ischemia, Renal osteodystrophy, Renal papillary necrosis, Renal tubular acidosis, Renal vein thrombosis, Secondary hypertension, Serpentine fibula-polycystic kidney syndrome, Shunt nephritis, Sickle cell nephropathy, Thin basement membrane disease, Transplant glomerulopathy, Tubulointerstitial nephritis and uveitis, Tubulopathy, Uremia, Uremic frost, Wunderlich syndrome, or a combination thereof.

In some embodiments, a compound disclosed herein can be used to treat a cancer. A compound disclosed herein can be used to treat, for example, acute leukemia, astrocytomas, biliary cancer (cholangiocarcinoma), bone cancer, breast cancer, brain stem glioma, bronchioloalveolar cell lung cancer, cancer of the adrenal gland, cancer of the anal region, cancer of the bladder, cancer of the endocrine system, cancer of the esophagus, cancer of the head or neck, cancer of the kidney, cancer of the parathyroid gland, cancer of the penis, cancer of the pleural/peritoneal membranes, cancer of the salivary gland, cancer of the small intestine, cancer of the thyroid gland, cancer of the ureter, cancer of the urethra, carcinoma of the cervix, carcinoma of the endometrium, carcinoma of the fallopian tubes, carcinoma of the renal pelvis, carcinoma of the vagina, carcinoma of the vulva, cervical cancer, chronic leukemia, colon cancer, colorectal cancer, cutaneous melanoma, ependymoma, epidermoid tumors, Ewings sarcoma, gastric cancer, glioblastoma, glioblastoma multiforme, glioma, hematologic malignancies, hepatocellular (liver) carcinoma, hepatoma, Hodgkin's Disease, intraocular melanoma, Kaposi sarcoma, lung cancer, lymphomas, medulloblastoma, melanoma, meningioma, mesothelioma, multiple myeloma, muscle cancer, neoplasms of the central nervous system (CNS), neuronal cancer, non-small cell lung cancer, osteosarcoma, ovarian cancer, pancreatic cancer, pediatric malignancies, pituitary adenoma, prostate cancer, rectal cancer, renal cell carcinoma, sarcoma of soft tissue, schwanoma, skin cancer, spinal axis tumors, squamous cell carcinomas, stomach cancer, synovial sarcoma, testicular cancer, uterine cancer, or tumors and their metastases, including refractory versions of any of the above cancers, or a combination thereof.

In some embodiments, a compound disclosed herein can be used to treat a disease characterized by changes in the vasculature, a disease characterized by decreased Tie2 activation, or a disease characterized by involvement of VEGF in pathogenesis. A compound disclosed herein can be used to treat, for example, acne rosacea, acute lung injury, acute respiratory distress syndrome (ARDS), adhesion formation from abdominal surgery, adipositas, albuminuria, allergic edema, allergy, angina, angiofibroma, arteriosclerosis, artery occlusion, ascites, atheroma, atherosclerosis, asthma, avascular necrosis, bacterial ulcers, *Bartonella bacilliformis* infection, Behcet's disease, Buerger's disease (thromboangiitis obliterans), cardiac fibrosis, cardiac hypertrophy, cardiomyopathy, carotid obstructive disease, cerebral infarction, chemical burns, COPD, Crohn's disease, cytokine-induced vascular leak, destabilized blood flow, diabetes (including non-insulin dependent diabetes mellitus), dysfunctional uterine bleeding, endometriosis, Epstein-Barr virus infection, erectile dysfunction, excessive hair growth, follicular cysts, foot ulcer (e.g., diabetic foot ulcer), fungal ulcers, giant cell arteritis, glomerulosclerosis, Graves' disease, Hashimoto's autoimmune thyroiditis, hemangioma, hemangioendothelioma, hemophilic joints, hemorrhage, hepatitis C, hereditary hemorrhagic telangiectasia (HHT), Herpes simplex infections, Herpes zoster infections, hypertension, idiopathic thrombocytopenic purpura, impaired wound healing, inflammatory and infectious processes (e.g. hepatitis, pneumonia, glomerulonephritis), interstitial fibrosis, ischemia, kidney disease, leishmaniasis, leukomalacia, lipid degeneration, liver regeneration, Lupus nephritis, Lyme disease, lymphoproliferative disorders, malaria (*Plasmodium* infection), Mooren ulcer, multiple sclerosis, mycobacterial infections, myocardial infarction, nasal polyps, nephropathy, neuronal inflammation, neuropathy, obesity, osteomyelitis, osteophyte, ovarian hyperstimulation, Paget's disease, pannus growth, peripheral artery disease, peritoneal sclerosis, pemphigoid, polyarteritis, protozoan infections, pseudoxanthoma elasticum, psoriasis, pulmonary hypertension, pyogenic granulomas, renal fibrosis, respiratory distress, rheumatoid arthritis, rickettsial infection, scar keloids, sepsis, sickle cell anemia, Stevens-Johnson disease, stroke, synovitis, systemic lupus erythematosus, syphilis, thyroid enlargement, thyroiditis, toxic shock syndrome, toxoplasmosis, trauma, ulcerative colitis, vascular leak, vascular leak syndrome, vascular malformations (e.g. Osler-Weber syndrome), vein occlusion, viral hemorrhagic fevers (e.g., dengue fever), vitamin A deficiency, warts, or Wegener's sarcoidosis, or a combination thereof.

Sequences

As used herein, the abbreviations for the L-enantiomeric and D-enantiomeric amino acids are as follows: alanine (A, Ala); arginine (R, Arg); asparagine (N, Asn); aspartic acid (D, Asp); cysteine (C, Cys); glutamic acid (E, Glu); glutamine (Q, Gln); glycine (G, Gly); histidine (H, His); isoleucine (I, Ile); leucine (L, Leu); lysine (K, Lys); methionine (M, Met); phenylalanine (F, Phe); proline (P, Pro); serine (S, Ser); threonine (T, Thr); tryptophan (W, Trp); tyrosine (Y, Tyr); valine (V, Val). In some embodiments, the amino acid is a L-enantiomer. In some embodiments, the amino acid is a D-enantiomer.

TABLE 2 shows the amino acid sequences of humanized $V_H$ antibody regions that bind HPTP-β (VE-PTP). SEQ ID NO: 1 is $V_{H1}$, SEQ ID NO: 2 is $V_{H2}$, SEQ ID NO: 3 is $V_{H3}$, and SEQ ID NO: 4 is $V_{H4}$.

TABLE 2

| SEQ ID NO: | Name | Amino acid sequence |
|---|---|---|
| 1 | $V_{H1}$ | EVQLVESGGGLVQPGGSLKLSCAASGFTFNA<br>NAMNWVRQASGKGLEWVGRIRTKSNNYATYY<br>AGSVKDRFTISRDDSKNTAYLQMNSLKTEDT<br>AAYYCVRDYYGSSAWITYWGQGTLVTVSS |
| 2 | $V_{H2}$ | EVQLVESGGGLVQPGGSLRLSCAASGFTFNA<br>NAMNWVRQAPGKGLEWVGRIRTKSNNYATYY<br>AGSVKDRFTISRDDSKNSLYLQMNSLKTEDT<br>AVYYCVRDYYGSSAWITYWGQGTLVTVSS |
| 3 | $V_{H3}$ | EVQLVESGGGLVQPGRSLRLSCTASGFTFNA<br>NAMNWVRQAPGKGLEWVGRIRTKSNNYATYY<br>AGSVKDRFTISRDDSKNIAYLQMNSLKTEDT<br>AVYYCVRDYYGSSAWITYWGQGTLVTVSS |
| 4 | $V_{H4}$ | LVQLVESGGGLVKPGGSLRLSCAASGFTFNA<br>NAMNWIRQAPGKGLEWVSRIRTKSNNYATYY<br>AGSVKDRFTISRDNAKNSLYLQMNSLRAEDT<br>AVHYCVRDYYGSSAWITYWGQGTLVTVSS |

TABLE 3 shows the amino acid sequences of humanized $V_L$ antibody regions that bind HPTP-β (VE-PTP). SEQ ID NO: 5 is $V_{L1}$, SEQ ID NO: 6 is $V_{L2}$, SEQ ID NO: 7 is $V_{L3}$, and SEQ ID NO: 8 is $V_{L4}$.

TABLE 3

| SEQ ID NO: | Name | Amino acid sequence |
|---|---|---|
| 5 | $V_{L1}$ | DVVMTQSPSFLSASVGDRVTITCKASQHVGTAVAWYQ<br>QRPGKAPKLLIYWASTRHTGVPSRFSGSGSGTEFTLT<br>ISSLQPEDFATYFCQQYSSYPFTFGGGTKLEIK |

TABLE 3-continued

| SEQ ID NO: | Name | Amino acid sequence |
|---|---|---|
| 6 | $V_{L2}$ | DIVMTQSPDSLAVSLGERATINCKASQHVGTAVAWYQ QKPGQPPKLLIYWASTRHTGVPDRFSGSGSGTDFTLT ISSLQAEDVAVYYCQQYSSYPFTFGQGTKLEIK |
| 7 | $V_{L3}$ | DIQMTQSPFSLSASVGDRVTITCKASQHVGTAVAWYQ QKPGKAPKLLIYWASTRHTGVPSRFSGSGSGTDFTLT ISSLQPEDFATYFCQQYSSYPFTFGGGTKLEIK |
| 8 | $V_{L4}$ | DIVMTQSPDSLAVSLGERATINCKASQHVGTAVAWYQ QKPEQPPKLLIYWASTRHTGVPDRFSGSGSGTDFTLT ISSLQAEDVAVYYCQQYSSYPFTFGGGTKVEIK |

Each of the $V_H$ domains can be synthesized in-frame with a constant domain sequence, for example, a human IgG1, IgG2, IgG3, IgG4, IgE, IgA1, IgA2, IgM, or IgD sequence. A DNA sequence encoding the entire heavy chain sequence can be codon optimized and verified.

Illustrative amino acid sequences of constant domain sequences are provided in TABLE 4. In some embodiments, a $V_H$ domain disclosed herein is synthesized in-frame with a human IgG1 constant domain sequence. A human IgG1 constant domain sequence can comprise SEQ ID NO: 220. In some embodiments, a $V_H$ domain disclosed herein is synthesized in-frame with a human IgG2 constant domain sequence. A human IgG2 constant domain sequence can comprise SEQ ID NO: 221. In some embodiments, a $V_H$ domain disclosed herein is synthesized in-frame with a human IgG3 constant domain sequence. A human IgG3 constant domain sequence can comprise SEQ ID NO: 222. In some embodiments, a $V_H$ domain disclosed herein is synthesized in-frame with a human IgG4 constant domain sequence. The human IgG4 isotype constant domain sequence can be mutated to a proline rather than a serine at position 228 to reduce Fab-arm exchange (stabilizing S228P mutation). An amino acid sequence of the IgG4 constant domain with S228P mutation can comprise SEQ ID NO: 9. In some embodiments, a $V_H$ domain disclosed herein is synthesized in-frame with a human IgE constant domain sequence. A human IgE constant domain sequence can comprise SEQ ID NO: 223. In some embodiments, a $V_H$ domain disclosed herein is synthesized in-frame with a human IgA1 constant domain sequence. A human IgA1 constant domain sequence can comprise SEQ ID NO: 224. In some embodiments, a $V_H$ domain disclosed herein is synthesized in-frame with a human IgA2 constant domain sequence. A human IgA2 constant domain sequence can comprise SEQ ID NO: 225. In some embodiments, a $V_H$ domain disclosed herein is synthesized in-frame with a human IgM constant domain sequence. A human IgM constant domain sequence can comprise SEQ ID NO: 226. In some embodiments, a $V_H$ domain disclosed herein is synthesized in-frame with a human IgD constant domain sequence. A human IgD constant domain sequence can comprise SEQ ID NO: 227.

TABLE 4

| SEQ ID NO: | Name | Amino acid sequence |
|---|---|---|
| 220 | IgG1 constant | ASTKGPSVFPLAPSSKSTSGGTAALGCLVKDYFPEPVTVSWNS GALTSGVHTFPAVLQSSGLYSLSSVVTVPSSSLGTQTYICNVN HKPSNTKVDKKVEPKSCDKTHTCPPCPAPELLGGPSVFLFPPK PKDTLMISRTPEVTCVVVDVSHEDPEVKFNWYVDGVEVHNA KTKPREEQYNSTYRVVSVLTVLHQDWLNGKEYKCKVSNKAL PAPIEKTISKAKGQPREPQVYTLPPSRDELTKNQVSLTCLVKGF YPSDIAVEWESNGQPENNYKTTPPVLDSDGSFFLYSKLTVDKS RWQQGNVFSCSVMHEALHNHYTQKSLSLSPGK |
| 221 | IgG2 constant | ASTKGPSVFPLAPCSRSTSESTAALGCLVKDYFPEPVTVSWNS GALTSGVHTFPAVLQSSGLYSLSSVVTVPSSNFGTQTYTCNVD HKPSNTKVDKTVERKCCVECPPCPAPPVAGPSVFLFPPKPKDT LMISRTPEVTCVVVDVSHEDPEVQFNWYVDGVEVHNAKTKP REEQFNSTFRVVSVLTVVHQDWLNGKEYKCKVSNKGLPAPIE KTISKTKGQPREPQVYTLPPSREEMTKNQVSLTCLVKGFYPSD ISVEWESNGQPENNYKTTPPMLDSDGSFFLYSKLTVDKSRWQ QGNVFSCSVMHEALHNHYTQKSLSLSPGK |
| 222 | IgG3 constant | ASTKGPSVFPLAPCSRSTSGGTAALGCLVKDYFPEPVTVSWNS GALTSGVHTFPAVLQSSGLYSLSSVVTVPSSSLGTQTYTCNVN HKPSNTKVDKRVELKTPLGDTTHTCPRCPEPKSCDTPPPCPRC PEPKSCDTPPPCPRCPEPKSCDTPPPCPRCPAPELLGGPSVFLFP PKPKDTLMISRTPEVTCVVVDVSHEDPEVQFKWYVDGVEVH NAKTKPREEQYNSTFRVVSVLTVLHQDWLNGKEYKCKVSNK ALPAPIEKTISKTKGQPREPQVYTLPPSREEMTKNQVSLTCLV KGFYPSDIAVEWESSGQPENNYNTTPPMLDSDGSFFLYSKLTV DKSRWQQGNIFSCSVMHEALHNRFTQKSLSLSPGK |
| 9 | IgG4 constant | ASTKGPSVFPLAPCSRSTSESTAALGCLVKDYFPEPVTVSWNS GALTSGVHTFPAVLQSSGLYSLSSVVTVPSSSLGTKTYTCNVD HKPSNTKVDKRVESKYGPPCPPCPAPEFLGGPSVFLFPPKPKD TLMISRTPEVTCVVVDVSQEDPEVQFNWYVDGVEVHNAKTK PREEQFNSTYRVVSVLTVLHQDWLNGKEYKCKVSNKGLPSSI EKTISKAKGQPREPQVYTLPPSQEEMTKNQVSLTCLVKGFYPS DIAVEWESNGQPENNYKTTPPVLDSDGSFFLYSRLTVDKSRW QEGNVFSCSVMHEALHNHYTQKSLSLSLGK |
| 223 | IgE constant | ASTQSPSVFPLTRCCKNIPSNATSVTLGCLATGYFPEPVMVTW DTGSLNGTTMTLPATTLTLSGHYATISLLTVSGAWAKQMFTC RVAHTPSSTDWVDNKTFSVCSRDFTPPTVKILQSSCDGGGHFP PTIQLLCLVSGYTPGTINITWLEDGQVMDVDLSTASTTQEGEL |

TABLE 4-continued

| SEQ ID NO: | Name | Amino acid sequence |
|---|---|---|
| | | ASTQSELTLSQKHWLSDRTYTCQVTYQGHTFEDSTKKCADSN<br>PRGVSAYLSRPSPFDLFIRKSPTITCLVVDLAPSKGTVNLTWSR<br>ASGKPVNHSTRKEEKQRNGTLTVTSTLPVGTRDWIEGETYQC<br>RVTHPHLPRALMRSTTKTSGPRAAPEVYAFATPEWPGSRDKR<br>TLACLIQNFMPEDISVQWLHNEVQLPDARHSTTQPRKTKGSG<br>FFVFSRLEVTRAEWEQKDEFICRAVHEAASPSQTVQRAVSVN<br>PGK |
| 224 | IgA1 constant | ASPTSPKVFPLSLCSTQPDGNVVIACLVQGFFPQEPLSVTWSES<br>GQGVTARNFPPSQDASGDLYTTSSQLTLPATQCLAGKSVTCH<br>VKHYTNPSQDVTVPCPVPSTPPTPSPSTPPTPSPSCCHPRLSLH<br>RPALEDLLLGSEANLTCTLTGLRDASGVTFTWTPSSGKSAVQ<br>GPPERDLCGCYSVSSVLPGCAEPWNHGKTFTCTAAYPESKTP<br>LTATLSKSGNTFRPEVHLLPPPSEELALNELVTLTCLARGFSPK<br>DVLVRWLQGSQELPREKYLTWASRQEPSQGTTTFAVTSILRV<br>AAEDWKKGDTFSCMVGHEALPLAFTQKTIDRLAGKPTHVNV<br>SVVMAEVDGTCY |
| 225 | IgGA2 constant | ASPTSPKVFPLSLDSTPQDGNVVVACLVQGFFPQEPLSVTWSE<br>SGQNVTARNFPPSQDASGDLYTTSSQLTLPATQCPDGKSVTC<br>HVKHYTNSSQDVTVPCRVPPPPPCCHPRLSLHRPALEDLLLGS<br>EANLTCTLTGLRDASGATFTWTPSSGKSAVQGPPERDLCGCY<br>SVSSVLPGCAQPWNHGETFTCTAAHPELKTPLTANITKSGNTF<br>RPEVHLLPPPSEELALNELVTLTCLARGFSPKDVLVRWLQGSQ<br>ELPREKYLTWASRQEPSQGTTTYAVTSILRVAAEDWKKGETF<br>SCMVGHEALPLAFTQKTIDRMAGKPTHINVSVVMAEADGTC<br>Y |
| 226 | IgM constant | GSASAPTLFPLVSCENSPSDTSSVAVGCLAQDFLPDSITFSWKY<br>KNNSDISSTRGFPSVLRGGKYAATSQVLLPSKDVMQGTDEHV<br>VCKVQHPNGNKEKNVPLPVIAELPPKVSVFVPPRDGFFGNPR<br>KSKLICQATGFSPRQIQVSWLREGKQVGSGVTTDQVQAEAKE<br>SGPTTYKVTSTLTIKESDWLGQSMFTCRVDHRGLTFQQNASS<br>MCVPDQDTAIRVFAIPPSFASIFLTKSTKLTCLVTDLTTYDSVTI<br>SWTRQNGEAVKTHTNISESHPNATFSAVGEASICEDDWNSGE<br>RFTCTVTHTDLPSPLKQTISRPKGVALHRPDVYLLPPAREQLN<br>LRESATITCLVTGFSPADVFVQWMQRGQPLSPEKYVTSAPMP<br>EPQAPGRYFAHSILTVSEEEWNTGETYTCVVAHEALPNRVTE<br>RTVDKSTGKPTLYNVSLVMSDTAGTCY |
| 227 | IgD constant | APTKAPDVFPIISGCRHPKDNSPVVLACLITGYHPTSVTVTWY<br>MGTQSQPQRTFPEIQRRDSYYMTSSQLSTPLQQWRQGEYKCV<br>VQHTASKSKKEIFRWPESPKAQASSVPTAQPQAEGSLAKATT<br>APATTRNTGRGGEEKKKEKEKEEQEERETKTPECPSHTQPLG<br>VYLLTPAVQDLWLRDKATFTCFVVGSDLKDAHLTWEVAGK<br>VPTGGVEEGLLERHSNGSQSQHSRLTLPRSLWNAGTSVTCTL<br>NHPSLPPQRLMALREPAAQAPVKLSLNLLASSDPPEAASWLL<br>CEVSGFSPPNILLMWLEDQREVNTSGFAPARPPPQPRSTTFWA<br>WSVLRVPAPPSPQPATYTCVVSHEDSRTLLNASRSLEVSYVTD<br>HGPMK |

Each of the $V_L$ domains can be synthesized in-frame with a human light chain constant domain sequence, e.g. a kappa (IgK) or lambda (IgL) chain. The entire light chain sequence can then be codon optimized, and the DNA sequence can be verified. TABLE 5 provides example light chain constant domain sequences.

In some embodiments, a $V_L$ domain disclosed herein is synthesized in-frame with a human IgK constant domain sequence. A human IgK constant domain sequence can comprise SEQ ID NO: 10. In some embodiments, a $V_L$ domain disclosed herein is synthesized in-frame with a human IgL constant domain sequence. A human IgL constant domain sequence can comprise SEQ ID NO: 228.

TABLE 5

| SEQ ID NO: | Name | Amino acid sequence |
|---|---|---|
| 10 | IgK constant | TVAAPSVFIFPPSDEQLKSGTASVVCLLNNFY<br>PREAKVQWKVDNALQSGNSQESVTEQDSKDST<br>YSLSSTLTLSKADYEKHKVYACEVTHQGLSSP<br>VTKSFNRGEC |
| 228 | IgL constant | GQPKANPTVTLFPPSSEELQANKATLVCLISD<br>FYPGAVTVAWKADGSPVKAGVETTKPSKQSNN<br>KYAASSYLSLTPEQWKSHRSYSCQVTHEGSTV<br>EKTVAPTECS |

Signal peptides can result in higher protein expression and/or secretion by a cell. The following signal peptides can be appended to all the constructs disclosed herein.

```
Heavy chain signal peptide (SEQ ID NO: 11):
MGWTLVFLFLLSVTAGVHS

Light chain signal peptide (SEQ ID NO: 12):
MVSSAQFLGLLLLCFQGTRC
```

Signal peptidases can cleave a signal peptide off a protein, for example, during a secretion process, generating a mature protein that does not comprise the signal peptide sequence. In some embodiments, a signal peptide is cleaved off a compound or antibody of the disclosure. In some embodiments, a mature compound or antibody of the disclosure does not comprise a signal peptide.

TABLE 6 and TABLE 7 list the full amino acid sequences of humanized heavy and light chains that bind HPTP-β (VE-PTP), respectively. HC1, HC2, HC3 and HC4 are the human IgG4 isotype constant domain with stabilizing S228P mutation joined to $V_{H1}$, $V_{H2}$, $V_{H3}$ and $V_{H4}$, respectively, and with signal peptide appended. Amino acids 1-19 of SEQ ID NOs: 13, 14, 15, and 16 are the heavy chain signal peptide (SEQ ID NO: 11). Also shown are HC1, HC2, HC3, and HC4 without the signal peptide appended (SEQ ID NOs: 246, 247, 248, and 249). In some embodiments, a mature compound or antibody of the disclosure does not comprise the signal peptide(s).

LC1, LC2, LC3 and LC4 are the human IgK isotype constant domain joined to $V_{L1}$, $V_{L2}$, $V_{L3}$, and $V_{L4}$, respectively, and with signal peptide appended. Amino acids 1-20 of SEQ ID NOs: 17, 18, 19, and 20 are the light chain signal peptide (SEQ ID NO: 12). Also shown are LC1, LC2, LC3, and LC4 without the signal peptide appended (SEQ ID NOs: 250, 251, 252, and 253). In some embodiments, a mature compound or antibody of the disclosure does not comprise the signal peptide(s).

TABLE 6

| SEQ ID NO: | Name | Amino acid sequence |
|---|---|---|
| 13 | signal peptide - HC1 | MGWTLVFLFLLSVTAGVHSEVQLVESGGGLVQPGGSLKLSCA<br>ASGFTFNANAMNWVRQASGKGLEWVGRIRTKSNNYATYYAG<br>SVKDRFTISRDDSKNTAYLQMNSLKTEDTAAYYCVRDYYGSS<br>AWITYWGQGTLVTVSSASTKGPSVFPLAPCSRSTSESTAALGCL<br>VKDYFPEPVTVSWNSGALTSGVHTFPAVLQSSGLYSLSSVVTV<br>PSSSLGTKTYTCNVDHKPSNTKVDKRVESKYGPPCPPCPAPEFL<br>GGPSVFLFPPKPKDTLMISRTPEVTCVVVDVSQEDPEVQFNWY<br>VDGVEVHNAKTKPREEQFNSTYRVVSVLTVLHQDWLNGKEY<br>KCKVSNKGLPSSIEKTISKAKGQPREPQVYTLPPSQEEMTKNQV<br>SLTCLVKGFYPSDIAVEWESNGQPENNYKTTPPVLDSDGSFFLY<br>SRLTVDKSRWQEGNVFSCSVMHEALHNHYTQKSLSLSLGK |
| 246 | HC1 | EVQLVESGGGLVQPGGSLKLSCAASGFTFNANAMNWVRQAS<br>GKGLEWVGRIRTKSNNYATYYAGSVKDRFTISRDDSKNTAYL<br>QMNSLKTEDTAAYYCVRDYYGSSAWITYWGQGTLVTVSSAST<br>KGPSVFPLAPCSRSTSESTAALGCLVKDYFPEPVTVSWNSGALT<br>SGVHTFPAVLQSSGLYSLSSVVTVPSSSLGTKTYTCNVDHKPSN<br>TKVDKRVESKYGPPCPPCPAPEFLGGPSVFLFPPKPKDTLMISR<br>TPEVTCVVVDVSQEDPEVQFNWYVDGVEVHNAKTKPREEQFN<br>STYRVVSVLTVLHQDWLNGKEYKCKVSNKGLPSSIEKTISKAK<br>GQPREPQVYTLPPSQEEMTKNQVSLTCLVKGFYPSDIAVEWES<br>NGQPENNYKTTPPVLDSDGSFFLYSRLTVDKSRWQEGNVFSCS<br>VMHEALHNHYTQKSLSLSLGK |
| 14 | signal peptide - HC2 | MGWTLVFLFLLSVTAGVHSEVQLVESGGGLVQPGGSLRLSCA<br>ASGFTFNANAMNWVRQAPGKGLEWVGRIRTKSNNYATYYAG<br>SVKDRFTISRDDSKNSLYLQMNSLKTEDTAVYYCVRDYYGSS<br>AWITYWGQGTLVTVSSASTKGPSVFPLAPCSRSTSESTAALGCL<br>VKDYFPEPVTVSWNSGALTSGVHTFPAVLQSSGLYSLSSVVTV<br>PSSSLGTKTYTCNVDHKPSNTKVDKRVESKYGPPCPPCPAPEFL<br>GGPSVFLFPPKPKDTLMISRTPEVTCVVVDVSQEDPEVQFNWY<br>VDGVEVHNAKTKPREEQFNSTYRVVSVLTVLHQDWLNGKEY<br>KCKVSNKGLPSSIEKTISKAKGQPREPQVYTLPPSQEEMTKNQV<br>SLTCLVKGFYPSDIAVEWESNGQPENNYKTTPPVLDSDGSFFLY<br>SRLTVDKSRWQEGNVFSCSVMHEALHNHYTQKSLSLSLGK |
| 247 | HC2 | EVQLVESGGGLVQPGGSLRLSCAASGFTFNANAMNWVRQAPG<br>KGLEWVGRIRTKSNNYATYYAGSVKDRFTISRDDSKNSLYLQ<br>MNSLKTEDTAVYYCVRDYYGSSAWITYWGQGTLVTVSSASTK<br>GPSVFPLAPCSRSTSESTAALGCLVKDYFPEPVTVSWNSGALTS<br>GVHTFPAVLQSSGLYSLSSVVTVPSSSLGTKTYTCNVDHKPSNT<br>KVDKRVESKYGPPCPPCPAPEFLGGPSVFLFPPKPKDTLMISRTP<br>EVTCVVVDVSQEDPEVQFNWYVDGVEVHNAKTKPREEQFNST<br>YRVVSVLTVLHQDWLNGKEYKCKVSNKGLPSSIEKTISKAKGQ<br>PREPQVYTLPPSQEEMTKNQVSLTCLVKGFYPSDIAVEWESNG<br>QPENNYKTTPPVLDSDGSFFLYSRLTVDKSRWQEGNVFSCSVM<br>HEALHNHYTQKSLSLSLGK |
| 15 | signal peptide - HC3 | MGWTLVFLFLLSVTAGVHSEVQLVESGGGLVQPGRSLRLSCT<br>ASGFTFNANAMNWVRQAPGKGLEWVGRIRTKSNNYATYYAG<br>SVKDRFTISRDDSKNIAYLQMNSLKTEDTAVYYCVRDYYGSSA<br>WITYWGQGTLVTVSSASTKGPSVFPLAPCSRSTSESTAALGCLV<br>KDYFPEPVTVSWNSGALTSGVHTFPAVLQSSGLYSLSSVVTVP<br>SSSLGTKTYTCNVDHKPSNTKVDKRVESKYGPPCPPCPAPEFL<br>GGPSVFLFPPKPKDTLMISRTPEVTCVVVDVSQEDPEVQFNWY<br>VDGVEVHNAKTKPREEQFNSTYRVVSVLTVLHQDWLNGKEY<br>KCKVSNKGLPSSIEKTISKAKGQPREPQVYTLPPSQEEMTKNQV<br>SLTCLVKGFYPSDIAVEWESNGQPENNYKTTPPVLDSDGSFFLY<br>SRLTVDKSRWQEGNVFSCSVMHEALHNHYTQKSLSLSLGK |

TABLE 6-continued

| SEQ ID NO: | Name | Amino acid sequence |
|---|---|---|
| 248 | HC3 | EVQLVESGGGLVQPGRSLRLSCTASGFTFNANAMNWVRQAPG KGLEWVGRIRTKSNNYATYYAGSVKDRFTISRDDSKNIAYLQ MNSLKTEDTAVYYCVRDYYGSSAWITYWGQGTLVTVSSASTK GPSVFPLAPCSRSTSESTAALGCLVKDYFPEPVTVSWNSGALTS GVHTFPAVLQSSGLYSLSSVVTVPSSSLGTKTYTCNVDHKPSNT KVDKRVESKYGPPCPPCPAPEFLGGPSVFLFPPKPKDTLMISRTP EVTCVVVDVSQEDPEVQFNWYVDGVEVHNAKTKPREEQFNST YRVVSVLTVLHQDWLNGKEYKCKVSNKGLPSSIEKTISKAKGQ PREPQVYTLPPSQEEMTKNQVSLTCLVKGFYPSDIAVEWESNG QPENNYKTTPPVLDSDGSFFLYSRLTVDKSRWQEGNVFSCSVM HEALHNHYTQKSLSLSLGK |
| 16 | signal peptide - HC4 | MGWTLVFLFLLSVTAGVHSLVQLVESGGGLVKPGGSLRLSCA ASGFTFNANAMNWIRQAPGKGLEWVSRIRTKSNNYATYYAGS VKDRFTISRDNAKNSLYLQMNSLRAEDTAVHYCVRDYYGSSA WITYWGQGTLVTVSSASTKGPSVFPLAPCSRSTSESTAALGCLV KDYFPEPVTVSWNSGALTSGVHTFPAVLQSSGLYSLSSVVTVP SSSLGTKTYTCNVDHKPSNTKVDKRVESKYGPPCPPCPAPEFL GGPSVFLEPPKPKDTLMISRTPEVTCVVVDVSQEDPEVQFNWY VDGVEVHNAKTKPREEQFNSTYRVVSVLTVLHQDWLNGKEY KCKVSNKGLPSSIEKTISKAKGQPREPQVYTLPPSQEEMTKNQV SLTCLVKGFYPSDIAVEWESNGQPENNYKTTPPVLDSDGSFFLY SRLTVDKSRWQEGNVFSCSVMHEALHNHYTQKSLSLSLGK |
| 249 | HC4 | LVQLVESGGGLVKPGGSLRLSCAASGFTENANAMNWIRQAPG KGLEWVSRIRTKSNNYATYYAGSVKDRFTISRDNAKNSLYLQ MNSLRAEDTAVHYCVRDYYGSSAWITYWGQGTLVTVSSASTK GPSVFPLAPCSRSTSESTAALGCLVKDYFPEPVTVSWNSGALTS GVHTFPAVLQSSGLYSLSSVVTVPSSSLGTKTYTCNVDHKPSNT KVDKRVESKYGPPCPPCPAPEFLGGPSVFLEPPKPKDTLMISRTP EVTCVVVDVSQEDPEVQFNWYVDGVEVHNAKTKPREEQFNST YRVVSVLTVLHQDWLNGKEYKCKVSNKGLPSSIEKTISKAKGQ PREPQVYTLPPSQEEMTKNQVSLTCLVKGFYPSDIAVEWESNG QPENNYKTTPPVLDSDGSFFLYSRLTVDKSRWQEGNVFSCSVM HEALHNHYTQKSLSLSLGK |

TABLE 7

| SEQ ID NO: | Name | Amino acid sequence |
|---|---|---|
| 17 | signal peptide-LC1 | MVSSAQFLGLLLLCFQGTRCDVVMTQSPSFLSASVGDRVTIT CKASQHVGTAVAWYQQRPGKAPKLLIYWASTRHTGVPSRF SGSGSGTEFTLTISSLQPEDFATYFCQQYSSYPFTFGGGTKLEI KRTVAAPSVFIFPPSDEQLKSGTASVVCLLNNFYPREAKVQ WKVDNALQSGNSQESVTEQDSKDSTYSLSSTLTLSKADYEK HKVYACEVTHQGLSSPVTKSFNRGEC |
| 250 | LC1 | DVVMTQSPSFLSASVGDRVTITCKASQHVGTAVAWYQQRP GKAPKLLIYWASTRHTGVPSRFSGSGSGTEFTLTISSLQPEDF ATYFCQQYSSYPFTFGGGTKLEIKRTVAAPSVFIFPPSDEQLK SGTASVVCLLNNFYPREAKVQWKVDNALQSGNSQESVTEQ DSKDSTYSLSSTLTLSKADYEKHKVYACEVTHQGLSSPVTK SFNRGEC |
| 18 | signal peptide-LC2 | MVSSAQFLGLLLLCFQGTRCDIVMTQSPDSLAVSLGERATIN CKASQHVGTAVAWYQQKPGQPPKLLIYWASTRHTGVPDRF SGSGSGTDFTLTISSLQAEDVAVYYCQQYSSYPFTFGQGTKL EIKRTVAAPSVFIFPPSDEQLKSGTASVVCLLNNFYPREAKV QWKVDNALQSGNSQESVTEQDSKDSTYSLSSTLTLSKADYE KHKVYACEVTHQGLSSPVTKSFNRGEC |
| 251 | LC2 | DIVMTQSPDSLAVSLGERATINCKASQHVGTAVAWYQQKP GQPPKLLIYWASTRHTGVPDRFSGSGSGTDFTLTISSLQAED VAVYYCQQYSSYPFTFGQGTKLEIKRTVAAPSVFIFPPSDEQ LKSGTASVVCLLNNFYPREAKVQWKVDNALQSGNSQESVT EQDSKDSTYSLSSTLTLSKADYEKHKVYACEVTHQGLSSPV TKSFNRGEC |
| 19 | signal peptide-LC3 | MVSSAQFLGLLLLCFQGTRCDIQMTQSPFSLSASVGDRVTIT CKASQHVGTAVAWYQQKPGKAPKLLIYWASTRHTGVPSRF SGSGSGTDFTLTISSLQPEDFATYFCQQYSSYPFTFGGGTKLE IKRTVAAPSVFIFPPSDEQLKSGTASVVCLLNNFYPREAKVQ WKVDNALQSGNSQESVTEQDSKDSTYSLSSTLTLSKADYEK HKVYACEVTHQGLSSPVTKSFNRGEC |

TABLE 7-continued

| SEQ ID NO: | Name | Amino acid sequence |
|---|---|---|
| 252 | LC3 | DIQMTQSPFSLSASVGDRVTITCKASQHVGTAVAWYQQKPG<br>KAPKLLIYWASTRHTGVPSRFSGSGSGTDFTLTISSLQPEDFA<br>TYFCQQYSSYPFTFGGGTKLEIKRTVAAPSVFIFPPSDEQLKS<br>GTASVVCLLNNFYPREAKVQWKVDNALQSGNSQESVTEQD<br>SKDSTYSLSSTLTLSKADYEKHKVYACEVTHQGLSSPVTKSF<br>NRGEC |
| 20 | signal peptide-LC4 | MVSSAQFLGLLLLCFQGTRCDIVMTQSPDSLAVSLGERATIN<br>CKASQHVGTAVAWYQQKPEQPPKLLIYWASTRHTGVPDRF<br>SGSGSGTDFTLTISSLQAEDVAVYYCQQYSSYPFTFGGGTKV<br>EIKRTVAAPSVFIFPPSDEQLKSGTASVVCLLNNFYPREAKV<br>QWKVDNALQSGNSQESVTEQDSKDSTYSLSSTLTLSKADYE<br>KHKVYACEVTHQGLSSPVTKSFNRGEC |
| 253 | LC4 | DIVMTQSPDSLAVSLGERATINCKASQHVGTAVAWYQQKP<br>EQPPKLLIYWASTRHTGVPDRFSGSGSGTDFTLTISSLQAED<br>VAVYYCQQYSSYPFTFGGGTKVEIKRTVAAPSVFIFPPSDEQ<br>LKSGTASVVCLLNNFYPREAKVQWKVDNALQSGNSQESVT<br>EQDSKDSTYSLSSTLTLSKADYEKHKVYACEVTHQGLSSPV<br>TKSFNRGEC |

Any of the $V_H$ regions disclosed herein can be combined with any of the $V_L$ regions disclosed herein, with or without additional sequences appended, to produce compounds that bind anti-HPTP-β (VE-PTP). For example, signal peptides and constant region sequences can be appended to $V_H$ and $V_L$ regions as shown in TABLE 6 and TABLE 7 respectively, and the resulting heavy and light chains can be paired in any combination to form antibodies. TABLE 8 shows 16 possible pairings of HC1-4 and LC1-4 that bind HPTP-β (VE-PTP). Transfection and expression of each of the anti-HPTP-β (VE-PTP) antibodies in TABLE 8 can be pursued.

TABLE 8

| | | | |
|---|---|---|---|
| HC1:LC1 | HC1:LC2 | HC1:LC3 | HC1:LC4 |
| HC2:LC1 | HC2:LC2 | HC2:LC3 | HC2:LC4 |
| HC3:LC1 | HC3:LC2 | HC3:LC3 | HC3:LC4 |
| HC4:LC1 | HC4:LC2 | HC4:LC3 | HC4:LC4 |

Antibodies or antigen-binding compounds specific for HPTP-β (VE-PTP) can be combined with antibodies or compounds that activate Tie2, inhibit VEGF, or inhibit VEGFR, to form multispecific compounds.

TABLE 9 provides sequences of collagen IV-derived biomimetic peptides. SEQ ID NO: 152 is AXT-107, an integrin-targeting collagen IV-derived biomimetic peptide that can inhibit VEGFR phosphorylation/activation/signaling and promote Tie2 phosphorylation/activation/signaling. SEQ ID NO: 153 provides a consensus sequence, wherein X is any standard amino acid or non-genetically encoded amino acid. In some embodiments, X at position 7 is M, A, or G; X at position 9 is F, A, Y, or G; X at position 0 is M, A, G, D-Alanine (dA), or norleucine (Nle); X at position 11 is F, A, Y, G, or 4-chlorophenylalanine (4-CiPhe): X at position 12 and position 18 are independently selected from 2-Aminobutyric acid (Abu), G, S, A, V, T, I, L, or Allylglycine (AllylGly).

TABLE 9

| SEQ ID NO: | Amino acid sequence |
|---|---|
| 152 | LRRFSTAPFAFIDINDVINF |
| 153 | LRRFSTXPXXXXNINNVXNF |

TABLE 10 provides sequences related to vasculotide, a synthetic Ang1 mimetic peptide that can act as a Tie2 agonist and activate Tie2 signaling. SEQ ID NO: 229 provides the sequence of a synthetic 7-mer that binds the Tie2 receptor. SEQ ID NO: 230 provides an 8-mer with a cysteine residue added at the N-terminus, allowing covalent tethering to a polyethylene glycol backbone to generate a tetrameric polyethylene oxide clustered version of the peptide.

TABLE 10

| SEQ ID NO: | Amino acid sequence |
|---|---|
| 229 | HHHRHSF |
| 230 | CHHHRHSF |

Antibodies or antigen-binding compounds specific for HPTP-β (VE-PTP) can be combined with antibodies or compounds specific to VEGF or VEGFR to form multispecific compounds that bind HPTP-β (VE-PTP) and VEGF or VEGFR. TABLE 11, TABLE 12, TABLE 13, TABLE 14, TABLE 15, and TABLE 17 provide example sequences of compounds specific for VEGF. TABLE 16 provides sequences of an antibody that binds VEGFR.

TABLE 11 provides sequences related to aflibercept, a recombinant protein comprising VEGF-binding portions of human VEGF receptors 1 and 2 fused to the Fc portion of human IgG1. SEQ ID NO: 21 is the full amino acid sequence of aflibercept. SEQ ID NO: 22 is a shortened sequence containing the VEGF-binding portions of human VEGF receptors 1 and 2 without the Fc portion of IgG.

TABLE 11

| SEQ ID NO: | Name | Amino acid sequence |
|---|---|---|
| 21 | $AFL_1$ | SDTGRPFVEMYSEIPEIIHMTEGRELVIPCRVTSPNITVT<br>LKKFPLDTLIPDGKRIIWDSRKGFIISNATYKEIGLLTCE<br>ATVNGHLYKTNYLTHRQTNTIIDVVLSPSHGIELSVGE<br>KLVLNCTARTELNVGIDFNWEYPSSKHQHKKLVNRDL<br>KTQSGSEMKKFLSTLTIDGVTRSDQGLYTCAASSGLMT<br>KKNSTFVRVHEKDKTHTCPPCPAPELLGGPSVFLFPPKP<br>KDTLMISRTPEVTCVVVDVSHEDPEVKFNWYVDGVEV<br>HNAKTKPREEQYNSTYRVVSVLTVLHQDWLNGKEYK |

TABLE 11-continued

| SEQ ID NO: | Name | Amino acid sequence |
|---|---|---|
| | | CKVSNKALPAPIEKTISKAKGQPREPQVYTLPPSRDELT KNQVSLTCLVKGFYPSDIAVEWESNGQPENNYKTTPPV LDSDGSFFLYSKLTVDKSRWQQGNVFSCSVMHEALHN HYTQKSLSLSPG |
| 22 | $AFL_2$ | SDTGRPFVEMYSEIPEIIHMTEGRELVIPCRVTSPNITVT LKKFPLDTLIPDGKRIIWDSRKGFIISNATYKEIGLLTCE ATVNGHLYKTNYLTHRQTNTIIDVVLSPSHGIELSVGE KLVLNCTARTELNVGIDFNWEYPSSKHQHKKLVNRDL KTQSGSEMKKFLSTLTIDGVTRSDQGLYTCAASSGLMT KKNSTFVRVHEK |

TABLE 12 provides the sequence of brolucizumab (SEQ ID NO: 23), a humanized single-chain antibody fragment (scFv) inhibitor of VEGF that binds to the receptor binding site of VEGF and thereby interferes with the interaction of VEGF with VEGFR1 and VEGFR2.

TABLE 12

| SEQ ID NO: | Name | Amino acid sequence |
|---|---|---|
| 23 | $BRO_{scFv1}$ | EIVMTQSPSTLSASVGDRVIITCQASEIIHSWLAWYQQ KPGKAPKLLIYLASTLASGVPSRFSGSGSGAEFTLTIS SLQPDDFATYYCQNVYLASTNGANFGQGTKLTVLGGGG GSGGGGSGGGGSGGGGSEVQLVESGGGLVQPGGSLRLS CTASGFSLTDYYYMTWVRQAPGKGLEWVGFIDPDDDPY YATWAKGRFTISRDNSKNTLYLQMNSLRAEDTAVYYCA GGDHNSGWGLDIWGQGTLVTVSS |

TABLE 13 provides sequences related to ranibizumab, a humanized monoclonal antibody fragment (Fab) that binds to and inhibits activity of VEGF. SEQ ID NO: 24 is the heavy chain sequence of ranibizumab. SEQ ID NO: 25 is the light chain sequence of ranibizumab. SEQ ID NO: 26 is a shortened sequence of the ranibizumab heavy chain that can be used in cloning a single-chain antibody fragment (scFv). SEQ ID NO: 27 is a shortened sequence of the ranibizumab light chain that can be used in cloning a single-chain antibody fragment (scFv). SEQ ID NO: 28 is a single-chain antibody fragment (scFv) comprising SEQ ID NO: 26, SEQ ID NO: 27, and SEQ ID NO: 33 (linker peptide, underlined).

TABLE 13

| SEQ ID NO: | Name | Amino acid sequence |
|---|---|---|
| 24 | $RAN_{H1}$ | EVQLVESGGGLVQPGGSLRLSCAASGYDFTHYGMNW VRQAPGKGLEWVGWINTYTGEPTYAADFKRRFTFSL DTSKSTAYLQMNSLRAEDTAVYYCAKYPYYYGTSHW YFDVWGQGTLVTVSSASTKGPSVFPLAPSSKSTSGG TAALGCLVKDYFPEPVTVSWNSGALTSGVHTFPAVL QSSGLYSLSSVVTVPSSSLGTQTYICNVNHKPSNTK VDKKVEPKSCDKTHL |
| 25 | $RAN_{L1}$ | DIQLTQSPSSLSASVGDRVTITCSASQDISNYLNWY QQKPGKAPKVLIYFTSSLHSGVPSRFSGSGSGTDFT LTISSLQPEDFATYYCQQYSTVPWTFGQGTKVEIKR TVAAPSVFIFPPSDEQLKSGTASVVCLLNNFYPREA KVQWKVDNALQSGNSQESVTEQDSKDSTYSLSSTLT LSKADYEKHKVYACEVTHQGLSSPVTKSFNRGEC |

TABLE 13-continued

| SEQ ID NO: | Name | Amino acid sequence |
|---|---|---|
| 26 | $RAN_{H2}$ | EVQLVESGGGLVQPGGSLRLSCAASGYDFTHYGMNW VRQAPGKGLEWVGWINTYTGEPTYAADFKRRFTFSL DTSKSTAYLQMNSLRAEDTAVYYCAKYPYYYGTSHW YFDVWGQGTLVTVSS |
| 27 | $RAN_{L2}$ | DIQLTQSPSSLSASVGDRVTITCSASQDISNYLNWY QQKPGKAPKVLIYFTSSLHSGVPSRFSGSGSGTDFT LTISSLQPEDFATYYCQQYSTVPWTFGQGTKVEIK |
| 28 | $RAN_{scFv1}$ | EVQLVESGGGLVQPGGSLRLSCAASGYDFTHYGMNW VRQAPGKGLEWVGWINTYTGEPTYAADFKRRFTFSL DTSKSTAYLQMNSLRAEDTAVYYCAKYPYYYGTSHW YFDVWGQGTLVTVSSGGGGSGGGGSGGGGSDIQLTQ SPSSLSASVGDRVTITCSASQDISNYLNWYQQKPGK APKVLIYFTSSLHSGVPSRFSGSGSGTDFTLTISSL QPEDFATYYCQQYSTVPWTFGQGTKVEIK |

TABLE 14 provides sequences related to bevacizumab, a humanized monoclonal antibody that that binds to and inhibits activity of VEGF. SEQ ID NO: 29 is the heavy chain sequence of bevacizumab. SEQ ID NO: 30 is the light chain sequence of bevacizumab.

TABLE 14

| SEQ ID NO: | Name | Amino acid sequence |
|---|---|---|
| 29 | $BEV_{H1}$ | EVQLVESGGGLVQPGGSLRLSCAASGYTFTNYGMNWVRQA PGKGLEWVGWINTYTGEPTYAADFKRRFTFSLDTSKSTAYL QMNSLRAEDTAVYYCAKYPHYYGSSHWYFDVWGQGTLVT VSSASTKGPSVFPLAPSSKSTSGGTAALGCLVKDYFPEPVTV SWNSGALTSGVHTFPAVLQSSGLYSLSSVVTVPSSSLGTQTY ICNVNHKPSNTKVDKKVEPKSCDKTHTCPPCPAPELLGGPSV FLFPPKPKDTLMISRTPEVTCVVVDVSHEDPEVKFNWYVDG VEVHNAKTKPREEQYNSTYRVVSVLTVLHQDWLNGKEYK CKVSNKALPAPIEKTISKAKGQPREPQVYTLPPSREEMTKNQ VSLTCLVKGFYPSDIAVEWESNGQPENNYKTTPPVLDSDGSF FLYSKLTVDKSRWQQGNVFSCSVMHEALHNHYTQKSLSLS PGK |
| 30 | $BEV_{L1}$ | DIQMTQSPSSLSASVGDRVTITCSASQDISNYLNWYQQKPGK APKVLIYFTSSLHSGVPSRFSGSGSGTDFTLTISSLQPEDFA TYYCQQYSTVPWTFGQGTKVEIKRTVAAPSVFIFPPSDEQLK SGTASVVCLLNNFYPREAKVQWKVDNALQSGNSQESVTEQDS KDSTYSLSSTLTLSKADYEKHKVYACEVTHQGLSSPVTKSF NRGEC |

TABLE 15 provides sequences related to conbercept, a recombinant protein comprising extracellular domains from VEGF receptors 1 and 2 fused to the Fc portion of human IgG1. SEQ ID NO: 154 is the full amino acid sequence of conbercept. SEQ ID NO: 155 is a shortened sequence containing sequences from VEGF receptors 1 and 2 without the Fc portion of JIgG.

TABLE 15

| SEQ ID NO: | Name | Amino acid sequence |
|---|---|---|
| 154 | $CON_1$ | GRPFVEMYSEIPEIIHMTEGRELVIPCRVTSPNITVTLKKFPL DTLIPDGKRIIWDSRKGFIISNATYKEIGLLTCEATVNGHLYK TNYLTHRQTNTIIDVVLSPSHGIELSVGEKLVLNCTARTELNV GIDFNWEYPSSKHQHKKLVNRDLKTQSGSEMKKFLSTLTID GVTRSDQGLYTCAASSGLMTKKNSTFVRVHEKPFVAFGSG MESLVEATVGERVRIPAKYLGYPPPEIKWYKNGIPLESNHTI |

TABLE 15-continued

| SEQ ID NO: | Name | Amino acid sequence |
|---|---|---|
| | | KAGHVLTIMEVSERDTGNYTVILTNPISKEKQSHVVSLVVY VPPGPGDKTHTCPLCPAPELLGGPSVFLEPPKPKDTLMISRTP EVTCVVVDVSHEDPEVKFNWYVDGVEVHNAKTKPREEQY NSTYRVVSVLTVLHQDWLNGKEYKCKVSNKALPAPIEKTIS KAKGQPREPQVYTLPPSRDELTKNQVSLTCLVKGFYPSDIAV EWESNGQPENNYKATPPVLDSDGSFFLYSKLTVDKSRWQQ GNVFSCSVMHEALHNHYTQKSLSLSPGK |
| 155 | $CON_2$ | GRPFVEMYSEIPEIIHMTEGRELVIPCRVTSPNITVTLKKFPL DTLIPDGKRIIWDSRKGFIISNATYKEIGLLTCEATVNGHLYK TNYLTHRQTNTIIDVVLSPSHGIELSVGEKLVLNCTARTELNV GIDFNWEYPSSKHQHKKLVNRDLKTQSGSEMKKFLSTLTID GVTRSDQGLYTCAASSGLMTKKNSTFVRVHEKPFVAFGSG MESLVEATVGERVRIPAKYLGYPPPEIKWYKNGIPLESNHTI KAGHVLTIMEVSERDTGNYTVILTNPISKEKQSHVVSLVVY VPPGPG |

TABLE 16 provides sequences related to ramucirumab, a humanized monoclonal antibody that binds to an extracellular domain of VEGFR2 and inhibits VEGFR2 signaling. SEQ ID NO: 156 is the heavy chain sequence of ramucirumab. SEQ ID NO: 157 is the light chain sequence of ramucirumab.

TABLE 16

| SEQ ID NO: | Name | Amino acid sequence |
|---|---|---|
| 156 | $RAM_{H1}$ | EVQLVQSGGGLVKPGGSLRLSCAASGFTFSSYSMNWVRQA PGKGLEWVSSISSSSSYIYYADSVKGRFTISRDNAKNSLY LQMNSLRAEDTAVYYCARVTDAFDIWGQGTMVTVSSASTK GPSVFPLAPSSKSTSGGTAALGCLVKDYFPEPVTVSWNSG ALTSGVHTFPAVLQSSGLYSLSSVVTVPSSSLGTQTYICN VNHKPSNTKVDKKVEPKSCDKTHTCPPCPAPELLGGPSVF |

TABLE 16-continued

| SEQ ID NO: | Name | Amino acid sequence |
|---|---|---|
| | | LFPPKPKDTLMISRTPEVTCVVVDVSHEDPEVKFNWYVDG VEVHNAKTKPREEQYNSTYRVVSVLTVLHQDWLNGKEYKC KVSNKALPAPIEKTISKAKGQPREPQVYTLPPSREEMTKN QVSLTCLVKGFYPSDIAVEWESNGQPENNYKTTPPVLDSD GSFFLYSKLTVDKSRWQQGNVFSCSVMHEALHNHYTQKSL SLSPGK |
| 157 | $RAM_{L1}$ | DIQMTQSPSSVSASIGDRVTITCRASQGIDNWLGWYQQKP GKAPKLLIYDASNLDTGVPSRFSGSGSGTYFTLTISSLQA EDFAVYFCQQAKAFPPTFGGGTKVDIKGTVAAPSVFIFPP SDEQLKSGTASVVCLLNNFYPREAKVQWKVDNALQSGNSQ ESVTEQDSKDSTYSLSSTLTLSKADYEKHKVYACEVTHQG LSSPVTKSFNRGEC |

TABLE 17 provides DARPin and DARPin-derived amino acid sequences that bind VEGF and inhibit VEGFR signaling. SEQ ID NOS: 158-168 comprise designed ankyrin repeats with binding specificity for VEGF. SEQ ID NO: 169 comprises designed ankyrin repeats with a binding specificity for VEGF and designed ankyrin repeats with a binding specificity for serum albumin. SEQ ID NO: 170 comprises designed ankyrin repeats with a binding specificity for VEGF, designed ankyrin repeats with a binding specificity for hepatocyte growth factor, and designed ankyrin repeats with a binding specificity for serum albumin. SEQ ID NOS: 171-177 comprise designed ankyrin repeats with a binding specificity for VEGF. SEQ ID NO: 173 provides the sequence of abicipar, which comprises designed ankyrin repeats with a binding specificity for VEGF. SEQ ID NOS: 178-190 provide individual designed ankyrin repeat sequence motifs with binding specificity for VEGF, wherein X represents any amino acid. SEQ ID NOS: 191-217 comprise designed ankyrin repeats with binding specificity for VEGF.

TABLE 17

| SEQ ID NO: | Amino acid sequence |
|---|---|
| 158 | DLGKKLLEAARAGQDDEVRILMANGADVNAFDWMGWTPLHLAAHE GHLEIVEVLLKNGADVNATDVSGYTPLHLAAADGHLEIVEVLLKHGA DVNTKDNTGWTPLHLSADLGHLEIVEVLLKNGADVNAQDKFGKTAF DISIDNGNEDLAEILQKAA |
| 159 | DLDKKLLEAARAGQDDEVRILLKAGADVNAKDYLGWTPLHLAAHEG HLEIVEVLLKAGADVNAKDVSGYTPLHLAAADGHLEIVEVLLKAGAD VNAKDNTGWTPLHLSADLGHLEIVEVLLKAGADVNAQDKFGKTAFDI SIDNGNEDLAEILQKAA |
| 160 | DLGKKLLEAARAGQDDEVRILMANGADVNTADSTGWTPLHLAAPWG HPEIVEVLLKNGADVNAHDYQGWTPLHLAATLGHLEIVEVLLKHGAD VNAQDKFGKTAFDISIDNGNEDLAEILQKAA |
| 161 | DLGKKLLEAARAGQDDEVRILMANGADVNTADSTGWTPLHLAVPWG HLEIVEVLLKYGADVNAKDFQGWTPLHLAAAIGHQEIVEVLLKNGAD VNAQDKFGKTAFDISIDNGNEDLAEILQKAA |
| 162 | DLDKKLLEAARAGQDDEVRILMANGADVNAKDSTGYTPLHLAAPWG HLEIVEVLLKAGADVNAKDYQGWTPLHLAAAVGHLEIVEVLLKAGA DVNAQDKSGKTPADLAADAGHEDIAEVLQKAA |
| 163 | DLGKKLLEAARAGQDDEVRILMANGADVNARDSTGWTPLHLAAPWG HPEIVEVLLKNGADVNAADFQGWTPLHLAAAVGHLEIVEVLLKHGAD VNAQDKFGKTAFDISIDNGNEDLAEILQKAA |
| 164 | DLDKKLLEAARAGQDDEVRILLKAGADVNAKDSTGWTPLHLAAPWG HPEIVEVLLKAGADVNAKDFQGWTPLHLAAAAGHLEIVEVLLKAGAD VNAQDKSGKTPADLAADAGHEDIAEVLQKAA |

TABLE 17-continued

| SEQ ID NO: | Amino acid sequence |
|---|---|
| 165 | DLGKKLLEAARAGQDDEVRILLKAGADVNAKDSTGWTPLHLAAPWG<br>HPEIVEVLLKAGADVNAKDFQGWTPLHLAAAAGHLEIVEVLLKAGAD<br>VNAQDKSGKTPADLAADAGHEDIAEVLQKAA |
| 166 | DLDKKLLEAARAGQDDEVRILLKAGADVNAKDSTGWTPLHLAAPWG<br>HPEIVEVLLKAGADVNAKDFQGWTPLHLAAAVGHLEIVEVLLKAGAD<br>VNAQDKSGKTPADLAADAGHEDIAEVLQKAA |
| 167 | DLDKKLLEAARAGQDDEVRILLKAGADVNAKDSTGWTPLHLAAPWG<br>HPEIVEVLLKAGADVNAKDYQGWTPLHLAAAVGHLEIVEVLLKAGA<br>DVNAQDKSGKTPADLAADAGHEDIAEVLQKAA |
| 168 | DLDKKLLEAARAGQDDEVRILMANGADVNAKDSTGWTPLHLAAPW<br>GHLEIVEVLLKAGADVNAKDFQGWTPLHLAAAVGHLEIVEVLLKAGA<br>DVNAQDKFGKTAFDISIDNGNEDLAEILQKAA |
| 169 | DLGKKLLEAARAGQDDEVRELLKAGADVNAKDYFSHTPLHLAARNG<br>HLKIVEVLLKAGADVNAKDFAGKTPLHLAANEGHLEIVEVLLKAGAD<br>VNAQDIFGKTPADIAADAGHEDIAEVLQKAAGSPTPTPTTPTPTPTTPTP<br>TPTGSDLDKKLLEAARAGQDDEVRILLKAGADVNAKDSTGWTPLHLA<br>APWGHPEIVEVLLKAGADVNAKDFQGWTPLHLAAAAGHLEIVEVLLK<br>AGADVNAQDKSGKTPADLAADAGHEDIAEVLQKAA |
| 170 | GSDLGKKLLEAARAGQDDEVRELLKAGADVNAKDYFSHTPLHLAAR<br>NGHLKIVEVLLKAGADVNAKDFAGKTPLHLAANEGHLEIVEVLLKAG<br>ADVNAQDIFGKTPADIAADAGHEDIAEVLQKAAGSPTPTPTTPTPTPTT<br>PTPTPTGSDLGKKLLEAARAGQDDEVRILLKAGADVNAKDRYGDTPL<br>HLAADIGHLEIVEVLLKAGADVNAEDYFGNTPLHLAASYGHLEIVEVL<br>LKAGADVNAKDDYGNTPLHLAANTGHLEIVEVLLKAGADVNAQDKS<br>GKTPADLAADAGHEDIAEVLQKAAGSPTPTPTTPTPTPTTPTPTPTGSD<br>LDKKLLEAARAGQDDEVRILLKAGADVNAKDSTGWTPLHLAAPWGH<br>PEIVEVLLKAGADVNAKDFQGWTPLHLAAAAGHLEIVEVLLKAGADV<br>NAQDKSGKTPADLAADAGHEDIAEVLQKAAGSPTPTPTTPTPTPTTPTP<br>TPTGSDLGKKLLEAARAGQDDEVRELLKAGADVNAKDYFSHTPLHLA<br>ARNGHLKIVEVLLKAGADVNAKDFAGKTPLHLAANEGHLEIVEVLLK<br>AGADVNAQDIFGKTPADIAADAGHEDIAEVLQKAA |
| 171 | GSDLGKKLLEAARAGQDDEVRILMANGADVNAFDWMGWTPLHLAA<br>HEGHLEIVEVLLKNGADVNATDVSGYTPLHLAAADGHLEIVEVLLKY<br>GADVNTKDNTGWTPLHLSADLGRLEIVEVLLKYGADVNAQDKFGKT<br>AFDISIDNGNEDLAEILQKAASGSPAGSPTSTEEGTSESATPESGPGTSTE<br>PSEGSAPGSPAGSPTSTEEGTSTEPSEGSAPGTSTEPSEGSAPGTSESATP<br>ESGPGSEPATSGSETPGSEPATSGSETPGSPAGSPTSTEEGTSESATPESG<br>PGTSTEPSEGSAPGTSTEPSEGSAPGSPAGSPTSTEEGTSTEPSEGSAPGT<br>STEPSEGSAPGTSESATPESGPGTSTEPSEGSAPGTSESATPESGPGSEPA<br>TSGSETPGTSTEPSEGSAPGTSTEPSEGSAPGTSESATPESGPGTSESATP<br>ESGPGSPAGSPTSTEEGTSESATPESGPGSEPATSGSETPGTSESATPESG<br>PGTSTEPSEGSAPGTSTEPSEGSAPGTSTEPSEGSAPGTSTEPSEGSAPGT<br>STEPSEGSAPGTSTEPSEGSAPGSPAGSPTSTEEGTSTEPSEGSAPGTSES<br>ATPESGPGSEPATSGSETPGTSESATPESGPGSEPATSGSETPGTSESATP<br>ESGPGTSTEPSEGSAPGTSESATPESGPGSPAGSPTSTEEGSPAGSPTSTE<br>EGSPAGSPTSTEEGTSESATPESGPGTSTEPSEGSAPGTSESATPESGPGS<br>EPATSGSETPGTSESATPESGPGSEPATSGSETPGTSESATPESGPGTSTE<br>PSEGSAPGSPAGSPTSTEEGTSESATPESGPGSEPATSGSETPGTSESATP<br>ESGPGSPAGSPTSTEEGSPAGSPTSTEEGTSTEPSEGSAPGTSESATPESG<br>PGTSESATPESGPGTSESATPESGPGSEPATSGSETPGSEPATSGSETPGS<br>PAGSPTSTEEGTSTEPSEGSAPGTSTEPSEGSAPGSEPATSGSETPGTSES<br>ATPESGPGTSTEPSEGSAPG |
| 172 | GSDLGKKLLEAARAGQDDEVRILMANGADVNAFDWMGWTPLHLAA<br>HEGHLEIVEVLLKNGADVNATDVSGYTPLHLAAADGHLEIVEVLLKH<br>GADVNTKDNTGWTPLHLSADLGHLEIVEVLLKNGADVNAQDKFGKT<br>AFDISIDNGNEDLAEILQKAAGGGSGGGSC |
| 173 | GSDLDKKLLEAARAGQDDEVRILMANGADVNARDSTGWTPLHLAAP<br>WGHPEIVEVLLKNGADVNAADFQGWTPLHLAAAVGHLEIVEVLLKY<br>GADVNAQDKFGKTAFDISIDNGNEDLAEILQKAAGGGSGGGSC |
| 174 | GSDLGKKLLEAARAGQDDEVRILMANGADVNTADSTGWTPLHLAVP<br>WGHLEIVEVLLKYGADVNAKDFQGWTPLHLAAAIGHQEIVEVLLKNG<br>ADVNAQDKFGKTAFDISIDNGNEDLAEILQKAAGSGSASPAAPAPASP<br>AAPAPSAPAASPAAPAPASPAAPAPSAPAASPAAPAPASPAAPAPSAPA<br>ASPAAPAPASPAAPAPSAPAASPAAPAPASPAAPAPSAPAASPAAPAPA<br>SPAAPAPSAPAASPAAPAPASPAAPAPSAPAASPAAPAPASPAAPAPSA<br>PAASPAAPAPASPAAPAPSAPAASPAAPAPASPAAPAPSAPAASPAAPA<br>PASPAAPAPSAPAASPAAPAPASPAAPAPSAPAASPAAPAPASPAAPAP<br>SAPAASPAAPAPASPAAPAPSAPAASPAAPAPASPAAPAPSAPAASPAA<br>PAPASPAAPAPSAPAASPAAPAPASPAAPAPSAPAASPAAPAPASPAAP |

TABLE 17-continued

| SEQ ID NO: | Amino acid sequence |
|---|---|
| | APSAPAASPAAPAPASPAAPAPSAPAASPAAPAPASPAAPAPSAPAASP AAPAPAS |
| 175 | GSDLGKKLLEAARVGQDDEVRILMADGADVNASDFKGDTPLHLAAS QGHLEIVEVLLKYGADVNAYDMLGWTPLHLAADLGHLEIVEVLLKY GADVNAQDRFGKTAFDISIDNGNEDLAEILQKAAGSPSTADGC |
| 176 | GSDLGKKLLEAVRAGQDDEVRILMTNGADVNAKDQFGFTPLQLAAY NGHLEIVEVLLKYGADVNAFDIFGWTPLHLAADLGHLEIVEVLLKNGA DVNAQDKFGRTAFDISIDNGNEDLAEILQKAASGSC |
| 177 | GSDLGKKLLEAARAGQDDEVRILMANGADVNAVDYIGWTPLHLAAA YGHLEIVEVLLKYSADVNAEDFAGYTPLHLAASNGHLEIVEVLLKYGA DVNTKDNTGWTPLHLSADLGHLEIVEVLLKYGADVNTQDKFGKTAFD ISIDNGNEDLAEILQKAAGSPSTADGC |
| 178 | XDXXGXTPLHLAAXXGHLEIVEVLLKXGADVNA |
| 179 | XDXXGWTPLHLAAXXGHLEIVEVLLKXGADVNA |
| 180 | XDXXGXTPLHLAAXXGHLEIVEVLLKXGADVNX |
| 181 | XDXXGWTPLHLXADLGXLEIVEVLLKXGADVNX |
| 182 | XDXXGXTPLHLAAXXGHXEIVEVLLKXGADVNA |
| 183 | XDXXGXTPLHLAAXXGHLEIVEVLLKXGADVNA |
| 184 | XDXXGWTPLHLAAXXGHLEIVEVLLKXGADVNA |
| 185 | XDXXGXTPLHLAAXXGHLEIVEVLLKXGADVNX |
| 186 | XDXXGXTPLHLXAXXGHLEIVEVLLKXGADVNA |
| 187 | XDFKXDTPLHLAAXXGHXEIVEVLLKXGADVNA |
| 188 | XDXLXXTPLHLAXXXGHLEIVEVLLKXGADVNA |
| 189 | XDXXGXTPLXLAAXXGHLEIVEVLLKXGADVNA |
| 190 | XDXXGWTXLHLAADLGXLEIVEVLLKXGADVNA |
| 191 | GSDLGKKLLEAARAGQDDEVRILMANGADVNAFDWMGWTPLHLAA HEGHLEIVEVLLKNGADVNATDVSGYTPLHLAAADGHLEIVEVLLKY GADVNTKDNTGWTPLHLSADLGHLEIVEVLLKYGADVNAQDKFGKT AFDISIDNGNEDLAEILQKAA |
| 192 | GSDLGKKLLEAARVGQDDEVRILMANGADVNAFDWMGWTPLHLAA HEGHLEIVEVLLKNGADVNATDVSGYTPLHLAAADGHLEIVEVLLKY GADVNTKDNTGWTPLHLSADLGHLEIVEVLLKYGADVNAQDKFGKT AFDISIDNGNEDLAEILQKAA |
| 193 | GSDLGKKLLEAARAGQDDEVRILMANGADVNAFDWMGWTPLHLAA HEGHLEIVEVLLKNGADVNATDVSGYTPLHLAAADGHLEIVEVLLKY GADVNTKDNTGWTPLHLSADLGRLEIVEVLLKYGADVNAQDKFGKT AFDISIDNGNEDLAEILQKAA |
| 194 | GSDLGKKLLEAARAGQDDEVRILMANGADVNAFDWMGWTPLHLAA HEGHLEIVEVLLKNGTDVNATDVSGYTPLHLAAADGHLEIVEVLLKY GADVNTKDNTGWTPLHLSADLGHLEIVEVLLKHGADVNAQDKFGKT AFDISIDNGNEDLAEILQKAA |
| 195 | GSDLGKKLLEAARAGQDDEVRILMANGADVNAFDWMGWTPLHLAA HEGHLEIVEVLLKNGADVNATDVSGYTPLHLAAADGHLEIVEVLLKH GADVNTKDNTGWTPLHLSADLGHLEIVEVLLKNGADVNAQDKFGKT AFDISIDNGNEDLAEILQKAA |
| 196 | GSDLGKKLLEAARAGQDDEVRILMANGADVNAFDWMGWTPLHLAA HEGHLEIVEVLLKNGADVNATDVSGYTPLHLAAADGHLEIVEVLLKH GADVNTKDNTGWTPLHLSADLGHLEIVEVLLKNGADINAQDKFGKTA FDISIDNGNEDLAEILQKAA |
| 197 | GSDLGKKLLEAARAGQDDEVRILMANGADVNAFDWMGWTPLHLAA HEGHLEIVEVLLKNGADVNATDVSGYTPLHLAAADGHLEIVEVLLKH GADVNTTDNTGWTPLHLSADLGHLEIVEVLLKYGADVNAQDKFGKT AFDISIDNGNEDLAEILQKAA |

TABLE 17-continued

| SEQ ID NO: | Amino acid sequence |
|---|---|
| 198 | GSDLGKKLLEAARAGQDDEVRILMANGADVNAFDYMGWTPLHLAAHNGHMEIVEVLLKYGADVNASDYSGYTPLHLAAADGHLEIVEVLLKYGADVNTKDNTGWTPLHLSADLGHLEIVEVLLKYGADVNAQDKFGKTAFDISIDNGNEDLAEILQKAA |
| 199 | GSDLGKKLLEAARAGQDDEVRILMANGADVNAVDYIGWTPLHLAAAYGHLEIVEVLLKYSADVNAEDFAGYTPLHLAASNGHLEIVEVLLKYGADVNTKDNTGWTPLHLSADLGHLEIVEVLLKYGADVNTQDKFGKTAFDISIDNGNEDLAEILQKAA |
| 200 | GSDLGKKLLEAARTGQDDEVRILMANGADVNATDYMGWTPLHLAAKVGHLEIVEVLLKYGADVNAEDYNGYTPLHLAAAMGHLEIAEVLLKYGADVNTKDNTGWTPLHLSADLGHLEIVEVLLKNGADVNAQDKFGKTAFDISIDNGNEDLAEILQKAA |
| 201 | GSDLGKKLLEAARAGQDDEVRILMANGADVNARDSTGWTPLHLAAPWGHPEIVEVLLKNGADVNAADFQGWTPLHLAAAVGHLEIVEVLLKYGADVNAQDKFGKTAFDISIDNGNEDLAEILQKAA |
| 202 | GSDLGKKLLEAARAGQDDEVRILMANGADVNARDSTGWTPLHLAAPWGHPEIVEVLLKNGADVNAADFQGWTPLHLAAAVGHLEIVEVLLKHGADVNAQDKFGKTAFDISIDNGNEDLAEILQKAA |
| 203 | GSDLGKKLLEAARAGQDDEVRILMANGADVNTADSTGWTPLHLAAPWGHPEIVEVLLKNGADVNAHDYQGWTPLHLAATLGHLEIVEVLLKYGADVNAQDKFGKTAFDISIDNGNEDLAEILQKAA |
| 204 | GSDLGKKLLEAARAGQDDEVRILMANGADVNTADSTGWTPLHLVAPWGHPEIVEVLLKHGADVNTHDYQGWTPLHLAATLGHLEIVEVLLRYGADVNAQDKFGKTAFDISIDNGNEDLAEILQKAA |
| 205 | GSDLGKKLLEAARAGQDDEVRILMANGADVNTADSTGWTPMHLAAPWGHPEIVEVLLKHGADVNAQDFQGWTPLHLAAAIGHLEIVEVLLKYGADVNAQDKFGKTAFDISIDNGNEDLAEILQKAA |
| 206 | GSDLGKKLLEAARAGQDDEVRILMANGADVNTADSTGWTPLHLAVPWGHLEIVEVLLKYGADVNAKDFQGWTPLHLAAAIGHQEIVEVLLKNGADVNAQDKFGKTAFDISIDNGNEDLAEILQKAA |
| 207 | GSDLGKKLLEAARVGQDDEVRILMADGADVNASDFKGDTPLHLAASQGHLEIVEVLLKYGADVNAYDMLGWTPLHLAADLGHLEIVEVLLKYGADVNAQDRFGKTAFDISIDNGNEDLAEILQKAA |
| 208 | GSDLGKKLLEAARVGQDDEVRILMANGADVNASDFKGDTPLHLAASQGHLEIVEVLLKNSADVNAFDLLGWTPLHLAADLGHLEIVEVLLKYGADVNAQDKFGKTAFDISIDNGNEDLAEILQKAA |
| 209 | GSDLGKKLLEAARVGQDDEVRILMANGADVNALDFKGDTPLHLAAASGHLEIVEVLLKNGADVNAHDMLSWTPLHLAGDLGHLEIVEVLLKYGADVNAQDRFGKTAFDISIDNGNEDLAEILQKAA |
| 210 | GSDLGKKLLEAVRAGQDDEVRILMTNGADVNAKDQFGFTPLQLAAYNGHLEIVEVLLKYGADVNAFDIFGWTPLHLAADLGHLEIVEVLLKNGADVNAQDKFGRTAFDISIDNGNEDLAEILQKAA |
| 211 | GSDLGKKLLEAVRAGQDDEVRILMANGADVNASDNQGTTPLHLAASHGHLEIVEVLLKYGADVNDAHDDLGWTPLHLSADLGHLEIVEVLLKYGADVNAQDKFGKTAFDISIDNGNEDLAEILQKAA |
| 212 | GSDLGKKLLEATRAGQDDEVRILMANGADVNASDNQGTTPLHLAASHGHLEIVEVLLKYGADVNDAHDDLGWTPLHLAADLGHLEIVEVLLKYGADVNAQDKFGKTAFDISIDNGNEDLAEILQKAA |
| 213 | GSDLGKKLLEAARVGQDDEVRILMADGADVNASDFKGDTPLHLAASQGHLEIVEVLLKYGADVNAYDMLGWTPLHLAADLGHLEIVEVLLKYGADVNAQDRFGKTAFDISIDNGNEDLAEILQKAA |
| 214 | GSDLGKKLLEAARVGQDDEVRILMANDADVNASDFKGDTPLHLAASQGHLEIVEVLLKYGADVNAYDMLGWTPLHLAADLGHLEIVEVLLKHGADVNAQDKFGKTAFDISIDNGNEDLAEILQKAA |
| 215 | GSDLGKKLLEAARAGQDDEVRILMANGADVNTLDFKSDTPLHLAAASGHLEIVEVLLKNGADVNAHDMLSWTPLHLAGDLGHLEIVEVLLKHGADVNAQDKFGKTAFDISIDNGNEDLAEILQKAA |

TABLE 17-continued

| SEQ ID NO: | Amino acid sequence |
|---|---|
| 216 | GSDLGKKLLEAARAGQDDEVRILMANGADVNAKDIYGRTPLHLAAL HGHPEIVEVLLKYGADVNANDYWGTTSLHLVAIWGHLEIVEVLLKYG ADVNAVDDIGQTPLHLAAAWGHLEIVEVLLKHGADVNAQDKFGKTA FDISIDNGNEDLAEILQKAA |
| 217 | GSDLGKKLLEAARAGQDDEVRILMANGADVNANDYDGMTPLHLAA MEGHLEIVEVLLKYGADVNANDHYGFTPLHLAWTGRLEIVEVLLKNG ADVNAADVFGRTPLHLAATSGHLEIVEVLLKYGADVNAQDKFGKTAF DISIDNGNEDLAEILQKAA |

Antibodies or antigen-binding compounds specific for VEGF can be combined with antibodies or antigen-binding compounds specific to HPTP-β (VE-PTP) to form multi-specific compounds, such as bispecific compounds that bind VEGF and HPTP-β (VE-PTP). Any compounds in this disclosure specific for VEGF can be combined with any compounds in this disclosure specific to HPTP-β (VE-PTP). Any of the compounds in this disclosure specific for VEGF or HPTP-β (VE-PTP) can be modified as necessary for the generation of a multispecific compound. Non-limiting examples of modifications necessary for the generation of a multispecific compound include the addition of amino acid residues, the removal of amino acid residues, the replacement of amino acid residues, and the use of linkers. In some embodiments, 1, 2, 3, 4, 5, 6, 7, 8, 9, 10, 11, 12, 13, 14, 15, 16, 17, 18, 19, 20, 21, 22, 23, 24, 25, or more residues can be added to an N-terminus and/or a C-terminus of a sequence disclosed herein, and the resulting sequence can be used in the generation of a multi-specific construct. In some embodiments, 1, 2, 3, 4, 5, 6, 7, 8, 9, 10, 11, 12, 13, 14, 15, 16, 17, 18, 19, 20, 21, 22, 23, 24, 25, or more residues can be removed from an N-terminus and/or a C-terminus of a sequence disclosed herein, and the remaining sequence can be used in the generation of a multi-specific construct. For example, N- and/or C-terminal residues can be removed from SEQ ID NO: 173 (e.g., to generate SEQ ID NO: 244), and the truncated sequence can be used in a multi-specific construct. In some embodiments, the sequences in any of SEQ ID NOS: 13-20 or 246-253 can be modified. For example, one or more C-terminal residues can be removed (e.g., the C-terminal lysine can be removed from any of SEQ ID NOS: 13-16 or 246-249, and the remaining residues (residues 1-467) can be used in a multi-specific construct).

A compound described herein can include a linker between different domains of the compound. A linker can be a chemical bond, for example, a covalent bond or a non-covalent bond. A linker as described herein can include a flexible or rigid linker.

A linker of the disclosure can include a chemical linker. For example, two amino acid sequences of the disclosure can be connected together by a chemical linker. Each chemical linker of the disclosure can be alkylene, alkenylene, alkynylene, heteroalkylene, cycloalkylene, heterocycloalkylene, arylene, or heteroarylene, any of which is optionally substituted. In some embodiments, a chemical linker of the disclosure can be an ester, ether, amide, thioether, or polyethyleneglycol (PEG). In some embodiments, a linker can reverse the order of the amino acids sequence in a compound, for example, so that the amino acid sequences linked by the linked are head-to-head, rather than head-to-tail. Non-limiting examples of such linkers include diesters of dicarboxylic acids, such as oxalyl diester, malonyl diester, succinyl diester, glutaryl diester, adipyl diester, pimetyl diester, fumaryl diester, maleyl diester, phthalyl diester, isophthalyl diester, and terephthalyl diester. Non-limiting examples of such linkers include diamides of dicarboxylic acids, such as oxalyl diamide, malonyl diamide, succinyl diamide, glutaryl diamide, adipyl diamide, pimetyl diamide, fumaryl diamide, maleyl diamide, phthalyl diamide, isophthalyl diamide, and terephthalyl diamide. Non-limiting examples of such linkers include diamides of diamino linkers, such as ethylene diamine, 1,2-di(methylamino)ethane, 1,3-diaminopropane, 1,3-di(methylamino) propane, 1,4-di(methylamino)butane, 1,5-di(methylamino) pentane, 1,6-di(methylamino)hexane, and pipyrizine.

Non-limiting examples of optional substituents include hydroxyl groups, sulfhydryl groups, halogens, amino groups, nitro groups, nitroso groups, cyano groups, azido groups, sulfoxide groups, sulfone groups, sulfonamide groups, carboxyl groups, carboxaldehyde groups, imine groups, alkyl groups, halo-alkyl groups, alkenyl groups, halo-alkenyl groups, alkynyl groups, halo-alkynyl groups, alkoxy groups, aryl groups, aryloxy groups, aralkyl groups, arylalkoxy groups, heterocyclyl groups, acyl groups, acyloxy groups, carbamate groups, amide groups, ureido groups, epoxy groups, and ester groups.

A linker can be a peptide. A linker can comprise a linker sequence, for example, a linker peptide sequence. A linker sequence can be, for example, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 51, 53, 54, 55, 56, 57, 58, 59, 60, 61, 62, 63, 64, 65, 66, 67, 68, 69, or 70 amino acid residues in length.

A flexible linker can have a sequence containing stretches of glycine and serine residues. The small size of the glycine and serine residues provides flexibility, and allows for mobility of the connected functional domains. The incorporation of serine or threonine can maintain the stability of the linker in aqueous solutions by forming hydrogen bonds with the water molecules, thereby reducing unfavorable interactions between the linker and protein moieties.

Flexible linkers can also contain additional amino acids such as threonine and alanine to maintain flexibility, as well as polar amino acids such as lysine and glutamine to improve solubility.

A flexible linker can comprise repeats of SEQ ID NO: 42 (GGGS), for example, SEQ ID NOS: 42-55. A flexible linker can comprise repeats of SEQ ID NO: 31 (GGGGS), for example, SEQ ID NOS: 31-41. Several other types of flexible linkers, including SEQ ID NO: 59 (KESGSVSSEQLAQFRSLD) and SEQ ID NO: 60 (EGKSSGSGSESKST), can also be used. The SEQ ID NO: 61 (GSAGSAAGSGEF) linker can also be used, in which large hydrophobic residues are minimized to maintain good solubility in aqueous solutions. The length of the flexible linkers can be adjusted to allow for proper folding or to achieve optimal biological activity of the fused proteins.

A rigid linker can have, for example, an alpha helix-structure. An alpha-helical rigid linker can act as a spacer between protein domains. A rigid linker can comprise repeats of SEQ ID NO: 62 (EAAAK), for example, SEQ ID NOS: 62-66. A rigid linker can comprise repeats of SEQ ID NO: 67 (EAAAR), for example, SEQ ID NOS: 67-72. A rigid linker can have a proline-rich sequence, (XP)n, with X designating alanine, lysine, glutamine, or any amino acid. The presence of proline in non-helical linkers can increase stiffness, and allow for effective separation of protein domains.

A linker can comprise any of the sequences disclosed in TABLE 18, which can be used to link any portion of a compound disclosed herein to any portion of another compound disclosed herein:

TABLE 18

| SEQ ID NO: | Sequence |
|---|---|
| 31 | GGGGS |
| 32 | GGGGSGGGGS |
| 33 | GGGGSGGGGSGGGGS |
| 34 | GGGGSGGGGSGGGGSGGGGS |
| 35 | GGGGSGGGGSGGGGSGGGGSGGGGS |
| 36 | GGGGSGGGGSGGGGSGGGGSGGGGSGGGGS |
| 37 | GGGGSGGGGSGGGGSGGGGSGGGGSGGGGSGGGGS |
| 38 | GGGGSGGGGSGGGGSGGGGSGGGGSGGGGSGGGGSGGGGS |
| 39 | GGGGSGGGGSGGGGSGGGGSGGGGSGGGGSGGGGSGGGGSGGGGS |
| 40 | GGGGSGGGGSGGGGSGGGGSGGGGSGGGGSGGGGSGGGGSGGGGSGGGGS |
| 41 | GGGGSGGGGSGGGGSGGGGSGGGGSGGGGSGGGGSGGGGSGGGGSGGGGSGGGGS |
| 42 | GGGS |
| 43 | GGGSGGGS |
| 44 | GGGSGGGSGGGS |
| 45 | GGGSGGGSGGGSGGGS |
| 46 | GGGSGGGSGGGSGGGSGGGS |
| 47 | GGGSGGGSGGGSGGGSGGGSGGGS |
| 48 | GGGSGGGSGGGSGGGSGGGSGGGSGGGS |
| 49 | GGGSGGGSGGGSGGGSGGGSGGGSGGGSGGGS |
| 50 | GGGSGGGSGGGSGGGSGGGSGGGSGGGSGGGSGGGS |
| 51 | GGGSGGGSGGGSGGGSGGGSGGGSGGGSGGGSGGGSGGGS |
| 52 | GGGSGGGSGGGSGGGSGGGSGGGSGGGSGGGSGGGSGGGSGGGS |
| 53 | GGGSGGGSGGGSGGGSGGGSGGGSGGGSGGGSGGGSGGGSGGGSGGGS |
| 54 | GGGSGGGSGGGSGGGSGGGSGGGSGGGSGGGSGGGSGGGSGGGSGGGSGGGS |
| 55 | GGGSGGGSGGGSGGGSGGGSGGGSGGGSGGGSGGGSGGGSGGGSGGGSGGGSGGGS |
| 56 | GG |
| 57 | GGGGGG |
| 58 | GGGGGGGG |
| 59 | KESGSVSSEQLAQFRSLD |
| 60 | EGKSSGSGSESKST |
| 61 | GSAGSAAGSGEF |
| 62 | EAAAK |
| 63 | EAAAKEAAAK |

TABLE 18-continued

| SEQ ID NO: | Sequence |
|---|---|
| 64 | EAAAKEAAAKEAAAKEAAAK |
| 65 | EAAAKEAAAKEAAAKEAAAKEAAAK |
| 66 | EAAAKEAAAKEAAAKEAAAKEAAAKEAAAK |
| 67 | EAAAR |
| 68 | EAAAREAAAR |
| 69 | EAAAREAAAREAAAR |
| 70 | EAAAREAAAREAAAREAAAR |
| 71 | EAAAREAAAREAAAREAAAREAAAR |
| 72 | EAAAREAAAREAAAREAAAREAAAREAAAR |
| 73 | AEAAAKEAAAKEAAAKEAAAKALEAEAAAKEAAAKEAAAKEAAAKA |
| 74 | PAPAP |
| 75 | AEAAAKEAAAKA |

The VEGF-binding and VEGFR-binding compounds described in TABLE 11, TABLE 12, TABLE 13, TABLE 14, TABLE 15, TABLE 16, and TABLE 17 can be combined with the HPTP-β (VE-PTP)-binding compounds described in TABLE 2, TABLE 3, TABLE 6, TABLE 7, and TABLE 8.

Any of the 16 antibodies described in TABLE 8 can be combined with aflibercept or aflibercept-related sequences to generate a bispecific antibody. Non-limiting schematic examples are presented in FIG. 2, FIG. 3, and FIG. 4. For example, SEQ ID NO: 22 can be appended onto SEQ ID NO: 14 or SEQ ID NO: 247 of antibody HC2:LC1 to generate a tetravalent bispecific antibody wherein the heavy chain of HC2:LC1 is appended with SEQ ID NO: 22 (FIG. 2). SEQ ID NO: 22 can be appended onto SEQ ID NO: 17 or SEQ ID NO: 250 of antibody HC2:LC1 to generate a tetravalent bispecific antibody, in which the light chain of HC2:LC1 is appended with SEQ ID NO: 22 (FIG. 3). SEQ ID NO: 22 can be appended onto SEQ ID NO: 14 or SEQ ID NO: 247, and SEQ ID NO: 22 can be appended onto SEQ ID NO: 17 or SEQ ID NO: 250 of antibody HC2:LC1 to generate a hexavalent bispecific antibody wherein the heavy and light chains of HC2:LC1 are appended with SEQ ID NO: 22 (FIG. 4).

Any of the 16 antibodies described in TABLE 8 can be combined with brolucizumab or brolucizumab-related sequences to generate a bispecific antibody. Non-limiting schematic examples are presented in FIG. 2, FIG. 3, and FIG. 4. For example, SEQ ID NO: 23 can be appended onto SEQ ID NO: 14 or SEQ ID NO: 247 of antibody HC2:LC1 to generate a tetravalent bispecific antibody wherein the heavy chain of HC2:LC1 is appended with SEQ ID NO: 23 (FIG. 2). SEQ ID NO: 23 can be appended onto SEQ ID NO: 17 or SEQ ID NO: 250 of antibody HC2:LC1 to generate a tetravalent bispecific antibody wherein the light chain of HC2:LC1 is appended with SEQ ID NO: 23 (FIG. 3). SEQ ID NO: 23 can be appended onto SEQ ID NO: 14 or SEQ ID NO: 247, and SEQ ID NO: 23 can be appended onto SEQ ID NO: 17 or SEQ ID NO: 250 of antibody HC2:LC1 to generate a hexavalent bispecific antibody wherein the heavy and light chains of HC2:LC1 are appended with SEQ ID NO: 23 (FIG. 4).

Any of the 16 antibodies described in TABLE 8 can be combined with ranibizumab or ranibizumab-related sequences to generate a bispecific antibody. Non-limiting schematic examples are presented in FIG. 2, FIG. 3, and FIG. 4. For example, SEQ ID NO: 28 can be appended onto SEQ ID NO: 14 or SEQ ID NO: 247 of antibody HC2:LC1 to generate a tetravalent bispecific antibody wherein the heavy chain of HC2:LC1 is appended with SEQ ID NO: 28 (FIG. 2). SEQ ID NO: 28 can be appended onto SEQ ID NO: 17 or SEQ ID NO: 250 of antibody HC2:LC1 to generate a tetravalent bispecific antibody wherein the light chain of HC2:LC1 is appended with SEQ ID NO: 28 (FIG. 3). SEQ ID NO: 28 can be appended onto SEQ ID NO: 14 or SEQ ID NO: 247, and SEQ ID NO: 28 can be appended onto SEQ ID NO: 17 or SEQ ID NO: 250 of antibody HC2:LC1 to generate a hexavalent bispecific antibody wherein the heavy and light chains of HC2:LC1 are appended with SEQ ID NO: 28 (FIG. 4).

Any of the 16 antibodies described in TABLE 8 can be combined with bevacizumab or bevacizumab-related sequences to generate a bispecific antibody. Non-limiting schematic examples are presented in FIG. 2, FIG. 3, and FIG. 4. For example, an antigen-binding scFv of bevacizumab could be generated as demonstrated for ranibizumab in TABLE 13. The bevacizumab-derived antigen-binding scFv can be appended onto SEQ ID NO: 14 or SEQ ID NO: 247 of antibody HC2:LC1 to generate a tetravalent bispecific antibody wherein the heavy chain of HC2:LC1 is appended with the bevacizumab-derived antigen-binding scFv (FIG. 2). The bevacizumab-derived antigen-binding scFv can be appended onto SEQ ID NO: 17 or SEQ ID NO: 250 of antibody HC2:LC1 to generate a tetravalent bispecific antibody, in which the light chain of HC2:LC1 is appended with the bevacizumab-derived antigen-binding scFv (FIG. 3). The bevacizumab-derived antigen-binding scFv can be appended onto SEQ ID NO: 14 or SEQ ID NO: 247, and the bevacizumab-derived antigen-binding scFv can be appended onto SEQ ID NO: 17 or SEQ ID NO: 250 of antibody HC2:LC1 to generate a hexavalent bispecific antibody, in which the heavy and light chains of HC2:LC1 are appended with the bevacizumab-derived antigen-binding scFv (FIG. 4).

Any of the 16 antibodies described in TABLE 8 can be combined with abicipar or abicipar-related sequences to generate a bispecific antibody. Non-limiting schematic examples are presented in FIG. 2, FIG. 3, and FIG. 4. For example, SEQ ID NO: 173 or SEQ ID NO: 244 can be appended onto SEQ ID NO: 14, SEQ ID NO: 247, residues 1-467 SEQ ID NO: 14, or residues 1-467 SEQ ID NO: 247 of antibody HC2:LC1 to generate a tetravalent bispecific antibody wherein the heavy chain of HC2:LC1 is appended with SEQ ID NO: 173 or SEQ ID NO: 244 (FIG. 2). SEQ ID NO: 173 or SEQ ID NO: 244 can be appended onto SEQ ID NO: 17 or SEQ ID NO: 250 of antibody HC2:LC1 to generate a tetravalent bispecific antibody, in which the light chain of HC2:LC1 is appended with SEQ ID NO: 173 or SEQ ID NO: 244 (FIG. 3). SEQ ID NO: 173 or SEQ ID NO: 244 can be appended onto SEQ ID NO: 14, SEQ ID NO: 247, residues 1-467 SEQ ID NO: 14, or residues 1-467 SEQ ID NO: 247, and SEQ ID NO: 173 or SEQ ID NO: 244 can be appended onto SEQ ID NO: 17 or SEQ ID NO: 250 of antibody HC2:LC1 to generate a hexavalent bispecific antibody wherein the heavy and light chains of HC2:LC1 are appended with SEQ ID NO: 173 or SEQ ID NO: 244 (FIG. 4).

Any of the 16 antibodies described in TABLE 8 can be combined with conbercept or conbercept-related sequences to generate a bispecific antibody. Non-limiting schematic examples are presented in FIG. 2, FIG. 3, and FIG. 4. For example, SEQ ID NO: 155 can be appended onto SEQ ID NO: 14 or SEQ ID NO: 247 of antibody HC2:LC1 to generate a tetravalent bispecific antibody wherein the heavy chain of HC2:LC1 is appended with SEQ ID NO: 155 (FIG. 2). SEQ ID NO: 155 can be appended onto SEQ ID NO: 17 or SEQ ID NO: 250 of antibody HC2:LC1 to generate a tetravalent bispecific antibody, in which the light chain of HC2:LC1 is appended with SEQ ID NO: 155 (FIG. 3). SEQ ID NO: 155 can be appended onto SEQ ID NO: 14 or SEQ ID NO: 247, and SEQ ID NO: 155 can be appended onto SEQ ID NO: 17 or SEQ ID NO: 250 of antibody HC2:LC1 to generate a hexavalent bispecific antibody wherein the heavy and light chains of HC2:LC1 are appended with SEQ ID NO: 155 (FIG. 4).

Any of the 16 antibodies described in TABLE 8 can be combined with ramucirumab or ramucirumab-related sequences to generate a bispecific antibody. Non-limiting schematic examples are presented in FIG. 2, FIG. 3, and FIG. 4. For example, an antigen-binding scFv of ramucirumab could be generated as demonstrated for ranibizumab in TABLE 13. The ramucirumab-derived antigen-binding scFv can be appended onto SEQ ID NO: 14 or SEQ ID NO: 247 of antibody HC2:LC1 to generate a tetravalent bispecific antibody wherein the heavy chain of HC2:LC1 is appended with the ramucirumab-derived antigen-binding scFv (FIG. 2). The ramucirumab-derived antigen-binding scFv can be appended onto SEQ ID NO: 17 or SEQ ID NO: 250 of antibody HC2:LC1 to generate a tetravalent bispecific antibody, in which the light chain of HC2:LC1 is appended with the ramucirumab-derived antigen-binding scFv (FIG. 3). The ramucirumab-derived antigen-binding scFv can be appended onto SEQ ID NO: 14 or SEQ ID NO: 247, and the ramucirumab-derived antigen-binding scFv can be appended onto SEQ ID NO: 17 or SEQ ID NO: 250 of antibody HC2:LC1 to generate a hexavalent bispecific antibody, in which the heavy and light chains of HC2:LC1 are appended with the ramucirumab-derived antigen-binding scFv (FIG. 4).

Any of the 16 antibodies described in TABLE 8 can be combined with DARPins, DARPin repeats, or sequences therefrom, to generate a multispecific antibody. Non-limiting schematic examples are presented in FIG. 2, FIG. 3, and FIG. 4. For example, an amino acid sequence comprising any of SEQ ID NOS: 158-217 can be appended onto SEQ ID NO: 14 or SEQ ID NO: 247 of antibody HC2:LC1 to generate a tetravalent bispecific antibody wherein the heavy chain of HC2:LC1 is appended with an amino acid sequence comprising any of SEQ ID NOS: 158-217 (FIG. 2). An amino acid sequence comprising any of SEQ ID NOS: 158-217 can be appended onto SEQ ID NO: 17 or SEQ ID NO: 250 of antibody HC2:LC1 to generate a tetravalent bispecific antibody, in which the light chain of HC2:LC1 is appended with an amino acid sequence comprising any of SEQ ID NOS: 158-217 (FIG. 3). An amino acid sequence comprising any of SEQ ID NOS: 158-217 can be appended onto SEQ ID NO: 14 or SEQ ID NO: 247 and onto SEQ ID NO: 17 or SEQ ID NO: 250 of antibody HC2:LC1 to generate a hexavalent bispecific antibody wherein the heavy and light chains of HC2:LC1 are appended with an amino acid sequence comprising any of SEQ ID NOS: 158-217 (FIG. 4).

The Tie2 activating compounds described in TABLE 9 and TABLE 10 can be combined with the HPTP-β (VE-PTP)-binding compounds described in TABLE 2, TABLE 3, TABLE 6, TABLE 7, and TABLE 8.

Any of the 16 antibodies described in TABLE 8 can be combined with collagen IV-derived biomimetic peptide sequences to generate a multispecific antibody. Non-limiting schematic examples are presented in FIG. 2, FIG. 3, and FIG. 4. For example, an amino acid sequence comprising SEQ ID NO: 152 or SEQ ID NO: 153 can be appended onto SEQ ID NO: 14 or SEQ ID NO: 247 of antibody HC2:LC1 to generate a tetravalent bispecific antibody wherein the heavy chain of HC2:LC1 is appended with an amino acid sequence comprising SEQ ID NO: 152 or SEQ ID NO: 153 (FIG. 2). An amino acid sequence comprising SEQ ID NO: 152 or SEQ ID NO: 153 can be appended onto SEQ ID NO: 17 or SEQ ID NO: 250 of antibody HC2:LC1 to generate a tetravalent bispecific antibody, in which the light chain of HC2:LC1 is appended with an amino acid sequence comprising SEQ ID NO: 152 or SEQ ID NO: 153 (FIG. 3). An amino acid sequence comprising SEQ ID NO: 152 or SEQ ID NO: 153 can be appended onto SEQ ID NO: 14 or SEQ ID NO: 247 and onto SEQ ID NO: 17 or SEQ ID NO: 250 of antibody HC2:LC1 to generate a hexavalent bispecific antibody wherein the heavy and light chains of HC2:LC1 are appended with an amino acid sequence comprising SEQ ID NO: 152 or SEQ ID NO: 153 (FIG. 4).

Any of the 16 antibodies described in TABLE 8 can be combined with Ang2 mimetics, or sequences therefrom, to generate a multispecific antibody. Non-limiting schematic examples are presented in FIG. 2, FIG. 3, and FIG. 4. For example, an amino acid sequence comprising any of SEQ ID NOS: 229-230 can be appended onto SEQ ID NO: 14 or SEQ ID NO: 247 of antibody HC2:LC1 to generate a tetravalent bispecific antibody wherein the heavy chain of HC2:LC1 is appended with an amino acid sequence comprising any of SEQ ID NOS: 229-230 (FIG. 2). An amino acid sequence comprising any of SEQ ID NOS: 229-230 can be appended onto SEQ ID NO: 17 or SEQ ID NO: 250 of antibody HC2:LC1 to generate a tetravalent bispecific antibody, in which the light chain of HC2:LC1 is appended with an amino acid sequence comprising any of SEQ ID NOS: 229-230 (FIG. 3). An amino acid sequence comprising any of SEQ ID NOS: 229-230 can be appended onto SEQ ID NO: 14 or SEQ ID NO: 247 and onto SEQ ID NO: 17 or SEQ ID NO: 250 of antibody HC2:LC1 to generate a hexavalent bispecific antibody wherein the heavy and light chains of HC2:LC1 are appended with an amino acid sequence comprising any of SEQ ID NOS: 229-230 (FIG. 4).

The Tie2 activating compounds described in TABLE 9 and TABLE 10 can be combined with the VEGF-binding and VEGFR-binding compounds described in TABLE 11, TABLE 12, TABLE 13, TABLE 14, TABLE 15, TABLE 16, and TABLE 17 to generate multi-specific compounds.

Any of the compounds in this disclosure, e.g., the multi-specific fusion constructs described above, can be modified as necessary to promote desirable protein folding or biological activity.

CDRs

Sequences in this disclosure can comprise complementarity determining regions (CDRs). CDRs can be identified by the Kabat method, the Chothia method, the IMGT method, or the Paratome method. A CDR of a sequence herein can be, for example, between 0 and 91 residues in length, between 0 and 25 residues in length, between 5 and 14 residues in length, about 0 residues in length, about 1 residue in length, about 2 residues in length, about 3 residues in length, about 4 residues in length, about 5 residues in length, about 6 residues in length, about 7 residues in length, about 8 residues in length, about 9 residues in length, about 10 residues in length, about 11 residues in length, about 12 residues in length, about 13 residues in length, about 14 residues in length, about 15 residues in length, about 16 residues in length, about 17 residues in length, about 18 residues in length, about 19 residues in length, about 20 residues in length, about 21 residues in length, about 22 residues in length, about 23 residues in length, about 24 residues in length, or about 25 residues in length.

A compound of this disclosure with a binding specificity for or an ability to modulate HPTP-β (VE-PTP) can comprise, for example, any of the CDRs in TABLE 19, TABLE 20, TABLE 21, TABLE 22, TABLE 23, or TABLE 24.

TABLE 19 provides non-limiting examples of HCDR1 sequences specific for HPTP-β (VE-PTP).

TABLE 19

| SEQ ID NO: | Amino acid sequence |
|---|---|
| 76 | ANAMN |
| 77 | GFTFNAN |
| 78 | GFTFNANA |
| 79 | FTFNANAMN |
| 80 | GFTFNANAMN |

TABLE 20 provides non-limiting examples of HCDR2 sequences specific for HPTP-β (VE-PTP).

TABLE 20

| SEQ ID NO: | Amino acid sequence |
|---|---|
| 81 | RIRTKSNNYATYYAGSVKD |
| 82 | RTKSNNYA |
| 83 | IRTKSNNYAT |
| 84 | WVGRIRTKSNNYATYY |
| 85 | WVGRIRTKSNNYATYYAGSVKD |
| 86 | WVSRIRTKSNNYATYY |
| 87 | WVSRIRTKSNNYATYYAGSVKD |

TABLE 21 provides non-limiting examples of HCDR3 sequences specific for HPTP-β (VE-PTP).

TABLE 21

| SEQ ID NO: | Amino acid sequence |
|---|---|
| 88 | DYYGSSAWITY |
| 89 | VRDYYGSSAWITY |
| 90 | RDYYGSSAWITY |

TABLE 22 provides non-limiting examples of LCDR1 sequences specific for HPTP-β (VE-PTP).

TABLE 22

| SEQ ID NO: | Amino acid sequence |
|---|---|
| 91 | KASQHVGTAVA |
| 92 | QHVGTA |
| 93 | QHVGTAVA |

TABLE 23 provides non-limiting examples of LCDR2 sequences specific for HPTP-β (VE-PTP).

TABLE 23

| SEQ ID NO: | Amino acid sequence |
|---|---|
| 94 | WASTRHT |
| 95 | WAS |
| 96 | LLIYWASTRHT |

TABLE 24 provides non-limiting examples of LCDR3 sequences specific for HPTP-β (VE-PTP).

TABLE 24

| SEQ ID NO: | Amino acid sequence |
|---|---|
| 97 | QQYSSYPFT |
| 98 | QQYSSYPF |

Compounds of this disclosure with a binding specificity for or an ability to modulate VEGF can comprise any of the CDRs in TABLE 25, TABLE 26, TABLE 27, TABLE 28, TABLE 29, or TABLE 30.

TABLE 25 provides non-limiting examples of HCDR1 sequences specific for VEGF.

TABLE 25

| SEQ ID NO: | Amino acid sequence |
|---|---|
| 99 | DYYYMT |
| 100 | GFSLTDYY |
| 101 | GFSLTDYYY |
| 102 | FSLTDYYYMT |
| 103 | GFSLTDYYYMT |
| 104 | HYGMN |
| 105 | GYDFTHY |
| 106 | GYDFTHYG |
| 107 | YDFTHYGMN |
| 108 | GYDFTHYGMN |
| 109 | NYGMN |
| 110 | GYTFTNY |
| 111 | GYTFTNYG |
| 112 | YTFTNYGMN |
| 113 | GYTFTNYGMN |

TABLE 26 provides non-limiting examples of HCDR2 sequences specific for VEGF.

TABLE 26

| SEQ ID NO: | Amino acid sequence |
|---|---|
| 114 | FIDPDDDPYYATWAKG |
| 115 | DPDDD |
| 116 | IDPDDDP |
| 117 | WVGFIDPDDDPYYATWA |
| 118 | WVGFIDPDDDPYYATWAKG |
| 119 | WINTYTGEPTYAADFKR |
| 120 | NTYTGE |
| 121 | INTYTGEP |
| 122 | WVGWINTYTGEPTY |
| 123 | WVGWINTYTGEPTYAADFKR |

TABLE 27 provides non-limiting examples of HCDR3 sequences specific for VEGF.

TABLE 27

| SEQ ID NO: | Amino acid sequence |
|---|---|
| 124 | GDHNSGWGLDI |
| 125 | AGGDHNSGWGLDI |
| 126 | YPYYYGTSHWYFDV |
| 127 | AKYPYYYGTSHWYFDV |

TABLE 27-continued

| SEQ ID NO: | Amino acid sequence |
|---|---|
| 128 | KYPYYYGTSHWYFDV |
| 129 | YPHYYGSSHWYFDV |
| 130 | AKYPHYYGSSHWYFDV |
| 131 | KYPHYYGSSHWYFDV |

TABLE 28 provides non-limiting examples of LCDR1 sequences specific for VEGF.

TABLE 28

| SEQ ID NO: | Amino acid sequence |
|---|---|
| 132 | QASEIIHSWLA |
| 133 | EIIHSW |
| 134 | EIIHSWLA |
| 135 | SASQDISNYLN |
| 136 | QDISNY |
| 137 | QDISNYLN |

TABLE 29 provides non-limiting examples of LCDR2 sequences specific for VEGF.

TABLE 29

| SEQ ID NO: | Amino acid sequence |
|---|---|
| 138 | LASTLAS |
| 139 | LAS |
| 140 | LLIYLASTLAS |
| 141 | FTSSLHS |
| 142 | FTS |
| 143 | VLIYFTSSLHS |

TABLE 30 provides non-limiting examples of LCDR3 sequences specific for VEGF.

TABLE 30

| SEQ ID NO: | Amino acid sequence |
|---|---|
| 144 | QNVYLASTNGAN |
| 145 | QQYSTVPWT |
| 146 | QQYSTVPW |

TABLE 31 provides aflibercept-derived sequences corresponding to the D2 domain of human VEGF receptor 1 (SEQ ID NO: 147) and the D3 domain of human VEGF receptor 2 (SEQ ID NO: 148).

TABLE 31

| SEQ ID NO: | Amino acid sequence |
|---|---|
| 147 | SDTGRPFVEMYSEIPEIIHMTEGRELVIPCR<br>VTSPNITVTLKKFPLDTLIPDGKRIIWDSRK<br>GFIISNATYKEIGLLTCEATVNGHLYKTNYL<br>THRQTNTII |
| 148 | DVVLSPSHGIELSVGEKLVLNCTARTELNVG<br>IDFNWEYPSSKHQHKKLVNRDLKTQSGSEMK<br>KFLSTLTIDGVTRSDQGLYTCAASSGLMTKK<br>NSTFVRVHEK |

TABLE 32 provides abicipar-derived sequences. SEQ ID NOS: 233-236 correspond to ankyrin repeats within abicipar. SEQ ID NOS: 237-242 provide consensus sequences for VEGF binding ankyrin repeats. In SEQ ID NO: 237, X1 is K, T, or Y; X2 is N or M; X3 is T or F; X4 is S or A; X5 is H or R; X6 is A, Y, H, or N; and X7 is A or T. In SEQ ID NO: 238, X1 is K, M, N, R, or V; X2 is Y, H, M, or V; X3 is F, L, M, or V; X4 is R, H, V, A, K, or N; X5 is F, D, H, T, Y, M, or K; and X6 is A, H, N, or Y. In SEQ ID NO: 239, X1 is L, S, or T; X2 is G, S, or C; X3 is S or A; X4 is Q, S, M, or N; X5 is L, M, or Q; and X6 is A, H, N, Y, or D. In SEQ ID NO: 240, X1 is K, S, I, N, T, or V; X2 is K, N, W, A, H, M, Q, or S; X3 is F, Q, L, H, or V; X4 is F or T; X5 is Q or H; X6 is Y or S; X7 is N, H, Y, or M; and X8 is A, H, N, or Y. In SEQ ID NO: 241, X1 is A, N, R, V, Y, E, H, I, K, L, Q, S, or T; X2 is S, A, N, R, D, F, L, P, T, or Y; X3 is T, V, S, A, L, or F; X4 is W, F, or H; X5 is P, I, A, L, S, T, V, or Y; X6 is W, F, I, L, T, or V; X7 is L or P; and X8 is A, H, N, or Y. In SEQ ID NO: 242, X1 is H, Q, A, K, R, D, I, L, M, N, V, or Y; X2 is Y, F, or H; X3 is Q, F, or T; X4 is W, M, G, H, N, or T; X5 is T, A, M, L, or V; X6 is I, L, V, D, or T; and X7 is A, H, N, or Y. SEQ ID NO: 244 provides a truncated sequence derived from abicipar that comprises designed ankyrin repeats with a binding specificity for VEGF.

TABLE 32

| SEQ ID NO: | Amino acid sequence |
|---|---|
| 233 | DLDKKLLEAARAGQDDEVRILMANGADVNARDS |
| 234 | TGWTPLHLAAPWGHPEIVEVLLKNGADVNAADF |
| 235 | QGWTPLHLAAAVGHLEIVEVLLKYGADVNAQDK |
| 236 | FGKTAFDISIDNGNEDLAEILQ |
| 237 | X1DX2X3GWTPLHLX4ADLGX5LEIVEVLLKX6GADVNX7 |
| 238 | X1DX2X3GWTPLHLAAX4X5GHLEIVEVLLKX6GADVNA |
| 239 | X1DFKX2DTPLHLAAX3X4GHX5EIVEVLLKX6GADVNA |
| 240 | X1DX2X3GX4TPLX5LAAX6X7GHLEIVEVLLKX8GADVNA |
| 241 | X1DX2X3GX4TPLHLAAX5X6GHX7EIVEVLLKX8GADVNA |
| 242 | X1DX2X3GX4TPLHLAAX5X6GHLEIVEVLLKX7GADVNA |
| 244 | DLDKKLLEAARAGQDDEVRILMANGADVNARDSTGWTPLHLA<br>APWGHPEIVEVLLKNGADVNAADFQGWTPLHLAAAVGHLEI<br>VEVLLKYGADVNAQDKFGKTAFDISIDNGNEDLAEILQKAA |

Homology

A sequence of a compound herein can have at least about 70% homology, at least about 71% homology, at least about 72% homology, at least about 73% homology, at least about 74% homology, at least about 75% homology, at least about 76% homology, at least about 77% homology, at least about 78% homology, at least about 79% homology, at least about 80% homology, at least about 81% homology, at least about 82% homology, at least about 83% homology, at least about 84% homology, at least about 85% homology, at least about 86% homology, at least about 87% homology, at least about 88% homology, at least about 89% homology, at least about 90% homology, at least about 91% homology, at least about 92% homology, at least about 93% homology, at least about 94% homology, at least about 95% homology, at least about 96% homology, at least about 97% homology, at least about 98% homology, at least about 99% homology, at least about 99.1% homology, at least about 99.2% homology, at least about 99.3% homology, at least about 99.4% homology, at least about 99.5% homology, at least about 99.6% homology, at least about 99.7% homology, at least about 99.8% homology, at least about 99.9% homology, at least about 99.91% homology, at least about 99.92% homology, at least about 99.93% homology, at least about 99.94% homology, at least about 99.95% homology, at least about 99.96% homology, at least about 99.97% homology, at least about 99.98% homology, or at least about 99.99% homology to an amino acid sequence provided herein.

Various methods and software programs can be used to determine the homology between two or sequences, such as NCBI BLAST, Clustal W, MAFFT, Clustal Omega, AlignMe, Praline, or another suitable method or algorithm.

Pharmaceutical Compositions

A pharmaceutical composition of the disclosure can be a combination of any pharmaceutical compounds described herein with other chemical components, such as carriers, stabilizers, diluents, dispersing agents, suspending agents, thickening agents, and/or excipients. The pharmaceutical composition facilitates administration of the compound to an organism.

Pharmaceutical formulations for administration can include aqueous solutions of the active compounds in water-soluble form. Suspensions of the active compounds can be prepared as oily injection suspensions. Suitable lipophilic solvents or vehicles include fatty oils such as sesame oil, or synthetic fatty acid esters, such as ethyl oleate or triglycerides, or liposomes. Aqueous injection suspensions can contain substances which increase the viscosity of the suspension, such as sodium carboxymethyl cellulose, sorbitol, or dextran. The suspension can also contain suitable stabilizers or agents which increase the solubility of the compounds to allow for the preparation of highly concentrated solutions. The active ingredient can be in powder form for constitution with a suitable vehicle, for example, sterile pyrogen-free water, before use.

In practicing the methods of treatment or use provided herein, therapeutically-effective amounts of the compounds described herein are administered in pharmaceutical compositions to a subject having a disease or condition to be treated. In some embodiments, the subject is a mammal such as a human. A therapeutically-effective amount can vary widely depending on the severity of the disease, the age and relative health of the subject, the potency of the compounds used, and other factors.

Pharmaceutical compositions can be formulated using one or more physiologically-acceptable carriers comprising excipients and auxiliaries, which facilitate processing of the active compounds into preparations that can be used pharmaceutically. Formulation can be modified depending upon the route of administration chosen. Pharmaceutical compositions comprising compounds described herein can be manufactured, for example, by mixing, dissolving, emulsifying, encapsulating, entrapping, or compression processes.

The pharmaceutical compositions can include at least one pharmaceutically-acceptable carrier, diluent, or excipient and compounds described herein as free-base or pharmaceutically-acceptable salt form. Pharmaceutical compositions can contain solubilizers, stabilizers, tonicity enhancing agents, buffers, and preservatives.

Methods for the preparation of compositions comprising the compounds described herein include formulating the compounds with one or more inert, pharmaceutically-acceptable excipients or carriers to form a solid, semi-solid, or liquid composition. Solid compositions include, for example, powders, tablets, dispersible granules, capsules, and cachets. Liquid compositions include, for example, solutions in which a compound is dissolved, emulsions comprising a compound, or a solution containing liposomes, micelles, or nanoparticles comprising a compound as disclosed herein. Semi-solid compositions include, for example, gels, suspensions and creams. The compositions can be in liquid solutions or suspensions, solid forms suitable for solution or suspension in a liquid prior to use, or as emulsions. These compositions can also contain minor amounts of nontoxic, auxiliary substances, such as wetting or emulsifying agents, pH buffering agents, and other pharmaceutically-acceptable additives.

Non-limiting examples of dosage forms suitable for use in the disclosure include liquid, powder, gel, nanosuspension, nanoparticle, microgel, aqueous or oily suspensions, emulsion, and any combination thereof.

Non-limiting examples of pharmaceutically-acceptable excipients suitable for use in the disclosure include binding agents, disintegrating agents, anti-adherents, anti-static agents, surfactants, anti-oxidants, coating agents, coloring agents, plasticizers, preservatives, suspending agents, emulsifying agents, anti-microbial agents, spheronization agents, and any combination thereof.

A composition of the disclosure can be, for example, an immediate release form or a controlled release formulation. An immediate release formulation can be formulated to allow the compounds to act rapidly. Non-limiting examples of immediate release formulations include readily dissolvable formulations. A controlled release formulation can be a pharmaceutical formulation that has been adapted such that release rates and release profiles of the active agent can be matched to physiological and chronotherapeutic requirements, or has been formulated to effect release of an active agent at a programmed rate. Non-limiting examples of controlled release formulations include granules, delayed release granules, hydrogels (e.g., of synthetic or natural origin), other gelling agents (e.g., gel-forming dietary fibers), matrix-based formulations (e.g., formulations comprising a polymeric material having at least one active ingredient dispersed through), granules within a matrix, polymeric mixtures, and granular masses.

In some, a controlled release formulation is a delayed release form. A delayed release form can be formulated to delay a compound's action for an extended period of time. A delayed release form can be formulated to delay the release of an effective dose of one or more compounds, for example, for about 4, about 8, about 12, about 16, or about 24 hours.

A controlled release formulation can be a sustained release form. A sustained release form can be formulated to sustain, for example, the compound's action over an extended period of time. A sustained release form can be formulated to provide an effective dose of any compound described herein (e.g., provide a physiologically-effective blood profile) over about 4, about 8, about 12, about 16, or about 24 hours.

The disclosed compositions can optionally comprise pharmaceutically-acceptable preservatives.

Non-limiting examples of pharmaceutically-acceptable excipients can be found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pennsylvania 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), each of which is incorporated by reference in its entirety.

A compound described herein can be conveniently formulated into pharmaceutical compositions composed of one or more pharmaceutically-acceptable carriers. See e.g., Remington's Pharmaceutical Sciences, latest edition, by E.W. Martin Mack Pub. Co., Easton, PA, incorporated by reference in its entirety, which discloses typical carriers and conventional methods of preparing pharmaceutical compositions. Such carriers can be carriers for administration of compositions to humans and non-humans, including solutions such as sterile water, saline, and buffered solutions at physiological pH. Pharmaceutical compositions can also include one or more additional active ingredients such as antimicrobial agents, anti-inflammatory agents, and anesthetics.

Non-limiting examples of pharmaceutically-acceptable carriers include saline, Ringer's solution, and dextrose solution. In some embodiments, the pH of the solution can be from about 5 to about 8, and can be from about 7 to about 7.5. Further carriers include sustained release preparations such as semipermeable matrices of solid hydrophobic polymers containing the compound. The matrices can be in the form of shaped articles, for example, films, liposomes, microparticles, or microcapsules.

Compositions suitable for topical administration can be used. In some embodiments, compositions of the disclosure can comprise a liquid comprising an active agent in solution, in suspension, or both. Liquid compositions can include gels. A liquid composition can be, for example, aqueous. A composition is an in situ gellable aqueous composition. In iteration, the composition is an in situ gellable aqueous solution. Such a composition can comprise a gelling agent in a concentration effective to promote gelling upon contact with the eye or lacrimal fluid in the exterior of the eye. Aqueous compositions can have ophthalmically-compatible pH and osmolality. The composition can comprise an ophthalmic depot formulation comprising an active agent for subconjunctival administration. Microparticles comprising an active agent can be embedded in a biocompatible, pharmaceutically-acceptable polymer or a lipid encapsulating agent. The depot formulations can be adapted to release all or substantially all the active material over an extended period of time. The polymer or lipid matrix, if present, can be adapted to degrade sufficiently to be transported from the site of administration after release of all or substantially all the active agent. The depot formulation can be a liquid formulation, comprising a pharmaceutical acceptable polymer and a dissolved or dispersed active agent. Upon injection, the polymer forms a depot at the injections site, for example, by gelifying or precipitating. The composition can comprise a solid article that can be inserted in a suitable location in the eye, such as between the eye and eyelid or in the conjuctival sac, where the article releases the active agent. Solid articles suitable for implantation in the eye in such fashion can comprise polymers and can be bioerodible or non-bioerodible.

Pharmaceutical formulations can include additional carriers, as well as thickeners, diluents, buffers, preservatives, and surface active agents in addition to the agents disclosed herein.

The pH of the disclosed composition can range from about 3 to about 12. The pH of the composition can be, for example, from about 3 to about 4, from about 4 to about 5, from about 5 to about 6, from about 6 to about 7, from about 7 to about 8, from about 8 to about 9, from about 9 to about 10, from about 10 to about 11, or from about 11 to about 12 pH units. The pH of the composition can be, for example, about 3, about 4, about 5, about 6, about 7, about 8, about 9, about 10, about 11, or about 12 pH units. The pH of the composition can be, for example, at least 3, at least 4, at least 5, at least 6, at least 7, at least 8, at least 9, at least 10, at least 11 or at least 12 pH units. The pH of the composition can be, for example, at most 3, at most 4, at most 5, at most 6, at most 7, at most 8, at most 9, at most 10, at most 11, or at most 12 pH units. A pharmaceutical formulation disclosed herein can have a pH of from about 5.5 to about 6.5. For example, a formulation of the present disclosure can have a pH of about 5.5, about 5.6, about 5.7, about 5.8, about 5.9, about 6.0, about 6.1, about 6.2, about 6.3, about 6.4, or about 6.5. In some embodiments, the pH is 6.2±0.3, 6.2±0.2, 6.2±0.1, about 6.2, or 6.2.

If the pH is outside the range desired by the formulator, the pH can be adjusted by using sufficient pharmaceutically-acceptable acids and bases.

Depending on the intended mode of administration, the pharmaceutical compositions can be in the form of solid, semi-solid or liquid dosage forms, such as, for example, tablets, suppositories, pills, capsules, powders, liquids, suspensions, lotions, creams, or gels, for example, in unit dosage form suitable for single administration of a precise dosage.

For solid compositions, nontoxic solid carriers include, for example, pharmaceutical grades of mannitol, lactose, starch, magnesium stearate, sodium saccharin, talc, cellulose, glucose, sucrose, and magnesium carbonate.

Non-limiting examples of pharmaceutically active agents suitable for combination with compositions of the disclosure include anti-infectives, i.e., aminoglycosides, antiviral agents, antimicrobials, anti-cholinergics/anti-spasmotics, antidiabetic agents, antihypertensive agents, anti-neoplastics, cardiovascular agents, central nervous system agents, coagulation modifiers, hormones, immunologic agents, immunosuppressive agents, and ophthalmic preparations.

In some embodiments, the pharmaceutical composition provided herein comprises a therapeutically effective amount of a compound in admixture with a pharmaceutically-acceptable carrier and/or excipient, for example, saline, phosphate buffered saline, phosphate and amino acids, polymers, polyols, sugar, buffers, preservatives, and other proteins. Illustrative agents include octylphenoxy polyethoxy ethanol compounds, polyethylene glycol monostearate compounds, polyoxyethylene sorbitan fatty acid esters, sucrose, fructose, dextrose, maltose, glucose, mannitol, dextran, sorbitol, inositol, galactitol, xylitol, lactose, trehalose, bovine or human serum albumin, citrate, acetate, Ringer's and Hank's solutions, cysteine, arginine, carnitine, alanine, glycine, lysine, valine, leucine, polyvinylpyrrolidone, polyethylene, and glycol.

In some embodiments, a pharmaceutical formulation disclosed herein can comprise: (i) a compound or antibody disclosed herein; (ii) a buffer; (iii) a non-ionic detergent; (iv) a tonicity agent; and (v) a stabilizer. In some embodiments, the pharmaceutical formulation disclosed herein is a stable liquid pharmaceutical formulation.

In some embodiments, an ophthalmic formulation disclosed herein can comprise: (i) a compound or antibody disclosed herein; (ii) a buffer; (iii) a non-ionic detergent; (iv) a tonicity agent; and (v) a stabilizer. In some embodiments, the ophthalmic formulation disclosed herein is a stable liquid pharmaceutical formulation or a stable liquid ophthalmic formulation.

In some embodiments, a pharmaceutical formulation or ophthalmic formulation disclosed herein is a liquid formulation that can comprise about 5 mg/mL to about 150 mg/mL of antibody or compound, about 7.5 mg/mL to about 140 mg/mL of antibody or compound, about 10 mg/mL to about 130 mg/mL of antibody or compound, about 10 mg/mL to about 100 mg/mL of antibody or compound, about 20 mg/mL to about 80 mg/mL of antibody or compound, or about 30 mg/mL to about 70 mg/mL of antibody or compound. For example, a formulation of the present disclosure can comprise about 5 mg/mL, about 10 mg/mL, about 15 mg/mL, about 20 mg/mL, about 25 mg/mL, about 30 mg/mL, about 35 mg/mL, about 40 mg/mL, about 50 mg/mL, about 60 mg/mL, about 70 mg/mL, about 80 mg/mL, about 90 mg/mL, about 100 mg/mL, about 120 mg/mL, about 140 mg/mL, or about 150 mg/mL of a compound, antibody, or antigen-binding fragment thereof described herein.

In some embodiments, a pharmaceutical formulation or ophthalmic formulation disclosed herein can comprise a buffer. In some embodiments, the buffer serves to maintain a stable pH and to help stabilize a compound or antibody disclosed herein. In some embodiments, the buffer or buffer system comprises at least one buffer that has a buffering range that overlaps fully or in part the range of pH 5.5-7.4. In some embodiments, the buffer has a pKa of about 6.2±0.5. In some embodiments, the buffer comprises a sodium phosphate buffer. In some embodiments, the sodium phosphate is present at a concentration of about 5 mM to about 15 mM, about 6 mM to about 14 mM, about 7 mM to about 13 mM, about 8 mM to about 12 mM, about 9 mM to about 11 mM, or about 10 mM. In certain embodiments, the buffer system comprises sodium phosphate at 10 mM, at a pH of 6.2±0.3 or 6.1±0.3.

In some embodiments, a pharmaceutical formulation or ophthalmic formulation disclosed herein can comprise a non-ionic detergent. In some embodiments, the non-ionic detergent is a nonionic polymer containing a polyoxyethylene moiety. In some embodiments, the non-ionic detergent is any one or more of polysorbate 20, poloxamer 188 or polyethylene glycol 3350. In some embodiments, the non-ionic detergent is polysorbate 20. In some embodiments, the non-ionic detergent is polysorbate 80. In some embodiments, a pharmaceutical formulation or ophthalmic formulation disclosed herein can contain about 0.01% to about 1% non-ionic detergent. For example, a formulation of the present disclosure can comprise about 0.0$^{0}$85%, about 0.01%, about 0.02%, about 0.03%, about 0.04%, about 0.05%, about 0.06%, about 0.07%, about 0.08%, about 0.09%, about 0.1%, about 0.11%, about 0.12%, about 0.13%, about 0.14%, about 0.15%, about 0.16%, about 0.17%, about 0.18%, about 0.19%, about 0.20%, about 0.21%, about 0.22%, about 0.23%, about 0.24%, about 0.25%, about 0.3%, about 0.4%, about 0.5%, about 0.6%, about 0.7%, about 0.8%, about 0.9%, about 1%, about 1.1%, about 1.15%, about 1.2%, about 1.25%, about 1.3%, about 1.35%, about 1.4%, about 1.45%, about 1.5%, about 1.55%, about 1.6%, about 1.65%, about 1.7%, about 1.75%, about 1.8%, about 1.85%, about 1.9%, about 1.95%, or about 2% polysorbate 20, polysorbate 80 or poloxamer 188.

In some embodiments, a pharmaceutical formulation or ophthalmic formulation disclosed herein can comprise a tonicity agent. In some embodiments, the tonicity agent is sodium chloride or potassium chloride. In some embodiments, the tonicity agent is sodium chloride. In some embodiments, the sodium chloride is present at a concentration of about 5 mM to about 100 mM, about 10 mM to about 50 mM, or about 40 mM.

In some embodiments, a pharmaceutical formulation or ophthalmic formulation disclosed herein can comprise a stabilizer. In some embodiments, the stabilizer is a thermal stabilizer that can stabilize an antibody or compound disclosed herein under conditions of thermal stress. In some embodiments, the stabilizer maintains greater than about 93% of the compound or antibody in a native conformation when the solution containing the compound or antibody and the thermal stabilizer is kept at about 45° C. for up to about 28 days. In some embodiments, the stabilizer prevents aggregation of the compound or antibody and less than 4% of the compound or antibody is aggregated when the solution containing the compound or antibody and the thermal stabilizer is kept at about 45° C. for up to about 28 days. In some embodiments, the stabilizer maintains greater than about 96% of the compound or antibody in a native conformation when the solution containing the compound or antibody and the thermal stabilizer is kept at about 37° C. for up to about 28 days. In some embodiments, the stabilizer prevents aggregation of the compound or antibody and less than about 2% of the compound or antibody is aggregated when the solution containing the compound or antibody and the thermal stabilizer is kept at about 37° C. for up to about 28 days.

In some embodiments, the thermal stabilizer is a sugar or sugar alcohol, for example, sucrose, sorbitol, glycerol, trehalose, or mannitol, or any combination thereof. In some embodiments, the stabilizer is a sugar. In some embodiments, the sugar is sucrose, mannitol or trehalose. In some embodiments, the stabilizer is sucrose. In some embodiments, a pharmaceutical formulation or ophthalmic formulation disclosed herein can comprise about 1% to about 20% sugar or sugar alcohol, about 2% to about 18% sugar or sugar alcohol, about 3% to about 15% sugar or sugar alcohol, about 4% to about 10% sugar or sugar alcohol, or about 5% sugar or sugar alcohol. For example, a pharmaceutical formulation or ophthalmic formulation of the present disclosure can comprise about 4%, about 5%, about 6%, about 7%, about 8%, about 9%, about 10%, about 11%, about 12%, about 13%, or about 14% sugar or sugar alcohol (e.g., sucrose, trehalose or mannitol). In some embodiments, the stabilizer is at a concentration of from about 1% w/v to about 20% w/v. In some embodiments, the stabilizer is sucrose at a concentration of from about 1% w/v to about 15% w/v, or from about 1% w/v to about 10% w/v. In some embodiments, the stabilizer is sucrose at a concentration of 5% w/v or about 5% w/v. In some embodiments, the stabilizer is sucrose at a concentration of 7.5% w/v or about 7.5% w/v. In some embodiments, the stabilizer is sucrose at a concentration of 10% w/v or about 10% w/v. In some embodiments, the stabilizer is sucrose at a concentration of 12.5% w/v or about 12.5% w/v. In some embodiments, the stabilizer is sucrose at a concentration of 15% w/v or about 15% w/v. In some embodiments, the stabilizer is sucrose at a concentration of 20% w/v or about 20% w/v.

Administration of Pharmaceutical Compositions

A pharmaceutical composition disclosed herein can be administered in a therapeutically-effective amount by various forms and routes including, for example, oral, topical, parenteral, intravenous injection, intravenous infusion, subcutaneous injection, subcutaneous infusion, intramuscular injection, intramuscular infusion, intradermal injection, intradermal infusion, intraperitoneal injection, intraperitoneal infusion, intracerebral injection, intracerebral infusion, subarachnoid injection, subarachnoid infusion, intraocular injection, intraspinal injection, intrasternal injection, ophthalmic administration, endothelial administration, local administration, intranasal administration, intrapulmonary administration, rectal administration, intraarterial administration, intrathecal administration, inhalation, intralesional administration, intradermal administration, epidural administration, absorption through epithelial or mucocutaneous linings (e.g., oral mucosa, rectal and intestinal mucosa), intracapsular administration, subcapsular administration, intracardiac administration, transtracheal administration, subcuticular administration, subarachnoid administration, subcapsular administration, intraspinal administration, or intrasternal administration.

A pharmaceutical composition can be administered in a local manner, for example, via injection of the compound directly into an organ, optionally in a depot or sustained release formulation or implant. A pharmaceutical composition can be provided in the form of a rapid release formulation, in the form of an extended release formulation, or in the form of an intermediate release formulation. A rapid release form can provide an immediate release. An extended release formulation can provide a controlled release or a sustained delayed release.

In some embodiments, a pump can be used for delivery of the pharmaceutical composition. In some embodiments, a pen delivery device can be used, for example, for subcutaneous delivery of a composition of the disclosure. Such a pen delivery device can be reusable or disposable. A reusable pen delivery device can use a replaceable cartridge that contains a pharmaceutical composition disclosed herein. Once all of the pharmaceutical composition within the cartridge has been administered and the cartridge is empty, the empty cartridge can readily be discarded and replaced with a new cartridge that contains the pharmaceutical composition. The pen delivery device can then be reused. A disposable pen has no replaceable cartridge. Rather, the disposable pen delivery device comes prefilled with the pharmaceutical composition held in a reservoir within the device. Once the reservoir is emptied of the pharmaceutical composition, the entire device is discarded.

A pharmaceutical composition disclosed herein can be administered, for example, to the eye via any suitable form or route including, for example, topical, oral, systemic, intravitreal, intracameral, intracanieral, subconjunctival, subtenon, retrobulbar, intraocular, intrastromal, intracorneal, posterior juxtascleral, periocular, subretinal, or suprachoroidal administration. The delivery method can include an invasive method for direct delivery of the composition to ocular cells. In some embodiments, a liquid pharmaceutical composition comprising an antibody or compound can be delivered via a subretinal injection, intravitreal injection (e.g., front, mid or back vitreal injection), intravitreal implant, intraorbital injection, intraorbital administration, subcutaneous injection, intracameral injection, intracanieral injection, subconjunctival injection, subconjunctival implant, injection into the anterior chamber via the temporal limbus, intrastromal injection, intracorneal injection, aqueous humor injection, subtenon injection, or subtenon implant. The compositions can be administered by injecting the formulation in any part of the eye including anterior chamber, posterior chamber, vitreous chamber (intravitreal), retina proper, and/or subretinal space.

A pharmaceutical composition disclosed herein can be delivered via a non-invasive method. Examples of non-invasive modes of administering the formulation can include using a needleless injection device, and topical administration, for example, eye drops to the cornea. Multiple administration routes can be employed for efficient delivery of the pharmaceutical composition. In some embodiments, the composition is delivered via multiple administration routes, for example, subretinal and intravitreous, to increase the efficiency of antibody delivery. In some embodiments, the subretinal and/or intravitreal injection is preceded by a vitrectomy.

In some embodiments, a liquid formulation comprising from 10 mg/mL to 120 mg/mL of antibody or compound is in a prefilled syringe and is administered intravitreally in a volume of up to about 500 μL. In some embodiments, a liquid formulation comprising from 10 mg/mL to 120 mg/mL of antibody or compound is in a prefilled syringe and is administered intravitreally in a volume of up to about 100 μL. In some embodiments, a liquid formulation comprising from 10 mg/mL to 120 mg/mL of antibody or compound is in a prefilled syringe and is administered intravitreally in a volume of about 50 μL.

A pharmaceutical composition disclosed herein can be targeted to any suitable ocular cell including, for example, endothelial cells such as vascular endothelial cells, cells of the retina such as retinal pigment epilthelium (RPE), corneal cells, fibroblasts, astrocytes, glial cells, pericytes, iris epithelial cells, cells of neural origin, ciliary epithelial cells, Müller cells, muscle cells surrounding and attached to the eye such as cells of the lateral rectus muscle, orbital fat cells, cells of the sclera and episclera, cells of the trabecular meshwork, or connective tissue cells.

Dosing

A compound, antibody, or therapeutic agent described herein can be administered before, during, or after the occurrence of a disease or condition, and the timing of administering a composition containing the compound, antibody, or therapeutic agent can vary. For example, the composition can be used as a prophylactic and can be administered continuously to subjects with a propensity to conditions or diseases in order to lessen a likelihood of the occurrence of the disease or condition. The composition can be administered to a subject already suffering from a disease or condition, in an amount sufficient to cure or at least partially arrest the symptoms of the disease or condition, or to cure, heal, improve, or ameliorate the condition. The composition can be administered to a subject during or as soon as possible after the onset of the symptoms. The administration of the compound, antibody, or therapeutic agent can be initiated within the first 48 hours of the onset of the symptoms, within the first 24 hours of the onset of the symptoms, within the first 6 hours of the onset of the symptoms, or within 3 hours of the onset of the symptoms. The initial administration can be via any practical route, such as by any route described herein using any formulation described herein. The compound, antibody, or therapeutic agent can be administered as soon as is practicable after the onset of a disease or condition is detected or suspected, and for a length of time necessary for the treatment of the disease, such as, for example, from about 1 month to about 3 months. The length of treatment can vary for each subject. Amounts effective for this use can vary based on the severity and course of the disease or condition, previous therapy, the subject's health status, weight, and response to the drugs, and the judgment of the treating physician. Improvement of clinical symptoms can be monitored, for example, by indirect ophthalmoscopy, fundus photography, fluorescein angiography, electroretinography, external eye examination, slit lamp biomicroscopy, applanation tonometry, pachymetry, optical coherence tomography, or autorefraction.

A pharmaceutical composition described herein can be in a unit dosage form suitable for a single administration of a precise dosage. In unit dosage form, the formulation can be divided into unit doses containing appropriate quantities of one or more compounds, antibodies or therapeutic agents. The unit dosage can be in the form of a package containing discrete quantities of the formulation. Non-limiting examples are packaged injectables, vials, and ampoules. An aqueous suspension composition disclosed herein can be packaged in a single-dose non-reclosable container. Multiple-dose reclosable containers can be used, for example, in combination with or without a preservative. A formulation for injection disclosed herein can be present in a unit dosage form, for example, in ampoules, or in multi-dose containers with a preservative.

Multiple compounds, antibodies or therapeutic agents disclosed herein can be administered in any order or simultaneously. If simultaneously, the multiple compounds, antibodies or therapeutic agents can be provided in a single, unified form, or in multiple forms, for example, as multiple separate injections or infusions. The compounds, antibodies or therapeutic agents can be packed together or separately, in a single package or in a plurality of packages. One or all of the compounds, antibodies or therapeutic agents can be given in multiple doses. If not simultaneous, the timing between the multiple doses can vary to as much as about a month.

An intraocular injection can be performed between any interval of time to improve efficiency of delivery and/or to minimize or avoid damage to surrounding tissue. The interval of time between two or more intraocular injections can be from, for example, about 1 minute to about 60 minutes, about 1 minute to about 5 minutes, about 5 minutes to about 10 minutes, about 10 minutes to about 15 minutes, about 15 minutes to about 20 minutes, about 20 minutes to about 25 minutes, about 25 minutes to about 30 minutes, about 30 minutes to about 35 minutes, about 35 minutes to about 40 minutes, about 40 minutes to about 45 minutes, about 45 minutes to about 50 minutes, about 50 minutes to about 55 minutes, or about 55 minutes to about 60 minutes.

An intraocular injection can be performed at any rate. The rate of intraocular injection can be from, for example, about 1 μL/sec to about 500 μL/sec, about 1 μL/sec to about 10 μL/sec, about 10 μL/sec to about 20 μL/sec, about 20 μL/sec to about 30 μL/sec, about 30 μL/sec to about 40 μL/sec, about 40 μL/sec to about 50 μL/sec, about 50 μL/sec to about 60 μL/sec, about 60 μL/sec to about 70 μL/sec, about 70 μL/sec to about 80 μL/sec, about 80 μL/sec to about 90 μL/sec, about 90 μL/sec to about 100 μL/sec, about 100 μL/sec to about 110 μL/sec, about 110 μL/sec to about 120 μL/sec, about 120 μL/sec to about 130 μL/sec, about 130 μL/sec to about 140 μL/sec, about 140 μL/sec to about 150 μL/sec, about 150 μL/sec to about 160 μL/sec, about 160 μL/sec to about 170 μL/sec, about 170 μL/sec to about 180 μL/sec, about 180 μL/sec to about 190 μL/sec, about 190

μL/sec to about 200 μL/sec, about 200 μL/sec to about 300 μL/sec, about 300 μL/sec to about 400 μL/sec, or about 400 μL/sec to about 500 μL/sec.

A compound, antibody, or therapeutic agent disclosed herein can be administered at a dosage of about 0.0001 mg/kg to about 1000 mg/kg, about 0.001 mg/kg to about 100 mg/kg, about 0.01 mg/kg to about 100 mg/kg, about 0.01 mg/kg to about 20 mg/kg, about 0.02 mg/kg to about 7 mg/kg, about 0.03 mg/kg to about 5 mg/kg, about 0.05 mg/kg to about 3 mg/kg, about 0.1 mg/kg to about 50 mg/kg, about 0.1 mg/kg to about 0.5 mg/kg, about 0.2 mg/kg to about 0.6 mg/kg, about 0.3 mg/kg to about 0.7 mg/kg, about 0.4 mg/kg to about 0.8 mg/kg, about 0.1 mg/kg to about 0.9 mg/kg, about 0.01 mg/kg to about 50 mg/kg, about 0.1 mg/kg to about 10 mg/kg, about 1 mg/kg to about 10 mg/kg, about 5 mg/kg to about 10 mg/kg, about 1 mg/kg to about 5 mg/kg, or about 3 mg/kg to about 7 mg/kg by mass of the subject.

A compound, antibody, or therapeutic agent described herein can be administered at any interval desired. The administration of the compound, antibody, or therapeutic agent can have regular or irregular dosing schedules to accommodate either the person administering the compound, antibody, or therapeutic agent or the subject receiving the compound, antibody, or therapeutic agent. For example, the compound, antibody, or therapeutic agent can be administered twice a day, once a day, five times a week, four times a week, three times a week, two times a week, once a week, once every two weeks, once every three weeks, once every four weeks, once a month, once every five weeks, once every six weeks, once every eight weeks, once every two months, once every twelve weeks, once every three months, once every four months, once every six months, once a year, or less frequently. In some embodiments, administration is every other week.

The amount administered can be of the same amount in each dose or the dosage can vary between doses. For example, a first amount can be administered in the morning and a second amount can be administered in the evening.

A compound, antibody, or therapeutic agent described herein can be administered in any amount necessary or convenient. For example, a compound described herein can be administered in an amount from about 0.05 mg to about 300 mg, about 0.1 mg to about 300 mg, about 0.1 mg to about 200 mg, about 0.1 mg to about 100 mg, about 0.05 mg to about 1.5 mg, about 0.1 mg to about 1.5 mg, about 0.05 mg to about 1 mg, about 1 mg to about 1.5 mg, about 0.5 mg to about 6 mg, about 1 mg to about 4 mg, about 2 mg to about 10 mg, about 10 mg to about 30 mg, about 30 mg to about 50 mg, about 50 mg to about 70 mg, about 70 mg to about 100 mg, or about 0.1 mg to about 1 mg, about 0.05 mg, about 0.06 mg, about 0.07 mg, about 0.08 mg, about 0.09 mg, about 0.1 mg, about 0.11 mg, about 0.12 mg, about 0.13 mg, about 0.14 mg, about 0.15 mg, about 0.16 mg, about 0.17, mg, about 0.18 mg, about 0.19 mg, about 0.2 mg, about 0.21 mg, about 0.22 mg, about 0.23 mg, about 0.24 mg, about 0.25 mg, about 0.26 mg, about 0.27, mg, about 0.28 mg, about 0.29 mg, about 0.3 mg, about 0.31 mg, about 0.32 mg, about 0.33 mg, about 0.34 mg, about 0.35 mg, about 0.36 mg, about 0.37, mg, about 0.38 mg, about 0.39 mg, about 0.4 mg, about 0.41 mg, about 0.42 mg, about 0.43 mg, about 0.44 mg, about 0.45 mg, about 0.46 mg, about 0.47, mg, about 0.48 mg, about 0.49 mg, about 0.5 mg, about 0.51 mg, about 0.52 mg, about 0.53 mg, about 0.54 mg, about 0.55 mg, about 0.56 mg, about 0.57, mg, about 0.58 mg, about 0.59 mg, about 0.6 mg, about 0.61 mg, about 0.62 mg, about 0.63 mg, about 0.64 mg, about 0.65 mg, about 0.66 mg, about 0.67, mg, about 0.68 mg, about 0.69 mg, about 0.7 mg, about 0.71 mg, about 0.72 mg, about 0.73 mg, about 0.74 mg, about 0.75 mg, about 0.76 mg, about 0.77, mg, about 0.78 mg, about 0.79 mg, about 0.8 mg, about 0.81 mg, about 0.82 mg, about 0.83 mg, about 0.84 mg, about 0.85 mg, about 0.86 mg, about 0.87, mg, about 0.88 mg, about 0.89 mg, about 0.9 mg, about 0.91 mg, about 0.92 mg, about 0.93 mg, about 0.94 mg, about 0.95 mg, about 0.96 mg, about 0.97, mg, about 0.98 mg, about 0.99 mg, about 1 mg, about 1.5 mg, about 2 mg, about 2.5 mg, about 3 mg, about 3.5 mg, about 4 mg, about 4.5 mg, about 5 mg, about 5.5 mg, about 6 mg, about 6.5 mg, about 7 mg, about 7.5 mg, about 8 mg, about 8.5 mg, about 9 mg, about 9.5 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 110 mg, about 120 mg, about 130 mg, about 140 mg, about 150 mg, about 160 mg, about 170 mg, about 180 mg, about 190 mg about 200 mg, about 210 mg, about 220 mg, about 230 mg, about 240 mg, about 250 mg, about 260 mg, about 270 mg, about 280 mg, about 290 mg, or about 300 mg per dose for a subject by any route of administration.

Combination Therapies

A pharmaceutical composition provided herein can be administered in conjunction with other therapies, for example, chemotherapy, radiation, surgery, anti-inflammatory agents, or vitamins. The other agents can be administered prior to, after, or concomitantly with the pharmaceutical composition.

In some embodiments, a compound or antibody described herein can be used singly or in combination with one or more therapeutic agents as a component of mixtures.

In some embodiments, the disclosure provides co-administration of a multispecific compound or antibody targeting, for example, HPTP-β (VE-PTP) and VEGF, with one or more additional anti-VEGF agents, which can stabilize the vasculature against neovascularization. In some embodiments, co-administration of the multispecific compound or antibody with one or more additional anti-VEGF agents can stabilize the vasculature against leakage. An anti-VEGF agent can be a compound, a recombinant protein, an antibody, an antigen-binding fragment, variant, or derivative thereof (e.g., a scFv), a protein comprising one or more designed ankyrin repeats, a designed ankyrin repeat protein (DARPin), an ankyrin protein, an ankyrin repeat protein, an affibody, an avimer, an adnectin, an anticalin, a Fynomer, a Kunitz domain, a knottin, a β-hairpin mimetic, or a peptide derived from one or more receptors, e.g. VEGF receptors, or the VEGF-binding portions of human VEGF receptors 1 and 2.

Non-limiting examples of anti-VEGF agents include bevacizumab (Avastin®), ranibizumab (Lucentis®), aflibercept (Eylea®), conbercept, brolucizumab, RTH258, VEGF receptor tyrosine kinase inhibitors such as sorafenib, sunitinib, axitinib, pazopanib, vandetinib, cabozantinib, regorafenib, and 4-(4-bromo-2-fluoroanilino)-6-methoxy-7-(1-methylpiperidin-4-ylmethoxy)quinazoline (ZD6474), VEGF variants, soluble VEGF receptor fragments or traps, aptamers capable of blocking VEGF or VEGFR (e.g. Pegaptanib), neutralizing anti-VEGFR antibodies or fragments thereof (e.g., ramucirumab, p1C11, 1121, 1121B), anti-KDR antibodies, anti-flt1 antibodies, low molecular weight inhibitors of VEGFR tyrosine kinases, DARPins that bind VEGF (e.g., abicipar, MP0112, MP0250), proteins comprising one or more designed ankyrin repeats that bind VEGF, adnectins (e.g., CT-322), anticalins (e.g., PRS-050), collagen IV-derived biomimetic peptides (e.g., AXT-107)

Further non-limiting examples of VEGF-modulating agents include anti-inflammatory agents, for example, dexamethasone, fluocinolone, and triamcinolone. The multispecific compound or antibody targeting, for example, HPTP-β (VE-PTP) and VEGF, can be administered in combination with any additional anti-VEGF agent in any combination, for example, at the beginning of treatment, at any time during treatment, or at any time after treatment with the additional anti-VEGF agent has concluded. In addition, the dosage of the multispecific compound or antibody can be adjusted during treatment. Also, the dosage of the additional anti-VEGF agent can be adjusted during treatment. The multispecific compound or antibody can be administered, for example, monthly, once every 3 months, once every 6 months, or yearly, wherein the additional anti-VEGF agent is administered at any frequency between treatments. Also disclosed herein are methods for treating a disease or condition as disclosed herein. The method comprises administering to a subject:

a) a therapeutically-effective amount of a multispecific compound or antibody targeting, for example, HPTP-β (VE-PTP) and VEGF; and b) a therapeutically-effective amount of an additional anti-VEGF agent;

wherein the administration of the multispecific compound or antibody and the additional anti-VEGF agent can be conducted as described herein.

In some embodiments, the disclosure provides co-administration of a multispecific compound or antibody targeting, for example, HPTP-β (VE-PTP) and VEGF, with one or more additional anti-HPTP-β (VE-PTP) agents, which can stabilize the vasculature against neovascularization. In some embodiments, co-administration of the multispecific compound or antibody with one or more additional anti-HPTP-β (VE-PTP) agents can stabilize the vasculature against leakage. An anti-HPTP-β (VE-PTP) agent can be a compound, a recombinant protein, an antibody, an antigen-binding fragment, variant, or derivative thereof (e.g., a scFv), a protein comprising one or more designed ankyrin repeats, a designed ankyrin repeat protein (DARPin), an ankyrin protein, an ankyrin repeat protein, an affibody, an avimer, an adnectin, an anticalin, a Fynomer, a Kunitz domain, a knottin, a β-hairpin mimetic, or a peptide derived from one or more receptors. In some embodiments, the additional anti-HPTP-β (VE-PTP) agent(s) can activate Tie2 signaling by promoting protein phosphorylation, such as phosphorylation of the Tie2 protein. In some embodiments, the additional anti-HPTP-β (VE-PTP) agent(s) can bind to HPTP-β (VE-PTP).

The multispecific compound or antibody targeting, for example, HPTP-β (VE-PTP) and VEGF, can be administered in combination with any additional anti-HPTP-β (VE-PTP) agent in any combination, for example, at the beginning of treatment, at any time during treatment, or at any time after treatment with the additional anti-HPTP-β (VE-PTP) agent has concluded. The dosage of the multispecific compound or antibody can be adjusted during treatment. The dosage of the additional anti-HPTP-β (VE-PTP) agent can be adjusted during treatment. The multispecific compound or antibody can be administered, for example, monthly, once every 3 months, once every 6 months, or yearly, wherein the additional anti-HPTP-β (VE-PTP) agent is administered at any frequency between treatments. Also disclosed herein are methods for treating a disease or condition as disclosed herein. The method comprises administering to a subject:

a) a therapeutically-effective amount of a multispecific compound or antibody targeting, for example, HPTP-β (VE-PTP) and VEGF; and b) a therapeutically-effective amount of an additional anti-HPTP-β (VE-PTP) agent;

wherein the administration of the multispecific compound or antibody and the additional anti-HPTP-β (VE-PTP) agent can be conducted as described herein.

In some embodiments, the disclosure provides co-administration of a multispecific compound or antibody targeting, for example, HPTP-β (VE-PTP) and VEGF, with one or more additional Tie2 receptor activating compounds. An additional Tie2 receptor activating compound can be, for example, an angiopoietin 1 recombinant protein, an Ang1 mimetic, a Tie2 agonist, a peptide, a HPTP-β (VE-PTP) phosphatase inhibitor, a Tie2-peptomimetic, a tetrameric polyethylene oxide clustered peptide, a collagen IV-biomimetic peptide, a compound, a recombinant protein, an antibody, an antigen-binding fragment, variant, or derivative thereof (e.g., an scFv), an affinibody, an avimer, an adnectin, a protein comprising one or more designed ankyrin repeats, a designed ankyrin repeat protein (DARPin), an ankyrin protein, an ankyrin repeat protein, an affibody, an avimer, an adnectin, an anticalin, a Fynomer, a Kunitz domain, a knottin, a β-hairpin mimetic, or a peptide derived from one or more receptors. In some embodiments, the one or more additional Tie2 receptor activating compounds are small molecules. In some embodiments, the one or more additional Tie2 receptor activating compounds improve drainage through ocular lymphatics, Schlemm's canal, or corneal limbal lymphatics. In some embodiments, the one or more additional Tie2 receptor activating compounds are administered as eye drops. In some embodiments, the one or more additional Tie2 receptor activating compounds are administered to treat primary open angle glaucoma, age-related macular degeneration, cardiovascular disease, or cystic kidney disease. In some embodiments, the one or more additional Tie2 receptor activating compounds can be, for example, MAN-01, AXT-107, or vasculotide. In some embodiments, a compound disclosed herein can be co-administered with, for example, MAN-01, AXT-107, or vasculotide.

The multispecific compound or antibody targeting, for example, HPTP-β (VE-PTP) and VEGF, can be administered in combination with any additional Tie2 receptor activating compound in any combination, for example, at the beginning of treatment, at any time during treatment, or at any time after treatment with the additional Tie2 receptor activating compound has concluded. The dosage of the multispecific compound or antibody can be adjusted during treatment. The dosage of the additional Tie2 receptor activating compound can be adjusted during treatment. The multispecific compound or antibody can be administered, for example, monthly, once every 3 months, once every 6 months, or yearly, wherein the additional Tie2 receptor activating compound is administered at any frequency between treatments with the multispecific compound or antibody. Also disclosed herein are methods for treating a disease or condition as disclosed herein. The method comprises administering to a subject:

a) a therapeutically-effective amount of a multispecific compound or antibody targeting, for example, HPTP-β (VE-PTP) and VEGF; and b) a therapeutically-effective amount of a Tie2 activator;

wherein the administration of the multispecific compound or antibody and the additional Tie2 receptor activating compound can be conducted as described herein.

Mouse Models

Oxygen-Induced Ischemic Retinopathy Model

The oxygen-induced ischemic retinopathy model can be considered to mimic aspects of proliferative retinal neovascularization and proliferative diabetic retinopathy. One week old mice can be placed in an airtight chamber and exposed to hyperoxia (75±3% oxygen) for five days, resulting in hyperoxia-induced neovascularization, for example, at the junction between the vascularized and avascular retina between postnatal day 17 and 21. Mice can be dosed with a compound of interest, for example, an antibody or compound of the disclosure, to determine the effect on neovascularization and/or vascular leakage. Neovascularization and/or vascular leakage can be assessed as described below.

Rho/VEGF Mouse Model

The Rho/VEGF mouse model can mimic aspects of neovascular age-related macular degeneration. Transgenic mice with vascular endothelial growth factor (VEGF) expression driven by the rhodopsin promoter (rho/VEGF mice) can develop retinal neovascularization, retinal angiomatous proliferation, and retinal vascular leakage. In rho/VEGF mice, VEGF expression in photoreceptors can begin between postnatal days 5 and 10, the period when the deep capillary bed is developing. Neovascularization can originate from the deep capillary bed of the retina and grow into the subretinal space. Mice can be dosed with a compound of interest, for example, an antibody or compound of the disclosure, to determine the effect on neovascularization and/or vascular leakage. Neovascularization and/or vascular leakage can be assessed as described below.

Tet/Opsin/VEGF Mouse Model

Mice with a VEGF under the control of a reverse tetracycline transactivator (rtTA) inducible promoter coupled to the rhodopsin promoter (Tet/opsin/VEGF mice) can be used as an inducible model of neovascularization, retinal vascular leakage, and retinal detachment. In these mice, VEGF transgene expression in the retina can be induced by administering doxycycline. Neovascularization can be evident by three to four days after VEGF induction. Neovascularization can be more extensive, and can cause outer retinal folds followed by total retinal detachment within about five days. Mice can be dosed with a compound of interest, for example, an antibody or compound of the disclosure, to determine the effect on neovascularization, vascular leakage, and/or retinal detachment. Neovascularization and/or vascular leakage can be assessed as described below. To assess retinal detachment, eyes can be frozen in cutting temperature embedding solution, ten micron sections cut through the entire eye, and sections stained with Hoechst. Sections can be examined by light microscopy, the mean length of the retinal detachment per section measured by image analysis, and the detached percentage of the retina calculated.

Tet/Opsin/Ang2 Mouse Model

Tet/opsin/Ang2 mice have inducible expression of Ang2 in the retina. These mice can be used to study the impact of Ang2 expression in various experimental conditions. For example, Tet/opsin/Ang2 mice can be used to determine the effect of Ang2 expression on neovascularization when VEGF levels are high versus low, or the effect of Ang2 expression in the oxygen induced ischemic retinopathy model. Mice can be dosed with a compound of interest, for example, an antibody or compound of the disclosure, to determine the impact of Ang2 expression on therapeutic efficacy.

Laser-Induced Choroidal Neovascularization Model

The laser-induced choroidal neovascularization model can be considered to mimic aspects of neovascular age-related macular degeneration. Anesthetized mice can have their pupils dilated, and burns can be delivered, for example, to the retina by a krypton laser using a slit lamp system and a cover glass as a contact lens. Multiple burns can be produced in a single eye, for example, burns in three locations per eye. Burns can cause rupture of Bruch's membrane. Choroidal neovascularization can be assessed at various time points after laser treatment, for example, one week, two weeks, or four weeks after laser treatment. Mice can be dosed with a compound of interest, for example, an antibody or compound of the disclosure, to determine the effect on neovascularization. Eyecups can be stained with FITC-labeled GSA, choroids flat mounted, and the area of choroidal neovascularization at each Bruch's membrane rupture site measured with fluorescence microscopy and image analysis. Neovascularization and/or vascular leakage can also be assessed as described below.

Assessment of Neovascularization

Neovascularization can be assessed using a range of techniques.

Fluorescein angiograms can be done by taking serial fundus photographs after injection of a dye to reveal blood vessels, allowing identification of the presence, location, and size of a neovascular complex. For example, an intraperitoneal injection of 0.3 mL of 1% fluorescein sodium can be given, serial fundus photographs taken, and the choroidal neovascularization area, total lesion area, and leakage area can be measured.

Eyes can be processed for evaluation by fluorescent, light, or electron microscopy. For example, mice can be perfused with fluorescently labelled dextran, or eyes can be injected with GSA or antibodies targeting PECAM. Eyes can be processed for observation under a fluorescent microscope, and the extent of neovascularization can be quantified, for example, by quantifying the area of neovascularization per retina, by quantifying the area of neovascularization at each Bruch's membrane rupture site, or by quantifying the number of nuclei of new vessels extending from the retina into the vitreous.

The area of retinal neovascularization can be determined, for example, using FITC-labeled GSA lectin and fluorescence microscopy. Eyes can be fixed in 10% formalin, dissected intact, washed with PBS, blocked in 8% swine serum, and stained with FITC-labeled GSA lectin for a time appropriate to stain retinal neovascularization and hyaloid vessels, but not normal retinal vessels (e.g., 40-50 minutes). Retinas can be flat mounted, digital images can be obtained with a fluorescent microscope and merged into a single image of the entire retina. Software can be used to measure the area of neovascularization per retina.

The area of subretinal neovascularization can be determined, for example, using FITC-labeled GSA lectin and fluorescence microscopy. Eyes can be fixed in 10% formalin, and retinas can be dissected, blocked with 5% swine serum, stained with FITC-conjugated GSA for two hours to stain vascular cells, and flat mounted with the photoreceptor side up. The area of subretinal neovascularization can be measured with fluorescence microscopy and image analysis.

Assessment of Retinal Vascular Leakage

Retinal vascular leakage can be assessed by measuring extravasated serum albumin using an immunofluorescent technique. For example, eyes can be fixed in 10% formalin, retinas can be dissected, washed, blocked, and stained using an anti-albumin antibody and a fluorescently-conjugated secondary antibody. The vessels can be labeled by counterstaining with GSA lectin, and retinas flat mounted. Retinas can be examined by fluorescence microscopy, and the area of albumin staining determined by image analysis. Retinal vascular leakage is relevant to, for example, diabetic macular edema and macular edema due to retinal vein occlusion.

Miles Assay for Vascular Leakage

The Miles assay can be used to assess vascular leakage in dermal subcutaneous blood vessels. Evans blue is a dye that binds albumin. Under physiologic conditions the endothelium is impermeable to albumin, so Evans blue bound albumin remains restricted within blood vessels. In pathologic conditions that promote increased vascular permeability, endothelial cells partially lose close contacts. The endothelium becomes permeable to small proteins such as albumin. Mice can be injected intravenously with 1% Evans blue dye in PBS, and injected intradermally with VEGF. Thirty minutes after intradermal injections, tissue at the intradermal injection sites can be excised and extracted in formamide to assess Evans blue dye extravasation. Vascular leakage can be quantified by measurement of the dye incorporated per milligram of tissue, for example, using optical density measurements and a standard curve. Mice can be dosed with a compound of interest, for example, an antibody or compound of the disclosure, to determine the effect on vascular leakage.

Cancer Models

The efficacy of a compound or antibody of the disclosure as a treatment for cancer can be tested in a range of cancer models. In some cancer models, cancer cells from a cell line can be implanted in a recipient animal, for example, a mouse. Non-limiting examples of suitable mouse strains include C57BL6, BALB/C, C3H, FVB/N, and FVB/N-Tg (MMTV-PyVT)634Mul. Non-limiting examples of suitable cancer cell lines include 4T1, E0771, and P0008. Cells of the 4T1 or E0771 cell lines can, for example, be implanted into a mammary pad as a model of breast cancer. 4T1 or E0771 cells can be implanted, for example, into the third mammary fat pad of female nude mice.

The size of solid tumors can be measured with calipers and tumor volume calculated. Tumors can be processed for histopathological evaluation or fluorescence microscopy, to assess, for example, tumor area, tumor grade, metastases count, metastases area, the number of cell nuclei per tumor focus, intratumoral vessel diameter, intratumoral vessel density, tumor vascular maturity, perivascular cell coverage, proximity between perivascular cells and endothelial cells, or to grade tumors foci as intravascular or extravascular.

Spontaneous metastasis models can be used to study the effects of a compound or antibody of the disclosure on metastasis. After tumor implant, a primary tumor can be resected (e.g., upon reaching 5 mm in size), and the animal later evaluated macroscopically or histopathologically for metastases, for example, to determine the number and size of metastases in the lungs, liver, lymph nodes, and bones.

To evaluate the impact of vessel stability on metastasis, a model can be used wherein tumor cells can be injected intravenously, and the animal subsequently evaluated for intravascular versus extravasated metastases. For example, 4T-1 cells can be injected intravenously, and the lungs processed for histopathologic evaluation to quantify intravascular versus extravascular metastases.

Metastases can be counted and measured macroscopically, for example, by immersing lungs in Bouin's solution, then examining them with a stereomicroscope.

To measure tumor vessel permeability in vivo, intravital multiphoton microscopy can be used. Animals can be injected with fluorescently labeled bovine serum albumin, for example, pre-treatment and post-treatment time points. At each time point, two distinct regions within the tumor can be selected and a 200 micron image stack recording BSA fluorescence taken through each region every ten minutes for an hour, using a multiphoton laser scanning microscope. The analysis approach can involve three-dimensional vessel tracing to create vessel metrics and a three-dimensional map of voxel intensity versus distance to the nearest vessel over time. Images can be corrected for sample movement over time with three-dimensional image registration. The normalized transvascular flux can be calculated.

Illustrative CDR Combinations

In some embodiments, an antibody or compound of this disclosure comprises a HCDR1. In some embodiments, an antibody or compound of this disclosure comprises a HCDR2. In some embodiments, an antibody or compound of this disclosure comprises a HCDR3. In some embodiments, an antibody or compound of this disclosure comprises a LCDR1. In some embodiments, an antibody or compound of this disclosure comprises a LCDR2. In some embodiments, an antibody or compound of this disclosure comprises a LCDR3.

In some embodiments, an antibody or compound of this disclosure comprises a HCDR1 and a HCDR2. In some embodiments, an antibody or compound of this disclosure comprises a HCDR1 and a HCDR3. In some embodiments, an antibody or compound of this disclosure comprises a HCDR1 and a LCDR1. In some embodiments, an antibody or compound of this disclosure comprises a HCDR1 and a LCDR2. In some embodiments, an antibody or compound of this disclosure comprises a HCDR1 and a LCDR3. In some embodiments, an antibody or compound of this disclosure comprises a HCDR2 and a HCDR3. In some embodiments, an antibody or compound of this disclosure comprises a HCDR2 and a LCDR1. In some embodiments, an antibody or compound of this disclosure comprises a HCDR2 and a LCDR2. In some embodiments, an antibody or compound of this disclosure comprises a HCDR2 and a LCDR3. In some embodiments, an antibody or compound of this disclosure comprises a HCDR3 and a LCDR1. In some embodiments, an antibody or compound of this disclosure comprises a HCDR3 and a LCDR2. In some embodiments, an antibody or compound of this disclosure comprises a HCDR3 and a LCDR3. In some embodiments, an antibody or compound of this disclosure comprises a LCDR1 and a LCDR2. In some embodiments, an antibody or compound of this disclosure comprises a LCDR1 and a LCDR3. In some embodiments, an antibody or compound of this disclosure comprises a LCDR2 and a LCDR3.

In some embodiments, an antibody or compound of this disclosure comprises a HCDR1, a HCDR2, and a HCDR3. In some embodiments, an antibody or compound of this disclosure comprises a HCDR1, a HCDR2, and a LCDR1. In some embodiments, an antibody or compound of this disclosure comprises a HCDR1, a HCDR2, and a LCDR2. In some embodiments, an antibody or compound of this disclosure comprises a HCDR1, a HCDR2, and a LCDR3. In some embodiments, an antibody or compound of this disclosure comprises a HCDR1, a HCDR3, and a LCDR1. In some embodiments, an antibody or compound of this disclosure comprises a HCDR1, a HCDR3, and a LCDR2. In some embodiments, an antibody or compound of this disclosure comprises a HCDR1, a HCDR3, and a LCDR3. In some embodiments, an antibody or compound of this disclosure comprises a HCDR1, a LCDR1, and a LCDR2. In some embodiments, an antibody or compound of this disclosure comprises a HCDR1, a LCDR1, and a LCDR3. In some embodiments, an antibody or compound of this disclosure comprises a HCDR1, a LCDR2, and a LCDR3. In some embodiments, an antibody or compound of this disclosure comprises a HCDR2, a HCDR3, and a LCDR1. In some embodiments, an antibody or compound of this disclosure comprises a HCDR2, a HCDR3, and a LCDR2. In some embodiments, an antibody or compound of this disclosure comprises a HCDR2, a HCDR3, and a LCDR3. In some embodiments, an antibody or compound of this disclosure comprises a HCDR2, a LCDR1, and a LCDR2. In some embodiments, an antibody or compound of this disclosure comprises a HCDR2, a LCDR1, and a LCDR3. In some embodiments, an antibody or compound of this disclosure comprises a HCDR2, a LCDR2, and a LCDR3. In some embodiments, an antibody or compound of this disclosure comprises a HCDR3, a LCDR1, and a LCDR2. In some embodiments, an antibody or compound of this disclosure comprises a HCDR3, a LCDR1, and a LCDR3. In some embodiments, an antibody or compound of this disclosure comprises a HCDR3, a LCDR2, and a LCDR3. In some embodiments, an antibody or compound of this disclosure comprises a LCDR1, a LCDR2, and a LCDR3.

In some embodiments, an antibody or compound of this disclosure comprises a HCDR1, a HCDR2, a HCDR3, and a LCDR1. In some embodiments, an antibody or compound of this disclosure comprises a HCDR1, a HCDR2, a HCDR3, and a LCDR2. In some embodiments, an antibody or compound of this disclosure comprises a HCDR1, a HCDR2, a HCDR3, and a LCDR3. In some embodiments, an antibody or compound of this disclosure comprises a HCDR1, a HCDR2, a LCDR1, and a LCDR2. In some embodiments, an antibody or compound of this disclosure comprises a HCDR1, a HCDR2, a LCDR1, and a LCDR3. In some embodiments, an antibody or compound of this disclosure comprises a HCDR1, a HCDR2, a LCDR2, and a LCDR3. In some embodiments, an antibody or compound of this disclosure comprises a HCDR1, a HCDR3, a LCDR1, and a LCDR2. In some embodiments, an antibody or compound of this disclosure comprises a HCDR1, a HCDR3, a LCDR1, and a LCDR3. In some embodiments, an antibody or compound of this disclosure comprises a HCDR1, a HCDR3, a LCDR2, and a LCDR3. In some embodiments, an antibody or compound of this disclosure comprises a HCDR1, a LCDR1, a LCDR2, and a LCDR3. In some embodiments, an antibody or compound of this disclosure comprises a HCDR2, a HCDR3, a LCDR1, and a LCDR2. In some embodiments, an antibody or compound of this disclosure comprises a HCDR2, a HCDR3, a LCDR1, and a LCDR3. In some embodiments, an antibody or compound of this disclosure comprises a HCDR2, a HCDR3, a LCDR2, and a LCDR3. In some embodiments, an antibody or compound of this disclosure comprises a HCDR2, a LCDR1, a LCDR2, and a LCDR3. In some embodiments, an antibody or compound of this disclosure comprises a HCDR3, a LCDR1, a LCDR2, and a LCDR3.

In some embodiments, an antibody or compound of this disclosure comprises a HCDR1, a HCDR2, a HCDR3, a LCDR1, and a LCDR2. In some embodiments, an antibody or compound of this disclosure comprises a HCDR1, a HCDR2, a HCDR3, a LCDR1, and a LCDR3. In some embodiments, an antibody or compound of this disclosure comprises a HCDR1, a HCDR2, a HCDR3, a LCDR2, and a LCDR3. In some embodiments, an antibody or compound of this disclosure comprises a HCDR1, a HCDR2, a LCDR1, a LCDR2, and a LCDR3. In some embodiments, an antibody or compound of this disclosure comprises a HCDR1, a HCDR3, a LCDR1, a LCDR2, and a LCDR3. In some embodiments, an antibody or compound of this disclosure comprises a HCDR2, a HCDR3, a LCDR1, a LCDR2, and a LCDR3.

In some embodiments, an antibody or compound of this disclosure comprises a HCDR1, a HCDR2, a HCDR3, a LCDR1, a LCDR2, and a LCDR3.

In some embodiments, an antibody or compound of this disclosure comprises any one of SEQ ID NOS: 76-80. In some embodiments, an antibody or compound of this disclosure comprises any one of SEQ ID NOS: 81-87. In some embodiments, an antibody or compound of this disclosure comprises any one of SEQ ID NOS: 88-90. In some embodiments, an antibody or compound of this disclosure comprises any one of SEQ ID NOS: 91-93. In some embodiments, an antibody or compound of this disclosure comprises any one of SEQ ID NOS: 94-96. In some embodiments, an antibody or compound of this disclosure comprises any one of SEQ ID NOS: 97-98.

In some embodiments, an antibody or compound of this disclosure comprises any one of SEQ ID NOS: 76-80 and any one of SEQ ID NOS: 81-87. In some embodiments, an antibody or compound of this disclosure comprises any one of SEQ ID NOS: 76-80 and any one of SEQ ID NOS: 88-90. In some embodiments, an antibody or compound of this disclosure comprises any one of SEQ ID NOS: 76-80 and any one of SEQ ID NOS: 91-93. In some embodiments, an antibody or compound of this disclosure comprises any one of SEQ ID NOS: 76-80 and any one of SEQ ID NOS: 94-96. In some embodiments, an antibody or compound of this disclosure comprises any one of SEQ ID NOS: 76-80 and any one of SEQ ID NOS: 97-98. In some embodiments, an antibody or compound of this disclosure comprises any one of SEQ ID NOS: 81-87 and any one of SEQ ID NOS: 88-90. In some embodiments, an antibody or compound of this disclosure comprises any one of SEQ ID NOS: 81-87 and any one of SEQ ID NOS: 91-93. In some embodiments, an antibody or compound of this disclosure comprises any one of SEQ ID NOS: 81-87 and any one of SEQ ID NOS: 94-96. In some embodiments, an antibody or compound of this disclosure comprises any one of SEQ ID NOS: 81-87 and any one of SEQ ID NOS: 97-98. In some embodiments, an antibody or compound of this disclosure comprises any one of SEQ ID NOS: 88-90 and any one of SEQ ID NOS: 91-93. In some embodiments, an antibody or compound of this disclosure comprises any one of SEQ ID NOS: 88-90 and any one of SEQ ID NOS: 94-96. In some embodiments, an antibody or compound of this disclosure comprises any one of SEQ ID NOS: 88-90 and any one of SEQ ID NOS: 97-98. In some embodiments, an antibody or compound of this disclosure comprises any one of SEQ ID NOS: 91-93 and any one of SEQ ID NOS: 94-96. In some embodiments, an antibody or compound of this disclosure comprises any one of SEQ ID NOS: 91-93 and any one of SEQ ID NOS: 97-98. In some embodiments, an antibody or compound of this disclosure comprises any one of SEQ ID NOS: 94-96 and any one of SEQ ID NOS: 97-98.

In some embodiments, an antibody or compound of this disclosure comprises any one of SEQ ID NOS: 76-80, any one of SEQ ID NOS: 81-87, and any one of SEQ ID NOS: 88-90. In some embodiments, an antibody or compound of this disclosure comprises any one of SEQ ID NOS: 76-80, any one of SEQ ID NOS: 81-87, and any one of SEQ ID NOS: 91-93. In some embodiments, an antibody or compound of this disclosure comprises any one of SEQ ID NOS: 76-80, any one of SEQ ID NOS: 81-87, and any one of SEQ ID NOS: 94-96. In some embodiments, an antibody or compound of this disclosure comprises any one of SEQ ID NOS: 76-80, any one of SEQ ID NOS: 81-87, and any one of SEQ ID NOS: 97-98. In some embodiments, an antibody or compound of this disclosure comprises any one of SEQ ID NOS: 76-80, any one of SEQ ID NOS: 88-90, and any one of SEQ ID NOS: 91-93. In some embodiments, an antibody or compound of this disclosure comprises any one of SEQ ID NOS: 76-80, any one of SEQ ID NOS: 88-90, and any one of SEQ ID NOS: 94-96. In some embodiments, an antibody or compound of this disclosure comprises any one of SEQ ID NOS: 76-80, any one of SEQ ID NOS: 88-90, and any one of SEQ ID NOS: 97-98. In some embodiments, an antibody or compound of this disclosure comprises any one of SEQ ID NOS: 76-80, any one of SEQ ID NOS: 91-93, and any one of SEQ ID NOS: 94-96. In some embodiments, an antibody or compound of this disclosure comprises any one of SEQ ID NOS: 76-80, any one of SEQ ID NOS: 91-93, and any one of SEQ ID NOS: 97-98. In some embodiments, an antibody or compound of this disclosure comprises any one of SEQ ID NOS: 76-80, any one of SEQ ID NOS: 94-96, and any one of SEQ ID NOS: 97-98. In some embodiments, an antibody or compound of this disclosure comprises any one of SEQ ID NOS: 81-87, any one of SEQ ID NOS: 88-90, and any one of SEQ ID NOS: 91-93. In some embodiments, an antibody or compound of this disclosure comprises any one of SEQ ID NOS: 81-87, any one of SEQ ID NOS: 88-90, and any one of SEQ ID NOS: 94-96. In some embodiments, an antibody or compound of this disclosure comprises any one of SEQ ID NOS: 81-87, any one of SEQ ID NOS: 88-90, and any one of SEQ ID NOS: 97-98. In some embodiments, an antibody or compound of this disclosure comprises any one of SEQ ID NOS: 81-87, any one of SEQ ID NOS: 91-93, and any one of SEQ ID NOS: 94-96. In some embodiments, an antibody or compound of this disclosure comprises any one of SEQ ID NOS: 81-87, any one of SEQ ID NOS: 91-93, and any one of SEQ ID NOS: 97-98. In some embodiments, an antibody or compound of this disclosure comprises any one of SEQ ID NOS: 81-87, any one of SEQ ID NOS: 94-96, and any one of SEQ ID NOS: 97-98. In some embodiments, an antibody or compound of this disclosure comprises any one of SEQ ID NOS: 88-90, any one of SEQ ID NOS: 91-93, and any one of SEQ ID NOS: 94-96. In some embodiments, an antibody or compound of this disclosure comprises any one of SEQ ID NOS: 88-90, any one of SEQ ID NOS: 91-93, and any one of SEQ ID NOS: 97-98. In some embodiments, an antibody or compound of this disclosure comprises any one of SEQ ID NOS: 88-90, any one of SEQ ID NOS: 94-96, and any one of SEQ ID NOS: 97-98. In some embodiments, an antibody or compound of this disclosure comprises any one of SEQ ID NOS: 91-93, any one of SEQ ID NOS: 94-96, and any one of SEQ ID NOS: 97-98.

In some embodiments, an antibody or compound of this disclosure comprises any one of SEQ ID NOS: 76-80, any one of SEQ ID NOS: 81-87, any one of SEQ ID NOS: 88-90, and any one of SEQ ID NOS: 91-93. In some embodiments, an antibody or compound of this disclosure comprises any one of SEQ ID NOS: 76-80, any one of SEQ ID NOS: 81-87, any one of SEQ ID NOS: 88-90, and any one of SEQ ID NOS: 94-96. In some embodiments, an antibody or compound of this disclosure comprises any one of SEQ ID NOS: 76-80, any one of SEQ ID NOS: 81-87, any one of SEQ ID NOS: 88-90, and any one of SEQ ID NOS: 97-98. In some embodiments, an antibody or compound of this disclosure comprises any one of SEQ ID NOS: 76-80, any one of SEQ ID NOS: 81-87, any one of SEQ ID NOS: 91-93, and any one of SEQ ID NOS: 94-96. In some embodiments, an antibody or compound of this disclosure comprises any one of SEQ ID NOS: 76-80, any one of SEQ ID NOS: 81-87, any one of SEQ ID NOS: 91-93, and any one of SEQ ID NOS: 97-98. In some embodiments, an antibody or compound of this disclosure comprises any one of SEQ ID NOS: 76-80, any one of SEQ ID NOS: 81-87, any one of SEQ ID NOS: 94-96, and any one of SEQ ID NOS: 97-98. In some embodiments, an antibody or compound of this disclosure comprises any one of SEQ ID NOS: 76-80, any one of SEQ ID NOS: 88-90, any one of SEQ ID NOS: 91-93, and any one of SEQ ID NOS: 94-96. In some embodiments, an antibody or compound of this disclosure comprises any one of SEQ ID NOS: 76-80, any one of SEQ ID NOS: 88-90, any one of SEQ ID NOS: 91-93, and any one of SEQ ID NOS: 97-98. In some embodiments, an antibody or compound of this disclosure comprises any one of SEQ ID NOS: 76-80, any one of SEQ ID NOS: 88-90, any one of SEQ ID NOS: 94-96, and any one of SEQ ID NOS: 97-98. In some embodiments, an antibody or compound of this disclosure comprises any one of SEQ ID NOS: 76-80, any one of SEQ ID NOS: 91-93, any one of SEQ ID NOS: 94-96, and any one of SEQ ID NOS: 97-98. In some embodiments, an antibody or compound of this disclosure comprises any one of SEQ ID NOS: 81-87, any one of SEQ ID NOS: 88-90, any one of SEQ ID NOS: 91-93, and any one of SEQ ID NOS: 94-96. In some embodiments, an antibody or compound of this disclosure comprises any one of SEQ ID NOS: 81-87, any one of SEQ ID NOS: 88-90, any one of SEQ ID NOS: 91-93, and any one of SEQ ID NOS: 97-98. In some embodiments, an antibody or compound of this disclosure comprises any one of SEQ ID NOS: 81-87, any one of SEQ ID NOS: 88-90, any one of SEQ ID NOS: 94-96, and any one of SEQ ID NOS: 97-98. In some embodiments, an antibody or compound of this disclosure comprises any one of SEQ ID NOS: 81-87, any one of SEQ ID NOS: 91-93, any one of SEQ ID NOS: 94-96, and any one of SEQ ID NOS: 97-98. In some embodiments, an antibody or compound of this disclosure comprises any one of SEQ ID NOS: 88-90, any one of SEQ ID NOS: 91-93, any one of SEQ ID NOS: 94-96, and any one of SEQ ID NOS: 97-98.

In some embodiments, an antibody or compound of this disclosure comprises any one of SEQ ID NOS: 76-80, any one of SEQ ID NOS: 81-87, any one of SEQ ID NOS: 88-90, any one of SEQ ID NOS: 91-93, and any one of SEQ ID NOS: 94-96. In some embodiments, an antibody or compound of this disclosure comprises any one of SEQ ID NOS: 76-80, any one of SEQ ID NOS: 81-87, any one of SEQ ID NOS: 88-90, any one of SEQ ID NOS: 91-93, and any one of SEQ ID NOS: 97-98. In some embodiments, an antibody or compound of this disclosure comprises any one of SEQ ID NOS: 76-80, any one of SEQ ID NOS: 81-87, any one of SEQ ID NOS: 88-90, any one of SEQ ID NOS: 94-96, and any one of SEQ ID NOS: 97-98. In some embodiments, an antibody or compound of this disclosure comprises any one of SEQ ID NOS: 76-80, any one of SEQ ID NOS: 81-87, any one of SEQ ID NOS: 91-93, any one of SEQ ID NOS: 94-96, and any one of SEQ ID NOS: 97-98. In some embodiments, an antibody or compound of this disclosure comprises any one of SEQ ID NOS: 76-80, any one of SEQ ID NOS: 88-90, any one of SEQ ID NOS: 91-93, any one of SEQ ID NOS: 94-96, and any one of SEQ ID NOS: 97-98. In some embodiments, an antibody or compound of this disclosure comprises any one of SEQ ID NOS: 81-87, any one of SEQ ID NOS: 88-90, any one of SEQ ID NOS: 91-93, any one of SEQ ID NOS: 94-96, and any one of SEQ ID NOS: 97-98.

In some embodiments, an antibody or compound of this disclosure comprises any one of SEQ ID NOS: 76-80, any one of SEQ ID NOS: 81-87, any one of SEQ ID NOS: 88-90, any one of SEQ ID NOS: 91-93, any one of SEQ ID NOS: 94-96, and any one of SEQ ID NOS: 97-98.

In some embodiments, an antibody or compound of this disclosure comprises SEQ ID NO: 76. In some embodiments, an antibody or compound of this disclosure comprises SEQ ID NO: 81. In some embodiments, an antibody or compound of this disclosure comprises SEQ ID NO: 88. In some embodiments, an antibody or compound of this disclosure comprises SEQ ID NO: 91. In some embodiments, an antibody or compound of this disclosure comprises SEQ ID NO: 94. In some embodiments, an antibody or compound of this disclosure comprises SEQ ID NO: 97. In some embodiments, an antibody or compound of this disclosure comprises SEQ ID NO: 77. In some embodiments, an antibody or compound of this disclosure comprises SEQ ID NO: 82.

In some embodiments, an antibody or compound of this disclosure comprises SEQ ID NO: 76 and SEQ ID NO: 81. In some embodiments, an antibody or compound of this disclosure comprises SEQ ID NO: 76 and SEQ ID NO: 88. In some embodiments, an antibody or compound of this disclosure comprises SEQ ID NO: 76 and SEQ ID NO: 91. In some embodiments, an antibody or compound of this disclosure comprises SEQ ID NO: 76 and SEQ ID NO: 94. In some embodiments, an antibody or compound of this disclosure comprises SEQ ID NO: 76 and SEQ ID NO: 97. In some embodiments, an antibody or compound of this disclosure comprises SEQ ID NO: 81 and SEQ ID NO: 88. In some embodiments, an antibody or compound of this disclosure comprises SEQ ID NO: 81 and SEQ ID NO: 91. In some embodiments, an antibody or compound of this disclosure comprises SEQ ID NO: 81 and SEQ ID NO: 94. In some embodiments, an antibody or compound of this disclosure comprises SEQ ID NO: 81 and SEQ ID NO: 97. In some embodiments, an antibody or compound of this disclosure comprises SEQ ID NO: 88 and SEQ ID NO: 91. In some embodiments, an antibody or compound of this disclosure comprises SEQ ID NO: 88 and SEQ ID NO: 94. In some embodiments, an antibody or compound of this disclosure comprises SEQ ID NO: 88 and SEQ ID NO: 97. In some embodiments, an antibody or compound of this disclosure comprises SEQ ID NO: 91 and SEQ ID NO: 94. In some embodiments, an antibody or compound of this disclosure comprises SEQ ID NO: 91 and SEQ ID NO: 97. In some embodiments, an antibody or compound of this disclosure comprises SEQ ID NO: 94 and SEQ ID NO: 97. In some embodiments, an antibody or compound of this disclosure comprises SEQ ID NO: 77 and SEQ ID NO: 82. In some embodiments, an antibody or compound of this disclosure comprises SEQ ID NO: 77 and SEQ ID NO: 88. In some embodiments, an antibody or compound of this disclosure comprises SEQ ID NO: 77 and SEQ ID NO: 91. In some embodiments, an antibody or compound of this disclosure comprises SEQ ID NO: 77 and SEQ ID NO: 94. In some embodiments, an antibody or compound of this disclosure comprises SEQ ID NO: 77 and SEQ ID NO: 97. In some embodiments, an antibody or compound of this disclosure comprises SEQ ID NO: 82 and SEQ ID NO: 88. In some embodiments, an antibody or compound of this disclosure comprises SEQ ID NO: 82 and SEQ ID NO: 91. In some embodiments, an antibody or compound of this disclosure comprises SEQ ID NO: 82 and SEQ ID NO: 94. In some embodiments, an antibody or compound of this disclosure comprises SEQ ID NO: 82 and SEQ ID NO: 97.

In some embodiments, an antibody or compound of this disclosure comprises SEQ ID NO: 76, SEQ ID NO: 81, and SEQ ID NO: 88. In some embodiments, an antibody or compound of this disclosure comprises SEQ ID NO: 76, SEQ ID NO: 81, and SEQ ID NO: 91. In some embodiments, an antibody or compound of this disclosure comprises SEQ ID NO: 76, SEQ ID NO: 81, and SEQ ID NO: 94. In some embodiments, an antibody or compound of this disclosure comprises SEQ ID NO: 76, SEQ ID NO: 81, and SEQ ID NO: 97. In some embodiments, an antibody or compound of this disclosure comprises SEQ ID NO: 76, SEQ ID NO: 88, and SEQ ID NO: 91. In some embodiments, an antibody or compound of this disclosure comprises SEQ ID NO: 76, SEQ ID NO: 88, and SEQ ID NO: 94. In some embodiments, an antibody or compound of this disclosure comprises SEQ ID NO: 76, SEQ ID NO: 88, and SEQ ID NO: 97. In some embodiments, an antibody or compound of this disclosure comprises SEQ ID NO: 76, SEQ ID NO: 91, and SEQ ID NO: 94. In some embodiments, an antibody or compound of this disclosure comprises SEQ ID NO: 76, SEQ ID NO: 91, and SEQ ID NO: 97. In some embodiments, an antibody or compound of this disclosure comprises SEQ ID NO: 76, SEQ ID NO: 94, and SEQ ID NO: 97. In some embodiments, an antibody or compound of this disclosure comprises SEQ ID NO: 81, SEQ ID NO: 88, and SEQ ID NO: 91. In some embodiments, an antibody or compound of this disclosure comprises SEQ ID NO: 81, SEQ ID NO: 88, and SEQ ID NO: 94. In some embodiments, an antibody or compound of this disclosure comprises SEQ ID NO: 81, SEQ ID NO: 88, and SEQ ID NO: 97. In some embodiments, an antibody or compound of this disclosure comprises SEQ ID NO: 81, SEQ ID NO: 91, and SEQ ID NO: 94. In some embodiments, an antibody or compound of this disclosure comprises SEQ ID NO: 81, SEQ ID NO: 91, and SEQ ID NO: 97. In some embodiments, an antibody or compound of this disclosure comprises SEQ ID NO: 81, SEQ ID NO: 94, and SEQ ID NO: 97. In some embodiments, an antibody or compound of this disclosure comprises SEQ ID NO: 88, SEQ ID NO: 91, and SEQ ID NO: 94. In some embodiments, an antibody or compound of this disclosure comprises SEQ ID NO: 88, SEQ ID NO: 91, and SEQ ID NO: 97. In some embodiments, an antibody or compound of this disclosure comprises SEQ ID NO: 88, SEQ ID NO: 94, and SEQ ID NO: 97. In some embodiments, an antibody or compound of this disclosure comprises SEQ ID NO: 91, SEQ ID NO: 94, and SEQ ID NO: 97. In some embodiments, an antibody or compound of this disclosure comprises SEQ ID NO: 77, SEQ ID NO: 82, and SEQ ID NO: 88. In some embodiments, an antibody or compound of this disclosure comprises SEQ ID NO: 77, SEQ ID NO: 82, and SEQ ID NO: 91. In some embodiments, an antibody or compound of this disclosure comprises SEQ ID NO: 77, SEQ ID NO: 82, and SEQ ID NO: 94. In some embodiments, an antibody or compound of this disclosure comprises SEQ ID NO: 77, SEQ ID NO: 82, and SEQ ID NO: 97. In some embodiments, an antibody or compound of this disclosure comprises SEQ ID NO: 77, SEQ ID NO: 88, and SEQ ID NO: 91. In some embodiments, an antibody or compound of this disclosure comprises SEQ ID NO: 77, SEQ ID NO: 88, and SEQ ID NO: 94. In some embodiments, an antibody or compound of this disclosure comprises SEQ ID NO: 77, SEQ ID NO: 88, and SEQ ID NO: 97. In some embodiments, an antibody or compound of this disclosure comprises SEQ ID NO: 77, SEQ ID NO: 91, and SEQ ID NO: 94. In some embodiments, an antibody or compound of this disclosure comprises SEQ ID NO: 77, SEQ ID NO: 91, and SEQ ID NO: 97. In some embodiments, an antibody or compound of this disclosure comprises SEQ ID NO: 77, SEQ ID NO: 94, and SEQ ID NO:

97. In some embodiments, an antibody or compound of this disclosure comprises SEQ ID NO: 82, SEQ ID NO: 88, and SEQ ID NO: 91. In some embodiments, an antibody or compound of this disclosure comprises SEQ ID NO: 82, SEQ ID NO: 88, and SEQ ID NO: 94. In some embodiments, an antibody or compound of this disclosure comprises SEQ ID NO: 82, SEQ ID NO: 88, and SEQ ID NO: 97. In some embodiments, an antibody or compound of this disclosure comprises SEQ ID NO: 82, SEQ ID NO: 91, and SEQ ID NO: 94. In some embodiments, an antibody or compound of this disclosure comprises SEQ ID NO: 82, SEQ ID NO: 91, and SEQ ID NO: 97. In some embodiments, an antibody or compound of this disclosure comprises SEQ ID NO: 82, SEQ ID NO: 94, and SEQ ID NO: 97.

In some embodiments, an antibody or compound of this disclosure comprises SEQ ID NO: 76, SEQ ID NO: 81, SEQ ID NO: 88, and SEQ ID NO: 91. In some embodiments, an antibody or compound of this disclosure comprises SEQ ID NO: 76, SEQ ID NO: 81, SEQ ID NO: 88, and SEQ ID NO: 94. In some embodiments, an antibody or compound of this disclosure comprises SEQ ID NO: 76, SEQ ID NO: 81, SEQ ID NO: 88, and SEQ ID NO: 97. In some embodiments, an antibody or compound of this disclosure comprises SEQ ID NO: 76, SEQ ID NO: 81, SEQ ID NO: 91, and SEQ ID NO: 94. In some embodiments, an antibody or compound of this disclosure comprises SEQ ID NO: 76, SEQ ID NO: 81, SEQ ID NO: 91, and SEQ ID NO: 97. In some embodiments, an antibody or compound of this disclosure comprises SEQ ID NO: 76, SEQ ID NO: 81, SEQ ID NO: 94, and SEQ ID NO: 97. In some embodiments, an antibody or compound of this disclosure comprises SEQ ID NO: 76, SEQ ID NO: 88, SEQ ID NO: 91, and SEQ ID NO: 94. In some embodiments, an antibody or compound of this disclosure comprises SEQ ID NO: 76, SEQ ID NO: 88, SEQ ID NO: 91, and SEQ ID NO: 97. In some embodiments, an antibody or compound of this disclosure comprises SEQ ID NO: 76, SEQ ID NO: 88, SEQ ID NO: 94, and SEQ ID NO: 97. In some embodiments, an antibody or compound of this disclosure comprises SEQ ID NO: 76, SEQ ID NO: 91, SEQ ID NO: 94, and SEQ ID NO: 97. In some embodiments, an antibody or compound of this disclosure comprises SEQ ID NO: 81, SEQ ID NO: 88, SEQ ID NO: 91, and SEQ ID NO: 94. In some embodiments, an antibody or compound of this disclosure comprises SEQ ID NO: 81, SEQ ID NO: 88, SEQ ID NO: 91, and SEQ ID NO: 97. In some embodiments, an antibody or compound of this disclosure comprises SEQ ID NO: 81, SEQ ID NO: 88, SEQ ID NO: 94, and SEQ ID NO: 97. In some embodiments, an antibody or compound of this disclosure comprises SEQ ID NO: 81, SEQ ID NO: 91, SEQ ID NO: 94, and SEQ ID NO: 97. In some embodiments, an antibody or compound of this disclosure comprises SEQ ID NO: 88, SEQ ID NO: 91, SEQ ID NO: 94, and SEQ ID NO: 97. In some embodiments, an antibody or compound of this disclosure comprises SEQ ID NO: 77, SEQ ID NO: 82, SEQ ID NO: 88, and SEQ ID NO: 91. In some embodiments, an antibody or compound of this disclosure comprises SEQ ID NO: 77, SEQ ID NO: 82, SEQ ID NO: 88, and SEQ ID NO: 94. In some embodiments, an antibody or compound of this disclosure comprises SEQ ID NO: 77, SEQ ID NO: 82, SEQ ID NO: 88, and SEQ ID NO: 97. In some embodiments, an antibody or compound of this disclosure comprises SEQ ID NO: 77, SEQ ID NO: 82, SEQ ID NO: 91, and SEQ ID NO: 94. In some embodiments, an antibody or compound of this disclosure comprises SEQ ID NO: 77, SEQ ID NO: 82, SEQ ID NO: 91, and SEQ ID NO: 97. In some embodiments, an antibody or compound of this disclosure comprises SEQ ID NO: 77, SEQ ID NO: 82, SEQ ID NO: 94, and SEQ ID NO: 97. In some embodiments, an antibody or compound of this disclosure comprises SEQ ID NO: 77, SEQ ID NO: 88, SEQ ID NO: 91, and SEQ ID NO: 94. In some embodiments, an antibody or compound of this disclosure comprises SEQ ID NO: 77, SEQ ID NO: 88, SEQ ID NO: 91, and SEQ ID NO: 97. In some embodiments, an antibody or compound of this disclosure comprises SEQ ID NO: 77, SEQ ID NO: 88, SEQ ID NO: 94, and SEQ ID NO: 97. In some embodiments, an antibody or compound of this disclosure comprises SEQ ID NO: 77, SEQ ID NO: 91, SEQ ID NO: 94, and SEQ ID NO: 97. In some embodiments, an antibody or compound of this disclosure comprises SEQ ID NO: 82, SEQ ID NO: 88, SEQ ID NO: 91, and SEQ ID NO: 94. In some embodiments, an antibody or compound of this disclosure comprises SEQ ID NO: 82, SEQ ID NO: 88, SEQ ID NO: 91, and SEQ ID NO: 97. In some embodiments, an antibody or compound of this disclosure comprises SEQ ID NO: 82, SEQ ID NO: 88, SEQ ID NO: 94, and SEQ ID NO: 97. In some embodiments, an antibody or compound of this disclosure comprises SEQ ID NO: 82, SEQ ID NO: 91, SEQ ID NO: 94, and SEQ ID NO: 97. In some embodiments, an antibody or compound of this disclosure comprises SEQ ID NO: 88, SEQ ID NO: 91, SEQ ID NO: 94, and SEQ ID NO: 97.

In some embodiments, an antibody or compound of this disclosure comprises SEQ ID NO: 76, SEQ ID NO: 81, SEQ ID NO: 88, SEQ ID NO: 91, and SEQ ID NO: 94. In some embodiments, an antibody or compound of this disclosure comprises SEQ ID NO: 76, SEQ ID NO: 81, SEQ ID NO: 88, SEQ ID NO: 91, and SEQ ID NO: 97. In some embodiments, an antibody or compound of this disclosure comprises SEQ ID NO: 76, SEQ ID NO: 81, SEQ ID NO: 88, SEQ ID NO: 94, and SEQ ID NO: 97. In some embodiments, an antibody or compound of this disclosure comprises SEQ ID NO: 76, SEQ ID NO: 81, SEQ ID NO: 91, SEQ ID NO: 94, and SEQ ID NO: 97. In some embodiments, an antibody or compound of this disclosure comprises SEQ ID NO: 76, SEQ ID NO: 88, SEQ ID NO: 91, SEQ ID NO: 94, and SEQ ID NO: 97. In some embodiments, an antibody or compound of this disclosure comprises SEQ ID NO: 81, SEQ ID NO: 88, SEQ ID NO: 91, SEQ ID NO: 94, and SEQ ID NO: 97. In some embodiments, an antibody or compound of this disclosure comprises SEQ ID NO: 77, SEQ ID NO: 82, SEQ ID NO: 88, SEQ ID NO: 91, and SEQ ID NO: 94. In some embodiments, an antibody or compound of this disclosure comprises SEQ ID NO: 77, SEQ ID NO: 82, SEQ ID NO: 88, SEQ ID NO: 91, and SEQ ID NO: 97. In some embodiments, an antibody or compound of this disclosure comprises SEQ ID NO: 77, SEQ ID NO: 82, SEQ ID NO: 88, SEQ ID NO: 94, and SEQ ID NO: 97. In some embodiments, an antibody or compound of this disclosure comprises SEQ ID NO: 77, SEQ ID NO: 82, SEQ ID NO: 91, SEQ ID NO: 94, and SEQ ID NO: 97. In some embodiments, an antibody or compound of this disclosure comprises SEQ ID NO: 82, SEQ ID NO: 88, SEQ ID NO: 91, SEQ ID NO: 94, and SEQ ID NO: 97.

In some embodiments, an antibody or compound of this disclosure comprises SEQ ID NO: 76, SEQ ID NO: 81, SEQ ID NO: 88, SEQ ID NO: 91, SEQ ID NO: 94, and SEQ ID NO: 97. In some embodiments, an antibody or compound of this disclosure comprises SEQ ID NO: 77, SEQ ID NO: 82, SEQ ID NO: 88, SEQ ID NO: 91, SEQ ID NO: 94, and SEQ ID NO: 97.

In some embodiments, an antibody or compound of this disclosure comprises SEQ ID NO: 78. In some embodiments, an antibody or compound of this disclosure comprises SEQ ID NO: 83. In some embodiments, an antibody or compound of this disclosure comprises SEQ ID NO: 89. In some embodiments, an antibody or compound of this disclosure comprises SEQ ID NO: 92. In some embodiments, an antibody or compound of this disclosure comprises SEQ ID NO: 95. In some embodiments, an antibody or compound of this disclosure comprises SEQ ID NO: 97.

In some embodiments, an antibody or compound of this disclosure comprises SEQ ID NO: 78 and SEQ ID NO: 83. In some embodiments, an antibody or compound of this disclosure comprises SEQ ID NO: 78 and SEQ ID NO: 89. In some embodiments, an antibody or compound of this disclosure comprises SEQ ID NO: 78 and SEQ ID NO: 92. In some embodiments, an antibody or compound of this disclosure comprises SEQ ID NO: 78 and SEQ ID NO: 95. In some embodiments, an antibody or compound of this disclosure comprises SEQ ID NO: 78 and SEQ ID NO: 97. In some embodiments, an antibody or compound of this disclosure comprises SEQ ID NO: 83 and SEQ ID NO: 89. In some embodiments, an antibody or compound of this disclosure comprises SEQ ID NO: 83 and SEQ ID NO: 92. In some embodiments, an antibody or compound of this disclosure comprises SEQ ID NO: 83 and SEQ ID NO: 95. In some embodiments, an antibody or compound of this disclosure comprises SEQ ID NO: 83 and SEQ ID NO: 97. In some embodiments, an antibody or compound of this disclosure comprises SEQ ID NO: 89 and SEQ ID NO: 92. In some embodiments, an antibody or compound of this disclosure comprises SEQ ID NO: 89 and SEQ ID NO: 95. In some embodiments, an antibody or compound of this disclosure comprises SEQ ID NO: 89 and SEQ ID NO: 97. In some embodiments, an antibody or compound of this disclosure comprises SEQ ID NO: 92 and SEQ ID NO: 95. In some embodiments, an antibody or compound of this disclosure comprises SEQ ID NO: 92 and SEQ ID NO: 97. In some embodiments, an antibody or compound of this disclosure comprises SEQ ID NO: 95 and SEQ ID NO: 97.

In some embodiments, an antibody or compound of this disclosure comprises SEQ ID NO: 78, SEQ ID NO: 83, and SEQ ID NO: 89. In some embodiments, an antibody or compound of this disclosure comprises SEQ ID NO: 78, SEQ ID NO: 83, and SEQ ID NO: 92. In some embodiments, an antibody or compound of this disclosure comprises SEQ ID NO: 78, SEQ ID NO: 83, and SEQ ID NO: 95. In some embodiments, an antibody or compound of this disclosure comprises SEQ ID NO: 78, SEQ ID NO: 83, and SEQ ID NO: 97. In some embodiments, an antibody or compound of this disclosure comprises SEQ ID NO: 78, SEQ ID NO: 89, and SEQ ID NO: 92. In some embodiments, an antibody or compound of this disclosure comprises SEQ ID NO: 78, SEQ ID NO: 89, and SEQ ID NO: 95. In some embodiments, an antibody or compound of this disclosure comprises SEQ ID NO: 78, SEQ ID NO: 89, and SEQ ID NO: 97. In some embodiments, an antibody or compound of this disclosure comprises SEQ ID NO: 78, SEQ ID NO: 92, and SEQ ID NO: 95. In some embodiments, an antibody or compound of this disclosure comprises SEQ ID NO: 78, SEQ ID NO: 92, and SEQ ID NO: 97. In some embodiments, an antibody or compound of this disclosure comprises SEQ ID NO: 78, SEQ ID NO: 95, and SEQ ID NO: 97. In some embodiments, an antibody or compound of this disclosure comprises SEQ ID NO: 83, SEQ ID NO: 89, and SEQ ID NO: 92. In some embodiments, an antibody or compound of this disclosure comprises SEQ ID NO: 83, SEQ ID NO: 89, and SEQ ID NO: 95. In some embodiments, an antibody or compound of this disclosure comprises SEQ ID NO: 83, SEQ ID NO: 89, and SEQ ID NO: 97. In some embodiments, an antibody or compound of this disclosure comprises SEQ ID NO: 83, SEQ ID NO: 92, and SEQ ID NO: 95. In some embodiments, an antibody or compound of this disclosure comprises SEQ ID NO: 83, SEQ ID NO: 92, and SEQ ID NO: 97. In some embodiments, an antibody or compound of this disclosure comprises SEQ ID NO: 83, SEQ ID NO: 95, and SEQ ID NO: 97. In some embodiments, an antibody or compound of this disclosure comprises SEQ ID NO: 89, SEQ ID NO: 92, and SEQ ID NO: 95. In some embodiments, an antibody or compound of this disclosure comprises SEQ ID NO: 89, SEQ ID NO: 92, and SEQ ID NO: 97. In some embodiments, an antibody or compound of this disclosure comprises SEQ ID NO: 89, SEQ ID NO: 95, and SEQ ID NO: 97. In some embodiments, an antibody or compound of this disclosure comprises SEQ ID NO: 92, SEQ ID NO: 95, and SEQ ID NO: 97.

In some embodiments, an antibody or compound of this disclosure comprises SEQ ID NO: 78, SEQ ID NO: 83, SEQ ID NO: 89, and SEQ ID NO: 92. In some embodiments, an antibody or compound of this disclosure comprises SEQ ID NO: 78, SEQ ID NO: 83, SEQ ID NO: 89, and SEQ ID NO: 95. In some embodiments, an antibody or compound of this disclosure comprises SEQ ID NO: 78, SEQ ID NO: 83, SEQ ID NO: 89, and SEQ ID NO: 97. In some embodiments, an antibody or compound of this disclosure comprises SEQ ID NO: 78, SEQ ID NO: 83, SEQ ID NO: 92, and SEQ ID NO: 95. In some embodiments, an antibody or compound of this disclosure comprises SEQ ID NO: 78, SEQ ID NO: 83, SEQ ID NO: 92, and SEQ ID NO: 97. In some embodiments, an antibody or compound of this disclosure comprises SEQ ID NO: 78, SEQ ID NO: 83, SEQ ID NO: 95, and SEQ ID NO: 97. In some embodiments, an antibody or compound of this disclosure comprises SEQ ID NO: 78, SEQ ID NO: 89, SEQ ID NO: 92, and SEQ ID NO: 95. In some embodiments, an antibody or compound of this disclosure comprises SEQ ID NO: 78, SEQ ID NO: 89, SEQ ID NO: 92, and SEQ ID NO: 97. In some embodiments, an antibody or compound of this disclosure comprises SEQ ID NO: 78, SEQ ID NO: 89, SEQ ID NO: 95, and SEQ ID NO: 97. In some embodiments, an antibody or compound of this disclosure comprises SEQ ID NO: 78, SEQ ID NO: 92, SEQ ID NO: 95, and SEQ ID NO: 97. In some embodiments, an antibody or compound of this disclosure comprises SEQ ID NO: 83, SEQ ID NO: 89, SEQ ID NO: 92, and SEQ ID NO: 95. In some embodiments, an antibody or compound of this disclosure comprises SEQ ID NO: 83, SEQ ID NO: 89, SEQ ID NO: 92, and SEQ ID NO: 97. In some embodiments, an antibody or compound of this disclosure comprises SEQ ID NO: 83, SEQ ID NO: 89, SEQ ID NO: 95, and SEQ ID NO: 97. In some embodiments, an antibody or compound of this disclosure comprises SEQ ID NO: 83, SEQ ID NO: 92, SEQ ID NO: 95, and SEQ ID NO: 97. In some embodiments, an antibody or compound of this disclosure comprises SEQ ID NO: 89, SEQ ID NO: 92, SEQ ID NO: 95, and SEQ ID NO: 97.

In some embodiments, an antibody or compound of this disclosure comprises SEQ ID NO: 78, SEQ ID NO: 83, SEQ ID NO: 89, SEQ ID NO: 92, and SEQ ID NO: 95. In some embodiments, an antibody or compound of this disclosure comprises SEQ ID NO: 78, SEQ ID NO: 83, SEQ ID NO: 89, SEQ ID NO: 92, and SEQ ID NO: 97. In some embodiments, an antibody or compound of this disclosure comprises SEQ ID NO: 78, SEQ ID NO: 83, SEQ ID NO: 89, SEQ ID NO: 95, and SEQ ID NO: 97. In some embodiments, an antibody or compound of this disclosure comprises SEQ ID NO: 78, SEQ ID NO: 83, SEQ ID NO: 92, SEQ ID NO: 95, and SEQ ID NO: 97. In some embodiments, an antibody or compound of this disclosure comprises SEQ ID NO: 78, SEQ ID NO: 89, SEQ ID NO: 92, SEQ ID NO: 95, and SEQ ID NO: 97. In some embodiments, an antibody or compound of this disclosure comprises SEQ ID NO: 83, SEQ ID NO: 89, SEQ ID NO: 92, SEQ ID NO: 95, and SEQ ID NO: 97.

In some embodiments, an antibody or compound of this disclosure comprises SEQ ID NO: 78, SEQ ID NO: 83, SEQ ID NO: 89, SEQ ID NO: 92, SEQ ID NO: 95, and SEQ ID NO: 97.

In some embodiments, an antibody or compound of this disclosure comprises SEQ ID NO: 79. In some embodiments, an antibody or compound of this disclosure comprises SEQ ID NO: 84. In some embodiments, an antibody or compound of this disclosure comprises SEQ ID NO: 90. In some embodiments, an antibody or compound of this disclosure comprises SEQ ID NO: 93. In some embodiments, an antibody or compound of this disclosure comprises SEQ ID NO: 96. In some embodiments, an antibody or compound of this disclosure comprises SEQ ID NO: 98. In some embodiments, an antibody or compound of this disclosure comprises SEQ ID NO: 86.

In some embodiments, an antibody or compound of this disclosure comprises SEQ ID NO: 79 and SEQ ID NO: 84. In some embodiments, an antibody or compound of this disclosure comprises SEQ ID NO: 79 and SEQ ID NO: 90. In some embodiments, an antibody or compound of this disclosure comprises SEQ ID NO: 79 and SEQ ID NO: 93. In some embodiments, an antibody or compound of this disclosure comprises SEQ ID NO: 79 and SEQ ID NO: 96. In some embodiments, an antibody or compound of this disclosure comprises SEQ ID NO: 79 and SEQ ID NO: 98. In some embodiments, an antibody or compound of this disclosure comprises SEQ ID NO: 84 and SEQ ID NO: 90. In some embodiments, an antibody or compound of this disclosure comprises SEQ ID NO: 84 and SEQ ID NO: 93. In some embodiments, an antibody or compound of this disclosure comprises SEQ ID NO: 84 and SEQ ID NO: 96. In some embodiments, an antibody or compound of this disclosure comprises SEQ ID NO: 84 and SEQ ID NO: 98. In some embodiments, an antibody or compound of this disclosure comprises SEQ ID NO: 90 and SEQ ID NO: 93. In some embodiments, an antibody or compound of this disclosure comprises SEQ ID NO: 90 and SEQ ID NO: 96. In some embodiments, an antibody or compound of this disclosure comprises SEQ ID NO: 90 and SEQ ID NO: 98. In some embodiments, an antibody or compound of this disclosure comprises SEQ ID NO: 93 and SEQ ID NO: 96. In some embodiments, an antibody or compound of this disclosure comprises SEQ ID NO: 93 and SEQ ID NO: 98. In some embodiments, an antibody or compound of this disclosure comprises SEQ ID NO: 96 and SEQ ID NO: 98. In some embodiments, an antibody or compound of this disclosure comprises SEQ ID NO: 79 and SEQ ID NO: 86. In some embodiments, an antibody or compound of this disclosure comprises SEQ ID NO: 86 and SEQ ID NO: 90. In some embodiments, an antibody or compound of this disclosure comprises SEQ ID NO: 86 and SEQ ID NO: 93. In some embodiments, an antibody or compound of this disclosure comprises SEQ ID NO: 86 and SEQ ID NO: 96. In some embodiments, an antibody or compound of this disclosure comprises SEQ ID NO: 86 and SEQ ID NO: 98.

In some embodiments, an antibody or compound of this disclosure comprises SEQ ID NO: 79, SEQ ID NO: 84, and SEQ ID NO: 90. In some embodiments, an antibody or compound of this disclosure comprises SEQ ID NO: 79, SEQ ID NO: 84, and SEQ ID NO: 93. In some embodiments, an antibody or compound of this disclosure comprises SEQ ID NO: 79, SEQ ID NO: 84, and SEQ ID NO: 96. In some embodiments, an antibody or compound of this disclosure comprises SEQ ID NO: 79, SEQ ID NO: 84, and SEQ ID NO: 98. In some embodiments, an antibody or compound of this disclosure comprises SEQ ID NO: 79, SEQ ID NO: 90, and SEQ ID NO: 93. In some embodiments, an antibody or compound of this disclosure comprises SEQ ID NO: 79, SEQ ID NO: 90, and SEQ ID NO: 96. In some embodiments, an antibody or compound of this disclosure comprises SEQ ID NO: 79, SEQ ID NO: 90, and SEQ ID NO: 98. In some embodiments, an antibody or compound of this disclosure comprises SEQ ID NO: 79, SEQ ID NO: 93, and SEQ ID NO: 96. In some embodiments, an antibody or compound of this disclosure comprises SEQ ID NO: 79, SEQ ID NO: 93, and SEQ ID NO: 98. In some embodiments, an antibody or compound of this disclosure comprises SEQ ID NO: 79, SEQ ID NO: 96, and SEQ ID NO: 98. In some embodiments, an antibody or compound of this disclosure comprises SEQ ID NO: 84, SEQ ID NO: 90, and SEQ ID NO: 93. In some embodiments, an antibody or compound of this disclosure comprises SEQ ID NO: 84, SEQ ID NO: 90, and SEQ ID NO: 96. In some embodiments, an antibody or compound of this disclosure comprises SEQ ID NO: 84, SEQ ID NO: 90, and SEQ ID NO: 98. In some embodiments, an antibody or compound of this disclosure comprises SEQ ID NO: 84, SEQ ID NO: 93, and SEQ ID NO: 96. In some embodiments, an antibody or compound of this disclosure comprises SEQ ID NO: 84, SEQ ID NO: 93, and SEQ ID NO: 98. In some embodiments, an antibody or compound of this disclosure comprises SEQ ID NO: 84, SEQ ID NO: 96, and SEQ ID NO: 98. In some embodiments, an antibody or compound of this disclosure comprises SEQ ID NO: 90, SEQ ID NO: 93, and SEQ ID NO: 96. In some embodiments, an antibody or compound of this disclosure comprises SEQ ID NO: 90, SEQ ID NO: 93, and SEQ ID NO: 98. In some embodiments, an antibody or compound of this disclosure comprises SEQ ID NO: 90, SEQ ID NO: 96, and SEQ ID NO: 98. In some embodiments, an antibody or compound of this disclosure comprises SEQ ID NO: 93, SEQ ID NO: 96, and SEQ ID NO: 98. In some embodiments, an antibody or compound of this disclosure comprises SEQ ID NO: 79, SEQ ID NO: 86, and SEQ ID NO: 90. In some embodiments, an antibody or compound of this disclosure comprises SEQ ID NO: 79, SEQ ID NO: 86, and SEQ ID NO: 93. In some embodiments, an antibody or compound of this disclosure comprises SEQ ID NO: 79, SEQ ID NO: 86, and SEQ ID NO: 96. In some embodiments, an antibody or compound of this disclosure comprises SEQ ID NO: 79, SEQ ID NO: 86, and SEQ ID NO: 98. In some embodiments, an antibody or compound of this disclosure comprises SEQ ID NO: 86, SEQ ID NO: 90, and SEQ ID NO: 93. In some embodiments, an antibody or compound of this disclosure comprises SEQ ID NO: 86, SEQ ID NO: 90, and SEQ ID NO: 96. In some embodiments, an antibody or compound of this disclosure comprises SEQ ID NO: 86, SEQ ID NO: 90, and SEQ ID NO: 98. In some embodiments, an antibody or compound of this disclosure comprises SEQ ID NO: 86, SEQ ID NO: 93, and SEQ ID NO: 96. In some embodiments, an antibody or compound of this disclosure comprises SEQ ID NO: 86, SEQ ID NO: 93, and SEQ ID NO: 98. In some embodiments, an antibody or compound of this disclosure comprises SEQ ID NO: 86, SEQ ID NO: 96, and SEQ ID NO: 98.

In some embodiments, an antibody or compound of this disclosure comprises SEQ ID NO: 79, SEQ ID NO: 84, SEQ ID NO: 90, and SEQ ID NO: 93. In some embodiments, an antibody or compound of this disclosure comprises SEQ ID NO: 79, SEQ ID NO: 84, SEQ ID NO: 90, and SEQ ID NO: 96. In some embodiments, an antibody or compound of this disclosure comprises SEQ ID NO: 79, SEQ ID NO: 84, SEQ ID NO: 90, and SEQ ID NO: 98. In some embodiments, an antibody or compound of this disclosure comprises SEQ ID NO: 79, SEQ ID NO: 84, SEQ ID NO: 93, and SEQ ID NO: 96. In some embodiments, an antibody or compound of this disclosure comprises SEQ ID NO: 79, SEQ ID NO: 84, SEQ ID NO: 93, and SEQ ID NO: 98. In some embodiments, an antibody or compound of this disclosure comprises SEQ ID NO: 79, SEQ ID NO: 84, SEQ ID NO: 96, and SEQ ID NO: 98. In some embodiments, an antibody or compound of this disclosure comprises SEQ ID NO: 79, SEQ ID NO: 90, SEQ ID NO: 93, and SEQ ID NO: 96. In some embodiments, an antibody or compound of this disclosure comprises SEQ ID NO: 79, SEQ ID NO: 90, SEQ ID NO: 93, and SEQ ID NO: 98. In some embodiments, an antibody or compound of this disclosure comprises SEQ ID NO: 79, SEQ ID NO: 90, SEQ ID NO: 96, and SEQ ID NO: 98. In some embodiments, an antibody or compound of this disclosure comprises SEQ ID NO: 79, SEQ ID NO: 93, SEQ ID NO: 96, and SEQ ID NO: 98. In some embodiments, an antibody or compound of this disclosure comprises SEQ ID NO: 84, SEQ ID NO: 90, SEQ ID NO: 93, and SEQ ID NO: 96. In some embodiments, an antibody or compound of this disclosure comprises SEQ ID NO: 84, SEQ ID NO: 90, SEQ ID NO: 93, and SEQ ID NO: 98. In some embodiments, an antibody or compound of this disclosure comprises SEQ ID NO: 84, SEQ ID NO: 90, SEQ ID NO: 96, and SEQ ID NO: 98. In some embodiments, an antibody or compound of this disclosure comprises SEQ ID NO: 84, SEQ ID NO: 93, SEQ ID NO: 96, and SEQ ID NO: 98. In some embodiments, an antibody or compound of this disclosure comprises SEQ ID NO: 90, SEQ ID NO: 93, SEQ ID NO: 96, and SEQ ID NO: 98. In some embodiments, an antibody or compound of this disclosure comprises SEQ ID NO: 79, SEQ ID NO: 86, SEQ ID NO: 90, and SEQ ID NO: 93. In some embodiments, an antibody or compound of this disclosure comprises SEQ ID NO: 79, SEQ ID NO: 86, SEQ ID NO: 90, and SEQ ID NO: 96. In some embodiments, an antibody or compound of this disclosure comprises SEQ ID NO: 79, SEQ ID NO: 86, SEQ ID NO: 90, and SEQ ID NO: 98. In some embodiments, an antibody or compound of this disclosure comprises SEQ ID NO: 79, SEQ ID NO: 86, SEQ ID NO: 93, and SEQ ID NO: 96. In some embodiments, an antibody or compound of this disclosure comprises SEQ ID NO: 79, SEQ ID NO: 86, SEQ ID NO: 93, and SEQ ID NO: 98. In some embodiments, an antibody or compound of this disclosure comprises SEQ ID NO: 79, SEQ ID NO: 86, SEQ ID NO: 96, and SEQ ID NO: 98. In some embodiments, an antibody or compound of this disclosure comprises SEQ ID NO: 86, SEQ ID NO: 90, SEQ ID NO: 93, and SEQ ID NO: 96. In some embodiments, an antibody or compound of this disclosure comprises SEQ ID NO: 86, SEQ ID NO: 90, SEQ ID NO: 93, and SEQ ID NO: 98. In some embodiments, an antibody or compound of this disclosure comprises SEQ ID NO: 86, SEQ ID NO: 90, SEQ ID NO: 96, and SEQ ID NO: 98. In some embodiments, an antibody or compound of this disclosure comprises SEQ ID NO: 86, SEQ ID NO: 93, SEQ ID NO: 96, and SEQ ID NO: 98.

In some embodiments, an antibody or compound of this disclosure comprises SEQ ID NO: 79, SEQ ID NO: 84, SEQ ID NO: 90, SEQ ID NO: 93, and SEQ ID NO: 96. In some embodiments, an antibody or compound of this disclosure comprises SEQ ID NO: 79, SEQ ID NO: 84, SEQ ID NO: 90, SEQ ID NO: 93, and SEQ ID NO: 98. In some embodiments, an antibody or compound of this disclosure comprises SEQ ID NO: 79, SEQ ID NO: 84, SEQ ID NO: 90, SEQ ID NO: 96, and SEQ ID NO: 98. In some embodiments, an antibody or compound of this disclosure comprises SEQ ID NO: 79, SEQ ID NO: 84, SEQ ID NO: 93, SEQ ID NO: 96, and SEQ ID NO: 98. In some embodiments, an antibody or compound of this disclosure comprises SEQ ID NO: 79, SEQ ID NO: 90, SEQ ID NO: 93, SEQ ID NO: 96, and SEQ ID NO: 98. In some embodiments, an antibody or compound of this disclosure comprises SEQ ID NO: 84, SEQ ID NO: 90, SEQ ID NO: 93, SEQ ID NO: 96, and SEQ ID NO: 98. In some embodiments, an antibody or compound of this disclosure comprises SEQ ID NO: 79, SEQ ID NO: 86, SEQ ID NO: 90, SEQ ID NO: 93, and SEQ ID NO: 96. In some embodiments, an antibody or compound of this disclosure comprises SEQ ID NO: 79, SEQ ID NO: 86, SEQ ID NO: 90, SEQ ID NO: 93, and SEQ ID NO: 98. In some embodiments, an antibody or compound of this disclosure comprises SEQ ID NO: 79, SEQ ID NO: 86, SEQ ID NO: 90, SEQ ID NO: 96, and SEQ ID NO: 98. In some embodiments, an antibody or compound of this disclosure comprises SEQ ID NO: 79, SEQ ID NO: 86, SEQ ID NO: 93, SEQ ID NO: 96, and SEQ ID NO: 98. In some embodiments, an antibody or compound of this disclosure comprises SEQ ID NO: 86, SEQ ID NO: 90, SEQ ID NO: 93, SEQ ID NO: 96, and SEQ ID NO: 98.

In some embodiments, an antibody or compound of this disclosure comprises SEQ ID NO: 79, SEQ ID NO: 84, SEQ ID NO: 90, SEQ ID NO: 93, SEQ ID NO: 96, and SEQ ID NO: 98. In some embodiments, an antibody or compound of this disclosure comprises SEQ ID NO: 79, SEQ ID NO: 86, SEQ ID NO: 90, SEQ ID NO: 93, SEQ ID NO: 96, and SEQ ID NO: 98.

In some embodiments, an antibody or compound of this disclosure comprises SEQ ID NO: 80. In some embodiments, an antibody or compound of this disclosure comprises SEQ ID NO: 85. In some embodiments, an antibody or compound of this disclosure comprises SEQ ID NO: 89. In some embodiments, an antibody or compound of this disclosure comprises SEQ ID NO: 91. In some embodiments, an antibody or compound of this disclosure comprises SEQ ID NO: 96. In some embodiments, an antibody or compound of this disclosure comprises SEQ ID NO: 97. In some embodiments, an antibody or compound of this disclosure comprises SEQ ID NO: 87.

In some embodiments, an antibody or compound of this disclosure comprises SEQ ID NO: 80 and SEQ ID NO: 85. In some embodiments, an antibody or compound of this disclosure comprises SEQ ID NO: 80 and SEQ ID NO: 89. In some embodiments, an antibody or compound of this disclosure comprises SEQ ID NO: 80 and SEQ ID NO: 91. In some embodiments, an antibody or compound of this disclosure comprises SEQ ID NO: 80 and SEQ ID NO: 96. In some embodiments, an antibody or compound of this disclosure comprises SEQ ID NO: 80 and SEQ ID NO: 97. In some embodiments, an antibody or compound of this disclosure comprises SEQ ID NO: 85 and SEQ ID NO: 89. In some embodiments, an antibody or compound of this disclosure comprises SEQ ID NO: 85 and SEQ ID NO: 91. In some embodiments, an antibody or compound of this disclosure comprises SEQ ID NO: 85 and SEQ ID NO: 96. In some embodiments, an antibody or compound of this disclosure comprises SEQ ID NO: 85 and SEQ ID NO: 97. In some embodiments, an antibody or compound of this disclosure comprises SEQ ID NO: 89 and SEQ ID NO: 91. In some embodiments, an antibody or compound of this disclosure comprises SEQ ID NO: 89 and SEQ ID NO: 96. In some embodiments, an antibody or compound of this disclosure comprises SEQ ID NO: 89 and SEQ ID NO: 97. In some embodiments, an antibody or compound of this disclosure comprises SEQ ID NO: 91 and SEQ ID NO: 96. In some embodiments, an antibody or compound of this disclosure comprises SEQ ID NO: 91 and SEQ ID NO: 97. In some embodiments, an antibody or compound of this disclosure comprises SEQ ID NO: 96 and SEQ ID NO: 97. In some embodiments, an antibody or compound of this disclosure comprises SEQ ID NO: 80 and SEQ ID NO: 87. In some embodiments, an antibody or compound of this disclosure comprises SEQ ID NO: 87 and SEQ ID NO: 89. In some embodiments, an antibody or compound of this disclosure comprises SEQ ID NO: 87 and SEQ ID NO: 91. In some embodiments, an antibody or compound of this disclosure comprises SEQ ID NO: 87 and SEQ ID NO: 96. In some embodiments, an antibody or compound of this disclosure comprises SEQ ID NO: 87 and SEQ ID NO: 97.

In some embodiments, an antibody or compound of this disclosure comprises SEQ ID NO: 80, SEQ ID NO: 85, and SEQ ID NO: 89. In some embodiments, an antibody or compound of this disclosure comprises SEQ ID NO: 80, SEQ ID NO: 85, and SEQ ID NO: 91. In some embodiments, an antibody or compound of this disclosure comprises SEQ ID NO: 80, SEQ ID NO: 85, and SEQ ID NO: 96. In some embodiments, an antibody or compound of this disclosure comprises SEQ ID NO: 80, SEQ ID NO: 85, and SEQ ID NO: 97. In some embodiments, an antibody or compound of this disclosure comprises SEQ ID NO: 80, SEQ ID NO: 89, and SEQ ID NO: 91. In some embodiments, an antibody or compound of this disclosure comprises SEQ ID NO: 80, SEQ ID NO: 89, and SEQ ID NO: 96. In some embodiments, an antibody or compound of this disclosure comprises SEQ ID NO: 80, SEQ ID NO: 89, and SEQ ID NO: 97. In some embodiments, an antibody or compound of this disclosure comprises SEQ ID NO: 80, SEQ ID NO: 91, and SEQ ID NO: 96. In some embodiments, an antibody or compound of this disclosure comprises SEQ ID NO: 80, SEQ ID NO: 91, and SEQ ID NO: 97. In some embodiments, an antibody or compound of this disclosure comprises SEQ ID NO: 80, SEQ ID NO: 96, and SEQ ID NO: 97. In some embodiments, an antibody or compound of this disclosure comprises SEQ ID NO: 85, SEQ ID NO: 89, and SEQ ID NO: 91. In some embodiments, an antibody or compound of this disclosure comprises SEQ ID NO: 85, SEQ ID NO: 89, and SEQ ID NO: 96. In some embodiments, an antibody or compound of this disclosure comprises SEQ ID NO: 85, SEQ ID NO: 89, and SEQ ID NO: 97. In some embodiments, an antibody or compound of this disclosure comprises SEQ ID NO: 85, SEQ ID NO: 91, and SEQ ID NO: 96. In some embodiments, an antibody or compound of this disclosure comprises SEQ ID NO: 85, SEQ ID NO: 91, and SEQ ID NO: 97. In some embodiments, an antibody or compound of this disclosure comprises SEQ ID NO: 85, SEQ ID NO: 96, and SEQ ID NO: 97. In some embodiments, an antibody or compound of this disclosure comprises SEQ ID NO: 89, SEQ ID NO: 91, and SEQ ID NO: 96. In some embodiments, an antibody or compound of this disclosure comprises SEQ ID NO: 89, SEQ ID NO: 91, and SEQ ID NO: 97. In some embodiments, an antibody or compound of this disclosure comprises SEQ ID NO: 89, SEQ ID NO: 96, and SEQ ID NO: 97. In some embodiments, an antibody or compound of this disclosure comprises SEQ ID NO: 91, SEQ ID NO: 96, and SEQ ID NO: 97. In some embodiments, an antibody or compound of this disclosure comprises SEQ ID NO: 80, SEQ ID NO: 87, and SEQ ID NO: 89. In some embodiments, an antibody or compound of this disclosure comprises SEQ ID NO: 80, SEQ ID NO: 87, and SEQ ID NO: 91. In some embodiments, an antibody or compound of this disclosure comprises SEQ ID NO: 80, SEQ ID NO: 87, and SEQ ID NO: 96. In some embodiments, an antibody or compound of this disclosure comprises SEQ ID NO: 80, SEQ ID NO: 87, and SEQ ID NO: 97. In some embodiments, an antibody or compound of this disclosure comprises SEQ ID NO: 87, SEQ ID NO: 89, and SEQ ID NO: 91. In some embodiments, an antibody or compound of this disclosure comprises SEQ ID NO: 87, SEQ ID NO: 89, and SEQ ID NO: 96. In some embodiments, an antibody or compound of this disclosure comprises SEQ ID NO: 87, SEQ ID NO: 89, and SEQ ID NO: 97. In some embodiments, an antibody or compound of this disclosure comprises SEQ ID NO: 87, SEQ ID NO: 91, and SEQ ID NO: 96. In some embodiments, an antibody or compound of this disclosure comprises SEQ ID NO: 87, SEQ ID NO: 91, and SEQ ID NO: 97. In some embodiments, an antibody or compound of this disclosure comprises SEQ ID NO: 87, SEQ ID NO: 96, and SEQ ID NO: 97.

In some embodiments, an antibody or compound of this disclosure comprises SEQ ID NO: 80, SEQ ID NO: 85, SEQ ID NO: 89, and SEQ ID NO: 91. In some embodiments, an antibody or compound of this disclosure comprises SEQ ID NO: 80, SEQ ID NO: 85, SEQ ID NO: 89, and SEQ ID NO: 96. In some embodiments, an antibody or compound of this disclosure comprises SEQ ID NO: 80, SEQ ID NO: 85, SEQ ID NO: 89, and SEQ ID NO: 97. In some embodiments, an antibody or compound of this disclosure comprises SEQ ID NO: 80, SEQ ID NO: 85, SEQ ID NO: 91, and SEQ ID NO: 96. In some embodiments, an antibody or compound of this disclosure comprises SEQ ID NO: 80, SEQ ID NO: 85, SEQ ID NO: 91, and SEQ ID NO: 97. In some embodiments, an antibody or compound of this disclosure comprises SEQ ID NO: 80, SEQ ID NO: 85, SEQ ID NO: 96, and SEQ ID NO: 97. In some embodiments, an antibody or compound of this disclosure comprises SEQ ID NO: 80, SEQ ID NO: 89, SEQ ID NO: 91, and SEQ ID NO: 96. In some embodiments, an antibody or compound of this disclosure comprises SEQ ID NO: 80, SEQ ID NO: 89, SEQ ID NO: 91, and SEQ ID NO: 97. In some embodiments, an antibody or compound of this disclosure comprises SEQ ID NO: 80, SEQ ID NO: 89, SEQ ID NO: 96, and SEQ ID NO: 97. In some embodiments, an antibody or compound of this disclosure comprises SEQ ID NO: 80, SEQ ID NO: 91, SEQ ID NO: 96, and SEQ ID NO: 97. In some embodiments, an antibody or compound of this disclosure comprises SEQ ID NO: 85, SEQ ID NO: 89, SEQ ID NO: 91, and SEQ ID NO: 96. In some embodiments, an antibody or compound of this disclosure comprises SEQ ID NO: 85, SEQ ID NO: 89, SEQ ID NO: 91, and SEQ ID NO: 97. In some embodiments, an antibody or compound of this disclosure comprises SEQ ID NO: 85, SEQ ID NO: 89, SEQ ID NO: 96, and SEQ ID NO: 97. In some embodiments, an antibody or compound of this disclosure comprises SEQ ID NO: 85, SEQ ID NO: 91, SEQ ID NO: 96, and SEQ ID NO: 97. In some embodiments, an antibody or compound of this disclosure comprises SEQ ID NO: 89, SEQ ID NO: 91, SEQ ID NO: 96, and SEQ ID NO: 97. In some embodiments, an antibody or compound of this disclosure comprises SEQ ID NO: 80, SEQ ID NO: 87, SEQ ID NO: 89, and SEQ ID NO: 91. In some embodiments, an antibody or compound of this disclosure comprises SEQ ID NO: 80, SEQ ID NO: 87, SEQ ID NO: 89, and SEQ ID NO: 96. In some embodiments, an antibody or compound of this disclosure comprises SEQ ID NO: 80, SEQ ID NO: 87, SEQ ID NO: 89, and SEQ ID NO: 97. In some embodiments, an antibody or compound of this disclosure comprises SEQ ID NO: 80, SEQ ID NO: 87, SEQ ID NO: 91, and SEQ ID NO: 96. In some embodiments, an antibody or compound of this disclosure comprises SEQ ID NO: 80, SEQ ID NO: 87, SEQ ID NO: 91, and SEQ ID NO: 97. In some embodiments, an antibody or compound of this disclosure comprises SEQ ID NO: 80, SEQ ID NO: 87, SEQ ID NO: 96, and SEQ ID NO: 97. In some embodiments, an antibody or compound of this disclosure comprises SEQ ID NO: 87, SEQ ID NO: 89, SEQ ID NO: 91, and SEQ ID NO: 96. In some embodiments, an antibody or compound of this disclosure comprises SEQ ID NO: 87, SEQ ID NO: 89, SEQ ID NO: 91, and SEQ ID NO: 97. In some embodiments, an antibody or compound of this disclosure comprises SEQ ID NO: 87, SEQ ID NO: 89, SEQ ID NO: 96, and SEQ ID NO: 97. In some embodiments, an antibody or compound of this disclosure comprises SEQ ID NO: 87, SEQ ID NO: 91, SEQ ID NO: 96, and SEQ ID NO: 97.

In some embodiments, an antibody or compound of this disclosure comprises SEQ ID NO: 80, SEQ ID NO: 85, SEQ ID NO: 89, SEQ ID NO: 91, and SEQ ID NO: 96. In some embodiments, an antibody or compound of this disclosure comprises SEQ ID NO: 80, SEQ ID NO: 85, SEQ ID NO: 89, SEQ ID NO: 91, and SEQ ID NO: 97. In some embodiments, an antibody or compound of this disclosure comprises SEQ ID NO: 80, SEQ ID NO: 85, SEQ ID NO: 89, SEQ ID NO: 96, and SEQ ID NO: 97. In some embodiments, an antibody or compound of this disclosure comprises SEQ ID NO: 80, SEQ ID NO: 85, SEQ ID NO: 91, SEQ ID NO: 96, and SEQ ID NO: 97. In some embodiments, an antibody or compound of this disclosure comprises SEQ ID NO: 80, SEQ ID NO: 89, SEQ ID NO: 91, SEQ ID NO: 96, and SEQ ID NO: 97. In some embodiments, an antibody or compound of this disclosure comprises SEQ ID NO: 85, SEQ ID NO: 89, SEQ ID NO: 91, SEQ ID NO: 96, and SEQ ID NO: 97. In some embodiments, an antibody or compound of this disclosure comprises SEQ ID NO: 80, SEQ ID NO: 87, SEQ ID NO: 89, SEQ ID NO: 91, and SEQ ID NO: 96. In some embodiments, an antibody or compound of this disclosure comprises SEQ ID NO: 80, SEQ ID NO: 87, SEQ ID NO: 89, SEQ ID NO: 91, and SEQ ID NO: 97. In some embodiments, an antibody or compound of this disclosure comprises SEQ ID NO: 80, SEQ ID NO: 87, SEQ ID NO: 89, SEQ ID NO: 96, and SEQ ID NO: 97. In some embodiments, an antibody or compound of this disclosure comprises SEQ ID NO: 80, SEQ ID NO: 87, SEQ ID NO: 91, SEQ ID NO: 96, and SEQ ID NO: 97. In some embodiments, an antibody or compound of this disclosure comprises SEQ ID NO: 87, SEQ ID NO: 89, SEQ ID NO: 91, SEQ ID NO: 96, and SEQ ID NO: 97.

In some embodiments, an antibody or compound of this disclosure comprises SEQ ID NO: 80, SEQ ID NO: 85, SEQ ID NO: 89, SEQ ID NO: 91, SEQ ID NO: 96, and SEQ ID NO: 97. In some embodiments, an antibody or compound of this disclosure comprises SEQ ID NO: 80, SEQ ID NO: 87, SEQ ID NO: 89, SEQ ID NO: 91, SEQ ID NO: 96, and SEQ ID NO: 97.

In some embodiments, an antibody or compound of this disclosure comprises any one of SEQ ID NOS: 99-113. In some embodiments, an antibody or compound of this disclosure comprises any one of SEQ ID NOS: 114-123. In some embodiments, an antibody or compound of this disclosure comprises any one of SEQ ID NOS: 124-131. In some embodiments, an antibody or compound of this disclosure comprises any one of SEQ ID NOS: 132-137. In some embodiments, an antibody or compound of this disclosure comprises any one of SEQ ID NOS: 138-143. In some embodiments, an antibody or compound of this disclosure comprises any one of SEQ ID NOS: 144-146.

In some embodiments, an antibody or compound of this disclosure comprises any one of SEQ ID NOS: 99-113 and any one of SEQ ID NOS: 114-123. In some embodiments, an antibody or compound of this disclosure comprises any one of SEQ ID NOS: 99-113 and any one of SEQ ID NOS: 124-131. In some embodiments, an antibody or compound of this disclosure comprises any one of SEQ ID NOS: 99-113 and any one of SEQ ID NOS: 132-137. In some embodiments, an antibody or compound of this disclosure comprises any one of SEQ ID NOS: 99-113 and any one of SEQ ID NOS: 138-143. In some embodiments, an antibody or compound of this disclosure comprises any one of SEQ ID NOS: 99-113 and any one of SEQ ID NOS: 144-146. In some embodiments, an antibody or compound of this disclosure comprises any one of SEQ ID NOS: 114-123 and any one of SEQ ID NOS: 124-131. In some embodiments, an antibody or compound of this disclosure comprises any one of SEQ ID NOS: 114-123 and any one of SEQ ID NOS: 132-137. In some embodiments, an antibody or compound of this disclosure comprises any one of SEQ ID NOS: 114-123 and any one of SEQ ID NOS: 138-143. In some embodiments, an antibody or compound of this disclosure comprises any one of SEQ ID NOS: 114-123 and any one of SEQ ID NOS: 144-146. In some embodiments, an antibody or compound of this disclosure comprises any one of SEQ ID NOS: 124-131 and any one of SEQ ID NOS: 132-137. In some embodiments, an antibody or compound of this disclosure comprises any one of SEQ ID NOS: 124-131 and any one of SEQ ID NOS: 138-143. In some embodiments, an antibody or compound of this disclosure comprises any one of SEQ ID NOS: 124-131 and any one of SEQ ID NOS: 144-146. In some embodiments, an antibody or compound of this disclosure comprises any one of SEQ ID NOS: 132-137 and any one of SEQ ID NOS: 138-143. In some embodiments, an antibody or compound of this disclosure comprises any one of SEQ ID NOS: 132-137 and any one of SEQ ID NOS: 144-146. In some embodiments, an antibody or compound of this disclosure comprises any one of SEQ ID NOS: 138-143 and any one of SEQ ID NOS: 144-146.

In some embodiments, an antibody or compound of this disclosure comprises any one of SEQ ID NOS: 99-113, any one of SEQ ID NOS: 114-123, and any one of SEQ ID NOS: 124-131. In some embodiments, an antibody or compound of this disclosure comprises any one of SEQ ID NOS: 99-113, any one of SEQ ID NOS: 114-123, and any one of SEQ ID NOS: 132-137. In some embodiments, an antibody or compound of this disclosure comprises any one of SEQ ID NOS: 99-113, any one of SEQ ID NOS: 114-123, and any one of SEQ ID NOS: 138-143. In some embodiments, an antibody or compound of this disclosure comprises any one of SEQ ID NOS: 99-113, any one of SEQ ID NOS: 114-123, and any one of SEQ ID NOS: 144-146. In some embodiments, an antibody or compound of this disclosure comprises any one of SEQ ID NOS: 99-113, any one of SEQ ID NOS: 124-131, and any one of SEQ ID NOS: 132-137. In some embodiments, an antibody or compound of this disclosure comprises any one of SEQ ID NOS: 99-113, any one of SEQ ID NOS: 124-131, and any one of SEQ ID NOS: 138-143. In some embodiments, an antibody or compound of this disclosure comprises any one of SEQ ID NOS: 99-113, any one of SEQ ID NOS: 124-131, and any one of SEQ ID NOS: 144-146. In some embodiments, an antibody or compound of this disclosure comprises any one of SEQ ID NOS: 99-113, any one of SEQ ID NOS: 132-137, and any one of SEQ ID NOS: 138-143. In some embodiments, an antibody or compound of this disclosure comprises any one of SEQ ID NOS: 99-113, any one of SEQ ID NOS: 132-137, and any one of SEQ ID NOS: 144-146. In some embodiments, an antibody or compound of this disclosure comprises any one of SEQ ID NOS: 99-113, any one of SEQ ID NOS: 138-143, and any one of SEQ ID NOS: 144-146. In some embodiments, an antibody or compound of this disclosure comprises any one of SEQ ID NOS: 114-123, any one of SEQ ID NOS: 124-131, and any one of SEQ ID NOS: 132-137. In some embodiments, an antibody or compound of this disclosure comprises any one of SEQ ID NOS: 114-123, any one of SEQ ID NOS: 124-131, and any one of SEQ ID NOS: 138-143. In some embodiments, an antibody or compound of this disclosure comprises any one of SEQ ID NOS: 114-123, any one of SEQ ID NOS: 124-131, and any one of SEQ ID NOS: 144-146. In some embodiments, an antibody or compound of this disclosure comprises any one of SEQ ID NOS: 114-123, any one of SEQ ID NOS: 132-137, and any one of SEQ ID NOS: 138-143. In some embodiments, an antibody or compound of this disclosure comprises any one of SEQ ID NOS: 114-123, any one of SEQ ID NOS: 132-137, and any one of SEQ ID NOS: 144-146. In some embodiments, an antibody or compound of this disclosure comprises any one of SEQ ID NOS: 114-123, any one of SEQ ID NOS: 138-143, and any one of SEQ ID NOS: 144-146. In some embodiments, an antibody or compound of this disclosure comprises any one of SEQ ID NOS: 124-131, any one of SEQ ID NOS: 132-137, and any one of SEQ ID NOS: 138-143. In some embodiments, an antibody or compound of this disclosure comprises any one of SEQ ID NOS: 124-131, any one of SEQ ID NOS: 132-137, and any one of SEQ ID NOS: 144-146. In some embodiments, an antibody or compound of this disclosure comprises any one of SEQ ID NOS: 124-131, any one of SEQ ID NOS: 138-143, and any one of SEQ ID NOS: 144-146. In some embodiments, an antibody or compound of this disclosure comprises any one of SEQ ID NOS: 132-137, any one of SEQ ID NOS: 138-143, and any one of SEQ ID NOS: 144-146.

In some embodiments, an antibody or compound of this disclosure comprises any one of SEQ ID NOS: 99-113, any one of SEQ ID NOS: 114-123, any one of SEQ ID NOS: 124-131, and any one of SEQ ID NOS: 132-137. In some embodiments, an antibody or compound of this disclosure comprises any one of SEQ ID NOS: 99-113, any one of SEQ ID NOS: 114-123, any one of SEQ ID NOS: 124-131, and any one of SEQ ID NOS: 138-143. In some embodiments, an antibody or compound of this disclosure comprises any one of SEQ ID NOS: 99-113, any one of SEQ ID NOS: 114-123, any one of SEQ ID NOS: 124-131, and any one of SEQ ID NOS: 144-146. In some embodiments, an antibody or compound of this disclosure comprises any one of SEQ ID NOS: 99-113, any one of SEQ ID NOS: 114-123, any one of SEQ ID NOS: 132-137, and any one of SEQ ID NOS: 138-143. In some embodiments, an antibody or compound of this disclosure comprises any one of SEQ ID NOS: 99-113, any one of SEQ ID NOS: 114-123, any one of SEQ ID NOS: 132-137, and any one of SEQ ID NOS: 144-146. In some embodiments, an antibody or compound of this disclosure comprises any one of SEQ ID NOS: 99-113, any one of SEQ ID NOS: 114-123, any one of SEQ ID NOS: 138-143, and any one of SEQ ID NOS: 144-146. In some embodiments, an antibody or compound of this disclosure comprises any one of SEQ ID NOS: 99-113, any one of SEQ ID NOS: 124-131, any one of SEQ ID NOS: 132-137, and any one of SEQ ID NOS: 138-143. In some embodiments, an antibody or compound of this disclosure comprises any one of SEQ ID NOS: 99-113, any one of SEQ ID NOS: 124-131, any one of SEQ ID NOS: 132-137, and any one of SEQ ID NOS: 144-146. In some embodiments, an antibody or compound of this disclosure comprises any one of SEQ ID NOS: 99-113, any one of SEQ ID NOS: 124-131, any one of SEQ ID NOS: 138-143, and any one of SEQ ID NOS: 144-146. In some embodiments, an antibody or compound of this disclosure comprises any one of SEQ ID NOS: 99-113, any one of SEQ ID NOS: 132-137, any one of SEQ ID NOS: 138-143, and any one of SEQ ID NOS: 144-146. In some embodiments, an antibody or compound of this disclosure comprises any one of SEQ ID NOS: 114-123, any one of SEQ ID NOS: 124-131, any one of SEQ ID NOS: 132-137, and any one of SEQ ID NOS: 138-143. In some embodiments, an antibody or compound of this disclosure comprises any one of SEQ ID NOS: 114-123, any one of SEQ ID NOS: 124-131, any one of SEQ ID NOS: 132-137, and any one of SEQ ID NOS: 144-146. In some embodiments, an antibody or compound of this disclosure comprises any one of SEQ ID NOS: 114-123, any one of SEQ ID NOS: 124-131, any one of SEQ ID NOS: 138-143, and any one of SEQ ID NOS: 144-146. In some embodiments, an antibody or compound of this disclosure comprises any one of SEQ ID NOS: 114-123, any one of SEQ ID NOS: 132-137, any one of SEQ ID NOS: 138-143, and any one of SEQ ID NOS: 144-146. In some embodiments, an antibody or compound of this disclosure comprises any one of SEQ ID NOS: 124-131, any one of SEQ ID NOS: 132-137, any one of SEQ ID NOS: 138-143, and any one of SEQ ID NOS: 144-146.

In some embodiments, an antibody or compound of this disclosure comprises any one of SEQ ID NOS: 99-113, any one of SEQ ID NOS: 114-123, any one of SEQ ID NOS: 124-131, any one of SEQ ID NOS: 132-137, and any one of SEQ ID NOS: 138-143. In some embodiments, an antibody or compound of this disclosure comprises any one of SEQ ID NOS: 99-113, any one of SEQ ID NOS: 114-123, any one of SEQ ID NOS: 124-131, any one of SEQ ID NOS: 132-137, and any one of SEQ ID NOS: 144-146. In some embodiments, an antibody or compound of this disclosure comprises any one of SEQ ID NOS: 99-113, any one of SEQ ID NOS: 114-123, any one of SEQ ID NOS: 124-131, any one of SEQ ID NOS: 138-143, and any one of SEQ ID NOS: 144-146. In some embodiments, an antibody or compound of this disclosure comprises any one of SEQ ID NOS: 99-113, any one of SEQ ID NOS: 114-123, any one of SEQ ID NOS: 132-137, any one of SEQ ID NOS: 138-143, and any one of SEQ ID NOS: 144-146. In some embodiments, an antibody or compound of this disclosure comprises any one of SEQ ID NOS: 99-113, any one of SEQ ID NOS: 124-131, any one of SEQ ID NOS: 132-137, any one of SEQ ID NOS: 138-143, and any one of SEQ ID NOS: 144-146. In some embodiments, an antibody or compound of this disclosure comprises any one of SEQ ID NOS: 114-123, any one of SEQ ID NOS: 124-131, any one of SEQ ID NOS: 132-137, any one of SEQ ID NOS: 138-143, and any one of SEQ ID NOS: 144-146.

In some embodiments, an antibody or compound of this disclosure comprises any one of SEQ ID NOS: 99-113, any one of SEQ ID NOS: 114-123, any one of SEQ ID NOS: 124-131, any one of SEQ ID NOS: 132-137, any one of SEQ ID NOS: 138-143, and any one of SEQ ID NOS: 144-146.

In some embodiments, an antibody or compound of this disclosure comprises SEQ ID NO 103, SEQ ID NO: 118, SEQ ID NO: 125, SEQ ID NO: 132, SEQ ID NO: 140, and SEQ ID NO: 144. In some embodiments, an antibody or compound of this disclosure comprises SEQ ID NO 108, SEQ ID NO: 123, SEQ ID NO: 127, SEQ ID NO: 135, SEQ ID NO: 143, and SEQ ID NO: 145. In some embodiments, an antibody or compound of this disclosure comprises SEQ ID NO 113, SEQ ID NO: 123, SEQ ID NO: 130, SEQ ID NO: 135, SEQ ID NO: 143, and SEQ ID NO: 145.

In some embodiments, an antibody or compound of this disclosure comprises SEQ ID NO: 80, SEQ ID NO: 85, SEQ ID NO: 89, SEQ ID NO: 91, SEQ ID NO: 96, SEQ ID NO: 97, SEQ ID NO 103, SEQ ID NO: 118, SEQ ID NO: 125, SEQ ID NO: 132, SEQ ID NO: 140, and SEQ ID NO: 144. In some embodiments, an antibody or compound of this disclosure comprises SEQ ID NO: 80, SEQ ID NO: 87, SEQ ID NO: 89, SEQ ID NO: 91, SEQ ID NO: 96, SEQ ID NO: 97, SEQ ID NO 103, SEQ ID NO: 118, SEQ ID NO: 125, SEQ ID NO: 132, SEQ ID NO: 140, and SEQ ID NO: 144. In some embodiments, an antibody or compound of this disclosure comprises SEQ ID NO: 80, SEQ ID NO: 85, SEQ ID NO: 89, SEQ ID NO: 91, SEQ ID NO: 96, SEQ ID NO: 97, SEQ ID NO 108, SEQ ID NO: 123, SEQ ID NO: 127, SEQ ID NO: 135, SEQ ID NO: 143, and SEQ ID NO: 145. In some embodiments, an antibody or compound of this disclosure comprises SEQ ID NO: 80, SEQ ID NO: 87, SEQ ID NO: 89, SEQ ID NO: 91, SEQ ID NO: 96, SEQ ID NO: 97, SEQ ID NO 108, SEQ ID NO: 123, SEQ ID NO: 127, SEQ ID NO: 135, SEQ ID NO: 143, and SEQ ID NO: 145. In some embodiments, an antibody or compound of this disclosure comprises SEQ ID NO: 80, SEQ ID NO: 85, SEQ ID NO: 89, SEQ ID NO: 91, SEQ ID NO: 96, SEQ ID NO: 97, SEQ ID NO 113, SEQ ID NO: 123, SEQ ID NO: 130, SEQ ID NO: 135, SEQ ID NO: 143, and SEQ ID NO: 145. In some embodiments, an antibody or compound of this disclosure comprises SEQ ID NO: 80, SEQ ID NO: 87, SEQ ID NO: 89, SEQ ID NO: 91, SEQ ID NO: 96, SEQ ID NO: 97, SEQ ID NO 113, SEQ ID NO: 123, SEQ ID NO: 130, SEQ ID NO: 135, SEQ ID NO: 143, and SEQ ID NO: 145.

EXAMPLES

Example 1: A Tetravalent Bispecific Antibody Comprising Antibody HC2:LC1 and Aflibercept-Derived Sequences To generate a tetravalent bispecific antibody in which the heavy chain of antibody HC2:LC1 was fused to an aflibercept-derived VEGF-binding domain, an amino acid sequence was generated comprising the following appended amino acid sequences, from N-terminus to C-terminus:

1) SEQ ID NO: 14 (heavy chain of antibody HC2:LC1);
2) SEQ ID NO: 31 (linker peptide, underlined); and
3) SEQ ID NO: 22 (aflibercept-derived sequence).

The resulting polypeptide (SEQ ID NO: 149) was co-expressed with SEQ ID NO: 17, to provide tetravalent, bispecific antibody HC2-AFL:LC1, comprising the sequences shown in TABLE 33. Amino acids 1-19 of SEQ ID NO: 149 are the heavy chain signal peptide (SEQ ID NO: 11). Amino acids 1-20 of SEQ ID NO: 17 are the light chain signal peptide (SEQ ID NO: 12). In some embodiments, a mature HC2-AFL:LC1 does not comprise the signal peptides. For example, a mature HC2-AFL:LC1 of the disclosure can comprise SEQ ID NO: 254 and SEQ ID NO: 250.

TABLE 33

| SEQ ID NO: | Name | Amino acid sequence |
|---|---|---|
| 149 | signal peptide-HC2-AFL | MGWTLVFLFLLSVTAGVHSEVQLVESGGGLVQPGGSLRLSCAASGFTFNANAMNWVRQAPGKGLEWVGRIRTKSNNYATYYAGSVKDRFTISRDDSKNSLYLQMNSLKTEDTAVYYCVRDYYGSSAWITYWGQGTLVTVSSASTKGPSVFPLAPCSRSTSESTAALGCLVKDYFPEPVTVSWNSGALTSGVHTFPAVLQSSGLYSLSSVVTVPSSSLGTKTYTCNVDHKPSNTKVDKRVESKYGPPCPPCPAPEFLGGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSLTCLVKGFYPSDIAVEWESNGQPENNYKTTPPVLDSDGSFFLYSRLTVDKSRWQEGNVFSCSVMHEALHNHYTQKSLSLSLGKGGGGSSDTGRPFVEMYSEIPEIIHMTEGRELVIPCRVTSPNITVTLKKFPLDTLIPDGKRIIWDSRKGFIISNATYKEIGLLTCEATVNGHLYKTNYLTHRQTNTIIDVVLSPSHGIELSVGEKLVLNCTARTELNVGIDFNWEYPSSKHQHKKLVNRDLKTQSGSEMKKFLSTLTIDGVTRSDQGLYTCAASSGLMTKKNSTFVRVHEK |
| 17 | Signal peptide-LC1 | MVSSAQFLGLLLLCFQGTRCDVVMTQSPSFLSASVGDRVTITCKASQHVGTAVAWYQQRPGKAPKLLIYWASTRHTGVPSRFSGSGSGTEFTLTISSLQPEDFATYFCQQYSSYPFTFGGGTKLEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| 254 | HC2-AFL | EVQLVESGGGLVQPGGSLRLSCAASGFTFNANAMNWVRQAPGKGLEWVGRIRTKSNNYATYYAGSVKDRFTISRDDSKNSLYLQMNSLKTEDTAVYYCVRDYYGSSAWITYWGQGTLVTVSSASTKGPSVFPLAPCSRSTSESTAALGCLVKDYFPEPVTVSWNSGALTSGVHTFPAVLQSSGLYSLSSVVTVPSSSLGTKTYTCNVDHKPSNTKVDKRVESKYGPPCPPCPAPEFLGGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSLTCLVKGFYPSDIAVEWESNGQPENNYKTTPPVLDSDGSFFLYSRLTVDKSRWQEGNVFSCSVMHEALHNHYTQKSLSLSLGKG |

TABLE 33-continued

| SEQ ID NO:Name | Amino acid sequence |
|---|---|
| | GGGSSDTGRPFVEMYSEIPEIIHMTEGRELVIPCRVTSPNITVT<br>LKKFPLDTLIPDGKRIIWDSRKGFIISNATYKEIGLLTCEATVN<br>GHLYKTNYLTHRQTNTIIDVVLSPSHGIELSVGEKLVLNCTA<br>RTELNVGIDFNWEYPSSKHQHKKLVNRDLKTQSGSEMKKF<br>LSTLTIDGVTRSDQGLYTCAASSGLMTKKNSTFVRVHEK |

Example 2: A Tetravalent Bispecific Antibody Comprising Antibody HC2:LC1 and Brolucizumab-Derived Sequences To generate a tetravalent bispecific antibody in which the heavy chain of antibody HC2:LC1 was fused to a brolucizumab-derived VEGF-binding domain, an amino acid sequence was generated comprising the following appended amino acid sequences, from N-terminus to C-terminus:

1) SEQ ID NO: 14 (heavy chain of antibody HC2:LC1);
2) SEQ ID NO: 31 (linker peptide, underlined); and
3) SEQ ID NO: 23 (brolucizumab-derived sequence).

The resulting polypeptide (SEQ ID NO: 150) was co-expressed with SEQ ID NO: 17, to provide tetravalent, bispecific antibody HC2-BRO:LC1, comprising the sequences shown in TABLE 34. Amino acids 1-19 of SEQ ID NO: 150 are the heavy chain signal peptide (SEQ ID NO: 11). Amino acids 1-20 of SEQ ID NO: 17 are the light chain signal peptide (SEQ ID NO: 12). In some embodiments, a mature HC2-BRO:LC1 does not comprise the signal peptides. For example, a mature HC2-BRO:LC1 of the disclosure can comprise SEQ ID NO: 255 and SEQ ID NO: 250.

TABLE 34

| SEQ ID NO | Name | Amino acid sequence |
|---|---|---|
| 150 | signal peptide-HC2-BRO | MGWTLVFLFLLSVTAGVHSEVQLVESGGGLVQPGGSLRLSC<br>AASGFTFNANAMNWVRQAPGKGLEWVGRIRTKSNNYATY<br>YAGSVKDRFTISRDDSKNSLYLQMNSLKTEDTAVYYCVRD<br>YYGSSAWITYWGQGTLVTVSSASTKGPSVFPLAPCSRSTSES<br>TAALGCLVKDYFPEPVTVSWNSGALTSGVHTFPAVLQSSGL<br>YSLSSVVTVPSSSLGTKTYTCNVDHKPSNTKVDKRVESKYG<br>PPCPPCPAPEFLGGPSVFLFPPKPKDTLMISRTPEVTCVVVDV<br>SQEDPEVQFNWYVDGVEVHNAKTKPREEQFNSTYRVVSVL<br>TVLHQDWLNGKEYKCKVSNKGLPSSIEKTISKAKGQPREPQ<br>VYTLPPSQEEMTKNQVSLTCLVKGFYPSDIAVEWESNGQPE<br>NNYKTTPPVLDSDGSFFLYSRLTVDKSRWQEGNVFSCSVMH<br>EALHNHYTQKSLSLSLGKGGGGSEIVMTQSPSTLSASVGDR<br>VIITCQASEIIHSWLAWYQQKPGKAPKLLIYLASTLASGVPSR<br>FSGSGSGAEFTLTISSLQPDDFATYYCQNVYLASTNGANFGQ<br>GTKLTVLGGGGGSGGGGSGGGGSGGGGSEVQLVESGGGLV<br>QPGGSLRLSCTASGFSLTDYYYMTWVRQAPGKGLEWVGFI<br>DPDDDPYYATWAKGRFTISRDNSKNTLYLQMNSLRAEDTA<br>VYYCAGGDHNSGWGLDIWGQGTLVTVSS |
| 17 | Signal peptide-LC1 | MVSSAQFLGLLLLCFQGTRCDVVMTQSPSFLSASVGDRVTIT<br>CKASQHVGTAVAWYQQRPGKAPKLLIYWASTRHTGVPSRF<br>SGSGSGTEFTLTISSLQPEDFATYFCQQYSSYPFTFGGGTKLEI<br>KRTVAAPSVFIFPPSDEQLKSGTASVVCLLNNFYPREAKVQ<br>WKVDNALQSGNSQESVTEQDSKDSTYSLSSTLTLSKADYEK<br>HKVYACEVTHQGLSSPVTKSFNRGEC |
| 255 | HC2-BRO | EVQLVESGGGLVQPGGSLRLSCAASGFTFNANAMNWVRQA<br>PGKGLEWVGRIRTKSNNYATYYAGSVKDRFTISRDDSKNSL<br>YLQMNSLKTEDTAVYYCVRDYYGSSAWITYWGQGTLVTV<br>SSASTKGPSVFPLAPCSRSTSESTAALGCLVKDYFPEPVTVS<br>WNSGALTSGVHTFPAVLQSSGLYSLSSVVTVPSSSLGTKTYT<br>CNVDHKPSNTKVDKRVESKYGPPCPPCPAPEFLGGPSVFLFP<br>PKPKDTLMISRTPEVTCVVVDVSQEDPEVQFNWYVDGVEV<br>HNAKTKPREEQFNSTYRVVSVLTVLHQDWLNGKEYKCKVS<br>NKGLPSSIEKTISKAKGQPREPQVYTLPPSQEEMTKNQVSLT<br>CLVKGFYPSDIAVEWESNGQPENNYKTTPPVLDSDGSFFLYS<br>RLTVDKSRWQEGNVFSCSVMHEALHNHYTQKSLSLSLGKG<br>GGGSEIVMTQSPSTLSASVGDRVIITCQASEIIHSWLAWYQQ<br>KPGKAPKLLIYLASTLASGVPSRFSGSGSGAEFTLTISSLQPD<br>DFATYYCQNVYLASTNGANFGQGTKLTVLGGGGGSGGGGS<br>GGGGSGGGGSEVQLVESGGGLVQPGGSLRLSCTASGFSLTD<br>YYYMTWVRQAPGKGLEWVGFIDPDDDPYYATWAKGRFTIS<br>RDNSKNTLYLQMNSLRAEDTAVYYCAGGDHNSGWGLDIW<br>GQGTLVTVSS |

Example 3: A Tetravalent Bispecific Antibody Comprising Antibody HC2:LC1 and Ranibizumab-Derived Sequences To generate a tetravalent bispecific antibody in which the heavy chain of antibody HC2:LC1 was fused to a ranibizumab-derived VEGF-binding domain, an amino acid sequence was generated comprising the following appended amino acid sequences, from N-terminus to C-terminus:

1) SEQ ID NO: 14 (heavy chain ofLantibody HC2:LC1);
2) SEQ ID NO: 31 (linker peptide, underlined); and
3) SEQ ID NO: 28 (ranibizumab-derived sequence).

The resulting polypeptide (SEQ ID NO: 151) was co-expressed with SEQ ID NO: 17, to provide tetravalent, bispecific antibody HC2-RAN:LC1, comprising the sequences shown in TABLE 35. Amino acids 1-19 of SEQ ID NO: 151 are the heavy chain signal peptide (SEQ ID NO: 11). Amino acids 1-20 of SEQ ID NO: 17 are the light chain signal peptide (SEQ ID NO: 12). In some embodiments, a mature HC2-RAN:LC1 does not comprise the signal peptides. For example, a mature HC2-RAN:LC1 of the disclosure can comprise SEQ ID NO: 256 and SEQ ID NO: 250.

TABLE 35

| SEQ ID NO: | Name | Amino acid sequence |
|---|---|---|
| 151 | Signal peptide-HC2-RAN | MGWTLVFLFLLSVTAGVHSEVQLVESGGGLVQPGGSLRLSCAASGFTFNANAMNWVRQAPGKGLEWVGRIRTKSNNYATYYAGSVKDRFTISRDDSKNSLYLQMNSLKTEDTAVYYCVRDYYGSSAWITYWGQGTLVTVSSASTKGPSVFPLAPCSRSTSESTAALGCLVKDYFPEPVTVSWNSGALTSGVHTFPAVLQSSGLYSLSSVVTVPSSSLGTKTYTCNVDHKPSNTKVDKRVESKYGPPCPPCPAPEFLGGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSLTCLVKGFYPSDIAVEWESNGQPENNYKTTPPVLDSDGSFFLYSRLTVDKSRWQEGNVFSCSVMHEALHNHYTQKSLSLSLGKGGGGSEVQLVESGGGLVQPGGSLRLSCAASGYDFTHYGMNWVRQAPGKGLEWVGWINTYTGEPTYAADFKRRFTFSLDTSKSTAYLQMNSLRAEDTAVYYCAKYPYYYGTSHWYFDVWGQGTLVTVSSGGGGSGGGGSGGGGSDIQLTQSPSSLSASVGDRVTITCSASQDISNYLNWYQQKPGKAPKVLIYFTSSLHSGVPSRFSGSGSGTDFTLTISSLQPEDFATYYCQQYSTVPWTFGQGTKVEIK |
| 17 | Signal peptide-LC1 | MVSSAQFLGLLLLCFQGTRCDVVMTQSPSFLSASVGDRVTITCKASQHVGTAVAWYQQRPGKAPKLLIYWASTRHTGVPSRFSGSGSGTEFTLTISSLQPEDFATYFCQQYSSYPFTFGGGTKLEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| 256 | HC2-RAN | EVQLVESGGGLVQPGGSLRLSCAASGFTFNANAMNWVRQAPGKGLEWVGRIRTKSNNYATYYAGSVKDRFTISRDDSKNSLYLQMNSLKTEDTAVYYCVRDYYGSSAWITYWGQGTLVTVSSASTKGPSVFPLAPCSRSTSESTAALGCLVKDYFPEPVTVSWNSGALTSGVHTFPAVLQSSGLYSLSSVVTVPSSSLGTKTYTCNVDHKPSNTKVDKRVESKYGPPCPPCPAPEFLGGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSLTCLVKGFYPSDIAVEWESNGQPENNYKTTPPVLDSDGSFFLYSRLTVDKSRWQEGNVFSCSVMHEALHNHYTQKSLSLSLGKGGGGSEVQLVESGGGLVQPGGSLRLSCAASGYDFTHYGMNWVRQAPGKGLEWVGWINTYTGEPTYAADFKRRFTFSLDTSKSTAYLQMNSLRAEDTAVYYCAKYPYYYGTSHWYFDVWGQGTLVTVSSGGGGSGGGGSGGGGSDIQLTQSPSSLSASVGDRVTITCSASQDISNYLNWYQQKPGKAPKVLIYFTSSLHSGVPSRFSGSGSGTDFTLTISSLQPEDFATYYCQQYSTVPWTFGQGTKVEIK |

Example 4: Characterization of Bispecific Compounds

The following multi-specific antibodies of the disclosure were generated: (i) HC2-RAN:LC1, (ii) HC2-AFL:LC1, (iii) HC2-BRO:LC1, (iv) HC2-ABI:LC1, (v) HC2:LC1-AFL, (vi) HC2:LC1-BRO, (vii) HC2:LC1-ABI, (viii) HC2-AFL:LC1-AFL, (ix) HC2-BRO:LC1-BRO, and (x) HC2-ABI:LC1-ABI. Enzyme-linked immunosorbent assays (ELISAs) were performed to determine binding of these antibodies to VEGF and HPTP-03 (VE-PTP). Binding to HPTP-03 (VE-PTP) was confirmed for all constructs, and binding to VEGF was confirmed for all constructs except for HC2-RAN:LC1.

Figure 16:
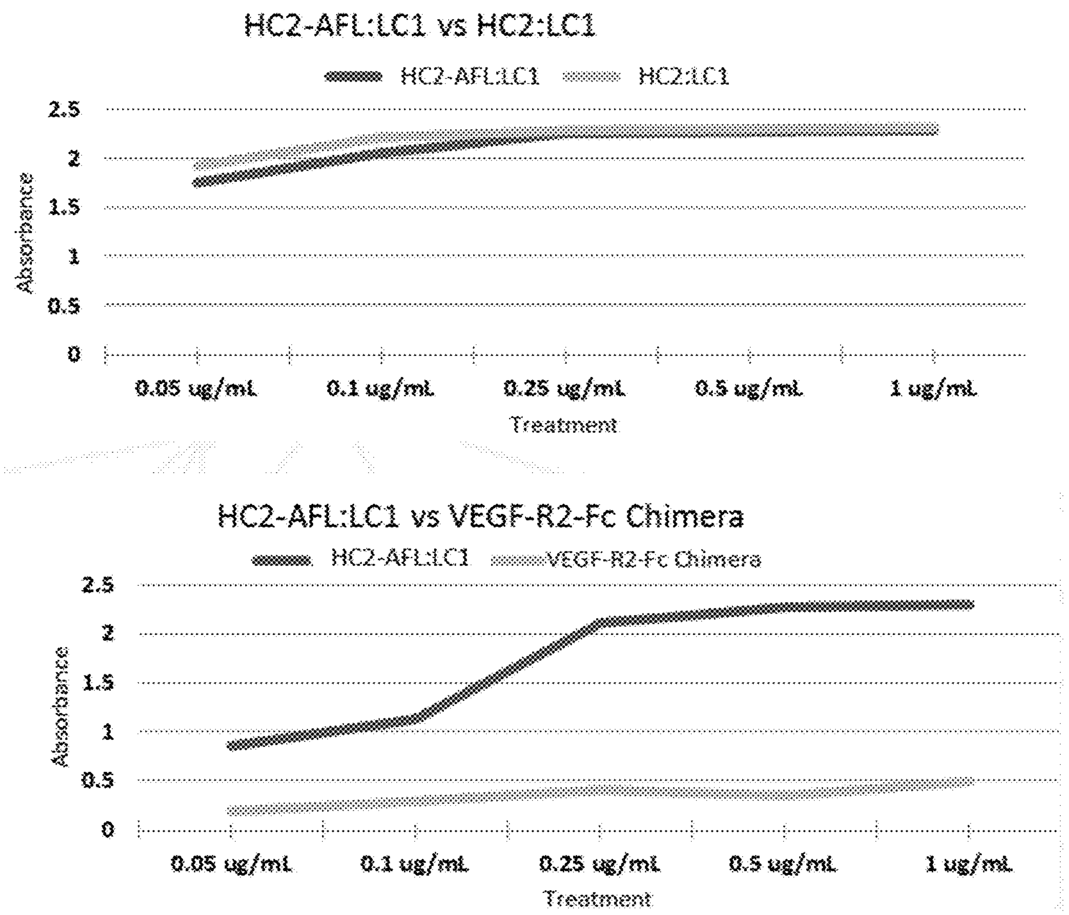
FIG. 16: ELISA data demonstrating binding of a tetravalent bispecific antibody HC2-AFL:LC1 to HPTP-β (top panel) and VEGF (bottom panel).
Figure 17:
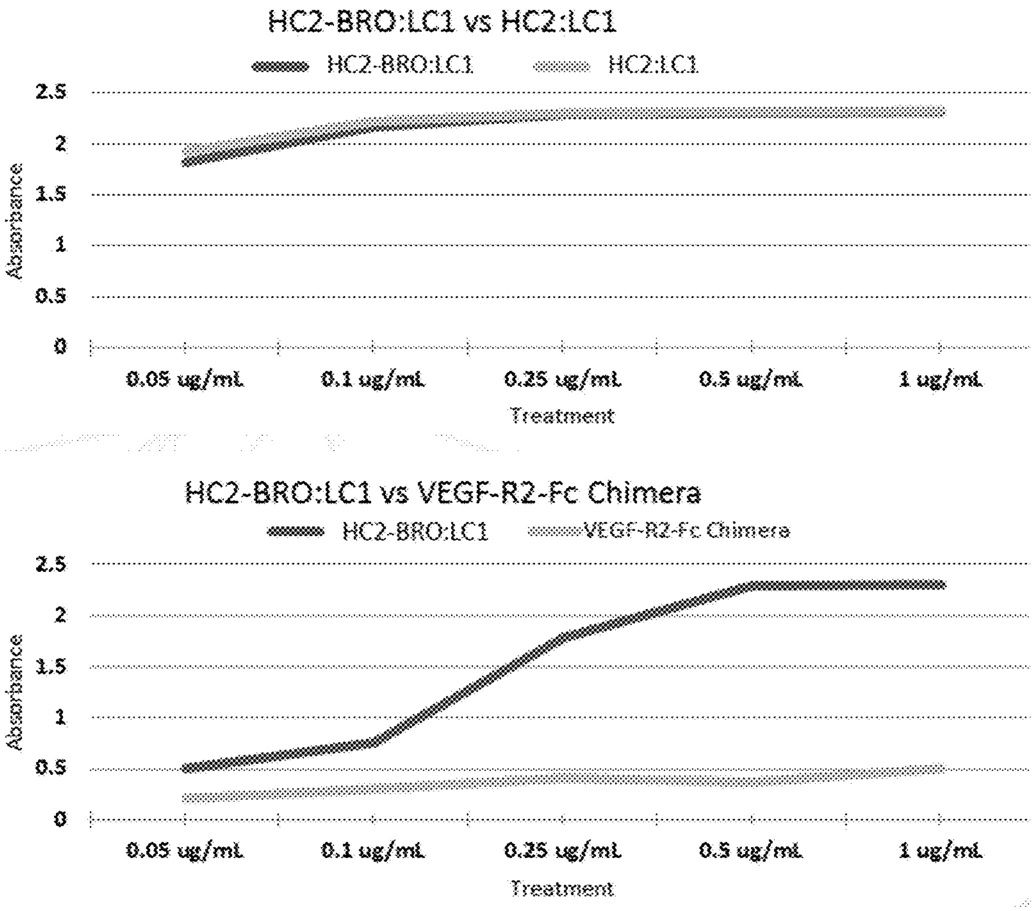
FIG. 17: ELISA data demonstrating binding of a tetravalent bispecific antibody HC2-BRO:LC1 to HPTP-β (top panel) and VEGF (bottom panel).
Figure 18:
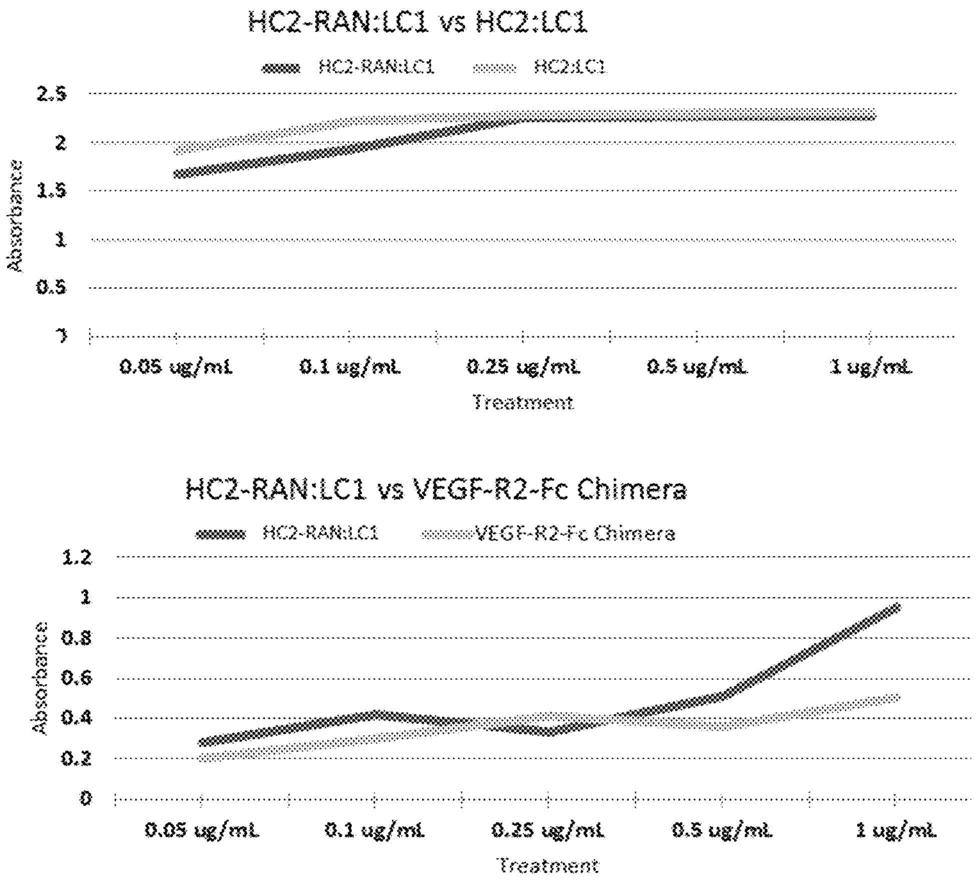
FIG. 18: ELISA data testing binding of a tetravalent bispecific antibody HC2-RAN:LC1 to HPTP-β (top panel) and VEGF (bottom panel).

The tetravalent, bispecific antibodies described in EXAMPLES 1-3 were produced and characterized as described in TABLE 36, FIG. 16, FIG. 17, and FIG. 18.

TABLE 36 provides results from small scale production and characterization of bispecific candidates.

TABLE 36

| Candidate Name | Yield (mg) | HC MW (Da)** | LC MW (Da)** | Intact MW (Da) |
|---|---|---|---|---|
| HC2-RAN:LC1 | 0.84 | 76113/76109 | 23400/23399 | 198981 |
| HC2-AFL:LC1 | 1.32 | 72756/72748 | 23400/23399 | 192270 |
| HC2-BRO:LC1 | 0.73 | 75882/75877 | 23400/23399 | 198532 |

**m/c = measured/calculated

FIG. 16 provides ELISA data demonstrating binding of a tetravalent bispecific antibody HC2-AFL:LC1 to HPTP-β (top panel) and VEGF (bottom panel). Binding is compared to controls (HC2:LC1 in top panel, VEGF-R2-Fc chimera in bottom panel).

FIG. 17 provides ELISA data demonstrating binding of a tetravalent bispecific antibody HC2-BRO:LC1 to HPTP-β (top panel) and VEGF (bottom panel). Binding is compared to controls (HC2:LC1 in top panel, VEGF-R2-Fc chimera in bottom panel).

FIG. 18 provides ELISA data evaluating binding of a tetravalent bispecific antibody HC2-RAN:LC1 to HPTP-β (top panel) and VEGF (bottom panel). Binding is compared to controls (HC2:LC1 in top panel, VEGF-R2-Fc chimera in bottom panel).

Example 5: A Tetravalent Bispecific Antibody Comprising Antibody HC2:LC1 and Abicipar-Derived Sequences To generate a tetravalent bispecific antibody in which the heavy chain of antibody HC2:LC1 was fused to an abicipar-derived VEGF-binding domain, an amino acid sequence was generated comprising the following appended amino acid sequences, from N-terminus to C-terminus:

1) Residues 1-467 of SEQ ID NO: 14 (heavy chain of antibody HC2:LC1);
2) SEQ ID NO: 31 (linker peptide, underlined); and
3) SEQ ID NO: 244 (abicipar-derived sequence).

The resulting polypeptide (SEQ ID NO: 231) was co-expressed with SEQ ID NO: 17, to provide tetravalent, bispecific antibody HC2-ABI:LC1, comprising the sequences shown in TABLE 37. Amino acids 1-19 of SEQ ID NO: 231 are the heavy chain signal peptide (SEQ ID NO: 11). Amino acids 1-20 of SEQ ID NO: 17 are the light chain signal peptide (SEQ ID NO: 12). In some embodiments, a mature HC2-ABI:LC1 does not comprise the signal peptides. For example, a mature HC2-ABI:LC1 of the disclosure can comprise SEQ ID NO: 257 and SEQ ID NO: 250.

TABLE 37

| SEQ ID NO: | Name | Amino acid sequence |
|---|---|---|
| 231 | Signal peptide-HC2-ABI | MGWTLVFLFLLSVTAGVHSEVQLVESGGGLVQPGGSLRLSC<br>AASGFTFNANAMNWVRQAPGKGLEWVGRIRTKSNNYATY<br>YAGSVKDRFTISRDDSKNSLYLQMNSLKTEDTAVYYCVRD<br>YYGSSAWITYWGQGTLVTVSSASTKGPSVFPLAPCSRSTSES<br>TAALGCLVKDYFPEPVTVSWNSGALTSGVHTFPAVLQSSGL<br>YSLSSVVTVPSSSLGTKTYTCNVDHKPSNTKVDKRVESKYG<br>PPCPPCPAPEFLGGPSVFLFPPKPKDTLMISRTPEVTCVVVDV<br>SQEDPEVQFNWYVDGVEVHNAKTKPREEQFNSTYRVVSVL<br>TVLHQDWLNGKEYKCKVSNKGLPSSIEKTISKAKGQPREPQ<br>VYTLPPSQEEMTKNQVSLTCLVKGFYPSDIAVEWESNGQPE<br>NNYKTTPPVLDSDGSFFLYSRLTVDKSRWQEGNVFSCSVMH<br>EALHNHYTQKSLSLSLGGGGGSDLDKKLLEAARAGQDDEV<br>RILMANGADVNARDSTGWTPLHLAAPWGHPEIVEVLLKNG<br>ADVNAADFQGWTPLHLAAAVGHLEIVEVLLKYGADVNAQ<br>DKFGKTAFDISIDNGNEDLAEILQKAA |
| 17 | Signal peptide-LC1 | MVSSAQFLGLLLLCFQGTRCDVVMTQSPSFLSASVGDRVTIT<br>CKASQHVGTAVAWYQQRPGKAPKLLIYWASTRHTGVPSRF<br>SGSGSGTEFTLTISSLQPEDFATYFCQQYSSYPFTFGGGTKLEI<br>KRTVAAPSVFIFPPSDEQLKSGTASVVCLLNNFYPREAKVQ<br>WKVDNALQSGNSQESVTEQDSKDSTYSLSSTLTLSKADYEK<br>HKVYACEVTHQGLSSPVTKSFNRGEC |
| 257 | HC2-ABI | EVQLVESGGGLVQPGGSLRLSCAASGFTENANAMNWVRQA<br>PGKGLEWVGRIRTKSNNYATYYAGSVKDRFTISRDDSKNSL<br>YLQMNSLKTEDTAVYYCVRDYYGSSAWITYWGQGTLVTV<br>SSASTKGPSVFPLAPCSRSTSESTAALGCLVKDYFPEPVTVS<br>WNSGALTSGVHTFPAVLQSSGLYSLSSVVTVPSSSLGTKTYT<br>CNVDHKPSNTKVDKRVESKYGPPCPPCPAPEFLGGPSVFLFP<br>PKPKDTLMISRTPEVTCVVVDVSQEDPEVQFNWYVDGVEV<br>HNAKTKPREEQFNSTYRVVSVLTVLHQDWLNGKEYKCKVS<br>NKGLPSSIEKTISKAKGQPREPQVYTLPPSQEEMTKNQVSLT<br>CLVKGFYPSDIAVEWESNGQPENNYKTTPPVLDSDGSFFLYS<br>RLTVDKSRWQEGNVFSCSVMHEALHNHYTQKSLSLSLGGG<br>GGSDLDKKLLEAARAGQDDEVRILMANGADVNARDSTGW |

TABLE 37-continued

| SEQ ID NO:Name | Amino acid sequence |
|---|---|
| | TPLHLAAPWGHPEIVEVLLKNGADVNAADFQGWTPLHLAA<br>AVGHLEIVEVLLKYGADVNAQDKFGKTAFDISIDNGNEDLA<br>EILQKAA |

Example 6: A Hexavalent Bispecific Antibody Comprising Antibody HC2:LC1 and Brolucizumab-Derived Sequences To generate a heavy chain with brolucizumab-derived VEGF-binding domains added at the C-terminus, an amino acid sequence was generated comprising the following appended amino acid sequences, from N-terminus to C-terminus:

1) SEQ ID NO: 14 (heavy chain of antibody HC2:LC1);

2) SEQ ID NO: 31 (linker peptide, underlined); and

3) SEQ ID NO: 23 (brolucizumab-derived sequence).

To generate a light chain with brolucizumab-derived VEGF-binding domains added at the C-terminus, an amino acid sequence was generated comprising the following appended amino acid sequences, from N-terminus to C-terminus:

1) SEQ ID NO: 17 (light chain of antibody HC2:LC1);

2) SEQ ID NO: 31 (linker peptide, underlined); and

3) SEQ ID NO: 23 (brolucizumab-derived sequence).

The resulting polypeptides, SEQ ID NO: 150 and SEQ ID NO: 218 were co-expressed to provide a hexavalent, bispecific antibody HC2-BRO:LC1-BRO shown in TABLE 38. Amino acids 1-19 of SEQ ID NO: 150 are the heavy chain signal peptide (SEQ ID NO: 11). Amino acids 1-20 of SEQ ID NO: 218 are the light chain signal peptide (SEQ ID NO: 12). In some embodiments, a mature HC2-BRO:LC1-BRO does not comprise the signal peptides. For example, a mature HC2-BRO:LC1-BRO of the disclosure can comprise SEQ ID NO: 255 and SEQ ID NO: 258.

TABLE 38

| SEQ ID NO: | Name | Amino acid sequence |
|---|---|---|
| 150 | Signal peptide-HC2-BRO | MGWTLVFLFLLSVTAGVHSEVQLVESGGGLVQPGGSLRLSC<br>AASGFTFNANAMNWVRQAPGKGLEWVGRIRTKSNNYATY<br>YAGSVKDRFTISRDDSKNSLYLQMNSLKTEDTAVYYCVRD<br>YYGSSAWITYWGQGTLVTVSSASTKGPSVFPLAPCSRSTSES<br>TAALGCLVKDYFPEPVTVSWNSGALTSGVHTFPAVLQSSGL<br>YSLSSVVTVPSSSLGTKTYTCNVDHKPSNTKVDKRVESKYG<br>PPCPPCPAPEFLGGPSVFLFPPKPKDTLMISRTPEVTCVVVDV<br>SQEDPEVQFNWYVDGVEVHNAKTKPREEQFNSTYRVVSVL<br>TVLHQDWLNGKEYKCKVSNKGLPSSIEKTISKAKGQPREPQ<br>VYTLPPSQEEMTKNQVSLTCLVKGFYPSDIAVEWESNGQPE<br>NNYKTTPPVLDSDGSFFLYSRLTVDKSRWQEGNVFSCSVMH<br>EALHNHYTQKSLSLSLGKGGGGSEIVMTQSPSTLSASVGDR<br>VIITCQASEIIHSWLAWYQQKPGKAPKLLIYLASTLASGVPSR<br>FSGSGSGAEFTLTISSLQPDDFATYYCQNVYLASTNGANFGQ<br>GTKLTVLGGGGGSGGGGSGGGGSGGGGSEVQLVESGGGLV<br>QPGGSLRLSCTASGFSLTDYYYMTWVRQAPGKGLEWVGFI<br>DPDDDPYYATWAKGRFTISRDNSKNTLYLQMNSLRAEDTA<br>VYYCAGGDHNSGWGLDIWGQGTLVTVSS |
| 218 | Signal peptide-LC1-BRO | MVSSAQFLGLLLLCFQGTRCDVVMTQSPSFLSASVGDRVTIT<br>CKASQHVGTAVAWYQQRPGKAPKLLIYWASTRHTGVPSRF<br>SGSGSGTEFTLTISSLQPEDFATYFCQQYSSYPFTFGGGTKLEI<br>KRTVAAPSVFIFPPSDEQLKSGTASVVCLLNNFYPREAKVQ<br>WKVDNALQSGNSQESVTEQDSKDSTYSLSSTLTLSKADYEK<br>HKVYACEVTHQGLSSPVTKSFNRGECGGGGSEIVMTQSPST<br>LSASVGDRVIITCQASEIIHSWLAWYQQKPGKAPKLLIYLAS<br>TLASGVPSRFSGSGSGAEFTLTISSLQPDDFATYYCQNVYLA<br>STNGANFGQGTKLTVLGGGGGSGGGGSGGGGSGGGGSEVQ<br>LVESGGGLVQPGGSLRLSCTASGFSLTDYYYMTWVRQAPG<br>KGLEWVGFIDPDDDPYYATWAKGRFTISRDNSKNTLYLQM<br>NSLRAEDTAVYYCAGGDHNSGWGLDIWGQGTLVTVSS |
| 258 | LC1-BRO | DVVMTQSPSFLSASVGDRVTITCKASQHVGTAVAWYQQRP<br>GKAPKLLIYWASTRHTGVPSRFSGSGSGTEFTLTISSLQPEDF<br>ATYFCQQYSSYPFTFGGGTKLEIKRTVAAPSVFIFPPSDEQLK<br>SGTASVVCLLNNFYPREAKVQWKVDNALQSGNSQESVTEQ<br>DSKDSTYSLSSTLTLSKADYEKHKVYACEVTHQGLSSPVTK<br>SFNRGECGGGGSEIVMTQSPSTLSASVGDRVIITCQASEIIHS<br>WLAWYQQKPGKAPKLLIYLASTLASGVPSRFSGSGSGAEFT<br>LTISSLQPDDFATYYCQNVYLASTNGANFGQGTKLTVLGGG<br>GGSGGGGSGGGGSGGGGSEVQLVESGGGLVQPGGSLRLSC<br>TASGFSLTDYYYMTWVRQAPGKGLEWVGFIDPDDDPYYAT<br>WAKGRFTISRDNSKNTLYLQMNSLRAEDTAVYYCAGGDHN<br>SGWGLDIWGQGTLVTVSS |

Example 7: A Hexavalent Bispecific Antibody Comprising Antibody HC2:LC1 and Aflibercept-Derived Sequences To generate a heavy chain with aflibercept-derived VEGF-binding domains added at the C-terminus, an amino acid sequence was generated comprising the following appended amino acid sequences, from N-terminus to C-terminus:

1) SEQ ID NO: 14 (heavy chain of antibody HC2:LC1);
2) SEQ ID NO: 31 (linker peptide, underlined); and
3) SEQ ID NO: 22 (aflibercept-derived sequence).

To generate a light chain with aflibercept-derived VEGF-binding domains added at the C-terminus, an amino acid sequence was generated comprising the following appended amino acid sequences, from N-terminus to C-terminus:

1) SEQ ID NO: 17 (light chain of antibody HC2:LC1);
2) SEQ ID NO: 31 (linker peptide, underlined); and
3) SEQ ID NO: 22 (aflibercept-derived sequence).

The resulting polypeptides, SEQ ID NO: 149 and SEQ ID NO: 219 were co-expressed to provide a hexavalent, bispecific antibody HC2-AFL:LC1-AFL shown in TABLE 39. Amino acids 1-19 of SEQ ID NO: 149 are the heavy chain signal peptide (SEQ ID NO: 11). Amino acids 1-20 of SEQ ID NO: 219 are the light chain signal peptide (SEQ ID NO: 12). In some embodiments, a mature HC2-AFL:LC1-AFL does not comprise the signal peptides. For example, a mature HC2-AFL:LC1-AFL of the disclosure can comprise SEQ ID NO: 254 and SEQ ID NO: 259.

TABLE 39

| SEQ ID NO: | Name | Amino acid sequence |
|---|---|---|
| 149 | Signal peptide-HC2-AFL | MGWTLVFLFLLSVTAGVHSEVQLVESGGGLVQPGGSLRLSCAASGFTFNANAMNWVRQAPGKGLEWVGRIRTKSNNYATYYAGSVKDRFTISRDDSKNSLYLQMNSLKTEDTAVYYCVRDYYGSSAWITYWGQGTLVTVSSASTKGPSVFPLAPCSRSTSESTAALGCLVKDYFPEPVTVSWNSGALTSGVHTFPAVLQSSGLYSLSSVVTVPSSSLGTKTYTCNVDHKPSNTKVDKRVESKYGPPCPPCPAPEFLGGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSLTCLVKGFYPSDIAVEWESNGQPENNYKTTPPVLDSDGSFFLYSRLTVDKSRWQEGNVFSCSVMHEALHNHYTQKSLSLSLGKGGGGSSDTGRPFVEMYSEIPEIIHMTEGRELVIPCRVTSPNITVTLKKFPLDTLIPDGKRIIWDSRKGFIISNATYKEIGLLTCEATVNGHLYKTNYLTHRQTNTIIDVVLSPSHGIELSVGEKLVLNCTARTELNVGIDFNWEYPSSKHQHKKLVNRDLKTQSGSEMKKFLSTLTIDGVTRSDQGLYTCAASSGLMTKKNSTFVRVHEK |
| 219 | Signal peptide-LC1-AFL | MVSSAQFLGLLLLCFQGTRCDVVMTQSPSFLSASVGDRVTITCKASQHVGTAVAWYQQRPGKAPKLLIYWASTRHTGVPSRFSGSGSGTEFTLTISSLQPEDFATYFCQQYSSYPFTFGGGTKLEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGECGGGGSSDTGRPFVEMYSEIPEIIHMTEGRELVIPCRVTSPNITVTLKKFPLDTLIPDGKRIIWDSRKGFIISNATYKEIGLLTCEATVNGHLYKTNYLTHRQTNTIIDVVLSPSHGIELSVGEKLVLNCTARTELNVGIDFNWEYPSSKHQHKKLVNRDLKTQSGSEMKKFLSTLTIDGVTRSDQGLYTCAASSGLMTKKNSTFVRVHEK |
| 259 | LC1-AFL | DVVMTQSPSFLSASVGDRVTITCKASQHVGTAVAWYQQRPGKAPKLLIYWASTRHTGVPSRFSGSGSGTEFTLTISSLQPEDFATYFCQQYSSYPFTFGGGTKLEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGECGGGGSSDTGRPFVEMYSEIPEIMMTEGRELVIPCRVTSPNITVTLKKFPLDTLIPDGKRIIWDSRKGFIISNATYKEIGLLTCEATVNGHLYKTNYLTHRQTNTIIDVVLSPSHGIELSVGEKLVLNCTARTELNVGIDFNWEYPSSKHQHKKLVNRDLKTQSGSEMKKFLSTLTIDGVTRSDQGLYTCAASSGLMTKKNSTFVRVHEK |

Example 8: A Hexavalent Bispecific Antibody Comprising Antibody HC2:LC1 and Ranibizumab-Derived Sequences To generate a heavy chain with ranibizumab-derived VEGF-binding domains added at the C-terminus, an amino acid sequence is generated comprising the following appended amino acid sequences, from N-terminus to C-terminus:

1) SEQ ID NO: 14 (heavy chain of antibody HC2:LC1);
2) SEQ ID NO: 31 (linker peptide, underlined); and
3) SEQ ID NO: 28 (ranibizumab-derived sequence).

To generate a light chain with ranibizumab-derived VEGF-binding domains added at the C-terminus, an amino acid sequence is generated comprising the following appended amino acid sequences, from N-terminus to C-terminus:

1) SEQ ID NO: 17 (light chain of antibody HC2:LC1);
2) SEQ ID NO: 31 (linker peptide, underlined); and
3) SEQ ID NO: 28 (ranibizumab-derived sequence).

The resulting polypeptides, SEQ ID NO: 151 and SEQ ID NO: 243 are co-expressed to provide a hexavalent, bispecific antibody HC2-RAN:LC1-RAN shown in TABLE 40. Amino acids 1-19 of SEQ ID NO: 151 are the heavy chain signal peptide (SEQ ID NO: 11). Amino acids 1-20 of SEQ ID NO: 243 are the light chain signal peptide (SEQ ID NO: 12). In some embodiments, a mature HC2-RAN:LC1-RAN does not comprise the signal peptides. For example, a mature HC2-RAN:LC1-RAN of the disclosure can comprise SEQ ID NO: 256 and SEQ ID NO: 260.

TABLE 40

| SEQ ID NO: | Name | Amino acid sequence |
|---|---|---|
| 151 | Signal peptide-HC2-RAN | MGWTLVFLFLLSVTAGVHSEVQLVESGGGLVQPGGSLRLSC<br>AASGFTFNANAMNWVRQAPGKGLEWVGRIRTKSNNYATY<br>YAGSVKDRFTISRDDSKNSLYLQMNSLKTEDTAVYYCVRD<br>YYGSSAWITYWGQGTLVTVSSASTKGPSVFPLAPCSRSTSES<br>TAALGCLVKDYFPEPVTVSWNSGALTSGVHTFPAVLQSSGL<br>YSLSSVVTVPSSSLGTKTYTCNVDHKPSNTKVDKRVESKYG<br>PPCPPCPAPEFLGGPSVFLFPPKPKDTLMISRTPEVTCVVVDV<br>SQEDPEVQFNWYVDGVEVHNAKTKPREEQFNSTYRVVSVL<br>TVLHQDWLNGKEYKCKVSNKGLPSSIEKTISKAKGQPREPQ<br>VYTLPPSQEEMTKNQVSLTCLVKGFYPSDIAVEWESNGQPE<br>NNYKTTPPVLDSDGSFFLYSRLTVDKSRWQEGNVFSCSVMH<br>EALHNHYTQKSLSLSLGKGGGGSEVQLVESGGGLVQPGGSL<br>RLSCAASGYDFTHYGMNWVRQAPGKGLEWVGWINTYTGE<br>PTYAADFKRRFTFSLDTSKSTAYLQMNSLRAEDTAVYYCAK<br>YPYYYGTSHWYFDVWGQGTLVTVSSGGGGSGGGGSGGGG<br>SDIQLTQSPSSLSASVGDRVTITCSASQDISNYLNWYQQKPG<br>KAPKVLIYFTSSLHSGVPSRFSGSGSGTDFTLTISSLQPEDFAT<br>YYCQQYSTVPWTFGQGTKVEIK |
| 243 | Signal peptide-LC1-RAN | MVSSAQFLGLLLLCFQGTRCDVVMTQSPSFLSASVGDRVTIT<br>CKASQHVGTAVAWYQQRPGKAPKLLIYWASTRHTGVPSRF<br>SGSGSGTEFTLTISSLQPEDFATYFCQQYSSYPFTFGGGTKLEI<br>KRTVAAPSVFIFPPSDEQLKSGTASVVCLLNNFYPREAKVQ<br>WKVDNALQSGNSQESVTEQDSKDSTYSLSSTLTLSKADYEK<br>HKVYACEVTHQGLSSPVTKSFNRGECGGGGSEVQLVESGG<br>GLVQPGGSLRLSCAASGYDFTHYGMNWVRQAPGKGLEWV<br>GWINTYTGEPTYAADFKRRFTFSLDTSKSTAYLQMNSLRAE<br>DTAVYYCAKYPYYYGTSHWYFDVWGQGTLVTVSSGGGGS<br>GGGGSGGGGSDIQLTQSPSSLSASVGDRVTITCSASQDISNYL<br>NWYQQKPGKAPKVLIYFTSSLHSGVPSRFSGSGSGTDFTLTI<br>SSLQPEDFATYYCQQYSTVPWTFGQGTKVEIK |
| 260 | LC1-RAN | DVVMTQSPSFLSASVGDRVTITCKASQHVGTAVAWYQQRP<br>GKAPKLLIYWASTRHTGVPSRFSGSGSGTEFTLTISSLQPEDF<br>ATYFCQQYSSYPFTFGGGTKLEIKRTVAAPSVFIFPPSDEQLK<br>SGTASVVCLLNNFYPREAKVQWKVDNALQSGNSQESVTEQ<br>DSKDSTYSLSSTLTLSKADYEKHKVYACEVTHQGLSSPVTK<br>SFNRGECGGGGSEVQLVESGGGLVQPGGSLRLSCAASGYDF<br>THYGMNWVRQAPGKGLEWVGWINTYTGEPTYAADFKRRF<br>TFSLDTSKSTAYLQMNSLRAEDTAVYYCAKYPYYYGTSHW<br>YFDVWGQGTLVTVSSGGGGSGGGGSGGGGSDIQLTQSPSSL<br>SASVGDRVTITCSASQDISNYLNWYQQKPGKAPKVLIYFTSS<br>LHSGVPSRFSGSGSGTDFTLTISSLQPEDFATYYCQQYSTVP<br>WTFGQGTKVEIK |

Example 9: A Hexavalent Bispecific Antibody Comprising Antibody HC2:LC1 and Abicipar-Derived Sequences To generate a heavy chain with abicipar-derived VEGF-binding domains added at the C-terminus, an amino acid sequence was generated comprising the following appended amino acid sequences, from N-terminus to C-terminus:

1) Residues 1-467 of SEQ ID NO: 14 (heavy chain of antibody HC2:LC1);
2) SEQ ID NO: 31 (linker peptide, underlined); and
3) SEQ ID NO: 244 (abicipar-derived sequence).

To generate a light chain with abicipar-derived VEGF-binding domains added at the C-terminus, an amino acid sequence was generated comprising the following appended amino acid sequences, from N-terminus to C-terminus:

1) SEQ ID NO: 17 (light chain of antibody HC2:LC1);
2) SEQ ID NO: 31 (linker peptide, underlined); and
3) SEQ ID NO: 244 (abicipar-derived sequence).

The resulting polypeptides, SEQ ID NO: 231 and SEQ ID NO: 232, were co-expressed to provide a hexavalent, bispecific antibody HC2-ABI:LC1-ABI shown in TABLE 41. Amino acids 1-19 of SEQ ID NO: 231 are the heavy chain signal peptide (SEQ ID NO: 11). Amino acids 1-20 of SEQ ID NO: 232 are the light chain signal peptide (SEQ ID NO: 12). In some embodiments, a mature HC2-ABI:LC1-ABI does not comprise the signal peptides. For example, a mature HC2-ABI:LC1-ABI of the disclosure can comprise SEQ ID NO: 257 and SEQ ID NO: 261.

TABLE 41

| SEQ ID NO: | Name | Amino acid sequence |
|---|---|---|
| 231 | Signal peptide-HC2-ABI | MGWTLVFLFLLSVTAGVHSEVQLVESGGGLVQPGGSLRLSC<br>AASGFTFNANAMNWVRQAPGKGLEWVGRIRTKSNNYATY<br>YAGSVKDRFTISRDDSKNSLYLQMNSLKTEDTAVYYCVRD<br>YYGSSAWITYWGQGTLVTVSSASTKGPSVFPLAPCSRSTSES<br>TAALGCLVKDYFPEPVTVSWNSGALTSGVHTFPAVLQSSGL<br>YSLSSVVTVPSSSLGTKTYTCNVDHKPSNTKVDKRVESKYG<br>PPCPPCPAPEFLGGPSVFLFPPKPKDTLMISRTPEVTCVVVDV<br>SQEDPEVQFNWYVDGVEVHNAKTKPREEQFNSTYRVVSVL<br>TVLHQDWLNGKEYKCKVSNKGLPSSIEKTISKAKGQPREPQ<br>VYTLPPSQEEMTKNQVSLTCLVKGFYPSDIAVEWESNGQPE<br>NNYKTTPPVLDSDGSFFLYSRLTVDKSRWQEGNVFSCSVMH<br>EALHNHYTQKSLSLSLGGGGGSDLDKKLLEAARAGQDDEV<br>RILMANGADVNARDSTGWTPLHLAAPWGHPEIVEVLLKNG<br>ADVNAADFQGWTPLHLAAAVGHLEIVEVLLKYGADVNAQ<br>DKFGKTAFDISIDNGNEDLAEILQKAA |
| 232 | Signal peptide-LC1-ABI | MVSSAQFLGLLLLCFQGTRCDVVMTQSPSFLSASVGDRVTIT<br>CKASQHVGTAVAWYQQRPGKAPKLLIYWASTRHTGVPSRF<br>SGSGSGTEFTLTISSLQPEDFATYFCQQYSSYPFTFGGGTKLEI<br>KRTVAAPSVFIFPPSDEQLKSGTASVVCLLNNFYPREAKVQ<br>WKVDNALQSGNSQESVTEQDSKDSTYSLSSTLTLSKADYEK<br>HKVYACEVTHQGLSSPVTKSFNRGECGGGGSDLDKKLLEA<br>ARAGQDDEVRILMANGADVNARDSTGWTPLHLAAPWGHP<br>EIVEVLLKNGADVNAADFQGWTPLHLAAAVGHLEIVEVLL<br>KYGADVNAQDKFGKTAFDISIDNGNEDLAEILQKAA |
| 261 | LC1-ABI | DVVMTQSPSFLSASVGDRVTITCKASQHVGTAVAWYQQRP<br>GKAPKLLIYWASTRHTGVPSRFSGSGSGTEFTLTISSLQPEDF<br>ATYFCQQYSSYPFTFGGGTKLEIKRTVAAPSVFIFPPSDEQLK<br>SGTASVVCLLNNFYPREAKVQWKVDNALQSGNSQESVTEQ<br>DSKDSTYSLSSTLTLSKADYEKHKVYACEVTHQGLSSPVTK<br>SFNRGECGGGGSDLDKKLLEAARAGQDDEVRILMANGADV<br>NARDSTGWTPLHLAAPWGHPEIVEVLLKNGADVNAADFQG<br>WTPLHLAAAVGHLEIVEVLLKYGADVNAQDKFGKTAFDISI<br>DNGNEDLAEILQKAA |

Example 10: A Tetravalent Bispecific Antibody Comprising Antibody HC2:LC1 and Brolucizumab-Derived Sequences To generate a light chain with brolucizumab-derived VEGF-binding domains added at the C-terminus, an amino acid sequence was generated comprising the following appended amino acid sequences, from N-terminus to C-terminus:

1) SEQ ID NO: 17 (light chain of antibody HC2:LC1);
2) SEQ ID NO: 31 (linker peptide, underlined); and
3) SEQ ID NO: 23 (brolucizumab-derived sequence).

The resulting polypeptide (SEQ ID NO: 218) was co-expressed with SEQ ID NO: 14, to provide tetravalent, bispecific antibody HC2:LC1-BRO, comprising the sequences shown in TABLE 42. Amino acids 1-19 of SEQ ID NO: 14 are the heavy chain signal peptide (SEQ ID NO: 11). Amino acids 1-20 of SEQ ID NO: 218 are the light chain signal peptide (SEQ ID NO: 12). In some embodiments, a mature HC2:LC1-BRO does not comprise the signal peptides. For example, a mature HC2:LC1-BRO of the disclosure can comprise SEQ ID NO: 247 and SEQ ID NO: 258.

TABLE 42

| SEQ ID NO: | Name | Amino acid sequence |
|---|---|---|
| 14 | Signal peptide-HC2 | MGWTLVFLFLLSVTAGVHSEVQLVESGGGLVQPGGSLRLSC AASGFTFNANAMNWVRQAPGKGLEWVGRIRTKSNNYATY YAGSVKDRFTISRDDSKNSLYLQMNSLKTEDTAVYYCVRD YYGSSAWITYWGQGTLVTVSSASTKGPSVFPLAPCSRSTSES TAALGCLVKDYFPEPVTVSWNSGALTSGVHTFPAVLQSSGL YSLSSVVTVPSSSLGTKTYTCNVDHKPSNTKVDKRVESKYG PPCPPCPAPEFLGGPSVFLFPPKPKDTLMISRTPEVTCVVVDV SQEDPEVQFNWYVDGVEVHNAKTKPREEQFNSTYRVVSVL TVLHQDWLNGKEYKCKVSNKGLPSSIEKTISKAKGQPREPQ VYTLPPSQEEMTKNQVSLTCLVKGFYPSDIAVEWESNGQPE NNYKTTPPVLDSDGSFFLYSRLTVDKSRWQEGNVFSCSVMH EALHNHYTQKSLSLSLGK |
| 218 | Signal peptide-LC1-BRO | MVSSAQFLGLLLLCFQGTRCDVVMTQSPSFLSASVGDRVTIT CKASQHVGTAVAWYQQRPGKAPKLLIYWASTRHTGVPSRF SGSGSGTEFTLTISSLQPEDFATYFCQQYSSYPFTFGGGTKLEI KRTVAAPSVFIFPPSDEQLKSGTASVVCLLNNFYPREAKVQ WKVDNALQSGNSQESVTEQDSKDSTYSLSSTLTLSKADYEK HKVYACEVTHQGLSSPVTKSFNRGEC<u>GGGGS</u>EIVMTQSPST LSASVGDRVIITCQASEIIHSWLAWYQQKPGKAPKWYLAS TLASGVPSRFSGSGSGAEFTLTISSLQPDDFATYYCQNVYLA STNGANFGQGTKLTVLGGGGGSGGGGSGGGGSGGGGSEVQ LVESGGGLVQPGGSLRLSCTASGFSLTDYYYMTWVRQAPG KGLEWVGFIDPDDDPYYATWAKGRFTISRDNSKNTLYLQM NSLRAEDTAVYYCAGGDHNSGWGLDIWGQGTLVTVSS |

Example 11: A Tetravalent Bispecific Antibody Comprising Antibody HC2:LC1 and Aflibercept-Derived Sequences To generate a light chain with aflibercept-derived VEGF-binding domains added at the C-terminus, an amino acid sequence was generated comprising the following appended amino acid sequences, from N-terminus to C-terminus:

1) SEQ ID NO: 17 (light chain of antibody HC2:LC1);
2) SEQ ID NO: 31 (linker peptide, underlined); and
3) SEQ ID NO: 22 (aflibercept-derived sequence).

The resulting polypeptide (SEQ ID NO: 219) was co-expressed with SEQ ID NO: 14, to provide tetravalent, bispecific antibody HC2:LC1-AFL, comprising the sequences shown in TABLE 43. Amino acids 1-19 of SEQ ID NO: 14 are the heavy chain signal peptide (SEQ ID NO: 11). Amino acids 1-20 of SEQ ID NO: 219 are the light chain signal peptide (SEQ ID NO: 12). In some embodiments, a mature HC2:LC1-AFL does not comprise the signal peptides. For example, a mature HC2:LC1-AFL of the disclosure can comprise SEQ ID NO: 247 and SEQ ID NO: 259.

TABLE 43

| SEQ ID NO: | Name | Amino acid sequence |
|---|---|---|
| 14 | Signal peptide-HC2 | MGWTLVFLFLLSVTAGVHSEVQLVESGGGLVQPGGSLRLSC<br>AASGFTFNANAMNWVRQAPGKGLEWVGRIRTKSNNYATY<br>YAGSVKDRFTISRDDSKNSLYLQMNSLKTEDTAVYYCVRD<br>YYGSSAWITYWGQGTLVTVSSASTKGPSVFPLAPCSRSTSES<br>TAALGCLVKDYFPEPVTVSWNSGALTSGVHTFPAVLQSSGL<br>YSLSSVVTVPSSSLGTKTYTCNVDHKPSNTKVDKRVESKYG<br>PPCPPCPAPEFLGGPSVFLFPPKPKDTLMISRTPEVTCVVVDV<br>SQEDPEVQFNWYVDGVEVHNAKTKPREEQFNSTYRVVSVL<br>TVLHQDWLNGKEYKCKVSNKGLPSSIEKTISKAKGQPREPQ<br>VYTLPPSQEEMTKNQVSLTCLVKGFYPSDIAVEWESNGQPE<br>NNYKTTPPVLDSDGSFFLYSRLTVDKSRWQEGNVFSCSVMH<br>EALHNHYTQKSLSLSLGK |
| 219 | Signal peptide-LC1-AFL | MVSSAQFLGLLLLCFQGTRCDVVMTQSPSFLSASVGDRVTIT<br>CKASQHVGTAVAWYQQRPGKAPKLLIYWASTRHTGVPSRF<br>SGSGSGTEFTLTISSLQPEDFATYFCQQYSSYPFTFGGGTKLEI<br>KRTVAAPSVFIFPPSDEQLKSGTASVVCLLNNFYPREAKVQ<br>WKVDNALQSGNSQESVTEQDSKDSTYSLSSTLTLSKADYEK<br>HKVYACEVTHQGLSSPVTKSFNRGECGGGGSSDTGRPFVEM<br>YSEIPEIIHMTEGRELVIPCRVTSPNITVTLKKFPLDTLIPDGK<br>RIIWDSRKGFIISNATYKEIGLLTCEATVNGHLYKTNYLTHR<br>QTNTIIDVVLSPSHGIELSVGEKLVLNCTARTELNVGIDFNW<br>EYPSSKHQHKKLVNRDLKTQSGSEMKKFLSTLTIDGVTRSD<br>QGLYTCAASSGLMTKKNSTFVRVHEK |

Example 12: A Tetravalent Bispecific Antibody Comprising Antibody HC2:LC1 and Ranibizumab-Derived Sequences To generate a light chain with ranibizumab-derived VEGF-binding domains added at the C-terminus, an amino acid sequence is generated comprising the following appended amino acid sequences, from N-terminus to C-terminus:

1) SEQ ID NO: 17 (light chain of antibody HC2:LC1);
2) SEQ ID NO: 31 (linker peptide, underlined); and
3) SEQ ID NO: 28 (ranibizumab-derived sequence).

The resulting polypeptide (SEQ ID NO: 243) is co-expressed with SEQ ID NO: 14, to provide tetravalent, bispecific antibody HC2:LC1-RAN, comprising the sequences shown in TABLE 44. Amino acids 1-19 of SEQ ID NO: 14 are the heavy chain signal peptide (SEQ ID NO: 11). Amino acids 1-20 of SEQ ID NO: 243 are the light chain signal peptide (SEQ ID NO: 12). In some embodiments, a mature HC2:LC1-RAN does not comprise the signal peptides. For example, a mature HC2:LC1-RAN of the disclosure can comprise SEQ ID NO: 247 and SEQ ID NO: 260.

TABLE 44

| SEQ ID NO: | Name | Amino acid sequence |
|---|---|---|
| 14 | Signal peptide-HC2 | MGWTLVFLFLLSVTAGVHSEVQLVESGGGLVQPGGSLRLSC<br>AASGFTFNANAMNWVRQAPGKGLEWVGRIRTKSNNYATY<br>YAGSVKDRFTISRDDSKNSLYLQMNSLKTEDTAVYYCVRD<br>YYGSSAWITYWGQGTLVTVSSASTKGPSVFPLAPCSRSTSES<br>TAALGCLVKDYFPEPVTVSWNSGALTSGVHTFPAVLQSSGL<br>YSLSSVVTVPSSSLGTKTYTCNVDHKPSNTKVDKRVESKYG<br>PPCPPCPAPEFLGGPSVFLFPPKPKDTLMISRTPEVTCVVVDV<br>SQEDPEVQFNWYVDGVEVHNAKTKPREEQFNSTYRVVSVL<br>TVLHQDWLNGKEYKCKVSNKGLPSSIEKTISKAKGQPREPQ<br>VYTLPPSQEEMTKNQVSLTCLVKGFYPSDIAVEWESNGQPE<br>NNYKTTPPVLDSDGSFFLYSRLTVDKSRWQEGNVFSCSVMH<br>EALHNHYTQKSLSLSLGK |
| 243 | Signal peptide-LC1-RAN | MVSSAQFLGLLLLCFQGTRCDVVMTQSPSFLSASVGDRVTIT<br>CKASQHVGTAVAWYQQRPGKAPKLLIYWASTRHTGVPSRF<br>SGSGSGTEFTLTISSLQPEDFATYFCQQYSSYPFTFGGGTKLEI<br>KRTVAAPSVFIFPPSDEQLKSGTASVVCLLNNFYPREAKVQ<br>WKVDNALQSGNSQESVTEQDSKDSTYSLSSTLTLSKADYEK<br>HKVYACEVTHQGLSSPVTKSFNRGECGGGGSEVQLVESGG<br>GLVQPGGSLRLSCAASGYDFTHYGMNWVRQAPGKGLEWV<br>GWINTYTGEPTYAADFKRRFTFSLDTSKSTAYLQMNSLRAE<br>DTAVYYCAKYPYYYGTSHWYFDVWGQGTLVTVSSGGGGS<br>GGGGSGGGGSDIQLTQSPSSLSASVGDRVTITCSASQDISNYL<br>NWYQQKPGKAPKVLIYFTSSLHSGVPSRFSGSGSGTDFTLTI<br>SSLQPEDFATYYCQQYSTVPWTFGQGTKVEIK |

Example 13: A Tetravalent Bispecific Antibody Comprising Antibody HC2:LC1 and Abicipar-Derived Sequences To generate a light chain with abicipar-derived VEGF-binding domains added at the C-terminus, an amino acid sequence was generated comprising the following appended amino acid sequences, from N-terminus to C-terminus:

1) SEQ ID NO: 17 (light chain of antibody HC2:LC1);
2) SEQ ID NO: 31 (linker peptide, underlined); and
3) SEQ ID NO: 244 (abicipar-derived sequence).

The resulting polypeptide (SEQ ID NO: 232) was co-expressed with SEQ ID NO: 245 (residues 1-467 of SEQ ID NO: 14), to provide tetravalent, bispecific antibody HC2:LC1-ABI, comprising the sequences shown in TABLE 45. Amino acids 1-19 of SEQ ID NO: 245 are the heavy chain signal peptide (SEQ ID NO: 11). Amino acids 1-20 of SEQ ID NO: 232 are the light chain signal peptide (SEQ ID NO: 12). In some embodiments, a mature HC2:LC1-ABI does not comprise the signal peptides. For example, a mature HC2:LC1-ABI of the disclosure can comprise SEQ ID NO: 247 and SEQ ID NO: 261.

Figure 19:
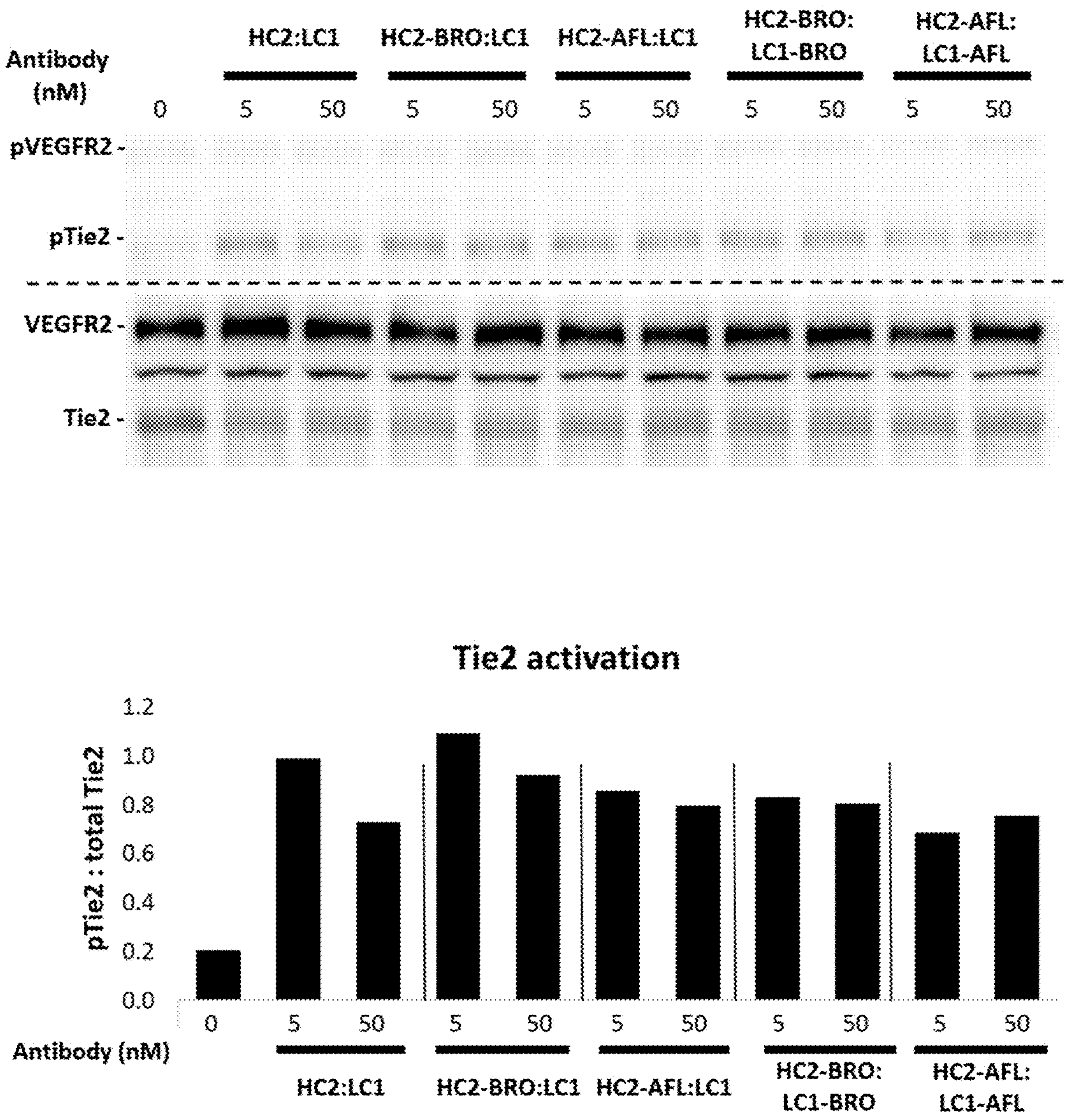
FIG. 19: Activation of Tie2 in HUVECs treated with tetravalent bispecific antibodies or hexavalent bispecific antibodies comprising brolucizumab-derived or aflibercept-derived VEGF-binding domains. As demonstrated by immunoprecipitation and western blot, all of the tested bispecific antibodies increased basal Tie2 activation (in the absence of exogenous Ang1 or Ang2), while basal VEGFR2 phosphorylation (in the absence of exogenous VEGF) was not affected.

FIG. 19: (i) HC2:LC1, a humanized monoclonal antibody specific for HPTP-β; (ii) HC2-BRO:LC1, a tetravalent bispecific antibody comprising brolucizumab-derived VEGF-binding domains fused to the C-termini of the heavy chains of HC2:LC1; (iii) HC2-AFL:LC1, a tetravalent bispecific antibody comprising aflibercept-derived VEGF-binding domains fused to the C-termini of the heavy chains of HC2:LC1; (iv) HC2-BRO:LC1-BRO, a hexavalent antibody comprising brolucizumab-derived VEGF-binding domains fused to the C-termini of the heavy chains and the light chains of HC2:LC1; or (v) HC2-AFL:LC1-AFL, a hexavalent antibody comprising aflibercept-derived VEGF-binding domains fused to the C-termini of the heavy chains and the light chains of HC2:LC1. After treatment, the cells were rinsed with ice cold PBS containing 1 mM NaOV and lysed in Complete Triton™ X Lysis Buffer (20 mM Tris-HCl, 137 mM NaCl, 10% Glycerol, 1% Triton™ X-100, 2 mM EDTA, 1 mM NaOV, 1 mM NaF, 1 mM PMSF, 1 μg/mL leupeptin, 1 g/mL pepstatin).

The lysates were immunoprecipitated with anti-Tie2 and anti-VEGFR2 antibodies. 1-10 μg of VEGFR2 antibody (MAB3573, #89109), TIE-2 antibody (Ab33), and 25 μL of

TABLE 45

| SEQ ID NO: | Name | Amino acid sequence |
|---|---|---|
| 245 | Signal peptide-HC2 | MGWTLVFLFLLSVTAGVHSEVQLVESGGGLVQPGGSLRLSC<br>AASGFTFNANAMNWVRQAPGKGLEWVGRIRTKSNNYATY<br>YAGSVKDRFTISRDDSKNSLYLQMNSLKTEDTAVYYCVRD<br>YYGSSAWITYWGQGTLVTVSSASTKGPSVFPLAPCSRSTSES<br>TAALGCLVKDYFPEPVTVSWNSGALTSGVHTFPAVLQSSGL<br>YSLSSVVTVPSSSLGTKTYTCNVDHKPSNTKVDKRVESKYG<br>PPCPPCPAPEFLGGPSVFLFPPKPKDTLMISRTPEVTCVVVDV<br>SQEDPEVQFNWYVDGVEVHNAKTKPREEQFNSTYRVVSVL<br>TVLHQDWLNGKEYKCKVSNKGLPSSIEKTISKAKGQPREPQ<br>VYTLPPSQEEMTKNQVSLTCLVKGFYPSDIAVEWESNGQPE<br>NNYKTTPPVLDSDGSFFLYSRLTVDKSRWQEGNVFSCSVMH<br>EALHNHYTQKSLSLSLG |
| 232 | Signal peptide-LC1-ABI | MVSSAQFLGLLLLCFQGTRCDVVMTQSPSFLSASVGDRVTIT<br>CKASQHVGTAVAWYQQRPGKAPKLLIYWASTRHTGVPSRF<br>SGSGSGTEFTLTISSLQPEDFATYFCQQYSSYPFTFGGGTKLEI<br>KRTVAAPSVFIFPPSDEQLKSGTASVVCLLNNFYPREAKVQ<br>WKVDNALQSGNSQESVTEQDSKDSTYSLSSTLTLSKADYEK<br>HKVYACEVTHQGLSSPVTKSFNRGECGGGGSDLDKKLLEA<br>ARAGQDDEVRILMANGADVNARDSTGWTPLHLAAPWGHP<br>EIVEVLLKNGADVNAADFQGWTPLHLAAAVGHLEIVEVLL<br>KYGADVNAQDKFGKTAFDISIDNGNEDLAEILQKAA |
| 262 | HC2 | EVQLVESGGGLVQPGGSLRLSCAASGFTFNANAMNWVRQA<br>PGKGLEWVGRIRTKSNNYATYYAGSVKDRFTISRDDSKNSL<br>YLQMNSLKTEDTAVYYCVRDYYGSSAWITYWGQGTLVTV<br>SSASTKGPSVFPLAPCSRSTSESTAALGCLVKDYFPEPVTVS<br>WNSGALTSGVHTFPAVLQSSGLYSLSSVVTVPSSSLGTKTYT<br>CNVDHKPSNTKVDKRVESKYGPPCPPCPAPEFLGGPSVFLFP<br>PKPKDTLMISRTPEVTCVVVDVSQEDPEVQFNWYVDGVEV<br>HNAKTKPREEQFNSTYRVVSVLTVLHQDWLNGKEYKCKVS<br>NKGLPSSIEKTISKAKGQPREPQVYTLPPSQEEMTKNQVSLT<br>CLVKGFYPSDIAVEWESNGQPENNYKTTPPVLDSDGSFFLYS<br>RLTVDKSRWQEGNVFSCSVMHEALHNHYTQKSLSLSLG |

Example 14: Bispecific Antibodies that Activate Tie2

Human Umbilical Cord Endothelial Cells (HUVECs) were seeded onto T75 flasks coated with porcine gelatin. Cell maintenance was performed using complete medium (EGM® or EGM®-2) and sub-cultured using Trypsin/EDTA into 100 mm dishes. After 3 days, the 100 mm dishes were rinsed, and treated in basal medium (EBM®, EBM®-2, OptiMEM™ I) for 30 minutes at 37° C./5% $CO_2$ with one of the following antibodies at 5 or 50 nM as indicated in Protein A/G agarose beads were added to 1 mL of HUVEC lysate, and the tubes were placed on a rotating platform for 1-3 days at 4° C. The IP reaction tubes were rinsed with 1 mL complete Triton™-X lysis buffer and resuspended in 2× loading dye containing DTT. The tubes were incubated at 95° C. for five minutes, spun down, and 25 μL loaded per well into a Tris Glycine gel. The samples were resolved on a gel, transferred to a PVDF membrane, and subjected to serial western blot to detect phosphotyrosine (phospho-Tie2 and phospho-VEGFR2), followed by re-probing to blot for total Tie2, and total VEGFR2. The gel was run at 125V for 75 minutes, before transfer to a PVDF membrane. The membranes were blocked in 5% BSA/0.05% Tween® Tris Wash Buffer for 1 hour at room temperature (RT) on a rotating platform. Primary antibodies (PY99; VEGFR2-A3; TIE-2 Ab33) were added for 1 hour at a 1:1000 dilution in wash buffer. Secondary antibody (anti-mouse hrp) was added for 1 hour at a 1:1000 dilution in wash buffer. The membranes were rinsed three times with 0.05-0.1% Tween® 20+Tris Buffered Saline (TBS) between steps. An ECL detection system was used to visualize bands. Re-probe was performed on lots treated with 200 mM Glycine for 24-48 h.

As shown in FIG. 19, all of the tested bispecific antibodies increased basal Tie2 activation in HUVECS, while basal VEGFR2 phosphorylation was not affected. The top panel provides a western blot showing Tie2 activation and VEGFR2 activation as shown through detection of phospho-Tie2 and phospho-VEGFR2, respectively (top half), and total Tie2 and VEGFR2 (bottom half). The bottom panel provides the densitometric ratios of phosphorylated Tie2 to total Tie2.

The assay was repeated with the following antibodies of the disclosure, which also enhanced Tie2 activation in the absence of exogenous Ang1: (i) HC2-RAN:LC1, (ii) HC2-ABI:LC1, (iii) HC2:LC1-AFL, (iv) HC2:LC1-BRO, (v) HC2:LC1-ABI, and (vi) HC2-ABI:LC1-ABI.

Figure 20:
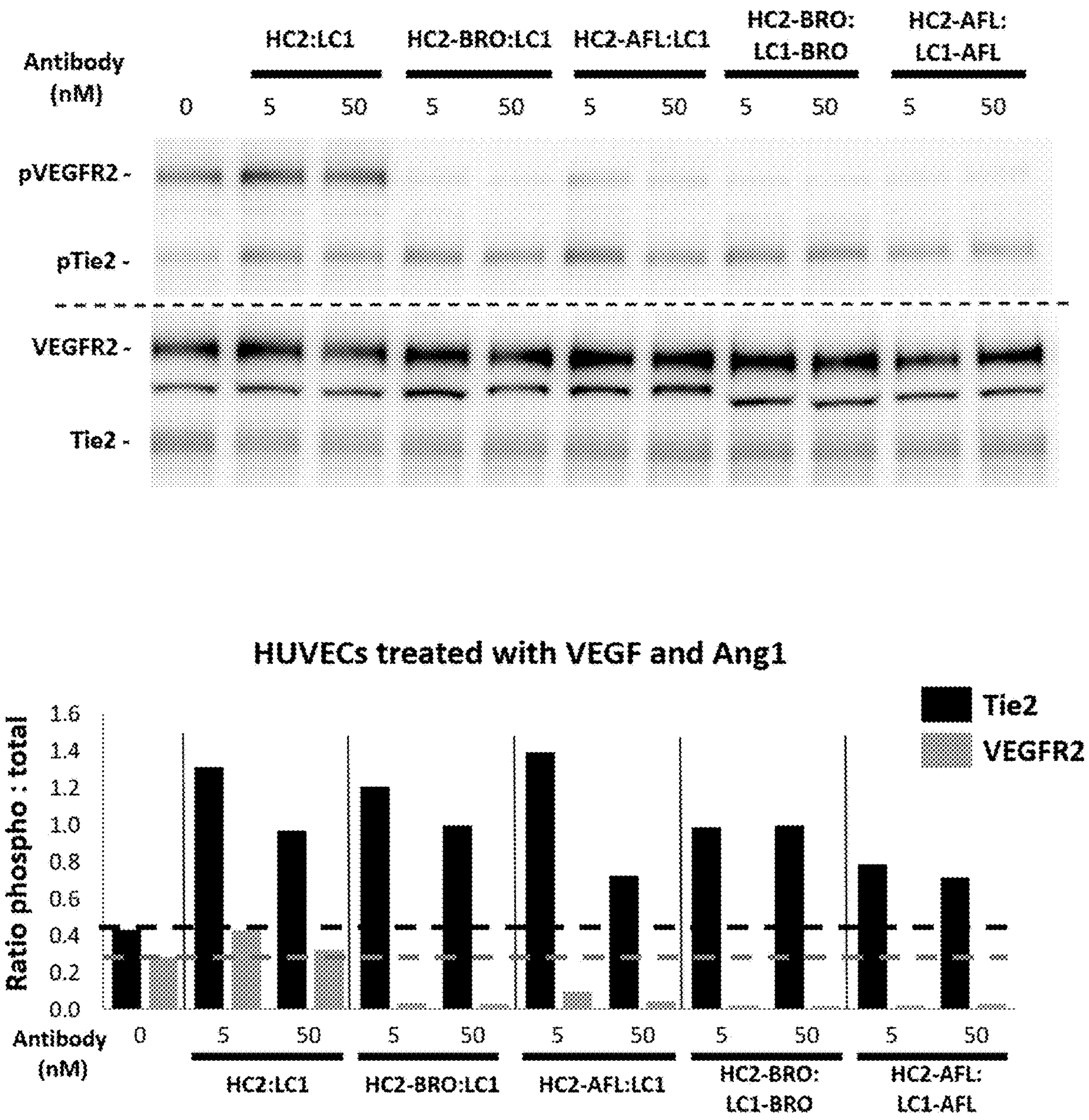
FIG. 20: Tetravalent bispecific and hexavalent bispecific antibodies comprising brolucizumab-derived or aflibercept-derived VEGF-binding domains enhance Tie2 activation and inhibit VEGFR2 activation in HUVECs treated with Ang1 and VEGF, as demonstrated by immunoprecipitation and western blot.

Example 15: Bispecific Antibodies Enhance Ang1-Mediated Tie2 Activation and Block VEGF-Mediated VEGFR2 Activation Human Umbilical Cord Endothelial Cells (HUVECs) were seeded onto T75 flasks coated with porcine gelatin. Cell maintenance was performed using complete medium (EGM® or EGM®-2) and sub-cultured using Trypsin/EDTA into 100 mm dishes. After 3 days, the 100 mm dishes were rinsed, and mock-pre-treated or pre-treated in basal medium (EBM®, EBM®-2, OptiMEM™ I) for 30 minutes at 37° C./5% $CO_2$ with one of the following antibodies at 5 or 50 nM as indicated in FIG. 20: (i) HC2:LC1, a humanized monoclonal antibody specific for HPTP-β; (ii) HC2-BRO:LC1, a tetravalent bispecific antibody comprising brolucizumab-derived VEGF-binding domains fused to the C-termini of the heavy chains of HC2:LC1; (iii) HC2-AFL:LC1, a tetravalent bispecific antibody comprising aflibercept-derived VEGF-binding domains fused to the C-termini of the heavy chains of HC2:LC1; (iv) HC2-BRO:LC1-BRO, a hexavalent antibody comprising brolucizumab-derived VEGF-binding domains fused to the C-termini of the heavy chains and the light chains of HC2:LC1; or (v) HC2-AFL:LC1-AFL, a hexavalent antibody comprising aflibercept-derived VEGF-binding domains fused to the C-termini of the heavy chains and the light chains of HC2:LC1. After pre-treatment, cells were treated with VEGF (5 ng/mL) and Ang1 (50 ng/mL) for 6 minutes at 37° C./5% $CO_2$ in basal medium (Phosphate buffered saline, PBS+0.2% Bovine Serum Albumin, or OptiMEM™ I). After treatment, the cells were rinsed with ice cold PBS containing 1 mM NaOV and lysed in Complete Triton™ X Lysis Buffer (20 mM Tris-HCl, 137 mM NaCl, 10% Glycerol, 1% Triton™ X-100, 2 mM EDTA, 1 mM NaOV, 1 mM NaF, 1 mM PMSF, 1 μg/mL leupeptin, 1 μg/mL pepstatin).

The lysates were immunoprecipitated with anti-Tie2 and anti-VEGFR2 antibodies. 1-10 μg of VEGFR2 antibody (MAB3573, #89109), TIE-2 antibody (Ab33), and 25 μL of Protein A/G agarose beads were added to 1 mL of HUVEC lysate, and the tubes were placed on a rotating platform for 1-3 days at 4° C. The IP reaction tubes were rinsed with 1 mL complete Triton™-X lysis buffer and resuspended in 2× loading dye containing DTT. The tubes were incubated at 95° C. for five minutes, spun down, and 25 μL loaded per well into a Tris Glycine gel. The samples were resolved on a gel, transferred to a PVDF membrane, and subjected to serial western blot to detect phosphotyrosine (phospho-Tie2 and phospho-VEGFR2), followed by re-probing to blot for total Tie2, and total VEGFR2. The gel was run at 125V for 75 minutes, before transfer to a PVDF membrane. The membranes were blocked in 5% BSA/0.05% Tween® Tris Wash Buffer for 1 hour at room temperature (RT) on a rotating platform. Primary antibodies (PY99; VEGFR2-A3; TIE-2 Ab33) were added for 1 hour at a 1:1000 dilution in wash buffer. Secondary antibody (anti-mouse hrp) was added for 1 hour at a 1:1000 dilution in wash buffer. The membranes were rinsed three times with 0.05-0.1% Tween® 20+Tris Buffered Saline (TBS) between steps. An ECL detection system was used to visualize bands. Re-probe was performed on lots treated with 200 mM Glycine for 24-48 h. Treatment with VEGF and Ang1 resulted in increased phosphorylation of VEGFR2 and Tie2 (FIG. 20). Treatment with the HC2:LC1 antibody, specific for HPTP-β, enhanced Ang1-mediated Tie2 activation in cells treated with Ang1 and VEGF. Treatment with the bispecific antibodies enhanced Ang1-mediated Tie2 activation and blocked VEGF-mediated VEGFR2 activation in cells treated with Ang1 and VEGF. The top panel provides a western blot showing Tie2 activation and VEGFR2 activation as shown through detection of phospho-Tie2 and phospho-VEGFR2, respectively (top half), and total Tie2 and VEGFR2 (bottom half). The lower panel provides the densitometric ratios of phosphorylated Tie2 to total Tie2 and phosphorylated VEGFR2 to total VEGFR2.

Example 16: Bispecific Antibodies Enhance Ang1-Mediated Tie2 Activation and Block VEGF-Mediated VEGFR2 Activation (Immunoprecipitation and Western Blot Assays)

Human Umbilical Cord Endothelial Cells (HUVECs) were seeded onto T75 flasks coated with porcine gelatin. Cell maintenance was performed using complete medium (EGM® or EGM®-2) and sub-cultured using Trypsin/EDTA into 100 mm dishes. After 3 days, the 100 mm dishes were rinsed, and pre-treated in basal medium (EBM®, EBM®-2, OptiMEM™ I) for 30 minutes at 37° C./5% $CO_2$ with one of multi-specific antibodies of the disclosure as indicated for each figure. After pre-treatment, the cells were mock-treated or treated with VEGF and Ang1 for 6 minutes at 37° C./5% $CO_2$ in basal medium (Phosphate buffered saline, PBS+0.2% Bovine Serum Albumin, or OptiMEM™ I). After treatment, the cells were rinsed with ice cold PBS containing 1 mM NaOV and lysed in Complete Triton™ X Lysis Buffer (20 mM Tris-HCl, 137 mM NaCl, 10% Glycerol, 1% Triton™ X-100, 2 mM EDTA, 1 mM NaOV, 1 mM NaF, 1 mM PMSF, 1 μg/mL leupeptin, 1 g/mL pepstatin).

The lysates were immunoprecipitated with anti-Tie2 and anti-VEGFR2 antibodies. 1-10 g of VEGFR2 antibody (MAB3573, #89109), TIE-2 antibody (Ab33), and 25 μL of Protein A/G agarose beads were added to 1 mL of HUVEC lysate, and the tubes were placed on a rotating platform for 1-3 days at 4° C. The IP reaction tubes were rinsed with 1 mL complete Triton™-X lysis buffer and resuspended in 2× loading dye containing DTT. The tubes were incubated at 95° C. for five minutes, spun down, and 25 μL loaded per well into a Tris Glycine gel. The samples were resolved on a gel, transferred to a PVDF membrane, and subjected to serial western blot to detect phosphotyrosine (phospho-Tie2 and phospho-VEGFR2), followed by re-probing to blot for total Tie2, and total VEGFR2. The gel was run at 125V for 75 minutes, before transfer to a PVDF membrane. The membranes were blocked in 5% BSA/0.05% Tween® Tris Wash Buffer for 1 hour at room temperature (RT) on a rotating platform. Primary antibodies (PY99; VEGFR2-A3; TIE-2 Ab33) were added for 1 hour at a 1:1000 dilution in wash buffer. Secondary antibody (anti-mouse hrp) was added for 1 hour at a 1:1000 dilution in wash buffer. The membranes were rinsed three times with 0.05-0.1% Tween® 20+Tris Buffered Saline (TBS) between steps. An ECL detection system was used to visualize bands. Re-probe was performed on lots treated with 200 mM Glycine for 24-48 h. The assay was repeated using different multi-specific antibodies of the disclosure, and different concentrations of VEGF and Ang1 as indicated for the following figures.

Figure 21A:
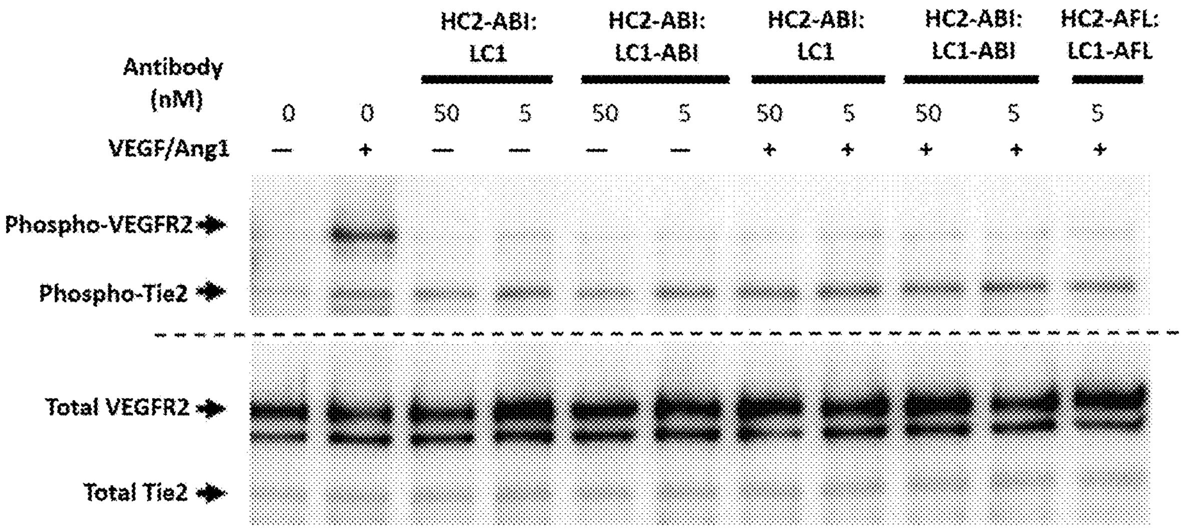
FIG. 21A, FIG. 21B, and FIG. 21C: Tetravalent bispecific and hexavalent bispecific antibodies comprising abicipar-derived or aflibercept-derived VEGF-binding domains enhance Tie2 activation and inhibit VEGFR2 activation in HUVECs, including HUVECs treated with Ang1 and VEGF.
Figure 21B:
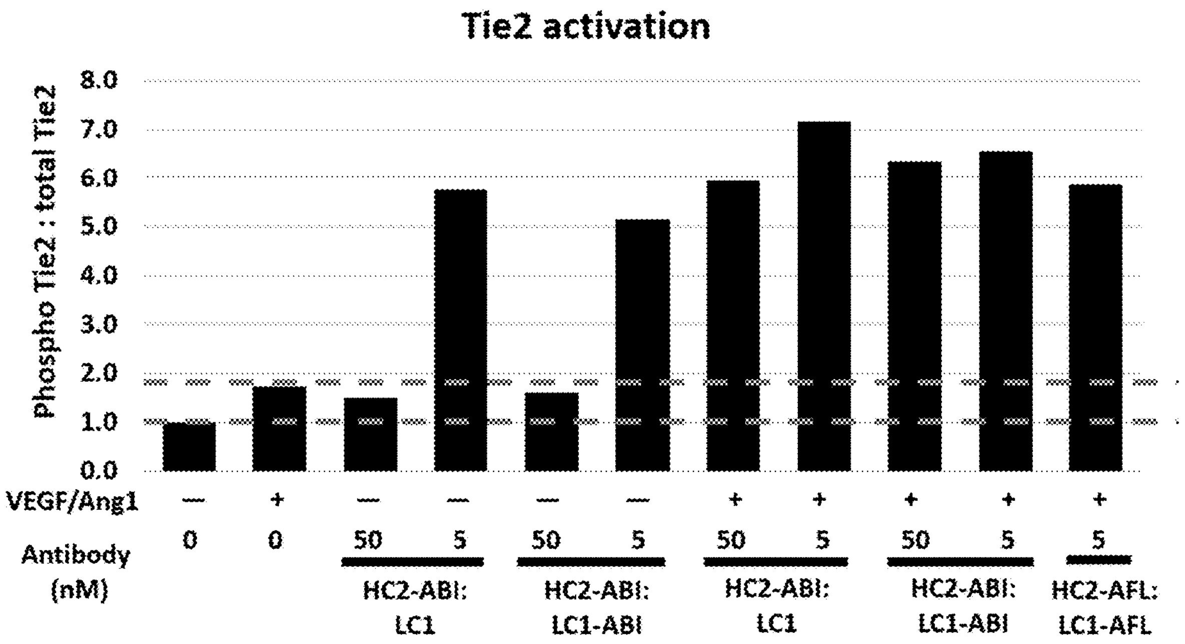
Figure 21C:
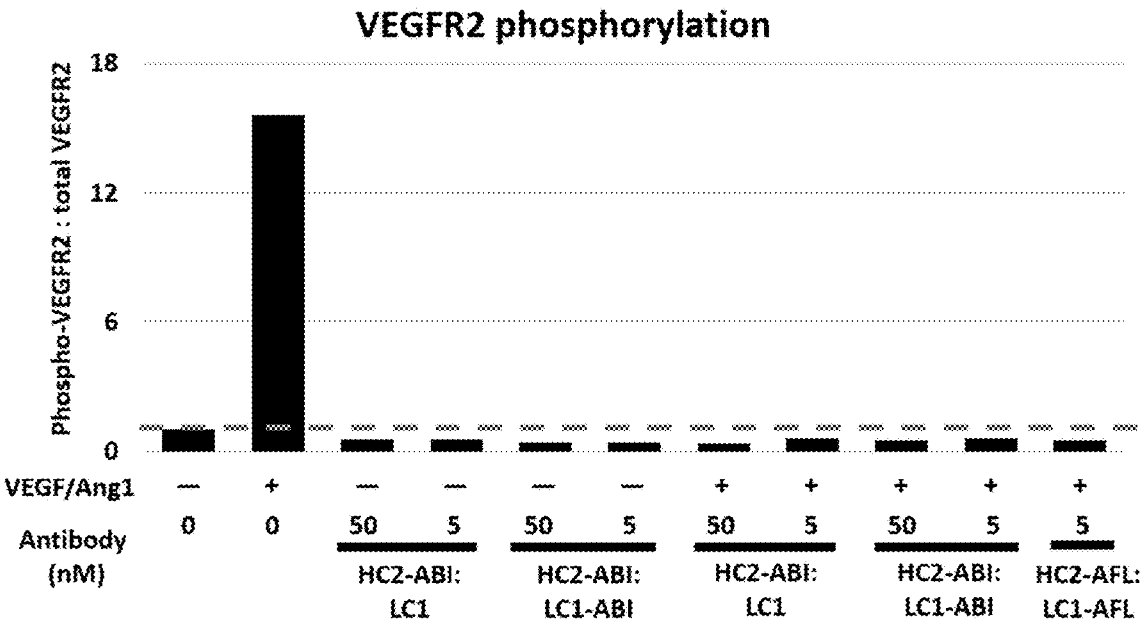

For FIG. 21A, FIG. 21B, and FIG. 21C, the cells were mock-pre-treated or pre-treated at 5 nM or 50 nM with one of: (i) HC2-ABI:LC1, a tetravalent bispecific antibody comprising abicipar-derived VEGF-binding domains fused to the C-termini of the heavy chains of HC2:LC1 (a humanized monoclonal antibody specific for HPTP-0); (ii) HC2-ABI:LC1-ABI, a hexavalent antibody comprising abicipar-derived VEGF-binding domains fused to the C-termini of the heavy chains and the light chains of HC2:LC1; or (iii) HC2-AFL:LC1-AFL, a hexavalent antibody comprising aflibercept-derived VEGF-binding domains fused to the C-termini of the heavy chains and the light chains of HC2:LC1. After pre-treatment, the cells were mock-treated (−) or treated (+) with VEGF (5 ng/mL) and Ang1 (50 ng/mL). Treatment with VEGF and Ang1 resulted in increased phosphorylation of VEGFR2 and Tie2 (FIG. 21A, FIG. 21B, and FIG. 21C). Treatment with the bispecific antibodies enhanced Tie2 activation and blocked VEGFR2 activation, including in cells treated with Ang1 and VEGF (FIG. 21A, FIG. 21B, and FIG. 21C). FIG. 21A provides a western blot showing Tie2 activation and VEGFR2 activation as shown through detection of phospho-Tie2 and phospho-VEGFR2, respectively (top half), and total Tie2 and VEGFR2 (bottom half). FIG. 21B provides the densitometric ratio of phosphorylated Tie2 to total Tie2, normalized to untreated cells. FIG. 21C provides the densitometric ratio of phosphorylated VEGFR2 to total VEGFR2, normalized to untreated cells.

Figure 22A:
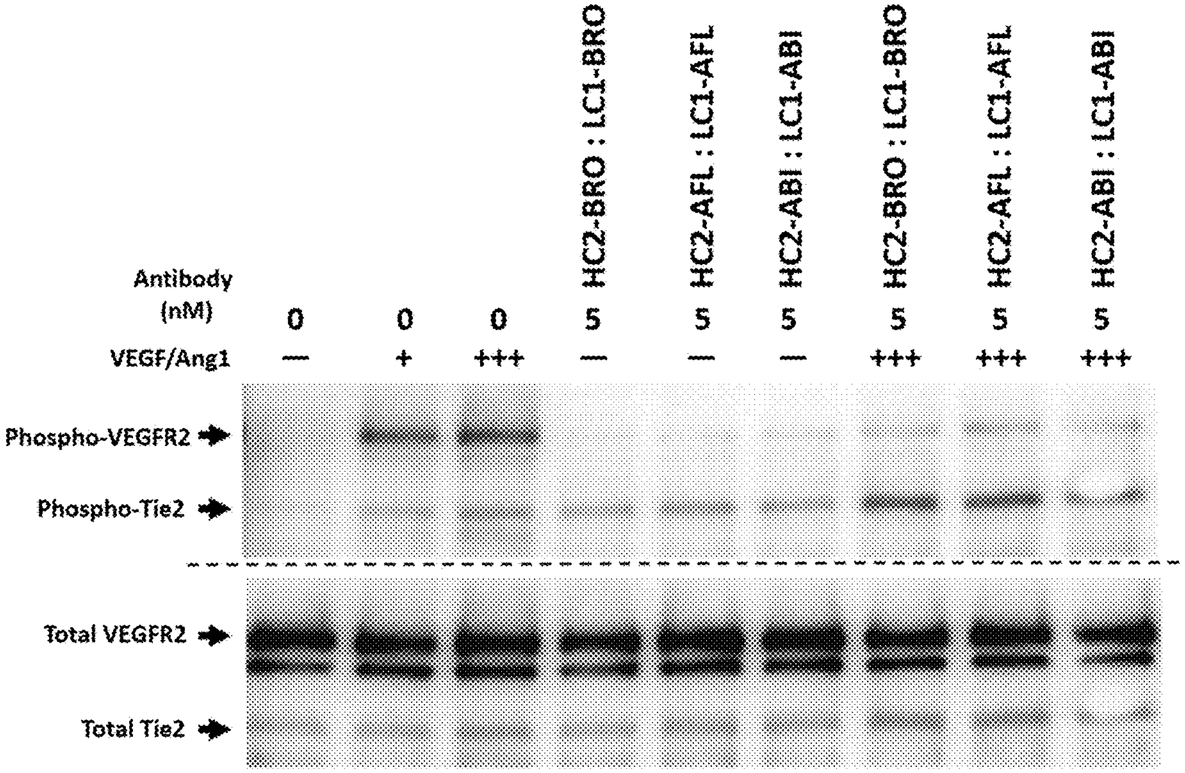
FIG. 22A, FIG. 22B, and FIG. 22C: Hexavalent bispecific antibodies comprising brolucizumab-derived, aflibercept-derived, or abicipar-derived VEGF-binding domains enhance Tie2 activation and inhibit VEGFR2 activation in HUVECs, including HUVECs treated with Ang1 and VEGF.
Figure 22B:
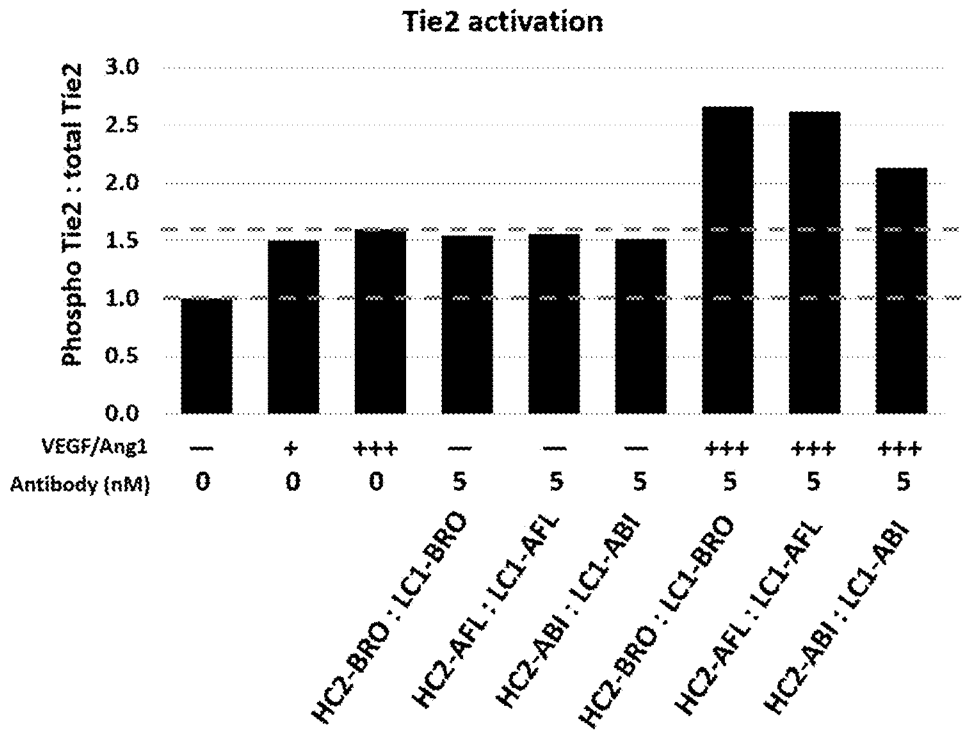
Figure 22C:
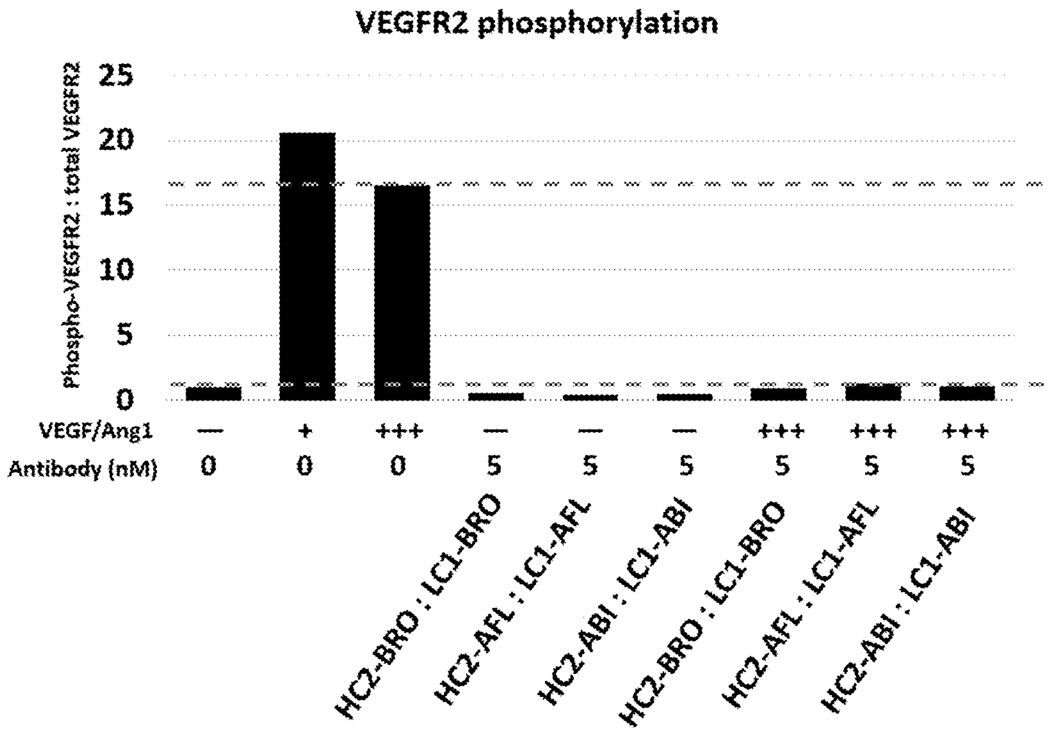

For FIG. 22A, FIG. 22B, and FIG. 22C, the cells were mock-pre-treated or pre-treated with one of the following antibodies at 5 nM: (i) HC2-BRO:LC1-BRO, a hexavalent antibody comprising brolucizumab-derived VEGF-binding domains fused to the C-termini of the heavy chains and the light chains of HC2:LC1 (a humanized monoclonal antibody specific for HPTP-β); (ii) HC2-AFL:LC1-AFL, a hexavalent antibody comprising aflibercept-derived VEGF-binding domains fused to the C-termini of the heavy chains and the light chains of HC2:LC1; or (iii) HC2-ABI:LC1:ABI, a hexavalent bispecific antibody comprising abicipar-derived VEGF-binding domains fused to the C-termini of the heavy chains and the light chains of HC2:LC1. After pre-treatment, the cells were mock-treated (−), treated with 5 ng/mL VEGF and 50 ng/mL Ang1 (+), or treated with 50 ng/mL VEGF and 250 ng/mL of Ang1 (+++). Treatment with VEGF and Ang1 resulted in increased phosphorylation of VEGFR2 and Tie2 (FIG. 22A, FIG. 22B, and FIG. 22C). Treatment with the bispecific antibodies enhanced Tie2 activation and blocked VEGFR2 activation, including in cells treated with Ang1 and VEGF. (FIG. 22A, FIG. 22B, and FIG. 22C). FIG. 22A provides a western blot showing Tie2 activation and VEGFR2 activation as shown through detection of phospho-Tie2 and phospho-VEGFR2, respectively (top half), and total Tie2 and VEGFR2 (bottom half). FIG. 22B provides the densitometric ratio of phosphorylated Tie2 to total Tie2, normalized to untreated cells. FIG. 22C provides the densitometric ratio of phosphorylated VEGFR2 to total VEGFR2, normalized to untreated cells.

Example 17: Bispecific Antibodies Enhance Ang1-Mediated Tie2 Activation and Block VEGF-Mediated VEGFR2 Activation (Electrochemiluminescence Assays)

Human Umbilical Cord Endothelial Cells (HUVECs) were seeded onto T75 flasks coated with porcine gelatin. Cell maintenance was performed using complete medium (EGM® or EGM®-2) and sub-cultured using Trypsin/EDTA into 100 mm dishes. After 3 days, the 100 mm dishes were rinsed, and mock-pre-treated or pre-treated in basal medium (EBM®, EBM®-2, OptiMEM™ I) for 30 minutes at 37° C./5% $CO_2$ with one the antibodies indicated below for each figure.

After pre-treatment, the cells were mock-treated or treated with VEGF and Ang1 for 6 minutes at 37° C./5% $CO_2$ in basal medium (Phosphate buffered saline, PBS+0.2% Bovine Serum Albumin, or OptiMEM™ I). After treatment, the cells were rinsed with ice cold PBS containing 1 mM NaOV and lysed in Complete Triton™ X Lysis Buffer (20 mM Tris-HCl, 137 mM NaCl, 10% Glycerol, 1% Triton™ X-100, 2 mM EDTA, 1 mM NaOV, 1 mM NaF, 1 mM PMSF, 1 μg/mL leupeptin, 1 g/mL pepstatin).

Phosphorylated Tie2 and phosphorylated VEGFR2 were quantified by electrochemiluminescence. Primary or capture Antibodies were spotted onto 96 well Sector® Imager plates. 5 μL of Tie2 antibody (30 g/mL, AF313) or VEGFR2 antibody (30 g/mL, 89109) were coated for 1 hour (at room temperature) or overnight (4° C.). Each plate was washed three times with TBS+0.02% Tween® 20 (this was performed between each step). Wells were blocked with MSD® Blocker A-3% in wash buffer for 1 hour on a rotating platform at room temperature. 25 μL of HUVEC lysates were added to each well directly and incubated for 1 hour on a rotating platform at room temperature. Detection antibody (1) was diluted to 2 μg/mL in 1% blocker/wash buffer (Ab33; AF2720/Y992; pTyr 1214; NB100 530), and 25 μL/well incubated for 1 hour on a rotating platform at room temperature. Detection antibody (2) was diluted to 1 μg/mL in 1% blocker/wash buffer (Goat anti-mouse, GAM; Goat anti-rabbit, GAR; both Sulfo Tag®-labeled) and 25 μL/well incubated for 1 hour on a rotating platform at room temperature. Signal was captured using 150 μL of Meso Scale Discovery (MSD®) read buffer in each well on an MSD® imager instrument. The assay was repeated using different multi-specific antibodies of the disclosure, and different concentrations of VEGF and Ang1 as indicated for the following figures.

Figure 23A:
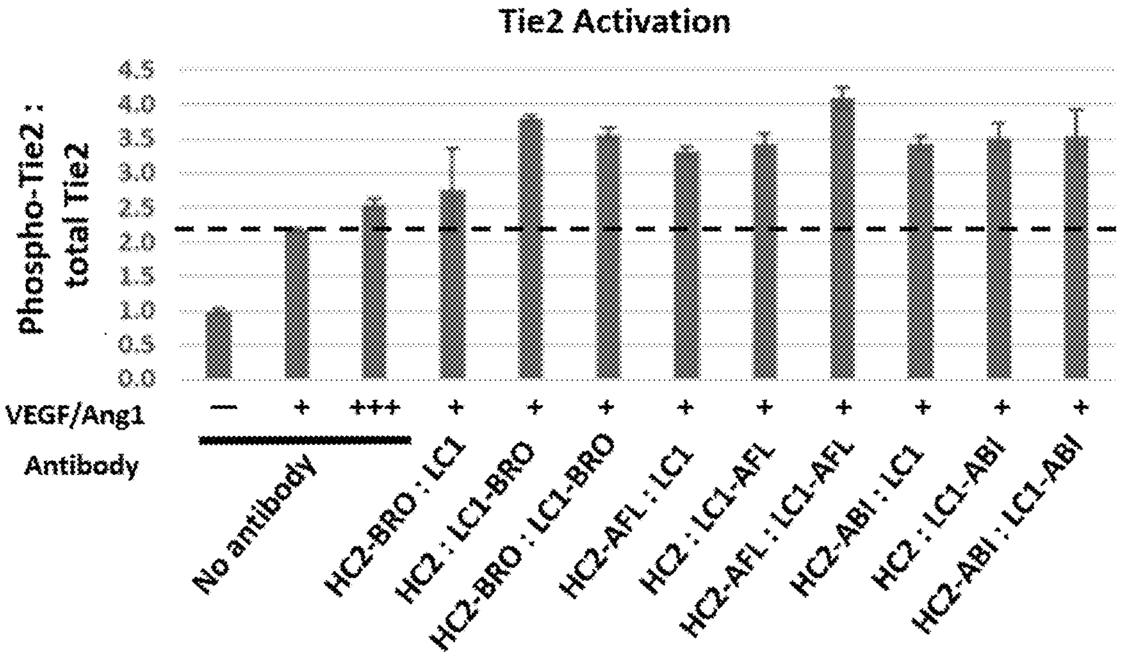
FIG. 23A and FIG. 23B: Tetravalent bispecific and hexavalent bispecific antibodies comprising brolucizumab-derived, aflibercept-derived, or abicipar-derived VEGF-binding domains enhance Tie2 activation and inhibit VEGFR2 activation in HUVECs treated with Ang1 and VEGF, as demonstrated by electrochemiluminescence signal quantification.
Figure 23B:
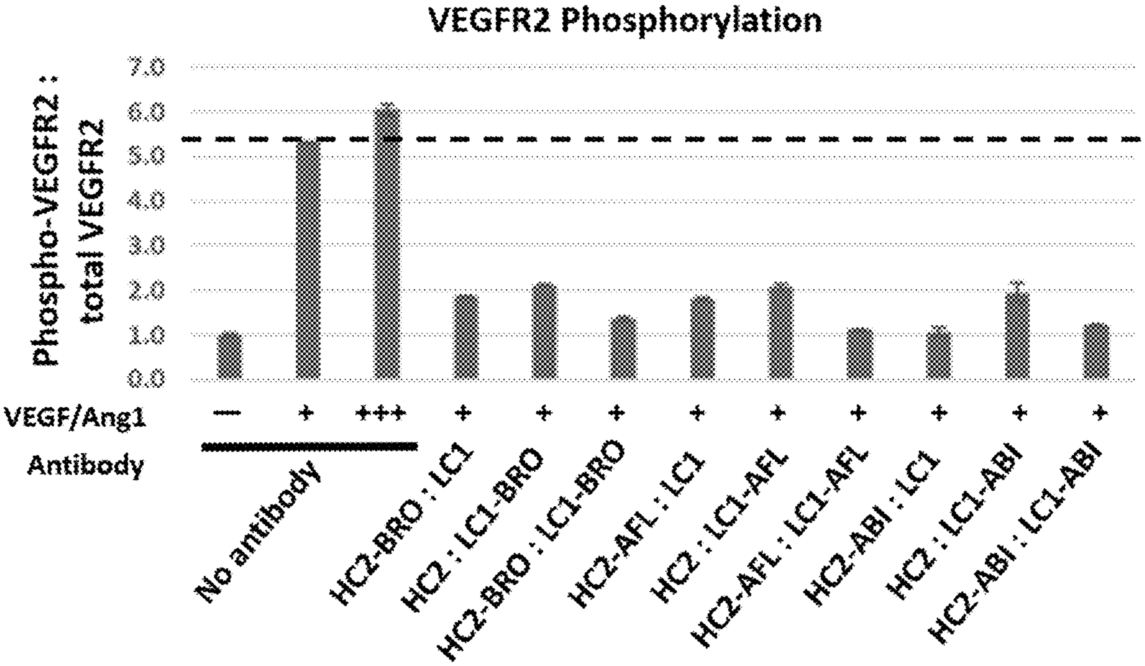

For FIG. 23A and FIG. 23B, the cells were mock-treated or pre-treated with one of the following antibodies at 5 nM: (i) HC2-BRO:LC1, a tetravalent bispecific antibody comprising brolucizumab-derived VEGF-binding domains fused to the C termini of the heavy chains of HC2:LC1 (a humanized monoclonal antibody specific for HPTP-β); (ii) HC2:LC1-BRO, a tetravalent bispecific antibody comprising brolucizumab-derived VEGF-binding domains fused to the C termini of the light chains of HC2:LC1; (iii) HC2-BRO:LC1-BRO, a hexavalent bispecific antibody comprising brolucizumab-derived VEGF-binding domains fused to the C termini of the heavy chains and the light chains of HC2:LC1; (iv) HC2-AFL:LC1, a tetravalent bispecific antibody comprising aflibercept-derived VEGF-binding domains fused to the C termini of the heavy chains of HC2:LC1; (v) HC2:LC1-AFL, a tetravalent bispecific antibody comprising aflibercept-derived VEGF-binding domains fused to the C termini of the light chains of HC2:LC1; (vi) HC2-AFL:LC1-AFL, a hexavalent bispecific antibody comprising aflibercept-derived VEGF-binding domains fused to the C termini of the heavy chains and the light chains of HC2:LC1; (vii) HC2-ABI:LC1, a tetravalent bispecific antibody comprising abicipar-derived VEGF-binding domains fused to the C termini of the heavy chains of HC2:LC1; (viii) HC2:LC1-ABI, a tetravalent bispecific antibody comprising abicipar-derived VEGF-binding domains fused to the C termini of the light chains of HC2:LC1; or (ix) HC2-ABI:LC1-ABI, a hexavalent bispecific antibody comprising abicipar-derived VEGF-binding domains fused to the C termini of the heavy chains and the light chains of HC2:LC1. FIG. 23A and FIG. 23B provide the ratio of phosphorylated Tie2 to total Tie2 and phosphorylated VEGFR2 to total VEGFR2, respectively, normalized to untreated cells. Treatments were as follows: mock-treated (−), treated with 5 ng/mL VEGF and 50 ng/mL Ang1 (+), or treated with 25 ng/mL VEGF and 250 ng/mL of Ang1 (+++). Treatment with VEGF and Ang1 resulted in increased phosphorylation of Tie2 (FIG. 23A) and VEGFR2 (FIG. 23B). Pre-treatment with the multi-specific antibodies enhanced Tie2 activation (FIG. 23A) and inhibited VEGFR2 activation (FIG. 23B) in cells treated with Ang1 and VEGF.

Figure 24A:
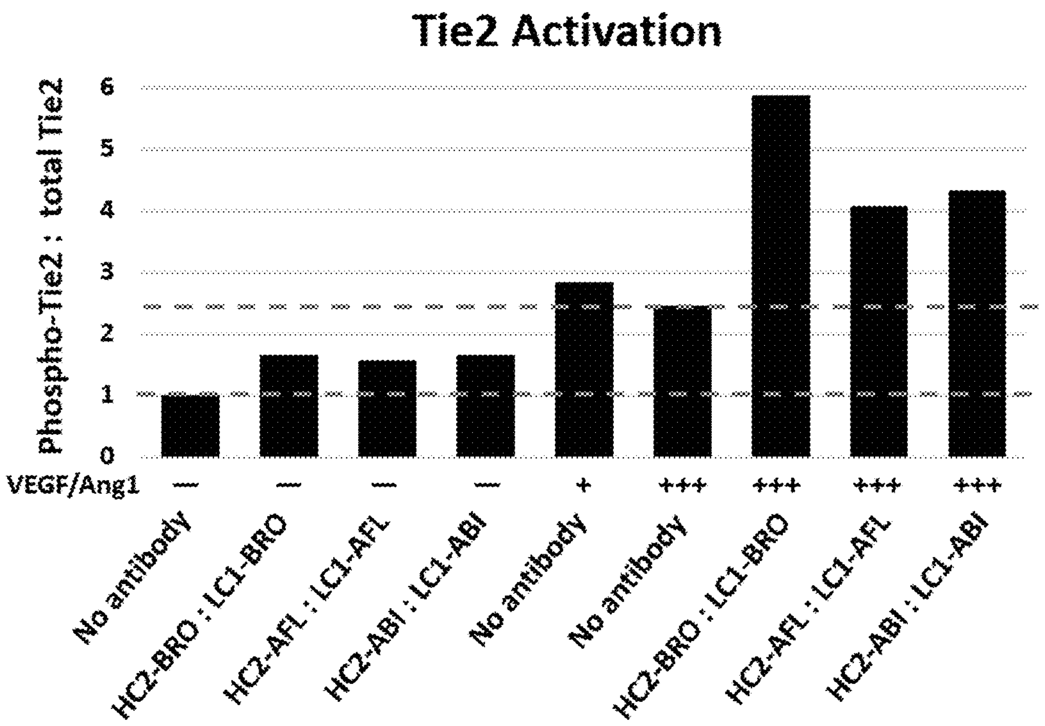
FIG. 24A and FIG. 24B: Hexavalent bispecific antibodies comprising brolucizumab-derived, aflibercept-derived, or abicipar-derived VEGF-binding domains enhance Tie2 activation and inhibit VEGFR2 activation in HUVECs treated with Ang1 and VEGF, as demonstrated by electrochemiluminescence signal quantification.
Figure 24B:
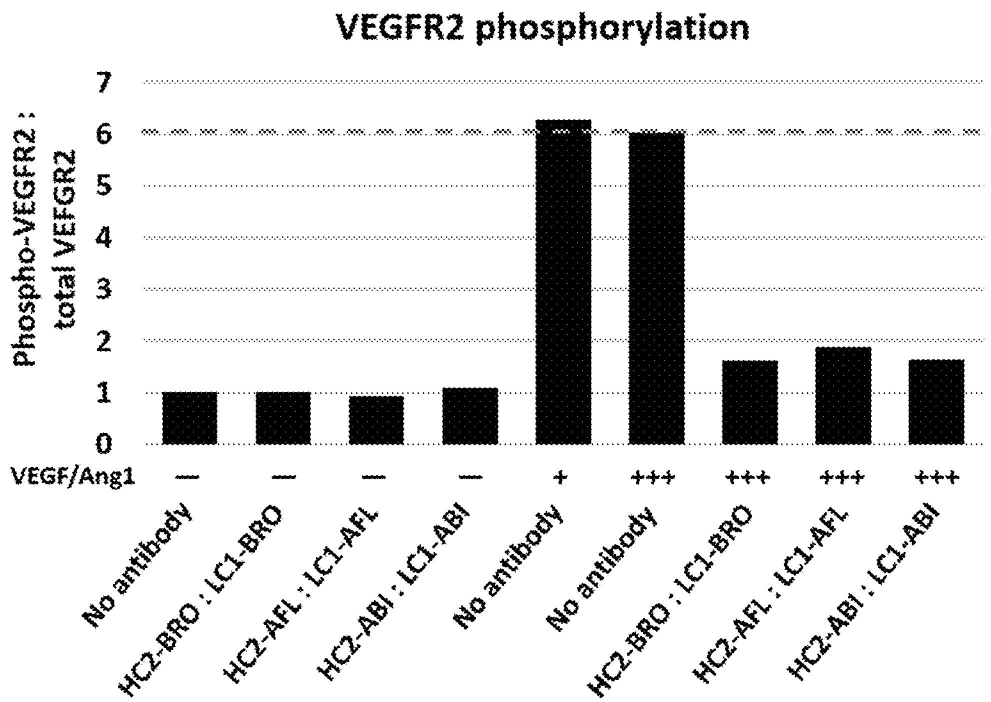

For FIG. 24A and FIG. 24B, the cells were mock-treated or pre-treated with one of the following antibodies at 5 nM: (i) HC2-BRO:LC1-BRO, a hexaavalent bispecific antibody comprising brolucizumab-derived VEGF-binding domains fused to the C termini of the heavy chains and the light chains of HC2:LC1 (a humanized monoclonal antibody specific for HPTP-β); (ii) HC2-AFL:LC1-AFL, a hexavalent bispecific antibody comprising aflibercept-derived VEGF-binding domains fused to the C termini of the heavy chains and the light chains of HC2:LC1; or (iii) HC2-ABI:LC1-ABI, a hexavalent bispecific antibody comprising abicipar-derived VEGF-binding domains fused to the C termini of the heavy chains and the light chains of HC2:LC1. FIG. 24A and FIG. 24B provide the ratio of phosphorylated Tie2 to total Tie2 and phosphorylated VEGFR2 to total VEGFR2, respectively, normalized to untreated cells. Treatments were as follows: mock-treated (−), treated with 5 ng/mL VEGF and 50 ng/mL Ang1 (+), or treated with 25 ng/mL VEGF and 250 ng/mL of Ang1 (+++). Treatment with VEGF and Ang1 resulted in increased phosphorylation of Tie2 (FIG. 24A) and VEGFR2 (FIG. 24B). Pre-treatment with the multi-specific antibodies enhanced Tie2 activation (FIG. 24A) and inhibited VEGFR2 activation (FIG. 24B) in cells treated with Ang1 and VEGF.

Figure 25A:
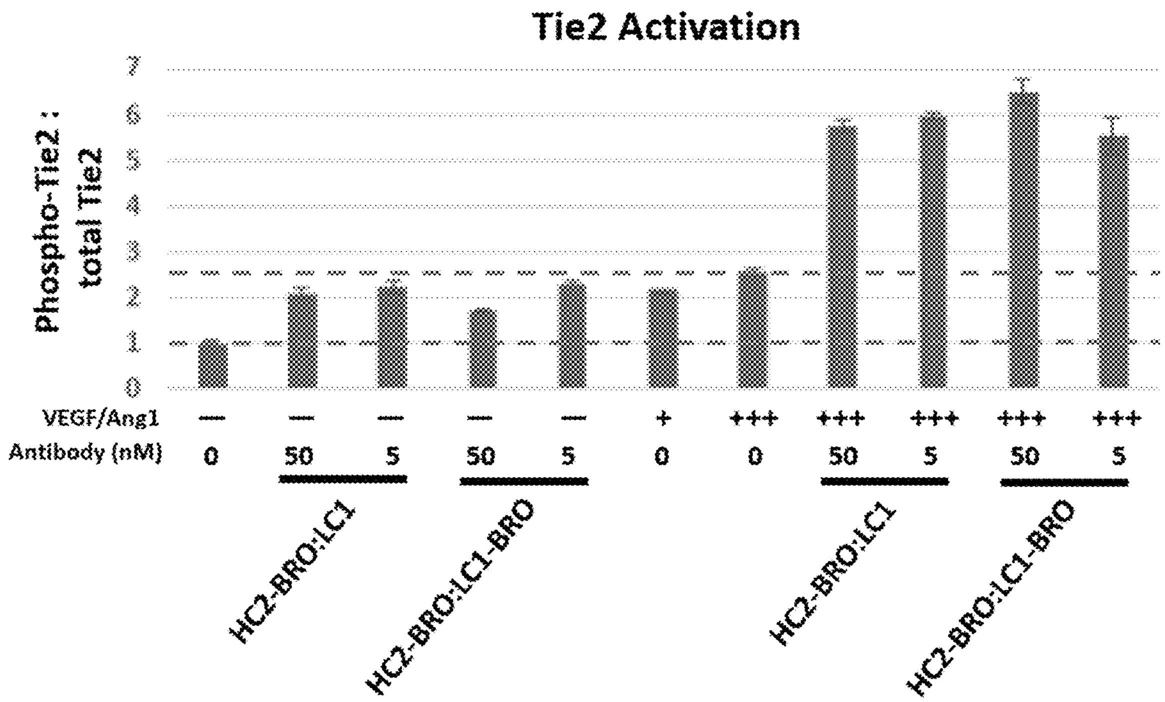
FIG. 25A and FIG. 25B: Tetravalent bispecific and hexavalent bispecific antibodies comprising brolucizumab-derived VEGF-binding domains enhance Tie2 activation and inhibit VEGFR2 activation in HUVECs treated with Ang1 and VEGF, as demonstrated by electrochemiluminescence signal quantification.
Figure 25B:
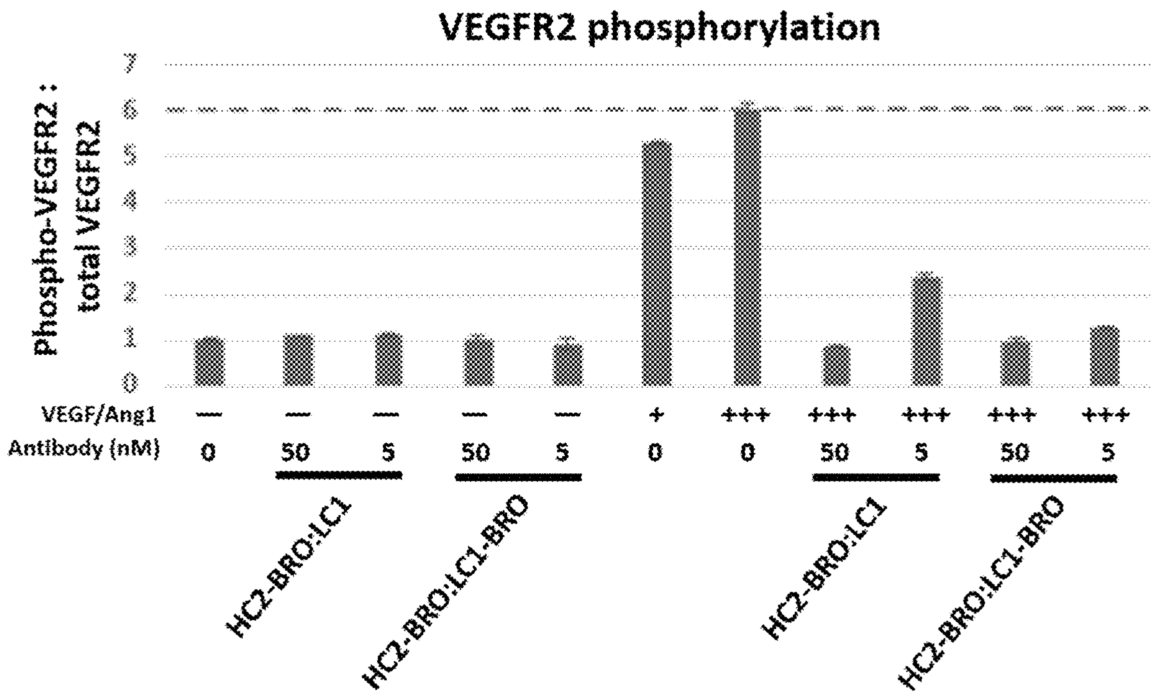

For FIG. 25A and FIG. 25B, the cells were mock-treated or pre-treated with one of the following antibodies at 5 or 50 nM: (i) HC2-BRO:LC1, a tetravalent bispecific antibody comprising brolucizumab-derived VEGF-binding domains fused to the C termini of the heavy chains of HC2:LC1 (a humanized monoclonal antibody specific for HPTP-0); or (ii) HC2-BRO:LC1-BRO, a hexavalent bispecific antibody comprising brolucizumab-derived VEGF-binding domains fused to the C termini of the heavy chains and the light chains of HC2:LC1. FIG. 25A and FIG. 25B provide the ratio of phosphorylated Tie2 to total Tie2 and phosphorylated VEGFR2 to total VEGFR2, respectively, normalized to untreated cells. Treatments were as follows: mock-treated (−), treated with 5 ng/mL VEGF and 50 ng/mL Ang1 (+), or treated with 25 ng/mL VEGF and 250 ng/mL of Ang1 (+++). Treatment with VEGF and Ang1 resulted in increased phosphorylation of Tie2 (FIG. 25A) and VEGFR2 (FIG. 25B). Pre-treatment with the multi-specific antibodies enhanced Tie2 activation (FIG. 25A) and inhibited VEGFR2 activation (FIG. 25B) in cells treated with Ang1 and VEGF.

Figure 26A:
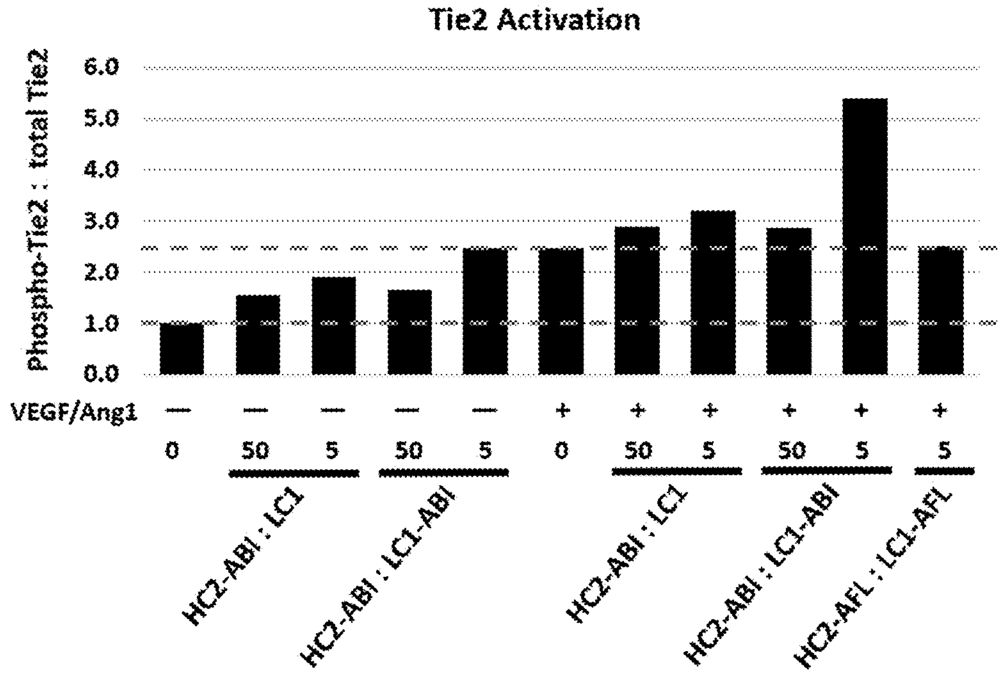
FIG. 26A and FIG. 26B: Tetravalent bispecific and hexavalent bispecific antibodies comprising abicipar-derived or aflibercept-derived VEGF-binding domains enhance Tie2 activation and inhibit VEGFR2 activation in HUVECs treated with Ang1 and VEGF, as demonstrated by electrochemiluminescence signal quantification.
Figure 26B:
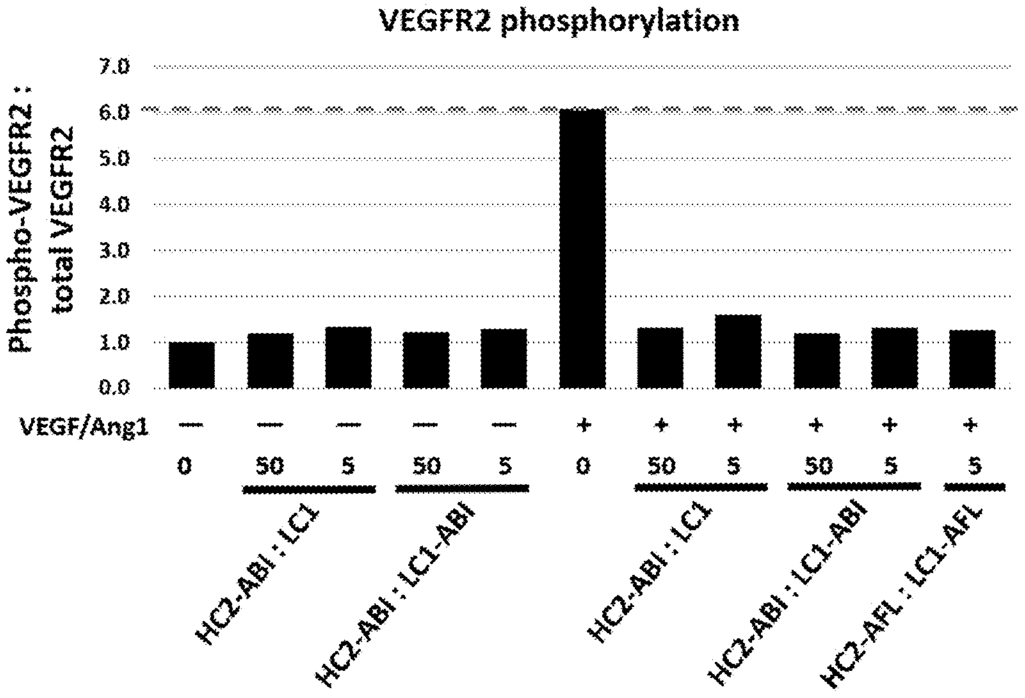

For FIG. 26A and FIG. 26B, the cells were mock-treated or pre-treated with one of the following antibodies at 5 nM or 50 nM: (i) HC2-ABI:LC1, a tetravalent bispecific antibody comprising abicipar-derived VEGF-binding domains fused to the C termini of the heavy chains of HC2:LC1 (a humanized monoclonal antibody specific for HPTP-β); (ii) HC2-ABI:LC1-ABI, a hexavalent bispecific antibody comprising abicipar-derived VEGF-binding domains fused to the C termini of the heavy chains and the light chains of HC2:LC1; or (iii) HC2-AFL:LC1:AFL, a hexavalent bispecific antibody comprising aflibercept-derived VEGF-binding domains fused to the C termini of the heavy chains and the light chains of HC2:LC1. FIG. 26A and FIG. 26B provide the ratio of phosphorylated Tie2 to total Tie2 and phosphorylated VEGFR2 to total VEGFR2, respectively, normalized to untreated cells. Treatments were as follows: mock-treated (−), or treated with 5 ng/mL VEGF and 50 ng/mL Ang1 (+). Treatment with VEGF and Ang1 resulted in increased phosphorylation of Tie2 (FIG. 26A) and VEGFR2 (FIG. 26B). Pre-treatment with the multi-specific antibodies enhanced Tie2 activation (FIG. 26A) and inhibited VEGFR2 activation (FIG. 26B) in cells treated with Ang1 and VEGF.

Figure 27A:
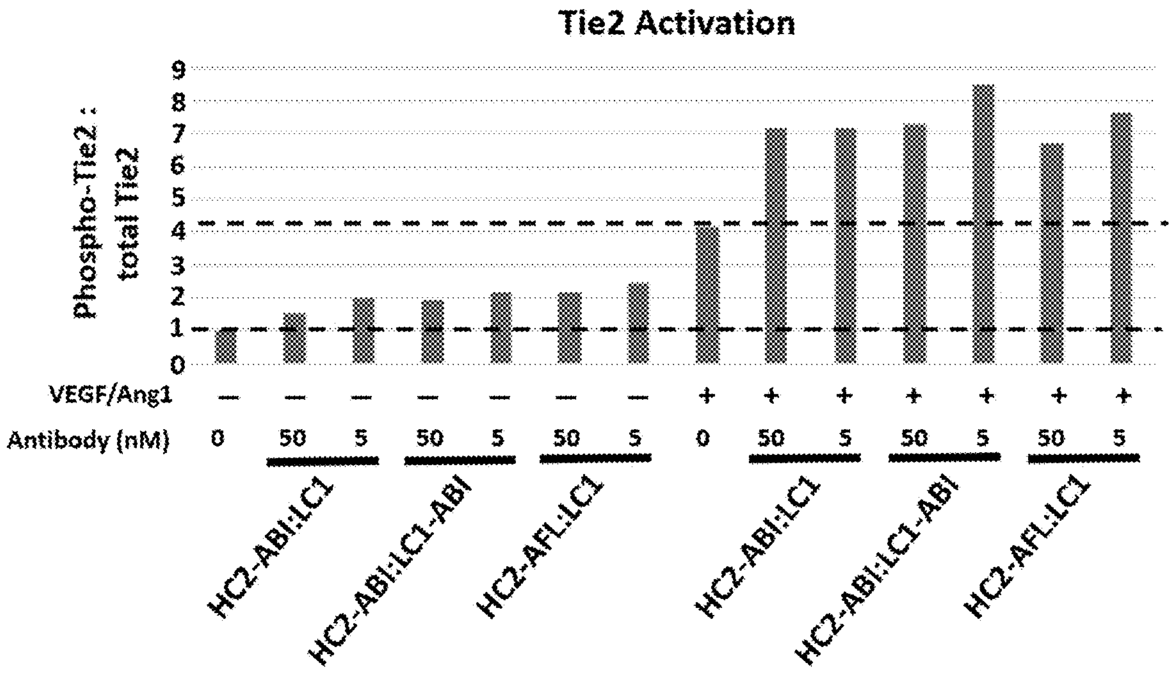
FIG. 27A and FIG. 27B: Tetravalent bispecific and hexavalent bispecific antibodies comprising abicipar-derived or aflibercept-derived VEGF-binding domains enhance Tie2 activation and inhibit VEGFR2 activation in HUVECs treated with Ang1 and VEGF, as demonstrated by electrochemiluminescence signal quantification.
Figure 27B:
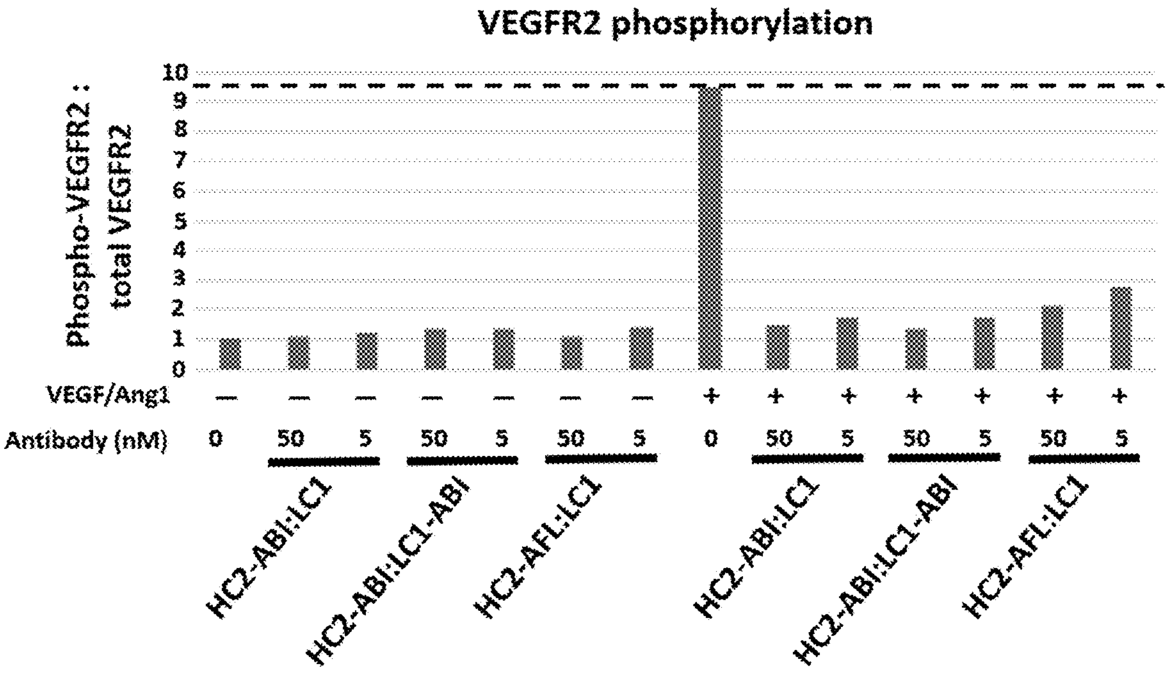

For FIG. 27A and FIG. 27B, the cells were mock-treated or pre-treated with one of the following antibodies at 5 nM or 50 nM: (i) HC2-ABI:LC1, a tetravalent bispecific antibody comprising abicipar-derived VEGF-binding domains fused to the C termini of the heavy chains of HC2:LC1 (a humanized monoclonal antibody specific for HPTP-β); (ii) HC2-ABI:LC1-ABI, a hexavalent bispecific antibody comprising abicipar-derived VEGF-binding domains fused to the C termini of the heavy chains and the light chains of HC2:LC1; or (iii) HC2-AFL:LC1, a tetravalent bispecific antibody comprising aflibercept-derived VEGF-binding domains fused to the C termini of the heavy chains of HC2:LC1. FIG. 27A and FIG. 27B provide the ratio of phosphorylated Tie2 to total Tie2 and phosphorylated VEGFR2 to total VEGFR2, respectively, normalized to untreated cells. Treatments were as follows: mock-treated (−), or treated with 25 ng/mL VEGF and 250 ng/mL Ang1 (+). Treatment with VEGF and Ang1 resulted in increased phosphorylation of Tie2 (FIG. 27A) and VEGFR2 (FIG. 27B). Pre-treatment with the multi-specific antibodies enhanced Tie2 activation (FIG. 27A) and inhibited VEGFR2 activation (FIG. 27B) in cells treated with Ang1 and VEGF.

Example 18: Multi-Specific Antibodies Bind HPTP-β and VEGF at High Affinity (Biacore™ Surface Plasmon Resonance Assays)

Biacore™ (a label-free, real-time biomolecular interaction analysis system using surface plasmon resonance) surface plasmon resonance assays were performed to determine the equilibrium dissociation constant ($K_D$) of antibodies of the disclosure for VEGF and HPTP-β (VE-PTP). Binding experiments were performed on Biacore™ 3000/Biacore™ T-200 instruments at 25° C.

The assay buffer contained 10 mM HEPES buffer (pH 7.4), 150 mM NaCl, 3 mM EDTA, and 0.05% P20 (polyoxyethylenesorbitan). The regeneration buffer contained 10 mM Glycine buffer (pH 1.75). The conjugation buffer contained 10 mM sodium acetate buffer (pH 5). A flow rate of 5 L/minute was used for capturing ligand. A flow rate of 30 L/minute was used for kinetic analysis.

For analysis of binding of antibodies to HPTP-0, polyhistidine tagged HPTP-β extracellular domain (ECD) ½ was immobilized on a chip surface via anti-His antibodies. Goat anti-His antibody was first immobilized on the surface of the chip by direct immobilization using EDC/NHS (N-ethyl-N'-(3-dimethyl aminopropyl carbodiimide)/N-hydroxy succinamide) coupling chemistry on flow cell 2 of the Biacore™ CM5 (Carboxymethylated dextran coated) chip. Unoccupied sites were blocked with 1M ethanolamine. The His-tagged ligand HPTP-β ½ ECD was captured at a response unit (RU) of 50. The analyte (antibody) was flowed over the chip at a single analyte concentration at a time. The binding of analyte to the ligand was monitored in real time to obtain on ($k_a$) and off ($k_d$) rates. The equilibrium constant ($K_D$) was calculated from the observed $k_a$ and $k_d$.

For analysis of binding of the antibodies to VEGF, the antibodies were immobilized on the surface of the chip by direct immobilization using EDC/NHS coupling chemistry on flow cell 2 of the Biacore™ CM5 chip. Unoccupied sites were blocked with 1M ethanolamine. The analyte (VEGF) was flowed over the chip at a single analyte concentration at a time. The binding of analyte to the ligand was monitored in real time to obtain on ($k_a$) and off ($k_d$) rates. The equilibrium constant ($K_D$) was calculated from the observed $k_a$ and $k_d$.

Scouting analysis was performed using 10 nM of analyte to determine approximate $K_D$. Chi square analysis was carried out between the actual sensorgram and the sensorgram generated from the BIAnalysis software to confirm the accuracy of the analysis; values of 1-2 were considered accurate and below 1 highly accurate.

TABLE 46 provides equilibrium dissociation constants based on scouting experiments performed at a single ligand concentration. NB=no significant binding detected.

TABLE 46

| Construct | VEGF $K_D$ | VEGF chi sq | HPTP-β $K_D$ | HPTP-β chi sq |
|---|---|---|---|---|
| HC2:LC1 | NB | NB | 7.32E−11M (73.2 pM) | 0.0439 |
| Aflibercept | 1.60E−10M (160 pM) | 0.278 | NB | NB |
| HC2-AFL:LC1 | 3.50E−10M (350 pM) | 0.13 | 3.20E−10M (320 pM) | 0.336 |
| HC2-BRO:LC1 | 1.12E−13M (112 fM) | 0.148 | 3.25E−10M (325 pM) | 0.323 |
| HC2-ABI:LC1 | 1.10E−13M (110 fM) | 1.68 | 1.22E−10M (122 pM) | 1.38 |
| HC2-RBZ:LC1 | NB | | 5.86E−13M (586 fM) | 0.16 |
| HC2:LC1-AFL | 8.25E−10M (825 pM) | 0.189 | 4.67E−10M (467 pM) | 1.48 |
| HC2:LC1-BRO | 3.51E−14M (35.1 fM) | 0.185 | 3.09E−10M (309 pM) | 0.691 |
| HC2:LC1-ABI | 5.19E−10M (519 pM) | 3.09 | 6.10E−11M (61 pM) | 1.47 |
| HC2-AFL:LC1-AFL | 5.57E−10M (557 pM) | 2.53 | 6.94E−11M (69.4 pM) | 3.14 |
| HC2-BRO:LC1-BRO | 1.79E−12M (1.79 pM) | 0.809 | 3.50E−12M (3.5 pM) | 2.15 |
| HC2-ABI:LC1-ABI | 6.80E−10M (680 pM) | 8.02 | 2.05E−10M (205 pM) | 1.18 |

Full kinetic analysis was performed using 0 nM, 0.625 nM, 1.25 nM, 5 nM, and 10 nM of the analyte to determine $K_D$. Chi square analysis was carried out between the actual sensorgram and the sensorgram generated from the BIAnalysis software to confirm the accuracy of the analysis; values of 1-2 were considered accurate and below 1 highly accurate.

TABLE 47 provides equilibrium dissociation constants based on full kinetic experiments performed at multiple ligand concentrations. NB=no significant binding detected.

TABLE 47

| Construct | VEGF $K_D$ | VEGF chi sq | HPTP-β $K_D$ | HPTP-β chi sq |
|---|---|---|---|---|
| HC2:LC1 | NB | NB | 1.21E−10M (121 pM) | 0.123 |
| Aflibercept | 3.75E−11M (37.5 pM) | 0.106 | NB | NB |
| HC2-AFL:LC1 | 4.63E−11M (46.3 pM) | 0.0875 | 2.19E−10M (219 pM) | 0.0295 |
| HC2-BRO:LC1 | 2.18E−13M (218 fM) | 0.452 | 1.54E−10M (154 pM) | 0.0817 |
| HC2-ABI:LC1 | 4.00E−14M (40 fM) | 0.223 | 1.03E−12M (1.03 pM) | 0.113 |

These results demonstrate that the multi-specific antibodies HC2-AFL:LC1, HC2-BRO:LC1, HC2-ABI:LC1, HC2:LC1-AFL, HC2:LC1-BRO, HC2:LC1-ABI, HC2-AFL:LC1-AFL, HC2-BRO:LC1-BRO, and HC2-ABI:LC1-ABI bind to HPTP-β and VEGF with high affinity.

Example 19: A Hexavalent Antibody Comprising Antibody HC2:LC1, Abicipar-Derived Sequences, and Brolucizumab-Derived Sequences To generate a heavy chain with abicipar-derived VEGF-binding domains added at the C-terminus, an amino acid sequence is generated comprising the following appended amino acid sequences, from N-terminus to C-terminus:

1) Residues 1-467 of SEQ ID NO: 14 (heavy chain of antibody HC2:LC1);
2) SEQ ID NO: 31 (linker peptide, underlined); and
3) SEQ ID NO: 244 (abicipar-derived sequence).

To generate a light chain with brolucizumab-derived VEGF-binding domains added at the C-terminus, an amino acid sequence is generated comprising the following appended amino acid sequences, from N-terminus to C-terminus:

1) SEQ ID NO: 17 (light chain of antibody HC2:LC1);
2) SEQ ID NO: 31 (linker peptide, underlined); and
3) SEQ ID NO: 23 (brolucizumab-derived sequence).

The resulting polypeptides, SEQ ID NO: 231 and SEQ ID NO: 218, are co-expressed to provide a hexavalent antibody HC2-ABI:LC1-BRO shown in TABLE 48. Amino acids 1-19 of SEQ ID NO: 231 are the heavy chain signal peptide (SEQ ID NO: 11). Amino acids 1-20 of SEQ ID NO: 218 are the light chain signal peptide (SEQ ID NO: 12). In some embodiments, a mature HC2-ABI:LC1-BRO does not comprise the signal peptides. For example, a mature HC2-ABI:LC1-BRO of the disclosure can comprise SEQ ID NO: 257 and SEQ ID NO: 258. The antibody is bispecific for target molecules, comprising a specificity for HPTP-β (VE-PTP) and VEGF. The antibody is trispecific for target epitopes, comprising a specificity for one HPTP-β (VE-PTP) epitope and for two VEGF epitopes.

TABLE 48

| SEQ ID NO: | Name | Amino acid sequence |
|---|---|---|
| 231 | Signal peptide-HC2-ABI | MGWTLVFLFLLSVTAGVHSEVQLVESGGGLVQPGGSLRLSC AASGFTFNANAMNWVRQAPGKGLEWVGRIRTKSNNYATY YAGSVKDRFTISRDDSKNSLYLQMNSLKTEDTAVYYCVRD YYGSSAWITYWGQGTLVTVSSASTKGPSVFPLAPCSRSTSES TAALGCLVKDYFPEPVTVSWNSGALTSGVHTFPAVLQSSGL YSLSSVVTVPSSSLGTKTYTCNVDHKPSNTKVDKRVESKYG PPCPPCPAPEFLGGPSVFLFPPKPKDTLMISRTPEVTCVVVDV SQEDPEVQFNWYVDGVEVHNAKTKPREEQFNSTYRVVSVL TVLHQDWLNGKEYKCKVSNKGLPSSIEKTISKAKGQPREPQ VYTLPPSQEEMTKNQVSLTCLVKGFYPSDIAVEWESNGQPE NNYKTTPPVLDSDGSFFLYSRLTVDKSRWQEGNVFSCSVMH EALHNHYTQKSLSLSLGGGGGSDLDKKLLEAARAGQDDEV RILMANGADVNARDSTGWTPLHLAAPWGHPEIVEVLLKNG ADVNAADFQGWTPLHLAAAVGHLEIVEVLLKYGADVNAQ DKFGKTAFDISIDNGNEDLAEILQKAA |
| 218 | Signal peptide-LC1-BRO | MVSSAQFLGLLLLCFQGTRCDVVMTQSPSFLSASVGDRVTIT CKASQHVGTAVAWYQQRPGKAPKLLIYWASTRHTGVPSRF SGSGSGTEFTLTISSLQPEDFATYFCQQYSSYPFTFGGGTKLEI KRTVAAPSVFIFPPSDEQLKSGTASVVCLLNNFYPREAKVQ WKVDNALQSGNSQESVTEQDSKDSTYSLSSTLTLSKADYEK HKVYACEVTHQGLSSPVTKSFNRGECGGGGSEIVMTQSPST LSASVGDRVIITCQASEIIHSWLAWYQQKPGKAPKLLIYLAS TLASGVPSRFSGSGSGAEFTLTISSLQPDDFATYYCQNVYLA STNGANFGQGTKLTVLGGGGGSGGGGSGGGGSGGGGSEVQ LVESGGGLVQPGGSLRLSCTASGFSLTDYYYMTWVRQAPG KGLEWVGFIDPDDDPYYATWAKGRFTISRDNSKNTLYLQM NSLRAEDTAVYYCAGGDHNSGWGLDIWGQGTLVTVSS |

Example 20: A Hexavalent Antibody Comprising Antibody HC2:LC1, Aflibercept-Derived Sequences, and Brolucizumab-Derived Sequences To generate a heavy chain with brolucizumab-derived VEGF-binding domains added at the C-terminus, an amino acid sequence is generated comprising the following appended amino acid sequences, from N-terminus to C-terminus:

1) SEQ ID NO: 14 (heavy chain of antibody HC2:LC1);
2) SEQ ID NO: 31 (linker peptide, underlined); and
3) SEQ ID NO: 23 (brolucizumab-derived sequence).

To generate a light chain with aflibercept-derived VEGF-binding domains added at the C-terminus, an amino acid sequence is generated comprising the following appended amino acid sequences, from N-terminus to C-terminus:

1) SEQ ID NO: 17 (light chain of antibody HC2:LC1);
2) SEQ ID NO: 31 (linker peptide, underlined); and
3) SEQ ID NO: 22 (aflibercept-derived sequence).

The resulting polypeptides, SEQ ID NO: 150 and SEQ ID NO: 219, are co-expressed to provide a hexavalent antibody HC2-BRO:LC1-AFL shown in TABLE 49. Amino acids 1-19 of SEQ ID NO: 150 are the heavy chain signal peptide (SEQ ID NO: 11). Amino acids 1-20 of SEQ ID NO: 219 are the light chain signal peptide (SEQ ID NO: 12). In some embodiments, a mature HC2-BRO:LC1-AFL does not comprise the signal peptides. For example, a mature HC2-BRO:LC1-AFL of the disclosure can comprise SEQ ID NO: 255 and SEQ ID NO: 259. The antibody is bispecific for target molecules, comprising a specificity for HPTP-β (VE-PTP) and VEGF. The antibody is trispecific for target epitopes, comprising a specificity for one HPTP-β (VE-PTP) epitope and for two VEGF epitopes.

TABLE 49

| SEQ ID NO: | Name | Amino acid sequence |
|---|---|---|
| 150 | Signal peptide-HC2-BRO | MGWTLVFLFLLSVTAGVHSEVQLVESGGGLVQPGGSLRLSC AASGFTFNANAMNWVRQAPGKGLEWVGRIRTKSNNYATY YAGSVKDRFTISRDDSKNSLYLQMNSLKTEDTAVYYCVRD YYGSSAWITYWGQGTLVTVSSASTKGPSVFPLAPCSRSTSES TAALGCLVKDYFPEPVTVSWNSGALTSGVHTFPAVLQSSGL YSLSSVVTVPSSSLGTKTYTCNVDHKPSNTKVDKRVESKYG PPCPPCPAPEFLGGPSVFLFPPKPKDTLMISRTPEVTCVVVDV SQEDPEVQFNWYVDGVEVHNAKTKPREEQFNSTYRVVSVL TVLHQDWLNGKEYKCKVSNKGLPSSIEKTISKAKGQPREPQ VYTLPPSQEEMTKNQVSLTCLVKGFYPSDIAVEWESNGQPE NNYKTTPPVLDSDGSFFLYSRLTVDKSRWQEGNVFSCSVMH EALHNHYTQKSLSLSLGKGGGGSEIVMTQSPSTLSASVGDR VIITCQASEIIHSWLAWYQQKPGKAPKLLIYLASTLASGVPSR FSGSGSGAEFTLTISSLQPDDFATYYCQNVYLASTNGANFGQ GTKLTVLGGGGGSGGGGSGGGGSGGGGSEVQLVESGGGLV QPGGSLRLSCTASGFSLTDYYYMTWVRQAPGKGLEWVGFI DPDDDPYYATWAKGRFTISRDNSKNTLYLQMNSLRAEDTA VYYCAGGDHNSGWGLDIWGQGTLVTVSS |

TABLE 49-continued

| SEQ ID NO: | Name | Amino acid sequence |
|---|---|---|
| 219 | Signal peptide-LC1- | MVSSAQFLGLLLLCFQGTRCDVVMTQSPSFLSASVGDRVTIT CKASQHVGTAVAWYQQRPGKAPKLLIYWASTRHTGVPSRF SGSGSGTEFTLTISSLQPEDFATYFCQQYSSYPFTFGGGTKLEI AFLKRTVAAPSVFIFPPSDEQLKSGTASVVCLLNNFYPREAKVQ WKVDNALQSGNSQESVTEQDSKDSTYSLSSTLTLSKADYEK HKVYACEVTHQGLSSPVTKSFNRGECGGGGSSDTGRPFVEM YSEIPEIIHMTEGRELVIPCRVTSPNITVTLKKFPLDTLIPDGK RIIWDSRKGFIISNATYKEIGLLTCEATVNGHLYKTNYLTHR QTNTIIDVVLSPSHGIELSVGEKLVLNCTARTELNVGIDFNW EYPSSKHQHKKLVNRDLKTQSGSEMKKFLSTLTIDGVTRSD QGLYTCAASSGLMTKKNSTFVRVHEK |

EMBODIMENTS

The following non-limiting embodiments provide illustrative examples of the disclosure, but do not limit the scope of the disclosure.

Embodiment 1. A compound comprising: (a) a first domain, wherein the first domain modulates a phosphatase, wherein the phosphatase modulates Tie2; and (b) a second domain that specifically binds a receptor tyrosine kinase agonist.

Embodiment 2. The compound of embodiment 1, wherein the compound is an antibody.

Embodiment 3. The compound of any one of embodiments 1-2, wherein the compound is a multispecific antibody.

Embodiment 4. The compound of any one of embodiments 1-3, wherein the compound is a tetravalent antibody.

Embodiment 5. The compound of any one of embodiments 1-3, wherein the compound is a hexavalent antibody.

Embodiment 6. The compound of any one of embodiments 1-5, wherein the compound is a bispecific antibody.

Embodiment 7. The compound of any one of embodiments 1-4 and 6, wherein the compound is a tetravalent bispecific antibody.

Embodiment 8. The compound of any one of embodiments 1-3 and 5-6, wherein the compound is a hexavalent bispecific antibody.

Embodiment 9. The compound of any one of embodiments 1-8, wherein the compound inhibits the phosphatase that modulates Tie2.

Embodiment 10. The compound of any one of embodiments 1-9, wherein the compound inhibits HPTP-β.

Embodiment 11. The compound of any one of embodiments 1-10, wherein the compound inhibits VE-PTP.

Embodiment 12. The compound of any one of embodiments 1-11, wherein the compound activates Tie2.

Embodiment 13. The compound of any one of embodiments 1-12, wherein the compound inhibits the receptor tyrosine kinase agonist.

Embodiment 14. The compound of any one of embodiments 1-13, wherein the compound inhibits VEGF receptor signaling.

Embodiment 15. The compound of any one of embodiments 1-14, wherein the compound inhibits a VEGF.

Embodiment 16. The compound of any one of embodiments 1-15, wherein the compound inhibits VEGF-A.

Embodiment 17. The compound of any one of embodiments 1-16, wherein the compound inhibits the phosphatase that modulates Tie2, and inhibits the receptor tyrosine kinase agonist.

Embodiment 18. The compound of any one of embodiments 1-17, wherein the phosphatase is HPTP-β, and the receptor tyrosine kinase agonist is a VEGF.

Embodiment 19. The compound of any one of embodiments 1-18, wherein the phosphatase is HPTP-β, and the receptor tyrosine kinase agonist is VEGF-A.

Embodiment 20. The compound of any one of embodiments 1-19, wherein the compound activates Tie2, and the receptor tyrosine kinase agonist is a VEGF.

Embodiment 21. The compound of any one of embodiments 1-20, wherein the compound activates Tie2, and the receptor tyrosine kinase agonist is VEGF-A.

Embodiment 22. The compound of any one of embodiments 1-21, wherein the phosphatase that modulates Tie2 signaling is a protein tyrosine phosphatase.

Embodiment 23. The compound of any one of embodiments 1-22, wherein the phosphatase that modulates Tie2 signaling is a receptor-like protein tyrosine phosphatase.

Embodiment 24. The compound of any one of embodiments 1-23, wherein the phosphatase that modulates Tie2 signaling is HPTP-β.

Embodiment 25. The compound of any one of embodiments 1-23, wherein the phosphatase that modulates Tie2 signaling is VE-PTP.

Embodiment 26. The compound of any one of embodiments 1-25, wherein the receptor tyrosine kinase agonist is a growth factor.

Embodiment 27. The compound of any one of embodiments 1-26, wherein the receptor tyrosine kinase agonist is a cysteine-knot growth factor superfamily member.

Embodiment 28. The compound of any one of embodiments 1-27, wherein the receptor tyrosine kinase agonist is a PDGF family member.

Embodiment 29. The compound of any one of embodiments 1-28, wherein the receptor tyrosine kinase agonist is a pro-angiogenic factor.

Embodiment 30. The compound of any one of embodiments 1-29, wherein the receptor tyrosine kinase agonist is a VEGF receptor agonist.

Embodiment 31. The compound of any one of embodiments 1-30, wherein the receptor tyrosine kinase agonist is a VEGF.

Embodiment 32. The compound of any one of embodiments 1-31, wherein the receptor tyrosine kinase agonist is VEGF-A.

Embodiment 33. The compound of any one of embodiments 1-32, wherein the first domain binds to HPTP-β.

Embodiment 34. The compound of any one of embodiments 1-33, wherein the first domain binds to VE-PTP.

Embodiment 35. The compound of any one of embodiments 1-34, wherein the first domain binds to an extracellular domain of HPTP-β.

Embodiment 36. The compound of any one of embodiments 1-34, wherein the first domain binds to a first FN3 repeat of an extracellular domain of HPTP-β.

Embodiment 37. The compound of any one of embodiments 1-36, wherein the second domain binds to a VEGF.

Embodiment 38. The compound of any one of embodiments 1-37, wherein the second domain binds to VEGF-A.

Embodiment 39. The compound of any one of embodiments 1-38, wherein the first domain binds to HPTP-β, and the receptor tyrosine kinase agonist is a VEGF.

Embodiment 40. The compound of any one of embodiments 1-39, wherein the first domain binds to HPTP-β, and the receptor tyrosine kinase agonist is VEGF-A.

Embodiment 41. The compound of any one of embodiments 1-40, wherein the first domain comprises a sequence that is at least 80% identical to any one of SEQ ID NOS: 76-98.

Embodiment 42. The compound of any one of embodiments 1-41, wherein the first domain comprises a sequence that is at least 80% identical to SEQ ID NO: 76, SEQ ID NO: 77, SEQ ID NO: 78, SEQ ID NO: 79, or SEQ ID NO: 80.

Embodiment 43. The compound of any one of embodiments 1-42, wherein the first domain comprises a sequence that is at least 80% identical to SEQ ID NO: 81, SEQ ID NO: 82, SEQ ID NO: 83, SEQ ID NO: 84, SEQ ID NO: 85, SEQ ID NO: 86, or SEQ ID NO: 87.

Embodiment 44. The compound of any one of embodiments 1-43, wherein the first domain comprises a sequence that is at least 80% identical to SEQ ID NO: 88, SEQ ID NO: 89, or SEQ ID NO: 90.

Embodiment 45. The compound of any one of embodiments 1-44, wherein the first domain comprises a sequence that is at least 80% identical to SEQ ID NO: 91, SEQ ID NO: 92, or SEQ ID NO: 93.

Embodiment 46. The compound of any one of embodiments 1-45, wherein the first domain comprises a sequence that is at least 80% identical to SEQ ID NO: 94, SEQ ID NO: 95, or SEQ ID NO: 96.

Embodiment 47. The compound of any one of embodiments 1-46, wherein the first domain comprises a sequence that is at least 80% identical to SEQ ID NO: 97 or SEQ ID NO: 98.

Embodiment 48. The compound of any one of embodiments 1-47, wherein the first domain comprises: (a) a sequence that is at least 80% identical to SEQ ID NO: 76, SEQ ID NO: 77, SEQ ID NO: 78, SEQ ID NO: 79, or SEQ ID NO: 80; (b) a sequence that is at least 80% identical to SEQ ID NO: 81, SEQ ID NO: 82, SEQ ID NO: 83, SEQ ID NO: 84, SEQ ID NO: 85, SEQ ID NO: 86, or SEQ ID NO: 87; (c) a sequence that is at least 80% identical to SEQ ID NO: 88, SEQ ID NO: 89, or SEQ ID NO: 90; (d) a sequence that is at least 80% identical to SEQ ID NO: 91, SEQ ID NO: 92, or SEQ ID NO: 93; (e) a sequence that is at least 80% identical to SEQ ID NO: 94, SEQ ID NO: 95, or SEQ ID NO: 96; and (f) a sequence that is at least 80% identical to SEQ ID NO: 97 or SEQ ID NO: 98.

Embodiment 49. The compound of any one of embodiments 1-48, wherein the second domain comprises a sequence that is at least 80% identical to SEQ ID NO: 22, SEQ ID NO: 23, SEQ ID NO: 28, or SEQ ID NO: 244.

Embodiment 50. The compound of any one of embodiments 1-49, wherein the second domain comprises a sequence that is at least 80% identical to any one of SEQ ID NOS: 99-146.

Embodiment 51. The compound of any one of embodiments 1-50, wherein the second domain comprises a sequence that is at least 80% identical to SEQ ID NO: 99, SEQ ID NO: 100, SEQ ID NO: 101, SEQ ID NO: 102, SEQ ID NO: 103, SEQ ID NO: 104, SEQ ID NO: 105, SEQ ID NO: 106, SEQ ID NO: 107, SEQ ID NO: 108, SEQ ID NO: 109, SEQ ID NO: 110, SEQ ID NO: 111, SEQ ID NO: 112, or SEQ ID NO: 113.

Embodiment 52. The compound of any one of embodiments 1-51, wherein the second domain comprises a sequence that is at least 80% identical to SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, SEQ ID NO: 122, or SEQ ID NO: 123.

Embodiment 53. The compound of any one of embodiments 1-52, wherein the second domain comprises a sequence that is at least 80% identical to SEQ ID NO: 124, SEQ ID NO: 125, SEQ ID NO: 126, SEQ ID NO: 127, SEQ ID NO: 128, SEQ ID NO: 129, SEQ ID NO: 130, or SEQ ID NO: 131.

Embodiment 54. The compound of any one of embodiments 1-53, wherein the second domain comprises a sequence that is at least 80% identical to SEQ ID NO: 132, SEQ ID NO: 133, SEQ ID NO: 134, SEQ ID NO: 135, SEQ ID NO: 136, or SEQ ID NO: 137.

Embodiment 55. The compound of any one of embodiments 1-54, wherein the second domain comprises a sequence that is at least 80% identical to SEQ ID NO: 138, SEQ ID NO: 139, SEQ ID NO: 140, SEQ ID NO: 141, SEQ ID NO: 142, or SEQ ID NO: 143.

Embodiment 56. The compound of any one of embodiments 1-55, wherein the second domain comprises a sequence that is at least 80% identical to SEQ ID NO: 144, SEQ ID NO: 145, or SEQ ID NO: 146.

Embodiment 57. The compound of any one of embodiments 1-56, wherein the second domain comprises: (a) a sequence that is at least 80% identical to SEQ ID NO: 99, SEQ ID NO: 100, SEQ ID NO: 101, SEQ ID NO: 102, SEQ ID NO: 103, SEQ ID NO: 104, SEQ ID NO: 105, SEQ ID NO: 106, SEQ ID NO: 107, SEQ ID NO: 108, SEQ ID NO: 109, SEQ ID NO: 110, SEQ ID NO: 111, SEQ ID NO: 112, or SEQ ID NO: 113; (b) a sequence that is at least 80% identical to SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, SEQ ID NO: 122, or SEQ ID NO: 123; (c) a sequence that is at least 80% identical to SEQ ID NO: 124, SEQ ID NO: 125, SEQ ID NO: 126, SEQ ID NO: 127, SEQ ID NO: 128, SEQ ID NO: 129, SEQ ID NO: 130, or SEQ ID NO: 131; (d) a sequence that is at least 80% identical to SEQ ID NO: 132, SEQ ID NO: 133, SEQ ID NO: 134, SEQ ID NO: 135, SEQ ID NO: 136, or SEQ ID NO: 137; (e) a sequence that is at least 80% identical to SEQ ID NO: 138, SEQ ID NO: 139, SEQ ID NO: 140, SEQ ID NO: 141, SEQ ID NO: 142, or SEQ ID NO: 143; and (f) a sequence that is at least 80% identical to SEQ ID NO: 144, SEQ ID NO: 145, or SEQ ID NO: 146.

Embodiment 58. The compound of any one of embodiments 1-57, wherein the second domain comprises a sequence that is at least 80% identical to SEQ ID NO: 147, SEQ ID NO: 148, or any one of SEQ ID NOS: 233-242.

Embodiment 59. The compound of any one of embodiments 1-58, wherein: (a) the first domain comprises a sequence that is at least 80% identical to any one of SEQ ID NOS: 76-98; and (b) the second domain comprises a sequence that is at least 80% identical to any one of SEQ ID NOS: 99-148 or any one of SEQ ID NOS: 233-242.

Embodiment 60. The compound of any one of embodiments 1-59, wherein: (a) the first domain comprises: (i) a sequence that is at least 80% identical to SEQ ID NO: 76, SEQ ID NO: 77, SEQ ID NO: 78, SEQ ID NO: 79, or SEQ ID NO: 80; (ii) a sequence that is at least 80% identical to SEQ ID NO: 81, SEQ ID NO: 82, SEQ ID NO: 83, SEQ ID NO: 84, SEQ ID NO: 85, SEQ ID NO: 86, or SEQ ID NO: 87; (iii) a sequence that is at least 80% identical to SEQ ID NO: 88, SEQ ID NO: 89, or SEQ ID NO: 90; (iv) a sequence that is at least 80% identical to SEQ ID NO: 91, SEQ ID NO: 92, or SEQ ID NO: 93; (v) a sequence that is at least 80% identical to SEQ ID NO: 94, SEQ ID NO: 95, or SEQ ID NO: 96; and (vi) a sequence that is at least 80% identical to SEQ ID NO: 97 or SEQ ID NO: 98; and (b) the second domain comprises: (i) a sequence that is at least 80% identical to SEQ ID NO: 99, SEQ ID NO: 100, SEQ ID NO: 101, SEQ ID NO: 102, SEQ ID NO: 103, SEQ ID NO: 104, SEQ ID NO: 105, SEQ ID NO: 106, SEQ ID NO: 107, SEQ ID NO: 108, SEQ ID NO: 109, SEQ ID NO: 110, SEQ ID NO: 111, SEQ ID NO: 112, or SEQ ID NO: 113; (ii) a sequence that is at least 80% identical to SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, SEQ ID NO: 122, or SEQ ID NO: 123; (iii) a sequence that is at least 80% identical to SEQ ID NO: 124, SEQ ID NO: 125, SEQ ID NO: 126, SEQ ID NO: 127, SEQ ID NO: 128, SEQ ID NO: 129, SEQ ID NO: 130, or SEQ ID NO: 131; (iv) a sequence that is at least 80% identical to SEQ ID NO: 132, SEQ ID NO: 133, SEQ ID NO: 134, SEQ ID NO: 135, SEQ ID NO: 136, or SEQ ID NO: 137; (v) a sequence that is at least 80% identical to SEQ ID NO: 138, SEQ ID NO: 139, SEQ ID NO: 140, SEQ ID NO: 141, SEQ ID NO: 142, or SEQ ID NO: 143; and (vi) a sequence that is at least 80% identical to SEQ ID NO: 144, SEQ ID NO: 145, or SEQ ID NO: 146.

Embodiment 61. The compound of any one of embodiments 1-60, wherein: (a) the first domain comprises a sequence that is at least 80% identical to SEQ ID NO: 76, SEQ ID NO: 77, SEQ ID NO: 78, SEQ ID NO: 79, or SEQ ID NO: 80; and (b) the second domain comprises a sequence that is at least 80% identical to SEQ ID NO: 22, SEQ ID NO: 147, SEQ ID NO: 148, SEQ ID NO: 244, or any one of SEQ ID NOS: 233-242.

Embodiment 62. The compound of any one of embodiments 1-61, wherein: (a) the first domain comprises a sequence that is at least 80% identical to SEQ ID NO: 81, SEQ ID NO: 82, SEQ ID NO: 83, SEQ ID NO: 84, SEQ ID NO: 85, SEQ ID NO: 86, or SEQ ID NO: 87; and (b) the second domain comprises a sequence that is at least 80% identical to SEQ ID NO: 22, SEQ ID NO: 147, SEQ ID NO: 148, SEQ ID NO: 244, or any one of SEQ ID NOS: 233-242.

Embodiment 63. The compound of any one of embodiments 1-62, wherein: (a) the first domain comprises a sequence that is at least 80% identical to SEQ ID NO: 88, SEQ ID NO: 89, or SEQ ID NO: 90; and (b) the second domain comprises a sequence that is at least 80% identical to SEQ ID NO: 22, SEQ ID NO: 147, SEQ ID NO: 148, SEQ ID NO: 244, or any one of SEQ ID NOS: 233-242.

Embodiment 64. The compound of any one of embodiments 1-63, wherein: (a) the first domain comprises a sequence that is at least 80% identical to SEQ ID NO: 91, SEQ ID NO: 92, or SEQ ID NO: 93; and (b) the second domain comprises a sequence that is at least 80% identical to SEQ ID NO: 22, SEQ ID NO: 147, SEQ ID NO: 148, SEQ ID NO: 244, or any one of SEQ ID NOS: 233-242.

Embodiment 65. The compound of any one of embodiments 1-64, wherein: (a) the first domain comprises a sequence that is at least 80% identical to SEQ ID NO: 94, SEQ ID NO: 95, or SEQ ID NO: 96; and (b) the second domain comprises a sequence that is at least 80% identical to SEQ ID NO: 22, SEQ ID NO: 147, SEQ ID NO: 148, SEQ ID NO: 244, or any one of SEQ ID NOS: 233-242.

Embodiment 66. The compound of any one of embodiments 1-65, wherein: (a) the first domain comprises a sequence that is at least 80% identical to SEQ ID NO: 97 or SEQ ID NO: 98; and (b) the second domain comprises a sequence that is at least 80% identical to SEQ ID NO: 22, SEQ ID NO: 147, SEQ ID NO: 148, SEQ ID NO: 244, or any one of SEQ ID NOS: 233-242.

Embodiment 67. The compound of any one of embodiments 1-66, wherein: (a) the first domain comprises: (i) a sequence that is at least 80% identical to SEQ ID NO: 76, SEQ ID NO: 77, SEQ ID NO: 78, SEQ ID NO: 79, or SEQ ID NO: 80; (ii) a sequence that is at least 80% identical to SEQ ID NO: 81, SEQ ID NO: 82, SEQ ID NO: 83, SEQ ID NO: 84, SEQ ID NO: 85, SEQ ID NO: 86, or SEQ ID NO: 87; (iii) a sequence that is at least 80% identical to SEQ ID NO: 88, SEQ ID NO: 89, or SEQ ID NO: 90; (iv) a sequence that is at least 80% identical to SEQ ID NO: 91, SEQ ID NO: 92, or SEQ ID NO: 93; (v) a sequence that is at least 80% identical to SEQ ID NO: 94, SEQ ID NO: 95, or SEQ ID NO: 96; and (vi) a sequence that is at least 80% identical to SEQ ID NO: 97 or SEQ ID NO: 98; and (b) the second domain comprises a sequence that is at least 80% identical to SEQ ID NO: 22, SEQ ID NO: 147, SEQ ID NO: 148, SEQ ID NO: 244, or any one of SEQ ID NOS: 233-242.

Embodiment 68. The compound of any one of embodiments 1-67, wherein the compound comprises: (a) a heavy chain sequence that is at least 80% identical to SEQ ID NO: 149, SEQ ID NO: 150, SEQ ID NO: 151, or SEQ ID NO: 231; and (b) a light chain sequence that is at least 80% identical to SEQ ID NO: 17, SEQ ID NO: 18, SEQ ID NO: 19, or SEQ ID NO: 20.

Embodiment 69. The compound of any one of embodiments 1-4, 6-7, and 9-68, wherein the compound is a tetravalent bispecific antibody comprising: (a) a sequence that is at least 80% identical to SEQ ID NO: 22, SEQ ID NO: 23, SEQ ID NO: 28, or SEQ ID NO: 244; (b) a sequence that is at least 80% identical to SEQ ID NO: 13, SEQ ID NO: 14, SEQ ID NO: 15, or SEQ ID NO: 16; (c) a sequence that is at least 80% identical to any one of SEQ ID NOS: 31-75; and (d) a sequence that is at least 80% identical to SEQ ID NO: 17, SEQ ID NO: 18, SEQ ID NO: 19, or SEQ ID NO: 20.

Embodiment 70. The compound of any one of embodiments 1-4, 6-7 and 9-69, wherein the compound is a tetravalent bispecific antibody comprising: (a) a first chain, wherein the first chain comprises a linker, wherein the linker comprises a sequence that is at least 80% identical to any one of SEQ ID NOS: 31-75, wherein the linker comprises a N-terminus and a C-terminus, wherein the N-terminus of the linker is attached to a C terminus of a sequence that is at least 80% identical to SEQ ID NO: 13, SEQ ID NO: 14, SEQ ID NO: 15, or SEQ ID NO: 16, and the C-terminus of the linker is attached to a N-terminus of a sequence that is at least 80% identical to SEQ ID NO: 22, SEQ ID NO: 23, SEQ ID NO: 28, or SEQ ID NO: 244; and (b) a second chain, wherein the second chain comprises a sequence that is at least 80% identical to SEQ ID NO: 17, SEQ ID NO: 18, SEQ ID NO: 19, or SEQ ID NO: 20.

Embodiment 71. The compound of any one of embodiments 1-4, 6-7, 9-67, and 69, wherein the compound is a tetravalent bispecific antibody comprising: (a) a first chain, wherein the first chain comprises a sequence that is at least 80% identical to SEQ ID NO: 13, SEQ ID NO: 14, SEQ ID NO: 15, or SEQ ID NO: 16; and (b) a second chain, wherein the second chain comprises a linker, wherein the linker comprises a sequence that is at least 80% identical to any one of SEQ ID NOS: 31-75, wherein the linker comprises a N-terminus and a C-terminus, wherein the N-terminus of the linker is attached to a C terminus of a sequence that is at least 80% identical to SEQ ID NO: 17, SEQ ID NO: 18, SEQ ID NO: 19, or SEQ ID NO: 20, and the C-terminus of the linker is attached to a N-terminus of a sequence that is at least 80% identical to SEQ ID NO: 22, SEQ ID NO: 23, SEQ ID NO: 28, or SEQ ID NO: 244.

Embodiment 72. The compound of any one of embodiments 1-3, 5-6, and 8-67, wherein the compound is a hexavalent bispecific antibody comprising: (a) a sequence that is at least 80% identical to SEQ ID NO: 22, SEQ ID NO: 23, SEQ ID NO: 28, or SEQ ID NO: 244; (b) a sequence that is at least 80% identical to SEQ ID NO: 13, SEQ ID NO: 14, SEQ ID NO: 15, or SEQ ID NO: 16; (c) a sequence that is at least 80% identical to any one of SEQ ID NOS: 31-75; and (d) a sequence that is at least 80% identical to SEQ ID NO: 17, SEQ ID NO: 18, SEQ ID NO: 19, or SEQ ID NO: 20.

Embodiment 73. The compound of any one of embodiments 1-3, 5-6, 8-67, and 72, wherein the compound is a hexavalent bispecific antibody comprising: (a) a first chain, wherein the first chain comprises a linker, wherein the linker comprises a sequence that is at least 80% identical to any one of SEQ ID NOS: 31-75, wherein the linker comprises a N-terminus and a C-terminus, wherein the N-terminus of the linker is attached to a C terminus of a sequence that is at least 80% identical to SEQ ID NO: 13, SEQ ID NO: 14, SEQ ID NO: 15, or SEQ ID NO: 16, and the C-terminus of the linker is attached to a N-terminus of a sequence that is at least 80% identical to SEQ ID NO: 22, SEQ ID NO: 23, SEQ ID NO: 28, or SEQ ID NO: 244; and (b) a second chain, wherein the second chain comprises a linker, wherein the linker comprises a sequence that is at least 80% identical to any one of SEQ ID NOS: 31-75, wherein the linker comprises a N-terminus and a C-terminus, wherein the N-terminus of the linker is attached to a C terminus of a sequence that is at least 80% identical to SEQ ID NO: 17, SEQ ID NO: 18, SEQ ID NO: 19, or SEQ ID NO: 20, and the C-terminus of the linker is attached to a N-terminus of a sequence that is at least 80% identical to SEQ ID NO: 22, SEQ ID NO: 23, SEQ ID NO: 28, or SEQ ID NO: 244.

Embodiment 74. The compound of any one of embodiments 1-67, wherein the compound comprises: (a) a heavy chain sequence that is at least 80% identical to SEQ ID NO: 245 or any one of SEQ ID NOS: 13-16; and (b) a light chain sequence that is at least 80% identical to SEQ ID NO: 218, SEQ ID NO: 219, SEQ ID NO: 232, or SEQ ID NO: 243.

Embodiment 75. The compound of any one of embodiments 1-67, wherein the compound comprises: (a) a heavy chain sequence that is at least 80% identical to SEQ ID NO: 149, SEQ ID NO: 150, SEQ ID NO: 151, or SEQ ID NO: 231; and (b) a light chain sequence that is at least 80% identical to SEQ ID NO: 218, SEQ ID NO: 219, SEQ ID NO: 232, or SEQ ID NO: 243.

Embodiment 76. The compound of any one of embodiments 1-75, wherein a binding affinity ($K_D$) of the compound to HPTP-β is about 30 fM to about 70 nM.

Embodiment 77. The compound of any one of embodiments 1-76, wherein a binding affinity ($K_D$) of the compound to the VEGF is about 30 fM to about 70 nM.

Embodiment 78. The compound of any one of embodiments 1-75, wherein a binding affinity ($K_D$) of the compound to HPTP-β is about 30 fM to about 70 nM, and a binding affinity ($K_D$) of the compound to VEGF is about 30 fM to about 70 nM.

Embodiment 79. A method of treating a condition in a subject in need thereof, the method comprising administering to the subject a therapeutically-effective amount of the compound of any one of embodiments 1-78.

Embodiment 80. The method of embodiment 79, wherein the condition is an ocular condition.

Embodiment 81. The method of any one of embodiments 79-80, wherein the condition is diabetic retinopathy.

Embodiment 82. The method of any one of embodiments 79-80, wherein the condition is neovascularization.

Embodiment 83. The method of any one of embodiments 79-80, wherein the condition is vascular leak.

Embodiment 84. The method of any one of embodiments 79-80, wherein the condition is increased intraocular pressure.

Embodiment 85. The method of any one of embodiments 79-80, wherein the condition is ocular edema.

Embodiment 86. The method of any one of embodiments 79-80 and 85, wherein the condition is diabetic macular edema.

Embodiment 87. The method of any one of embodiments 79-80, wherein the condition is ocular hypertension.

Embodiment 88. The method of any one of embodiments 79-80, wherein the condition is ocular inflammation.

Embodiment 89. The method of any one of embodiments 79-80, wherein the condition is glaucoma.

Embodiment 90. The method of any one of embodiments 79-89, wherein the administration is to an eye of the subject.

Embodiment 91. The method of any one of embodiments 79-90, wherein the administration is intravitreal.

Embodiment 92. The method of any one of embodiments 79-89, wherein the administration is subcutaneous.

Embodiment 93. The method of any one of embodiments 79-90, wherein the administration is topical.

Embodiment 94. The method of any one of embodiments 79-93, wherein the subject is human.

Embodiment 95. The method of any one of embodiments 79-94, wherein the therapeutically-effective amount is from about 0.25 mg to about 200 mg.

Embodiment 96. The method of any one of embodiments 79-95, wherein the therapeutically-effective amount is from about 1 mg/kg to about 10 mg/kg.

Embodiment 97. The method of any one of embodiments 79-95, wherein the therapeutically-effective amount is from about 1 mg to about 50 mg.

Embodiment 98. The method of any one of embodiments 79-95, wherein the therapeutically-effective amount is from about 50 mg to about 200 mg.

Embodiment 99. The compound of any one of embodiments 1-67, wherein the compound comprises: (a) a heavy chain sequence that is at least 80% identical to SEQ ID NO: 254, SEQ ID NO: 255, SEQ ID NO: 256, or SEQ ID NO: 257; and (b) a light chain sequence that is at least 80% identical to SEQ ID NO: 250, SEQ ID NO: 251, SEQ ID NO: 252, or SEQ ID NO: 253.

Embodiment 100. The compound of any one of embodiments 1-4, 6-7, and 9-68, wherein the compound is a tetravalent bispecific antibody comprising: (a) a sequence that is at least 80% identical to SEQ ID NO: 22, SEQ ID NO: 23, SEQ ID NO: 28, or SEQ ID NO: 244; (b) a sequence that is at least 80% identical to SEQ ID NO: 246, SEQ ID NO: 247, SEQ ID NO: 248, or SEQ ID NO: 249; (c) a sequence that is at least 80% identical to any one of SEQ ID NOS: 31-75; and (d) a sequence that is at least 80% identical to SEQ ID NO: 250, SEQ ID NO: 251, SEQ ID NO: 252, or SEQ ID NO: 253.

Embodiment 101. The compound of any one of embodiments 1-4, 6-7 and 9-69, wherein the compound is a tetravalent bispecific antibody comprising: (a) a first chain, wherein the first chain comprises a linker, wherein the linker comprises a sequence that is at least 80% identical to any one of SEQ ID NOS: 31-75, wherein the linker comprises a N-terminus and a C-terminus, wherein the N-terminus of the linker is attached to a C terminus of a sequence that is at least 80% identical to SEQ ID NO: 246, SEQ ID NO: 247, SEQ ID NO: 248, or SEQ ID NO: 249, and the C-terminus of the linker is attached to a N-terminus of a sequence that is at least 80% identical to SEQ ID NO: 22, SEQ ID NO: 23, SEQ ID NO: 28, or SEQ ID NO: 244; and (b) a second chain, wherein the second chain comprises a sequence that is at least 80% identical to SEQ ID NO: 250, SEQ ID NO: 251, SEQ ID NO: 252, or SEQ ID NO: 253.

Embodiment 102. The compound of any one of embodiments 1-4, 6-7, 9-67, and 69, wherein the compound is a tetravalent bispecific antibody comprising: (a) a first chain, wherein the first chain comprises a sequence that is at least 80% identical to SEQ ID NO: 246, SEQ ID NO: 247, SEQ ID NO: 248, or SEQ ID NO: 249; and (b) a second chain, wherein the second chain comprises a linker, wherein the linker comprises a sequence that is at least 80% identical to any one of SEQ ID NOS: 31-75, wherein the linker comprises a N-terminus and a C-terminus, wherein the N-terminus of the linker is attached to a C terminus of a sequence that is at least 80% identical to SEQ ID NO: 250, SEQ ID NO: 251, SEQ ID NO: 252, or SEQ ID NO: 253, and the C-terminus of the linker is attached to a N-terminus of a sequence that is at least 80% identical to SEQ ID NO: 22, SEQ ID NO: 23, SEQ ID NO: 28, or SEQ ID NO: 244.

Embodiment 103. The compound of any one of embodiments 1-3, 5-6, and 8-67, wherein the compound is a hexavalent bispecific antibody comprising: (a) a sequence that is at least 80% identical to SEQ ID NO: 22, SEQ ID NO: 23, SEQ ID NO: 28, or SEQ ID NO: 244; (b) a sequence that is at least 80% identical to SEQ ID NO: 246, SEQ ID NO: 247, SEQ ID NO: 248, or SEQ ID NO: 249; (c) a sequence that is at least 80% identical to any one of SEQ ID NOS: 31-75; and (d) a sequence that is at least 80% identical to SEQ ID NO: 250, SEQ ID NO: 251, SEQ ID NO: 252, or SEQ ID NO: 253.

Embodiment 104. The compound of any one of embodiments 1-3, 5-6, 8-67, and 72, wherein the compound is a hexavalent bispecific antibody comprising: (a) a first chain, wherein the first chain comprises a linker, wherein the linker comprises a sequence that is at least 80% identical to any one of SEQ ID NOS: 31-75, wherein the linker comprises a N-terminus and a C-terminus, wherein the N-terminus of the linker is attached to a C terminus of a sequence that is at least 80% identical to SEQ ID NO: 246, SEQ ID NO: 247, SEQ ID NO: 248, or SEQ ID NO: 249, and the C-terminus of the linker is attached to a N-terminus of a sequence that is at least 80% identical to SEQ ID NO: 22, SEQ ID NO: 23, SEQ ID NO: 28, or SEQ ID NO: 244; and (b) a second chain, wherein the second chain comprises a linker, wherein the linker comprises a sequence that is at least 80% identical to any one of SEQ ID NOS: 31-75, wherein the linker comprises a N-terminus and a C-terminus, wherein the N-terminus of the linker is attached to a C terminus of a sequence that is at least 80% identical to SEQ ID NO: 250, SEQ ID NO: 251, SEQ ID NO: 252, or SEQ ID NO: 253, and the C-terminus of the linker is attached to a N-terminus of a sequence that is at least 80% identical to SEQ ID NO: 22, SEQ ID NO: 23, SEQ ID NO: 28, or SEQ ID NO: 244.

Embodiment 105. The compound of any one of embodiments 1-67, wherein the compound comprises: (a) a heavy chain sequence that is at least 80% identical to SEQ ID NO: 262 or any one of SEQ ID NOS: 246-249; and (b) a light chain sequence that is at least 80% identical to SEQ ID NO: 258, SEQ ID NO: 259, SEQ ID NO: 261, or SEQ ID NO: 260.

Embodiment 106. The compound of any one of embodiments 1-3, 5-6, and 8-67, wherein the compound comprises: (a) a heavy chain sequence that is at least 80% identical to SEQ ID NO: 254, SEQ ID NO: 255, SEQ ID NO: 256, or SEQ ID NO: 257; and (b) a light chain sequence that is at least 80% identical to SEQ ID NO: 258, SEQ ID NO: 259, SEQ ID NO: 261, or SEQ ID NO: 260.

What is claimed is:

1. A method of treating an ocular condition in a subject in need thereof, comprising administering to the subject a therapeutically effective amount of an antibody comprising:

(a) a first domain that activates Tie2, wherein the first domain comprises an amino acid sequence that is any one of SEQ ID NOs: 76-80, an amino acid sequence that is any one of SEQ ID NOs: 81-87, an amino acid sequence that is any one of SEQ ID NOs: 88-90, an amino acid sequence that is any one of SEQ ID NOs: 91-93, an amino acid sequence that is any one of SEQ ID NOs: 94-96, and an amino acid sequence that is any one of SEQ ID NOs: 97-98; and (b) a second domain that specifically binds a receptor tyrosine kinase agonist, wherein the second domain comprises an amino acid sequence that is any one of SEQ ID NOs: 99-113, an amino acid sequence that is any one of SEQ ID NOs: 114-123, an amino acid sequence that is any one of SEQ ID NOs: 124-131, an amino acid sequence that is any one of SEQ ID NOs: 132-137, an amino acid sequence that is any one of SEQ ID NOs: 138-143, and an amino acid sequence that is any one of SEQ ID NOs: 144-146.

2. The method of claim 1, wherein the ocular condition is diabetic retinopathy.

3. The method of claim 1, wherein the ocular condition is neovascularization.

4. The method of claim 1, wherein the ocular condition is vascular leak.

5. The method of claim 1, wherein the ocular condition is increased intraocular pressure.

6. The method of claim 1, wherein the ocular condition is ocular edema.

7. The method of claim 1, wherein the ocular condition is diabetic macular edema.

8. The method of claim 1, wherein the ocular condition is wet age-related macular degeneration.

9. The method of claim 1 wherein the ocular condition is ocular inflammation.

10. The method of claim 1, wherein the ocular condition is retinal vein occlusion.

11. The method of claim 1, wherein the administering is to an eye of the subject.

12. The method of claim 1, wherein the administering is intravitreal.

13. The method of claim 1, wherein the administering is subcutaneous.

14. The method of claim 1, wherein the subject is a human.

15. The method of claim 1, wherein the therapeutically effective amount is from about 0.25 mg to about 200 mg.

16. The method of claim 1, wherein the therapeutically effective amount is from about 1 mg/kg to about 10 mg/kg.

17. The method of claim 1, wherein the antibody inhibits HPTP-β.

18. The method of claim 1, wherein the antibody inhibits VE-PTP.

19. The method of claim 1, wherein the antibody inhibits VEGF.

* * * * *

UNITED STATES PATENT AND TRADEMARK OFFICE

CERTIFICATE OF CORRECTION

PATENT NO. : 12,398,204 B2
APPLICATION NO. : 18/528957
DATED : August 26, 2025
INVENTOR(S) : Peters It is certified that error appears in the above-identified patent and that said Letters Patent is hereby corrected as shown below:

On the Title Page

Item [73], insert -- (73) Assignee: EyePoint Pharmaceuticals, Inc., Watertown, MA (US) --

In the Claims

In Column 222, Claim 9, Line 18, delete "claim 1" and insert -- claim 1, --

Signed and Sealed this
Eighteenth Day of November, 2025

John A. Squires
*Director of the United States Patent and Trademark Office*

SEQUENCE LISTING

```
Sequence total quantity: 262
SEQ ID NO: 1            moltype = AA  length = 122
FEATURE                 Location/Qualifiers
source                  1..122
                        mol_type = protein
                        note = Synthetic polypeptide
                        organism = synthetic construct
SEQUENCE: 1
EVQLVESGGG LVQPGGSLKL SCAASGFTFN ANAMNWVRQA SGKGLEWVGR IRTKSNNYAT  60
YYAGSVKDRF TISRDDSKNT AYLQMNSLKT EDTAAYYCVR DYYGSSAWIT YWGQGTLVTV  120
SS                                                                 122

SEQ ID NO: 2            moltype = AA  length = 122
FEATURE                 Location/Qualifiers
source                  1..122
                        mol_type = protein
                        note = Synthetic polypeptide
                        organism = synthetic construct
SEQUENCE: 2
EVQLVESGGG LVQPGGSLRL SCAASGFTFN ANAMNWVRQA PGKGLEWVGR IRTKSNNYAT  60
YYAGSVKDRF TISRDDSKNS LYLQMNSLKT EDTAVYYCVR DYYGSSAWIT YWGQGTLVTV  120
SS                                                                 122

SEQ ID NO: 3            moltype = AA  length = 122
FEATURE                 Location/Qualifiers
source                  1..122
                        mol_type = protein
                        note = Synthetic polypeptide
                        organism = synthetic construct
```

-continued

```
SEQUENCE: 3
EVQLVESGGG LVQPGRSLRL SCTASGFTFN ANAMNWVRQA PGKGLEWVGR IRTKSNNYAT  60
YYAGSVKDRF TISRDDSKNI AYLQMNSLKT EDTAVYYCVR DYYGSSAWIT YWGQGTLVTV  120
SS                                                                122

SEQ ID NO: 4           moltype = AA  length = 122
FEATURE                Location/Qualifiers
source                 1..122
                       mol_type = protein
                       note = Synthetic polypeptide
                       organism = synthetic construct
SEQUENCE: 4
LVQLVESGGG LVKPGGSLRL SCAASGFTFN ANAMNWIRQA PGKGLEWVSR IRTKSNNYAT  60
YYAGSVKDRF TISRDNAKNS LYLQMNSLRA EDTAVHYCVR DYYGSSAWIT YWGQGTLVTV  120
SS                                                                122

SEQ ID NO: 5           moltype = AA  length = 107
FEATURE                Location/Qualifiers
source                 1..107
                       mol_type = protein
                       note = Synthetic polypeptide
                       organism = synthetic construct
SEQUENCE: 5
DVVMTQSPSF LSASVGDRVT ITCKASQHVG TAVAWYQQRP GKAPKLLIYW ASTRHTGVPS  60
RFSGSGSGTE FTLTISSLQP EDFATYFCQQ YSSYPFTFGG GTKLEIK               107

SEQ ID NO: 6           moltype = AA  length = 107
FEATURE                Location/Qualifiers
source                 1..107
                       mol_type = protein
                       note = Synthetic polypeptide
                       organism = synthetic construct
SEQUENCE: 6
DIVMTQSPDS LAVSLGERAT INCKASQHVG TAVAWYQQKP GQPPKLLIYW ASTRHTGVPD  60
RFSGSGSGTD FTLTISSLQA EDVAVYYCQQ YSSYPFTFGQ GTKLEIK               107

SEQ ID NO: 7           moltype = AA  length = 107
FEATURE                Location/Qualifiers
source                 1..107
                       mol_type = protein
                       note = Synthetic polypeptide
                       organism = synthetic construct
SEQUENCE: 7
DIQMTQSPFS LSASVGDRVT ITCKASQHVG TAVAWYQQKP GKAPKLLIYW ASTRHTGVPS  60
RFSGSGSGTD FTLTISSLQP EDFATYFCQQ YSSYPFTFGG GTKLEIK               107

SEQ ID NO: 8           moltype = AA  length = 107
FEATURE                Location/Qualifiers
source                 1..107
                       mol_type = protein
                       note = Synthetic polypeptide
                       organism = synthetic construct
SEQUENCE: 8
DIVMTQSPDS LAVSLGERAT INCKASQHVG TAVAWYQQKP EQPPKLLIYW ASTRHTGVPD  60
RFSGSGSGTD FTLTISSLQA EDVAVYYCQQ YSSYPFTFGG GTKVEIK               107

SEQ ID NO: 9           moltype = AA  length = 327
FEATURE                Location/Qualifiers
source                 1..327
                       mol_type = protein
                       organism = Homo sapiens
SEQUENCE: 9
ASTKGPSVFP LAPCSRSTSE STAALGCLVK DYFPEPVTVS WNSGALTSGV HTFPAVLQSS  60
GLYSLSSVVT VPSSSLGTKT YTCNVDHKPS NTKVDKRVES KYGPPCPPCP APEFLGGPSV  120
FLFPPKPKDT LMISRTPEVT CVVVDVSQED PEVQFNWYVD GVEVHNAKTK PREEQFNSTY  180
RVVSVLTVLH QDWLNGKEYK CKVSNKGLPS SIEKTISKAK GQPREPQVYT LPPSQEEMTK  240
NQVSLTCLVK GFYPSDIAVE WESNGQPENN YKTTPPVLDS DGSFFLYSRL TVDKSRWQEG  300
NVFSCSVMHE ALHNHYTQKS LSLSLGK                                     327

SEQ ID NO: 10          moltype = AA  length = 106
FEATURE                Location/Qualifiers
source                 1..106
                       mol_type = protein
                       organism = Homo sapiens
SEQUENCE: 10
TVAAPSVFIF PPSDEQLKSG TASVVCLLNN FYPREAKVQW KVDNALQSGN SQESVTEQDS  60
KDSTYSLSST LTLSKADYEK HKVYACEVTH QGLSSPVTKS FNRGEC                106

SEQ ID NO: 11          moltype = AA  length = 19
```

-continued

```
FEATURE                Location/Qualifiers
source                 1..19
                       mol_type = protein
                       note = Synthetic peptide
                       organism = synthetic construct
SEQUENCE: 11
MGWTLVFLFL LSVTAGVHS                                           19

SEQ ID NO: 12          moltype = AA  length = 20
FEATURE                Location/Qualifiers
source                 1..20
                       mol_type = protein
                       note = Synthetic peptide
                       organism = synthetic construct
SEQUENCE: 12
MVSSAQFLGL LLLCFQGTRC                                          20

SEQ ID NO: 13          moltype = AA  length = 468
FEATURE                Location/Qualifiers
source                 1..468
                       mol_type = protein
                       note = Synthetic polypeptide
                       organism = synthetic construct
SEQUENCE: 13
MGWTLVFLFL LSVTAGVHSE VQLVESGGGL VQPGGSLKLS CAASGFTFNA NAMNWVRQAS  60
GKGLEWVGRI RTKSNNYATY YAGSVKDRFT ISRDDSKNTA YLQMNSLKTE DTAAYYCVRD  120
YYGSSAWITY WGQGTLVTVS SASTKGPSVF PLAPCSRSTS ESTAALGCLV KDYFPEPVTV  180
SWNSGALTSG VHTFPAVLQS SGLYSLSSVV TVPSSSLGTK TYTCNVDHKP SNTKVDKRVE  240
SKYGPPCPPC PAPEFLGGPS VFLFPPKPKD TLMISRTPEV TCVVVDVSQE DPEVQFNWYV  300
DGVEVHNAKT KPREEQFNST YRVVSVLTVL HQDWLNGKEY KCKVSNKGLP SSIEKTISKA  360
KGQPREPQVY TLPPSQEEMT KNQVSLTCLV KGFYPSDIAV EWESNGQPEN NYKTTPPVLD  420
SDGSFFLYSR LTVDKSRWQE GNVFSCSVMH EALHNHYTQK SLSLSLGK            468

SEQ ID NO: 14          moltype = AA  length = 468
FEATURE                Location/Qualifiers
source                 1..468
                       mol_type = protein
                       note = Synthetic polypeptide
                       organism = synthetic construct
SEQUENCE: 14
MGWTLVFLFL LSVTAGVHSE VQLVESGGGL VQPGGSLRLS CAASGFTFNA NAMNWVRQAP  60
GKGLEWVGRI RTKSNNYATY YAGSVKDRFT ISRDDSKNSL YLQMNSLKTE DTAVYYCVRD  120
YYGSSAWITY WGQGTLVTVS SASTKGPSVF PLAPCSRSTS ESTAALGCLV KDYFPEPVTV  180
SWNSGALTSG VHTFPAVLQS SGLYSLSSVV TVPSSSLGTK TYTCNVDHKP SNTKVDKRVE  240
SKYGPPCPPC PAPEFLGGPS VFLFPPKPKD TLMISRTPEV TCVVVDVSQE DPEVQFNWYV  300
DGVEVHNAKT KPREEQFNST YRVVSVLTVL HQDWLNGKEY KCKVSNKGLP SSIEKTISKA  360
KGQPREPQVY TLPPSQEEMT KNQVSLTCLV KGFYPSDIAV EWESNGQPEN NYKTTPPVLD  420
SDGSFFLYSR LTVDKSRWQE GNVFSCSVMH EALHNHYTQK SLSLSLGK            468

SEQ ID NO: 15          moltype = AA  length = 468
FEATURE                Location/Qualifiers
source                 1..468
                       mol_type = protein
                       note = Synthetic polypeptide
                       organism = synthetic construct
SEQUENCE: 15
MGWTLVFLFL LSVTAGVHSE VQLVESGGGL VQPGRSLRLS CTASGFTFNA NAMNWVRQAP  60
GKGLEWVGRI RTKSNNYATY YAGSVKDRFT ISRDDSKNIA YLQMNSLKTE DTAVYYCVRD  120
YYGSSAWITY WGQGTLVTVS SASTKGPSVF PLAPCSRSTS ESTAALGCLV KDYFPEPVTV  180
SWNSGALTSG VHTFPAVLQS SGLYSLSSVV TVPSSSLGTK TYTCNVDHKP SNTKVDKRVE  240
SKYGPPCPPC PAPEFLGGPS VFLFPPKPKD TLMISRTPEV TCVVVDVSQE DPEVQFNWYV  300
DGVEVHNAKT KPREEQFNST YRVVSVLTVL HQDWLNGKEY KCKVSNKGLP SSIEKTISKA  360
KGQPREPQVY TLPPSQEEMT KNQVSLTCLV KGFYPSDIAV EWESNGQPEN NYKTTPPVLD  420
SDGSFFLYSR LTVDKSRWQE GNVFSCSVMH EALHNHYTQK SLSLSLGK            468

SEQ ID NO: 16          moltype = AA  length = 468
FEATURE                Location/Qualifiers
source                 1..468
                       mol_type = protein
                       note = Synthetic polypeptide
                       organism = synthetic construct
SEQUENCE: 16
MGWTLVFLFL LSVTAGVHSL VQLVESGGGL VKPGGSLRLS CAASGFTFNA NAMNWIRQAP  60
GKGLEWVSRI RTKSNNYATY YAGSVKDRFT ISRDNAKNSL YLQMNSLRAE DTAVHYCVRD  120
YYGSSAWITY WGQGTLVTVS SASTKGPSVF PLAPCSRSTS ESTAALGCLV KDYFPEPVTV  180
SWNSGALTSG VHTFPAVLQS SGLYSLSSVV TVPSSSLGTK TYTCNVDHKP SNTKVDKRVE  240
SKYGPPCPPC PAPEFLGGPS VFLFPPKPKD TLMISRTPEV TCVVVDVSQE DPEVQFNWYV  300
DGVEVHNAKT KPREEQFNST YRVVSVLTVL HQDWLNGKEY KCKVSNKGLP SSIEKTISKA  360
KGQPREPQVY TLPPSQEEMT KNQVSLTCLV KGFYPSDIAV EWESNGQPEN NYKTTPPVLD  420
```

-continued

```
SDGSFFLYSR LTVDKSRWQE GNVFSCSVMH EALHNHYTQK SLSLSLGK             468

SEQ ID NO: 17          moltype = AA  length = 234
FEATURE                Location/Qualifiers
source                 1..234
                       mol_type = protein
                       note = Synthetic polypeptide
                       organism = synthetic construct
SEQUENCE: 17
MVSSAQFLGL LLLCFQGTRC DVVMTQSPSF LSASVGDRVT ITCKASQHVG TAVAWYQQRP  60
GKAPKLLIYW ASTRHTGVPS RFSGSGSGTE FTLTISSLQP EDFATYFCQQ YSSYPFTFGG  120
GTKLEIKRTV AAPSVFIFPP SDEQLKSGTA SVVCLLNNFY PREAKVQWKV DNALQSGNSQ  180
ESVTEQDSKD STYSLSSTLT LSKADYEKHK VYACEVTHQG LSSPVTKSFN RGEC        234

SEQ ID NO: 18          moltype = AA  length = 234
FEATURE                Location/Qualifiers
source                 1..234
                       mol_type = protein
                       note = Synthetic polypeptide
                       organism = synthetic construct
SEQUENCE: 18
MVSSAQFLGL LLLCFQGTRC DIVMTQSPDS LAVSLGERAT INCKASQHVG TAVAWYQQKP  60
GQPPKLLIYW ASTRHTGVPD RFSGSGSGTD FTLTISSLQA EDVAVYYCQQ YSSYPFTFGQ  120
GTKLEIKRTV AAPSVFIFPP SDEQLKSGTA SVVCLLNNFY PREAKVQWKV DNALQSGNSQ  180
ESVTEQDSKD STYSLSSTLT LSKADYEKHK VYACEVTHQG LSSPVTKSFN RGEC        234

SEQ ID NO: 19          moltype = AA  length = 234
FEATURE                Location/Qualifiers
source                 1..234
                       mol_type = protein
                       note = Synthetic polypeptide
                       organism = synthetic construct
SEQUENCE: 19
MVSSAQFLGL LLLCFQGTRC DIQMTQSPFS LSASVGDRVT ITCKASQHVG TAVAWYQQKP  60
GKAPKLLIYW ASTRHTGVPS RFSGSGSGTD FTLTISSLQP EDFATYFCQQ YSSYPFTFGG  120
GTKLEIKRTV AAPSVFIFPP SDEQLKSGTA SVVCLLNNFY PREAKVQWKV DNALQSGNSQ  180
ESVTEQDSKD STYSLSSTLT LSKADYEKHK VYACEVTHQG LSSPVTKSFN RGEC        234

SEQ ID NO: 20          moltype = AA  length = 234
FEATURE                Location/Qualifiers
source                 1..234
                       mol_type = protein
                       note = Synthetic polypeptide
                       organism = synthetic construct
SEQUENCE: 20
MVSSAQFLGL LLLCFQGTRC DIVMTQSPDS LAVSLGERAT INCKASQHVG TAVAWYQQKP  60
EQPPKLLIYW ASTRHTGVPD RFSGSGSGTD FTLTISSLQA EDVAVYYCQQ YSSYPFTFGG  120
GTKVEIKRTV AAPSVFIFPP SDEQLKSGTA SVVCLLNNFY PREAKVQWKV DNALQSGNSQ  180
ESVTEQDSKD STYSLSSTLT LSKADYEKHK VYACEVTHQG LSSPVTKSFN RGEC        234

SEQ ID NO: 21          moltype = AA  length = 431
FEATURE                Location/Qualifiers
source                 1..431
                       mol_type = protein
                       note = Synthetic polypeptide
                       organism = synthetic construct
SEQUENCE: 21
SDTGRPFVEM YSEIPEIIHM TEGRELVIPC RVTSPNITVT LKKFPLDTLI PDGKRIIWDS  60
RKGFIISNAT YKEIGLLTCE ATVNGHLYKT NYLTHRQTNT IIDVVLSPSH GIELSVGEKL  120
VLNCTARTEL NVGIDFNWEY PSSKHQHKKL VNRDLKTQSG SEMKKFLSTL TIDGVTRSDQ  180
GLYTCAASSG LMTKKNSTFV RVHEKDKTHT CPPCPAPELL GGPSVFLFPP KPKDTLMISR  240
TPEVTCVVVD VSHEDPEVKF NWYVDGVEVH NAKTKPREEQ YNSTYRVVSV LTVLHQDWLN  300
GKEYKCKVSN KALPAPIEKT ISKAKGQPRE PQVYTLPPSR DELTKNQVSL TCLVKGFYPS  360
DIAVEWESNG QPENNYKTTP PVLDSDGSFF LYSKLTVDKS RWQQGNVFSC SVMHEALHNH  420
YTQKSLSLSP G                                                      431

SEQ ID NO: 22          moltype = AA  length = 205
FEATURE                Location/Qualifiers
source                 1..205
                       mol_type = protein
                       note = Synthetic polypeptide
                       organism = synthetic construct
SEQUENCE: 22
SDTGRPFVEM YSEIPEIIHM TEGRELVIPC RVTSPNITVT LKKFPLDTLI PDGKRIIWDS  60
RKGFIISNAT YKEIGLLTCE ATVNGHLYKT NYLTHRQTNT IIDVVLSPSH GIELSVGEKL  120
VLNCTARTEL NVGIDFNWEY PSSKHQHKKL VNRDLKTQSG SEMKKFLSTL TIDGVTRSDQ  180
GLYTCAASSG LMTKKNSTFV RVHEK                                       205

SEQ ID NO: 23          moltype = AA  length = 251
```

-continued

```
FEATURE                 Location/Qualifiers
source                  1..251
                        mol_type = protein
                        note = Synthetic polypeptide
                        organism = synthetic construct
SEQUENCE: 23
EIVMTQSPST LSASVGDRVI ITCQASEIIH SWLAWYQQKP GKAPKLLIYL ASTLASGVPS  60
RFSGSGSGAE FTLTISSLQP DDFATYYCQN VYLASTNGAN FGQGTKLTVL GGGGGSGGGG  120
SGGGGSGGGG SEVQLVESGG GLVQPGGSLR LSCTASGFSL TDYYYMTWVR QAPGKGLEWV  180
GFIDPDDDPY YATWAKGRFT ISRDNSKNTL YLQMNSLRAE DTAVYYCAGG DHNSGWGLDI  240
WGQGTLVTVS S                                                      251

SEQ ID NO: 24           moltype = AA  length = 231
FEATURE                 Location/Qualifiers
source                  1..231
                        mol_type = protein
                        note = Synthetic polypeptide
                        organism = synthetic construct
SEQUENCE: 24
EVQLVESGGG LVQPGGSLRL SCAASGYDFT HYGMNWVRQA PGKGLEWVGW INTYTGEPTY  60
AADFKRRFTF SLDTSKSTAY LQMNSLRAED TAVYYCAKYP YYYGTSHWYF DVWGQGTLVT  120
VSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSCDKTH L           231

SEQ ID NO: 25           moltype = AA  length = 214
FEATURE                 Location/Qualifiers
source                  1..214
                        mol_type = protein
                        note = Synthetic polypeptide
                        organism = synthetic construct
SEQUENCE: 25
DIQLTQSPSS LSASVGDRVT ITCSASQDIS NYLNWYQQKP GKAPKVLIYF TSSLHSGVPS  60
RFSGSGSGTD FTLTISSLQP EDFATYYCQQ YSTVPWTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 26           moltype = AA  length = 123
FEATURE                 Location/Qualifiers
source                  1..123
                        mol_type = protein
                        note = Synthetic polypeptide
                        organism = synthetic construct
SEQUENCE: 26
EVQLVESGGG LVQPGGSLRL SCAASGYDFT HYGMNWVRQA PGKGLEWVGW INTYTGEPTY  60
AADFKRRFTF SLDTSKSTAY LQMNSLRAED TAVYYCAKYP YYYGTSHWYF DVWGQGTLVT  120
VSS                                                               123

SEQ ID NO: 27           moltype = AA  length = 107
FEATURE                 Location/Qualifiers
source                  1..107
                        mol_type = protein
                        note = Synthetic polypeptide
                        organism = synthetic construct
SEQUENCE: 27
DIQLTQSPSS LSASVGDRVT ITCSASQDIS NYLNWYQQKP GKAPKVLIYF TSSLHSGVPS  60
RFSGSGSGTD FTLTISSLQP EDFATYYCQQ YSTVPWTFGQ GTKVEIK               107

SEQ ID NO: 28           moltype = AA  length = 245
FEATURE                 Location/Qualifiers
source                  1..245
                        mol_type = protein
                        note = Synthetic polypeptide
                        organism = synthetic construct
SEQUENCE: 28
EVQLVESGGG LVQPGGSLRL SCAASGYDFT HYGMNWVRQA PGKGLEWVGW INTYTGEPTY  60
AADFKRRFTF SLDTSKSTAY LQMNSLRAED TAVYYCAKYP YYYGTSHWYF DVWGQGTLVT  120
VSSGGGGSGG GGSGGGGSDI QLTQSPSSLS ASVGDRVTIT CSASQDISNY LNWYQQKPGK  180
APKVLIYFTS SLHSGVPSRF SGSGSGTDFT LTISSLQPED FATYYCQQYS TVPWTFGQGT  240
KVEIK                                                             245

SEQ ID NO: 29           moltype = AA  length = 453
FEATURE                 Location/Qualifiers
source                  1..453
                        mol_type = protein
                        note = Synthetic polypeptide
                        organism = synthetic construct
SEQUENCE: 29
EVQLVESGGG LVQPGGSLRL SCAASGYTFT NYGMNWVRQA PGKGLEWVGW INTYTGEPTY  60
AADFKRRFTF SLDTSKSTAY LQMNSLRAED TAVYYCAKYP HYYGSSHWYF DVWGQGTLVT  120
```

-continued

```
VSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSCDKTH TCPPCPAPEL  240
LGGPSVFLFP PKPKDTLMIS RTPEVTCVVV DVSHEDPEVK FNWYVDGVEV HNAKTKPREE  300
QYNSTYRVVS VLTVLHQDWL NGKEYKCKVS NKALPAPIEK TISKAKGQPR EPQVYTLPPS  360
REEMTKNQVS LTCLVKGFYP SDIAVEWESN GQPENNYKTT PPVLDSDGSF FLYSKLTVDK  420
SRWQQGNVFS CSVMHEALHN HYTQKSLSLS PGK                              453

SEQ ID NO: 30          moltype = AA  length = 214
FEATURE                Location/Qualifiers
source                 1..214
                       mol_type = protein
                       note = Synthetic polypeptide
                       organism = synthetic construct
SEQUENCE: 30
DIQMTQSPSS LSASVGDRVT ITCSASQDIS NYLNWYQQKP GKAPKVLIYF TSSLHSGVPS  60
RFSGSGSGTD FTLTISSLQP EDFATYYCQQ YSTVPWTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                             214

SEQ ID NO: 31          moltype = AA  length = 5
FEATURE                Location/Qualifiers
source                 1..5
                       mol_type = protein
                       note = Synthetic peptide
                       organism = synthetic construct
SEQUENCE: 31
GGGGS                                                             5

SEQ ID NO: 32          moltype = AA  length = 10
FEATURE                Location/Qualifiers
source                 1..10
                       mol_type = protein
                       note = Synthetic peptide
                       organism = synthetic construct
SEQUENCE: 32
GGGGSGGGGS                                                        10

SEQ ID NO: 33          moltype = AA  length = 15
FEATURE                Location/Qualifiers
source                 1..15
                       mol_type = protein
                       note = Synthetic peptide
                       organism = synthetic construct
SEQUENCE: 33
GGGGSGGGGS GGGGS                                                  15

SEQ ID NO: 34          moltype = AA  length = 20
FEATURE                Location/Qualifiers
source                 1..20
                       mol_type = protein
                       note = Synthetic peptide
                       organism = synthetic construct
SEQUENCE: 34
GGGGSGGGGS GGGGSGGGGS                                             20

SEQ ID NO: 35          moltype = AA  length = 25
FEATURE                Location/Qualifiers
source                 1..25
                       mol_type = protein
                       note = Synthetic peptide
                       organism = synthetic construct
SEQUENCE: 35
GGGGSGGGGS GGGGSGGGGS GGGGS                                       25

SEQ ID NO: 36          moltype = AA  length = 30
FEATURE                Location/Qualifiers
source                 1..30
                       mol_type = protein
                       note = Synthetic polypeptide
                       organism = synthetic construct
SEQUENCE: 36
GGGGSGGGGS GGGGSGGGGS GGGGSGGGGS                                  30

SEQ ID NO: 37          moltype = AA  length = 35
FEATURE                Location/Qualifiers
source                 1..35
                       mol_type = protein
                       note = Synthetic polypeptide
                       organism = synthetic construct
```

```
SEQUENCE: 37
GGGGSGGGGS GGGGSGGGGS GGGGSGGGGS GGGGS                    35

SEQ ID NO: 38          moltype = AA  length = 40
FEATURE                Location/Qualifiers
source                 1..40
                       mol_type = protein
                       note = Synthetic polypeptide
                       organism = synthetic construct
SEQUENCE: 38
GGGGSGGGGS GGGGSGGGGS GGGGSGGGGS GGGGSGGGGS               40

SEQ ID NO: 39          moltype = AA  length = 45
FEATURE                Location/Qualifiers
source                 1..45
                       mol_type = protein
                       note = Synthetic polypeptide
                       organism = synthetic construct
SEQUENCE: 39
GGGGSGGGGS GGGGSGGGGS GGGGSGGGGS GGGGSGGGGS GGGGS         45

SEQ ID NO: 40          moltype = AA  length = 50
FEATURE                Location/Qualifiers
source                 1..50
                       mol_type = protein
                       note = Synthetic polypeptide
                       organism = synthetic construct
SEQUENCE: 40
GGGGSGGGGS GGGGSGGGGS GGGGSGGGGS GGGGSGGGGS GGGGSGGGGS    50

SEQ ID NO: 41          moltype = AA  length = 55
FEATURE                Location/Qualifiers
source                 1..55
                       mol_type = protein
                       note = Synthetic polypeptide
                       organism = synthetic construct
SEQUENCE: 41
GGGGSGGGGS GGGGSGGGGS GGGGSGGGGS GGGGSGGGGS GGGGSGGGGS GGGGS   55

SEQ ID NO: 42          moltype = AA  length = 4
FEATURE                Location/Qualifiers
source                 1..4
                       mol_type = protein
                       note = Synthetic peptide
                       organism = synthetic construct
SEQUENCE: 42
GGGS                                                      4

SEQ ID NO: 43          moltype = AA  length = 8
FEATURE                Location/Qualifiers
source                 1..8
                       mol_type = protein
                       note = Synthetic peptide
                       organism = synthetic construct
SEQUENCE: 43
GGGSGGGS                                                  8

SEQ ID NO: 44          moltype = AA  length = 12
FEATURE                Location/Qualifiers
source                 1..12
                       mol_type = protein
                       note = Synthetic peptide
                       organism = synthetic construct
SEQUENCE: 44
GGGSGGGSGG GS                                             12

SEQ ID NO: 45          moltype = AA  length = 16
FEATURE                Location/Qualifiers
source                 1..16
                       mol_type = protein
                       note = Synthetic peptide
                       organism = synthetic construct
SEQUENCE: 45
GGGSGGGSGG GSGGGS                                         16

SEQ ID NO: 46          moltype = AA  length = 20
FEATURE                Location/Qualifiers
source                 1..20
                       mol_type = protein
```

```
                        note = Synthetic peptide
                        organism = synthetic construct
SEQUENCE: 46
GGGSGGGSGG GSGGGSGGGS                                           20

SEQ ID NO: 47           moltype = AA  length = 24
FEATURE                 Location/Qualifiers
source                  1..24
                        mol_type = protein
                        note = Synthetic peptide
                        organism = synthetic construct
SEQUENCE: 47
GGGSGGGSGG GSGGGSGGGS GGGS                                      24

SEQ ID NO: 48           moltype = AA  length = 28
FEATURE                 Location/Qualifiers
source                  1..28
                        mol_type = protein
                        note = Synthetic peptide
                        organism = synthetic construct
SEQUENCE: 48
GGGSGGGSGG GSGGGSGGGS GGGSGGGS                                  28

SEQ ID NO: 49           moltype = AA  length = 32
FEATURE                 Location/Qualifiers
source                  1..32
                        mol_type = protein
                        note = Synthetic polypeptide
                        organism = synthetic construct
SEQUENCE: 49
GGGSGGGSGG GSGGGSGGGS GGGSGGGSGG GS                             32

SEQ ID NO: 50           moltype = AA  length = 36
FEATURE                 Location/Qualifiers
source                  1..36
                        mol_type = protein
                        note = Synthetic polypeptide
                        organism = synthetic construct
SEQUENCE: 50
GGGSGGGSGG GSGGGSGGGS GGGSGGGSGG GSGGGS                         36

SEQ ID NO: 51           moltype = AA  length = 40
FEATURE                 Location/Qualifiers
source                  1..40
                        mol_type = protein
                        note = Synthetic polypeptide
                        organism = synthetic construct
SEQUENCE: 51
GGGSGGGSGG GSGGGSGGGS GGGSGGGSGG GSGGGSGGGS                     40

SEQ ID NO: 52           moltype = AA  length = 44
FEATURE                 Location/Qualifiers
source                  1..44
                        mol_type = protein
                        note = Synthetic polypeptide
                        organism = synthetic construct
SEQUENCE: 52
GGGSGGGSGG GSGGGSGGGS GGGSGGGSGG GSGGGSGGGS GGGS                44

SEQ ID NO: 53           moltype = AA  length = 48
FEATURE                 Location/Qualifiers
source                  1..48
                        mol_type = protein
                        note = Synthetic polypeptide
                        organism = synthetic construct
SEQUENCE: 53
GGGSGGGSGG GSGGGSGGGS GGGSGGGSGG GSGGGSGGGS GGGSGGGS            48

SEQ ID NO: 54           moltype = AA  length = 52
FEATURE                 Location/Qualifiers
source                  1..52
                        mol_type = protein
                        note = Synthetic polypeptide
                        organism = synthetic construct
SEQUENCE: 54
GGGSGGGSGG GSGGGSGGGS GGGSGGGSGG GSGGGSGGGS GGGSGGGSGG GS       52

SEQ ID NO: 55           moltype = AA  length = 56
FEATURE                 Location/Qualifiers
```

-continued

```
source                  1..56
                        mol_type = protein
                        note = Synthetic polypeptide
                        organism = synthetic construct
SEQUENCE: 55
GGGSGGGSGG GSGGGSGGGS GGGSGGGSGG GSGGGSGGGS GGGSGGGSGG GSGGGS      56

SEQ ID NO: 56           moltype =   length =
SEQUENCE: 56
000

SEQ ID NO: 57           moltype = AA  length = 6
FEATURE                 Location/Qualifiers
source                  1..6
                        mol_type = protein
                        note = Synthetic peptide
                        organism = synthetic construct
SEQUENCE: 57
GGGGGG                                                             6

SEQ ID NO: 58           moltype = AA  length = 8
FEATURE                 Location/Qualifiers
source                  1..8
                        mol_type = protein
                        note = Synthetic peptide
                        organism = synthetic construct
SEQUENCE: 58
GGGGGGGG                                                           8

SEQ ID NO: 59           moltype = AA  length = 18
FEATURE                 Location/Qualifiers
source                  1..18
                        mol_type = protein
                        note = Synthetic peptide
                        organism = synthetic construct
SEQUENCE: 59
KESGSVSSEQ LAQFRSLD                                                18

SEQ ID NO: 60           moltype = AA  length = 14
FEATURE                 Location/Qualifiers
source                  1..14
                        mol_type = protein
                        note = Synthetic peptide
                        organism = synthetic construct
SEQUENCE: 60
EGKSSGSGSE SKST                                                    14

SEQ ID NO: 61           moltype = AA  length = 12
FEATURE                 Location/Qualifiers
source                  1..12
                        mol_type = protein
                        note = Synthetic peptide
                        organism = synthetic construct
SEQUENCE: 61
GSAGSAAGSG EF                                                      12

SEQ ID NO: 62           moltype = AA  length = 5
FEATURE                 Location/Qualifiers
source                  1..5
                        mol_type = protein
                        note = Synthetic peptide
                        organism = synthetic construct
SEQUENCE: 62
EAAAK                                                              5

SEQ ID NO: 63           moltype = AA  length = 10
FEATURE                 Location/Qualifiers
source                  1..10
                        mol_type = protein
                        note = Synthetic peptide
                        organism = synthetic construct
SEQUENCE: 63
EAAAKEAAAK                                                         10

SEQ ID NO: 64           moltype = AA  length = 20
FEATURE                 Location/Qualifiers
source                  1..20
                        mol_type = protein
                        note = Synthetic peptide
```

```
                        organism = synthetic construct
SEQUENCE: 64
EAAAKEAAAK EAAAKEAAAK                                              20

SEQ ID NO: 65           moltype = AA  length = 25
FEATURE                 Location/Qualifiers
source                  1..25
                        mol_type = protein
                        note = Synthetic peptide
                        organism = synthetic construct
SEQUENCE: 65
EAAAKEAAAK EAAAKEAAAK EAAAK                                        25

SEQ ID NO: 66           moltype = AA  length = 30
FEATURE                 Location/Qualifiers
source                  1..30
                        mol_type = protein
                        note = Synthetic polypeptide
                        organism = synthetic construct
SEQUENCE: 66
EAAAKEAAAK EAAAKEAAAK EAAAKEAAAK                                   30

SEQ ID NO: 67           moltype = AA  length = 5
FEATURE                 Location/Qualifiers
source                  1..5
                        mol_type = protein
                        note = Synthetic peptide
                        organism = synthetic construct
SEQUENCE: 67
EAAAR                                                              5

SEQ ID NO: 68           moltype = AA  length = 10
FEATURE                 Location/Qualifiers
source                  1..10
                        mol_type = protein
                        note = Synthetic peptide
                        organism = synthetic construct
SEQUENCE: 68
EAAAREAAAR                                                         10

SEQ ID NO: 69           moltype = AA  length = 15
FEATURE                 Location/Qualifiers
source                  1..15
                        mol_type = protein
                        note = Synthetic peptide
                        organism = synthetic construct
SEQUENCE: 69
EAAAREAAAR EAAAR                                                   15

SEQ ID NO: 70           moltype = AA  length = 20
FEATURE                 Location/Qualifiers
source                  1..20
                        mol_type = protein
                        note = Synthetic peptide
                        organism = synthetic construct
SEQUENCE: 70
EAAAREAAAR EAAAREAAAR                                              20

SEQ ID NO: 71           moltype = AA  length = 25
FEATURE                 Location/Qualifiers
source                  1..25
                        mol_type = protein
                        note = Synthetic peptide
                        organism = synthetic construct
SEQUENCE: 71
EAAAREAAAR EAAAREAAAR EAAAR                                        25

SEQ ID NO: 72           moltype = AA  length = 30
FEATURE                 Location/Qualifiers
source                  1..30
                        mol_type = protein
                        note = Synthetic polypeptide
                        organism = synthetic construct
SEQUENCE: 72
EAAAREAAAR EAAAREAAAR EAAAREAAAR                                   30

SEQ ID NO: 73           moltype = AA  length = 46
FEATURE                 Location/Qualifiers
source                  1..46
```

```
                         mol_type = protein
                         note = Synthetic polypeptide
                         organism = synthetic construct
SEQUENCE: 73
AEAAAKEAAA KEAAAKEAAA KALEAEAAAK EAAAKEAAAK EAAAKA                    46

SEQ ID NO: 74            moltype = AA  length = 5
FEATURE                  Location/Qualifiers
source                   1..5
                         mol_type = protein
                         note = Synthetic peptide
                         organism = synthetic construct
SEQUENCE: 74
PAPAP                                                                 5

SEQ ID NO: 75            moltype = AA  length = 12
FEATURE                  Location/Qualifiers
source                   1..12
                         mol_type = protein
                         note = Synthetic peptide
                         organism = synthetic construct
SEQUENCE: 75
AEAAAKEAAA KA                                                         12

SEQ ID NO: 76            moltype = AA  length = 5
FEATURE                  Location/Qualifiers
source                   1..5
                         mol_type = protein
                         note = Synthetic peptide
                         organism = synthetic construct
SEQUENCE: 76
ANAMN                                                                 5

SEQ ID NO: 77            moltype = AA  length = 7
FEATURE                  Location/Qualifiers
source                   1..7
                         mol_type = protein
                         note = Synthetic peptide
                         organism = synthetic construct
SEQUENCE: 77
GFTFNAN                                                               7

SEQ ID NO: 78            moltype = AA  length = 8
FEATURE                  Location/Qualifiers
source                   1..8
                         mol_type = protein
                         note = Synthetic peptide
                         organism = synthetic construct
SEQUENCE: 78
GFTFNANA                                                              8

SEQ ID NO: 79            moltype = AA  length = 9
FEATURE                  Location/Qualifiers
source                   1..9
                         mol_type = protein
                         note = Synthetic peptide
                         organism = synthetic construct
SEQUENCE: 79
FTFNANAMN                                                             9

SEQ ID NO: 80            moltype = AA  length = 10
FEATURE                  Location/Qualifiers
source                   1..10
                         mol_type = protein
                         note = Synthetic peptide
                         organism = synthetic construct
SEQUENCE: 80
GFTFNANAMN                                                            10

SEQ ID NO: 81            moltype = AA  length = 19
FEATURE                  Location/Qualifiers
source                   1..19
                         mol_type = protein
                         note = Synthetic peptide
                         organism = synthetic construct
SEQUENCE: 81
RIRTKSNNYA TYYAGSVKD                                                  19

SEQ ID NO: 82            moltype = AA  length = 8
```

-continued

```
FEATURE                Location/Qualifiers
source                 1..8
                       mol_type = protein
                       note = Synthetic peptide
                       organism = synthetic construct
SEQUENCE: 82
RTKSNNYA                                                                   8

SEQ ID NO: 83          moltype = AA  length = 10
FEATURE                Location/Qualifiers
source                 1..10
                       mol_type = protein
                       note = Synthetic peptide
                       organism = synthetic construct
SEQUENCE: 83
IRTKSNNYAT                                                                 10

SEQ ID NO: 84          moltype = AA  length = 16
FEATURE                Location/Qualifiers
source                 1..16
                       mol_type = protein
                       note = Synthetic peptide
                       organism = synthetic construct
SEQUENCE: 84
WVGRIRTKSN NYATYY                                                          16

SEQ ID NO: 85          moltype = AA  length = 22
FEATURE                Location/Qualifiers
source                 1..22
                       mol_type = protein
                       note = Synthetic peptide
                       organism = synthetic construct
SEQUENCE: 85
WVGRIRTKSN NYATYYAGSV KD                                                   22

SEQ ID NO: 86          moltype = AA  length = 16
FEATURE                Location/Qualifiers
source                 1..16
                       mol_type = protein
                       note = Synthetic peptide
                       organism = synthetic construct
SEQUENCE: 86
WVSRIRTKSN NYATYY                                                          16

SEQ ID NO: 87          moltype = AA  length = 22
FEATURE                Location/Qualifiers
source                 1..22
                       mol_type = protein
                       note = Synthetic peptide
                       organism = synthetic construct
SEQUENCE: 87
WVSRIRTKSN NYATYYAGSV KD                                                   22

SEQ ID NO: 88          moltype = AA  length = 11
FEATURE                Location/Qualifiers
source                 1..11
                       mol_type = protein
                       note = Synthetic peptide
                       organism = synthetic construct
SEQUENCE: 88
DYYGSSAWIT Y                                                               11

SEQ ID NO: 89          moltype = AA  length = 13
FEATURE                Location/Qualifiers
source                 1..13
                       mol_type = protein
                       note = Synthetic peptide
                       organism = synthetic construct
SEQUENCE: 89
VRDYYGSSAW ITY                                                             13

SEQ ID NO: 90          moltype = AA  length = 12
FEATURE                Location/Qualifiers
source                 1..12
                       mol_type = protein
                       note = Synthetic peptide
                       organism = synthetic construct
SEQUENCE: 90
RDYYGSSAWI TY                                                              12
```

```
SEQ ID NO: 91           moltype = AA  length = 11
FEATURE                 Location/Qualifiers
source                  1..11
                        mol_type = protein
                        note = Synthetic peptide
                        organism = synthetic construct
SEQUENCE: 91
KASQHVGTAV A                                                  11

SEQ ID NO: 92           moltype = AA  length = 6
FEATURE                 Location/Qualifiers
source                  1..6
                        mol_type = protein
                        note = Synthetic peptide
                        organism = synthetic construct
SEQUENCE: 92
QHVGTA                                                        6

SEQ ID NO: 93           moltype = AA  length = 8
FEATURE                 Location/Qualifiers
source                  1..8
                        mol_type = protein
                        note = Synthetic peptide
                        organism = synthetic construct
SEQUENCE: 93
QHVGTAVA                                                      8

SEQ ID NO: 94           moltype = AA  length = 7
FEATURE                 Location/Qualifiers
source                  1..7
                        mol_type = protein
                        note = Synthetic peptide
                        organism = synthetic construct
SEQUENCE: 94
WASTRHT                                                       7

SEQ ID NO: 95           moltype =   length =
SEQUENCE: 95
000

SEQ ID NO: 96           moltype = AA  length = 11
FEATURE                 Location/Qualifiers
source                  1..11
                        mol_type = protein
                        note = Synthetic peptide
                        organism = synthetic construct
SEQUENCE: 96
LLIYWASTRH T                                                  11

SEQ ID NO: 97           moltype = AA  length = 9
FEATURE                 Location/Qualifiers
source                  1..9
                        mol_type = protein
                        note = Synthetic peptide
                        organism = synthetic construct
SEQUENCE: 97
QQYSSYPFT                                                     9

SEQ ID NO: 98           moltype = AA  length = 8
FEATURE                 Location/Qualifiers
source                  1..8
                        mol_type = protein
                        note = Synthetic peptide
                        organism = synthetic construct
SEQUENCE: 98
QQYSSYPF                                                      8

SEQ ID NO: 99           moltype = AA  length = 6
FEATURE                 Location/Qualifiers
source                  1..6
                        mol_type = protein
                        note = Synthetic peptide
                        organism = synthetic construct
SEQUENCE: 99
DYYYMT                                                        6

SEQ ID NO: 100          moltype = AA  length = 8
FEATURE                 Location/Qualifiers
```

```
source                  1..8
                        mol_type = protein
                        note = Synthetic peptide
                        organism = synthetic construct
SEQUENCE: 100
GFSLTDYY                                                                    8

SEQ ID NO: 101          moltype = AA  length = 9
FEATURE                 Location/Qualifiers
source                  1..9
                        mol_type = protein
                        note = Synthetic peptide
                        organism = synthetic construct
SEQUENCE: 101
GFSLTDYYY                                                                   9

SEQ ID NO: 102          moltype = AA  length = 10
FEATURE                 Location/Qualifiers
source                  1..10
                        mol_type = protein
                        note = Synthetic peptide
                        organism = synthetic construct
SEQUENCE: 102
FSLTDYYYMT                                                                  10

SEQ ID NO: 103          moltype = AA  length = 11
FEATURE                 Location/Qualifiers
source                  1..11
                        mol_type = protein
                        note = Synthetic peptide
                        organism = synthetic construct
SEQUENCE: 103
GFSLTDYYYM T                                                                11

SEQ ID NO: 104          moltype = AA  length = 5
FEATURE                 Location/Qualifiers
source                  1..5
                        mol_type = protein
                        note = Synthetic peptide
                        organism = synthetic construct
SEQUENCE: 104
HYGMN                                                                       5

SEQ ID NO: 105          moltype = AA  length = 7
FEATURE                 Location/Qualifiers
source                  1..7
                        mol_type = protein
                        note = Synthetic peptide
                        organism = synthetic construct
SEQUENCE: 105
GYDFTHY                                                                     7

SEQ ID NO: 106          moltype = AA  length = 8
FEATURE                 Location/Qualifiers
source                  1..8
                        mol_type = protein
                        note = Synthetic peptide
                        organism = synthetic construct
SEQUENCE: 106
GYDFTHYG                                                                    8

SEQ ID NO: 107          moltype = AA  length = 9
FEATURE                 Location/Qualifiers
source                  1..9
                        mol_type = protein
                        note = Synthetic peptide
                        organism = synthetic construct
SEQUENCE: 107
YDFTHYGMN                                                                   9

SEQ ID NO: 108          moltype = AA  length = 10
FEATURE                 Location/Qualifiers
source                  1..10
                        mol_type = protein
                        note = Synthetic peptide
                        organism = synthetic construct
SEQUENCE: 108
GYDFTHYGMN                                                                  10
```

-continued

```
SEQ ID NO: 109          moltype = AA  length = 5
FEATURE                 Location/Qualifiers
source                  1..5
                        mol_type = protein
                        note = Synthetic peptide
                        organism = synthetic construct
SEQUENCE: 109
NYGMN                                                                       5

SEQ ID NO: 110          moltype = AA  length = 7
FEATURE                 Location/Qualifiers
source                  1..7
                        mol_type = protein
                        note = Synthetic peptide
                        organism = synthetic construct
SEQUENCE: 110
GYTFTNY                                                                     7

SEQ ID NO: 111          moltype = AA  length = 8
FEATURE                 Location/Qualifiers
source                  1..8
                        mol_type = protein
                        note = Synthetic peptide
                        organism = synthetic construct
SEQUENCE: 111
GYTFTNYG                                                                    8

SEQ ID NO: 112          moltype = AA  length = 9
FEATURE                 Location/Qualifiers
source                  1..9
                        mol_type = protein
                        note = Synthetic peptide
                        organism = synthetic construct
SEQUENCE: 112
YTFTNYGMN                                                                   9

SEQ ID NO: 113          moltype = AA  length = 10
FEATURE                 Location/Qualifiers
source                  1..10
                        mol_type = protein
                        note = Synthetic peptide
                        organism = synthetic construct
SEQUENCE: 113
GYTFTNYGMN                                                                  10

SEQ ID NO: 114          moltype = AA  length = 16
FEATURE                 Location/Qualifiers
source                  1..16
                        mol_type = protein
                        note = Synthetic peptide
                        organism = synthetic construct
SEQUENCE: 114
FIDPDDDPYY ATWAKG                                                           16

SEQ ID NO: 115          moltype = AA  length = 5
FEATURE                 Location/Qualifiers
source                  1..5
                        mol_type = protein
                        note = Synthetic peptide
                        organism = synthetic construct
SEQUENCE: 115
DPDDD                                                                       5

SEQ ID NO: 116          moltype = AA  length = 7
FEATURE                 Location/Qualifiers
source                  1..7
                        mol_type = protein
                        note = Synthetic peptide
                        organism = synthetic construct
SEQUENCE: 116
IDPDDDP                                                                     7

SEQ ID NO: 117          moltype = AA  length = 17
FEATURE                 Location/Qualifiers
source                  1..17
                        mol_type = protein
                        note = Synthetic peptide
                        organism = synthetic construct
SEQUENCE: 117
```

```
WVGFIDPDDD PYYATWA                                                  17

SEQ ID NO: 118          moltype = AA  length = 19
FEATURE                 Location/Qualifiers
source                  1..19
                        mol_type = protein
                        note = Synthetic peptide
                        organism = synthetic construct
SEQUENCE: 118
WVGFIDPDDD PYYATWAKG                                                19

SEQ ID NO: 119          moltype = AA  length = 17
FEATURE                 Location/Qualifiers
source                  1..17
                        mol_type = protein
                        note = Synthetic peptide
                        organism = synthetic construct
SEQUENCE: 119
WINTYTGEPT YAADFKR                                                  17

SEQ ID NO: 120          moltype = AA  length = 6
FEATURE                 Location/Qualifiers
source                  1..6
                        mol_type = protein
                        note = Synthetic peptide
                        organism = synthetic construct
SEQUENCE: 120
NTYTGE                                                              6

SEQ ID NO: 121          moltype = AA  length = 8
FEATURE                 Location/Qualifiers
source                  1..8
                        mol_type = protein
                        note = Synthetic peptide
                        organism = synthetic construct
SEQUENCE: 121
INTYTGEP                                                            8

SEQ ID NO: 122          moltype = AA  length = 14
FEATURE                 Location/Qualifiers
source                  1..14
                        mol_type = protein
                        note = Synthetic peptide
                        organism = synthetic construct
SEQUENCE: 122
WVGWINTYTG EPTY                                                     14

SEQ ID NO: 123          moltype = AA  length = 20
FEATURE                 Location/Qualifiers
source                  1..20
                        mol_type = protein
                        note = Synthetic peptide
                        organism = synthetic construct
SEQUENCE: 123
WVGWINTYTG EPTYAADFKR                                               20

SEQ ID NO: 124          moltype = AA  length = 11
FEATURE                 Location/Qualifiers
source                  1..11
                        mol_type = protein
                        note = Synthetic peptide
                        organism = synthetic construct
SEQUENCE: 124
GDHNSGWGLD I                                                        11

SEQ ID NO: 125          moltype = AA  length = 13
FEATURE                 Location/Qualifiers
source                  1..13
                        mol_type = protein
                        note = Synthetic peptide
                        organism = synthetic construct
SEQUENCE: 125
AGGDHNSGWG LDI                                                      13

SEQ ID NO: 126          moltype = AA  length = 14
FEATURE                 Location/Qualifiers
source                  1..14
                        mol_type = protein
                        note = Synthetic peptide
```

```
                         organism = synthetic construct
SEQUENCE: 126
YPYYYGTSHW YFDV                                                  14

SEQ ID NO: 127           moltype = AA  length = 16
FEATURE                  Location/Qualifiers
source                   1..16
                         mol_type = protein
                         note = Synthetic peptide
                         organism = synthetic construct
SEQUENCE: 127
AKYPYYYGTS HWYFDV                                                16

SEQ ID NO: 128           moltype = AA  length = 15
FEATURE                  Location/Qualifiers
source                   1..15
                         mol_type = protein
                         note = Synthetic peptide
                         organism = synthetic construct
SEQUENCE: 128
KYPYYYGTSH WYFDV                                                 15

SEQ ID NO: 129           moltype = AA  length = 14
FEATURE                  Location/Qualifiers
source                   1..14
                         mol_type = protein
                         note = Synthetic peptide
                         organism = synthetic construct
SEQUENCE: 129
YPHYYGSSHW YFDV                                                  14

SEQ ID NO: 130           moltype = AA  length = 16
FEATURE                  Location/Qualifiers
source                   1..16
                         mol_type = protein
                         note = Synthetic peptide
                         organism = synthetic construct
SEQUENCE: 130
AKYPHYYGSS HWYFDV                                                16

SEQ ID NO: 131           moltype = AA  length = 15
FEATURE                  Location/Qualifiers
source                   1..15
                         mol_type = protein
                         note = Synthetic peptide
                         organism = synthetic construct
SEQUENCE: 131
KYPHYYGSSH WYFDV                                                 15

SEQ ID NO: 132           moltype = AA  length = 11
FEATURE                  Location/Qualifiers
source                   1..11
                         mol_type = protein
                         note = Synthetic peptide
                         organism = synthetic construct
SEQUENCE: 132
QASEIIHSWL A                                                     11

SEQ ID NO: 133           moltype = AA  length = 6
FEATURE                  Location/Qualifiers
source                   1..6
                         mol_type = protein
                         note = Synthetic peptide
                         organism = synthetic construct
SEQUENCE: 133
EIIHSW                                                           6

SEQ ID NO: 134           moltype = AA  length = 8
FEATURE                  Location/Qualifiers
source                   1..8
                         mol_type = protein
                         note = Synthetic peptide
                         organism = synthetic construct
SEQUENCE: 134
EIIHSWLA                                                         8

SEQ ID NO: 135           moltype = AA  length = 11
FEATURE                  Location/Qualifiers
source                   1..11
```

```
                        mol_type = protein
                        note = Synthetic peptide
                        organism = synthetic construct
SEQUENCE: 135
SASQDISNYL N                                                    11

SEQ ID NO: 136          moltype = AA  length = 6
FEATURE                 Location/Qualifiers
source                  1..6
                        mol_type = protein
                        note = Synthetic peptide
                        organism = synthetic construct
SEQUENCE: 136
QDISNY                                                          6

SEQ ID NO: 137          moltype = AA  length = 8
FEATURE                 Location/Qualifiers
source                  1..8
                        mol_type = protein
                        note = Synthetic peptide
                        organism = synthetic construct
SEQUENCE: 137
QDISNYLN                                                        8

SEQ ID NO: 138          moltype = AA  length = 7
FEATURE                 Location/Qualifiers
source                  1..7
                        mol_type = protein
                        note = Synthetic peptide
                        organism = synthetic construct
SEQUENCE: 138
LASTLAS                                                         7

SEQ ID NO: 139          moltype =   length =
SEQUENCE: 139
000

SEQ ID NO: 140          moltype = AA  length = 11
FEATURE                 Location/Qualifiers
source                  1..11
                        mol_type = protein
                        note = Synthetic peptide
                        organism = synthetic construct
SEQUENCE: 140
LLIYLASTLA S                                                    11

SEQ ID NO: 141          moltype = AA  length = 7
FEATURE                 Location/Qualifiers
source                  1..7
                        mol_type = protein
                        note = Synthetic peptide
                        organism = synthetic construct
SEQUENCE: 141
FTSSLHS                                                         7

SEQ ID NO: 142          moltype =   length =
SEQUENCE: 142
000

SEQ ID NO: 143          moltype = AA  length = 11
FEATURE                 Location/Qualifiers
source                  1..11
                        mol_type = protein
                        note = Synthetic peptide
                        organism = synthetic construct
SEQUENCE: 143
VLIYFTSSLH S                                                    11

SEQ ID NO: 144          moltype = AA  length = 12
FEATURE                 Location/Qualifiers
source                  1..12
                        mol_type = protein
                        note = Synthetic peptide
                        organism = synthetic construct
SEQUENCE: 144
QNVYLASTNG AN                                                   12

SEQ ID NO: 145          moltype = AA  length = 9
FEATURE                 Location/Qualifiers
```

```
source                  1..9
                        mol_type = protein
                        note = Synthetic peptide
                        organism = synthetic construct
SEQUENCE: 145
QQYSTVPWT                                                   9

SEQ ID NO: 146          moltype = AA  length = 8
FEATURE                 Location/Qualifiers
source                  1..8
                        mol_type = protein
                        note = Synthetic peptide
                        organism = synthetic construct
SEQUENCE: 146
QQYSTVPW                                                    8

SEQ ID NO: 147          moltype = AA  length = 102
FEATURE                 Location/Qualifiers
source                  1..102
                        mol_type = protein
                        organism = Homo sapiens
SEQUENCE: 147
SDTGRPFVEM YSEIPEIIHM TEGRELVIPC RVTSPNITVT LKKFPLDTLI PDGKRIIWDS  60
RKGFIISNAT YKEIGLLTCE ATVNGHLYKT NYLTHRQTNT II                     102

SEQ ID NO: 148          moltype = AA  length = 103
FEATURE                 Location/Qualifiers
source                  1..103
                        mol_type = protein
                        organism = Homo sapiens
SEQUENCE: 148
DVVLSPSHGI ELSVGEKLVL NCTARTELNV GIDFNWEYPS SKHQHKKLVN RDLKTQSGSE  60
MKKFLSTLTI DGVTRSDQGL YTCAASSGLM TKKNSTFVRV HEK                    103

SEQ ID NO: 149          moltype = AA  length = 678
FEATURE                 Location/Qualifiers
source                  1..678
                        mol_type = protein
                        note = Synthetic polypeptide
                        organism = synthetic construct
SEQUENCE: 149
MGWTLVFLFL LSVTAGVHSE VQLVESGGGL VQPGGSLRLS CAASGFTFNA NAMNWVRQAP  60
GKGLEWVGRI RTKSNNYATY YAGSVKDRFT ISRDDSKNSL YLQMNSLKTE DTAVYYCVRD  120
YYGSSAWITY WGQGTLVTVS SASTKGPSVF PLAPCSRSTS ESTAALGCLV KDYFPEPVTV  180
SWNSGALTSG VHTFPAVLQS SGLYSLSSVV TVPSSSLGTK TYTCNVDHKP SNTKVDKRVE  240
SKYGPPCPPC PAPEFLGGPS VFLFPPKPKD TLMISRTPEV TCVVVDVSQE DPEVQFNWYV  300
DGVEVHNAKT KPREEQFNST YRVVSVLTVL HQDWLNGKEY KCKVSNKGLP SSIEKTISKA  360
KGQPREPQVY TLPPSQEEMT KNQVSLTCLV KGFYPSDIAV EWESNGQPEN NYKTTPPVLD  420
SDGSFFLYSR LTVDKSRWQE GNVFSCSVMH EALHNHYTQK SLSLSLGKGG GGSSDTGRPF  480
VEMYSEIPEI IHMTEGRELV IPCRVTSPNI TVTLKKFPLD TLIPDGKRII WDSRKGFIIS  540
NATYKEIGLL TCEATVNGHL YKTNYLTHRQ TNTIIDVVLS PSHGIELSVG EKLVLNCTAR  600
TELNVGIDFN WEYPSSKHQH KKLVNRDLKT QSGSEMKKFL STLTIDGVTR SDQGLYTCAA  660
SSGLMTKKNS TFVRVHEK                                                678

SEQ ID NO: 150          moltype = AA  length = 724
FEATURE                 Location/Qualifiers
source                  1..724
                        mol_type = protein
                        note = Synthetic polypeptide
                        organism = synthetic construct
SEQUENCE: 150
MGWTLVFLFL LSVTAGVHSE VQLVESGGGL VQPGGSLRLS CAASGFTFNA NAMNWVRQAP  60
GKGLEWVGRI RTKSNNYATY YAGSVKDRFT ISRDDSKNSL YLQMNSLKTE DTAVYYCVRD  120
YYGSSAWITY WGQGTLVTVS SASTKGPSVF PLAPCSRSTS ESTAALGCLV KDYFPEPVTV  180
SWNSGALTSG VHTFPAVLQS SGLYSLSSVV TVPSSSLGTK TYTCNVDHKP SNTKVDKRVE  240
SKYGPPCPPC PAPEFLGGPS VFLFPPKPKD TLMISRTPEV TCVVVDVSQE DPEVQFNWYV  300
DGVEVHNAKT KPREEQFNST YRVVSVLTVL HQDWLNGKEY KCKVSNKGLP SSIEKTISKA  360
KGQPREPQVY TLPPSQEEMT KNQVSLTCLV KGFYPSDIAV EWESNGQPEN NYKTTPPVLD  420
SDGSFFLYSR LTVDKSRWQE GNVFSCSVMH EALHNHYTQK SLSLSLGKGG GGSEIVMTQS  480
PSTLSASVGD RVIITCQASE IIHSWLAWYQ QKPGKAPKLL IYLASTLASG VPSRFSGSGS  540
GAEFTLTISS LQPDDFATYY CQNVYLASTN GANFGQGTKL TVLGGGGGSG GGGSGGGGSG  600
GGGSEVQLVE SGGGLVQPGG SLRLSCTASG FSLTDYYYMT WVRQAPGKGL EWVGFIDPDD  660
DPYYATWAKG RFTISRDNSK NTLYLQMNSL RAEDTAVYYC AGGDHNSGWG LDIWGQGTLV  720
TVSS                                                               724

SEQ ID NO: 151          moltype = AA  length = 718
FEATURE                 Location/Qualifiers
source                  1..718
                        mol_type = protein
```

```
                         note = Synthetic polypeptide
                         organism = synthetic construct
SEQUENCE: 151
MGWTLVFLFL LSVTAGVHSE VQLVESGGGL VQPGGSLRLS CAASGFTFNA NAMNWVRQAP  60
GKGLEWVGRI RTKSNNYATY YAGSVKDRFT ISRDDSKNSL YLQMNSLKTE DTAVYYCVRD  120
YYGSSAWITY WGQGTLVTVS SASTKGPSVF PLAPCSRSTS ESTAALGCLV KDYFPEPVTV  180
SWNSGALTSG VHTFPAVLQS SGLYSLSSVV TVPSSSLGTK TYTCNVDHKP SNTKVDKRVE  240
SKYGPPCPPC PAPEFLGGPS VFLFPPKPKD TLMISRTPEV TCVVVDVSQE DPEVQFNWYV  300
DGVEVHNAKT KPREEQFNST YRVVSVLTVL HQDWLNGKEY KCKVSNKGLP SSIEKTISKA  360
KGQPREPQVY TLPPSQEEMT KNQVSLTCLV KGFYPSDIAV EWESNGQPEN NYKTTPPVLD  420
SDGSFFLYSR LTVDKSRWQE GNVFSCSVMH EALHNHYTQK SLSLSLGKGG GGSEVQLVES  480
GGGLVQPGGS LRLSCAASGY DFTHYGMNWV RQAPGKGLEW VGWINTYTGE PTYAADFKRR  540
FTFSLDTSKS TAYLQMNSLR AEDTAVYYCA KYPYYYGTSH WYFDVWGQGT LVTVSSGGGG  600
SGGGGSGGGG SDIQLTQSPS SLSASVGDRV TITCSASQDI SNYLNWYQQK PGKAPKVLIY  660
FTSSLHSGVP SRFSGSGSGT DFTLTISSLQ PEDFATYYCQ QYSTVPWTFG QGTKVEIK    718

SEQ ID NO: 152           moltype = AA  length = 20
FEATURE                  Location/Qualifiers
source                   1..20
                         mol_type = protein
                         note = Synthetic peptide
                         organism = synthetic construct
SEQUENCE: 152
LRRFSTAPFA FIDINDVINF                                              20

SEQ ID NO: 153           moltype = AA  length = 20
FEATURE                  Location/Qualifiers
MOD_RES                  7
                         note = Any amino acid
MOD_RES                  9..12
                         note = Any amino acid
MOD_RES                  18
                         note = Any amino acid
source                   1..20
                         mol_type = protein
                         note = Synthetic peptide
                         organism = synthetic construct
SEQUENCE: 153
LRRFSTXPXX XXNINNVXNF                                              20

SEQ ID NO: 154           moltype = AA  length = 526
FEATURE                  Location/Qualifiers
source                   1..526
                         mol_type = protein
                         note = Synthetic polypeptide
                         organism = synthetic construct
SEQUENCE: 154
GRPFVEMYSE IPEIIHMTEG RELVIPCRVT SPNITVTLKK FPLDTLIPDG KRIIWDSRKG  60
FIISNATYKE IGLLTCEATV NGHLYKTNYL THRQTNTIID VVLSPSHGIE LSVGEKLVLN  120
CTARTELNVG IDFNWEYPSS KHQHKKLVNR DLKTQSGSEM KKFLSTLTID GVTRSDQGLY  180
TCAASSGLMT KKNSTFVRVH EKPFVAFGSG MESLVEATVG ERVRIPAKYL GYPPPEIKWY  240
KNGIPLESNH TIKAGHVLTI MEVSERDTGN YTVILTNPIS KEKQSHVVSL VVYVPPGPGD  300
KTHTCPLCPA PELLGGPSVF LFPPKPKDTL MISRTPEVTC VVVDVSHEDP EVKFNWYVDG  360
VEVHNAKTKP REEQYNSTYR VVSVLTVLHQ DWLNGKEYKC KVSNKALPAP IEKTISKAKG  420
QPREPQVYTL PPSRDELTKN QVSLTCLVKG FYPSDIAVEW ESNGQPENNY KATPPVLDSD  480
GSFFLYSKLT VDKSRWQQGN VFSCSVMHEA LHNHYTQKSL SLSPGK                 526

SEQ ID NO: 155           moltype = AA  length = 299
FEATURE                  Location/Qualifiers
source                   1..299
                         mol_type = protein
                         note = Synthetic polypeptide
                         organism = synthetic construct
SEQUENCE: 155
GRPFVEMYSE IPEIIHMTEG RELVIPCRVT SPNITVTLKK FPLDTLIPDG KRIIWDSRKG  60
FIISNATYKE IGLLTCEATV NGHLYKTNYL THRQTNTIID VVLSPSHGIE LSVGEKLVLN  120
CTARTELNVG IDFNWEYPSS KHQHKKLVNR DLKTQSGSEM KKFLSTLTID GVTRSDQGLY  180
TCAASSGLMT KKNSTFVRVH EKPFVAFGSG MESLVEATVG ERVRIPAKYL GYPPPEIKWY  240
KNGIPLESNH TIKAGHVLTI MEVSERDTGN YTVILTNPIS KEKQSHVVSL VVYVPPGPG   299

SEQ ID NO: 156           moltype = AA  length = 446
FEATURE                  Location/Qualifiers
source                   1..446
                         mol_type = protein
                         note = Synthetic polypeptide
                         organism = synthetic construct
SEQUENCE: 156
EVQLVQSGGG LVKPGGSLRL SCAASGFTFS SYSMNWVRQA PGKGLEWVSS ISSSSSYIYY  60
ADSVKGRFTI SRDNAKNSLY LQMNSLRAED TAVYYCARVT DAFDIWGQGT MVTVSSASTK  120
```

-continued

```
GPSVFPLAPS SKSTSGGTAA LGCLVKDYFP EPVTVSWNSG ALTSGVHTFP AVLQSSGLYS  180
LSSVVTVPSS SLGTQTYICN VNHKPSNTKV DKKVEPKSCD KTHTCPPCPA PELLGGPSVF  240
LFPPKPKDTL MISRTPEVTC VVVDVSHEDP EVKFNWYVDG VEVHNAKTKP REEQYNSTYR  300
VVSVLTVLHQ DWLNGKEYKC KVSNKALPAP IEKTISKAKG QPREPQVYTL PPSREEMTKN  360
QVSLTCLVKG FYPSDIAVEW ESNGQPENNY KTTPPVLDSD GSFFLYSKLT VDKSRWQQGN  420
VFSCSVMHEA LHNHYTQKSL SLSPGK                                      446

SEQ ID NO: 157         moltype = AA  length = 214
FEATURE                Location/Qualifiers
source                 1..214
                       mol_type = protein
                       note = Synthetic polypeptide
                       organism = synthetic construct
SEQUENCE: 157
DIQMTQSPSS VSASIGDRVT ITCRASQGID NWLGWYQQKP GKAPKLLIYD ASNLDTGVPS  60
RFSGSGSGTY FTLTISSLQA EDFAVYFCQQ AKAFPPTFGG GTKVDIKGTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 158         moltype = AA  length = 157
FEATURE                Location/Qualifiers
source                 1..157
                       mol_type = protein
                       note = Synthetic polypeptide
                       organism = synthetic construct
SEQUENCE: 158
DLGKKLLEAA RAGQDDEVRI LMANGADVNA FDWMGWTPLH LAAHEGHLEI VEVLLKNGAD  60
VNATDVSGYT PLHLAAADGH LEIVEVLLKH GADVNTKDNT GWTPLHLSAD LGHLEIVEVL  120
LKNGADVNAQ DKFGKTAFDI SIDNGNEDLA EILQKAA                           157

SEQ ID NO: 159         moltype = AA  length = 157
FEATURE                Location/Qualifiers
source                 1..157
                       mol_type = protein
                       note = Synthetic polypeptide
                       organism = synthetic construct
SEQUENCE: 159
DLDKKLLEAA RAGQDDEVRI LLKAGADVNA KDYLGWTPLH LAAHEGHLEI VEVLLKAGAD  60
VNAKDVSGYT PLHLAAADGH LEIVEVLLKA GADVNAKDNT GWTPLHLSAD LGHLEIVEVL  120
LKAGADVNAQ DKFGKTAFDI SIDNGNEDLA EILQKAA                           157

SEQ ID NO: 160         moltype = AA  length = 124
FEATURE                Location/Qualifiers
source                 1..124
                       mol_type = protein
                       note = Synthetic polypeptide
                       organism = synthetic construct
SEQUENCE: 160
DLGKKLLEAA RAGQDDEVRI LMANGADVNT ADSTGWTPLH LAAPWGHPEI VEVLLKNGAD  60
VNAHDYQGWT PLHLAATLGH LEIVEVLLKH GADVNAQDKF GKTAFDISID NGNEDLAEIL  120
QKAA                                                              124

SEQ ID NO: 161         moltype = AA  length = 124
FEATURE                Location/Qualifiers
source                 1..124
                       mol_type = protein
                       note = Synthetic polypeptide
                       organism = synthetic construct
SEQUENCE: 161
DLGKKLLEAA RAGQDDEVRI LMANGADVNT ADSTGWTPLH LAVPWGHLEI VEVLLKYGAD  60
VNAKDFQGWT PLHLAAAIGH QEIVEVLLKN GADVNAQDKF GKTAFDISID NGNEDLAEIL  120
QKAA                                                              124

SEQ ID NO: 162         moltype = AA  length = 124
FEATURE                Location/Qualifiers
source                 1..124
                       mol_type = protein
                       note = Synthetic polypeptide
                       organism = synthetic construct
SEQUENCE: 162
DLDKKLLEAA RAGQDDEVRI LMANGADVNA KDSTGYTPLH LAAPWGHLEI VEVLLKAGAD  60
VNAKDYQGWT PLHLAAAVGH LEIVEVLLKA GADVNAQDKS GKTPADLAAD AGHEDIAEVL  120
QKAA                                                              124

SEQ ID NO: 163         moltype = AA  length = 124
FEATURE                Location/Qualifiers
source                 1..124
                       mol_type = protein
                       note = Synthetic polypeptide
```

```
                        organism = synthetic construct
SEQUENCE: 163
DLGKKLLEAA RAGQDDEVRI LMANGADVNA RDSTGWTPLH LAAPWGHPEI VEVLLKNGAD  60
VNAADFQGWT PLHLAAAVGH LEIVEVLLKH GADVNAQDKF GKTAFDISID NGNEDLAEIL  120
QKAA                                                              124

SEQ ID NO: 164          moltype = AA  length = 124
FEATURE                 Location/Qualifiers
source                  1..124
                        mol_type = protein
                        note = Synthetic polypeptide
                        organism = synthetic construct
SEQUENCE: 164
DLDKKLLEAA RAGQDDEVRI LLKAGADVNA KDSTGWTPLH LAAPWGHPEI VEVLLKAGAD  60
VNAKDFQGWT PLHLAAAAGH LEIVEVLLKA GADVNAQDKS GKTPADLAAD AGHEDIAEVL  120
QKAA                                                              124

SEQ ID NO: 165          moltype = AA  length = 124
FEATURE                 Location/Qualifiers
source                  1..124
                        mol_type = protein
                        note = Synthetic polypeptide
                        organism = synthetic construct
SEQUENCE: 165
DLGKKLLEAA RAGQDDEVRI LLKAGADVNA KDSTGWTPLH LAAPWGHPEI VEVLLKAGAD  60
VNAKDFQGWT PLHLAAAAGH LEIVEVLLKA GADVNAQDKS GKTPADLAAD AGHEDIAEVL  120
QKAA                                                              124

SEQ ID NO: 166          moltype = AA  length = 124
FEATURE                 Location/Qualifiers
source                  1..124
                        mol_type = protein
                        note = Synthetic polypeptide
                        organism = synthetic construct
SEQUENCE: 166
DLDKKLLEAA RAGQDDEVRI LLKAGADVNA KDSTGWTPLH LAAPWGHPEI VEVLLKAGAD  60
VNAKDFQGWT PLHLAAAVGH LEIVEVLLKA GADVNAQDKS GKTPADLAAD AGHEDIAEVL  120
QKAA                                                              124

SEQ ID NO: 167          moltype = AA  length = 124
FEATURE                 Location/Qualifiers
source                  1..124
                        mol_type = protein
                        note = Synthetic polypeptide
                        organism = synthetic construct
SEQUENCE: 167
DLDKKLLEAA RAGQDDEVRI LLKAGADVNA KDSTGWTPLH LAAPWGHPEI VEVLLKAGAD  60
VNAKDYQGWT PLHLAAAVGH LEIVEVLLKA GADVNAQDKS GKTPADLAAD AGHEDIAEVL  120
QKAA                                                              124

SEQ ID NO: 168          moltype = AA  length = 124
FEATURE                 Location/Qualifiers
source                  1..124
                        mol_type = protein
                        note = Synthetic polypeptide
                        organism = synthetic construct
SEQUENCE: 168
DLDKKLLEAA RAGQDDEVRI LMANGADVNA KDSTGWTPLH LAAPWGHLEI VEVLLKAGAD  60
VNAKDFQGWT PLHLAAAVGH LEIVEVLLKA GADVNAQDKF GKTAFDISID NGNEDLAEIL  120
QKAA                                                              124

SEQ ID NO: 169          moltype = AA  length = 272
FEATURE                 Location/Qualifiers
source                  1..272
                        mol_type = protein
                        note = Synthetic polypeptide
                        organism = synthetic construct
SEQUENCE: 169
DLGKKLLEAA RAGQDDEVRE LLKAGADVNA KDYFSHTPLH LAARNGHLKI VEVLLKAGAD  60
VNAKDFAGKT PLHLAANEGH LEIVEVLLKA GADVNAQDIF GKTPADIAAD AGHEDIAEVL  120
QKAAGSPTPT PTTPTPTPTT PTPTPTGSDL DKKLLEAARA GQDDEVRILL KAGADVNAKD  180
STGWTPLHLA APWGHPEIVE VLLKAGADVN AKDFQGWTPL HLAAAAGHLE IVEVLLKAGA  240
DVNAQDKSGK TPADLAADAG HEDIAEVLQK AA                                272

SEQ ID NO: 170          moltype = AA  length = 603
FEATURE                 Location/Qualifiers
source                  1..603
                        mol_type = protein
                        note = Synthetic polypeptide
```

```
                         organism = synthetic construct
SEQUENCE: 170
GSDLGKKLLE AARAGQDDEV RELLKAGADV NAKDYFSHTP LHLAARNGHL KIVEVLLKAG  60
ADVNAKDFAG KTPLHLAANE GHLEIVEVLL KAGADVNAQD IFGKTPADIA ADAGHEDIAE 120
VLQKAAGSPT PTPTTPTPTP TTPTPTPTGS DLGKKLLEAA RAGQDDEVRI LLKAGADVNA 180
KDRYGDTPLH LAADIGHLEI VEVLLKAGAD VNAEDYFGNT PLHLAASYGH LEIVEVLLKA 240
GADVNAKDDY GNTPLHLAAN TGHLEIVEVL LKAGADVNAQ DKSGKTPADL AADAGHEDIA 300
EVLQKAAGSP TPTPTTPTPT PTTPTPTPTG SDLDKKLLEA ARAGQDDEVR ILLKAGADVN 360
AKDSTGWTPL HLAAPWGHPE IVEVLLKAGA DVNAKDFQGW TPLHLAAAAG HLEIVEVLLK 420
AGADVNAQDK SGKTPADLAA DAGHEDIAEV LQKAAGSPTP TPTTPTPTPT TPTPTPTGSD 480
LGKKLLEAAR AGQDDEVREL LKAGADVNAK DYFSHTPLHL AARNGHLKIV EVLLKAGADV 540
NAKDFAGKTP LHLAANEGHL EIVEVLLKAG ADVNAQDIFG KTPADIAADA GHEDIAEVLQ 600
KAA                                                               603

SEQ ID NO: 171           moltype = AA  length = 1025
FEATURE                  Location/Qualifiers
source                   1..1025
                         mol_type = protein
                         note = Synthetic polypeptide
                         organism = synthetic construct
SEQUENCE: 171
GSDLGKKLLE AARAGQDDEV RILMANGADV NAFDWMGWTP LHLAAHEGHL EIVEVLLKNG  60
ADVNATDVSG YTPLHLAAAD GHLEIVEVLL KYGADVNTKD NTGWTPLHLS ADLGRLEIVE 120
VLLKYGADVN AQDKFGKTAF DISIDNGNED LAEILQKAAS GSPAGSPTST EEGTSESATP 180
ESGPGTSTEP SEGSAPGSPA GSPTSTEEGT STEPSEGSAP GTSTEPSEGS APGTSESATP 240
ESGPGSEPAT SGSETPGSEP ATSGSETPGS PAGSPTSTEE GTSESATPES GPGTSTEPSE 300
GSAPGTSTEP SEGSAPGSPA GSPTSTEEGT STEPSEGSAP GTSTEPSEGS APGTSESATP 360
ESGPGTSTEP SEGSAPGTSE SATPESGPGS EPATSGSETP GTSTEPSEGS APGTSTEPSE 420
GSAPGTSESA TPESGPGTSE SATPESGPGS PAGSPTSTEE GTSESATPES GPGSEPATSG 480
SETPGTSESA TPESGPGTST EPSEGSAPGT STEPSEGSAP GTSTEPSEGS APGTSTEPSE 540
GSAPGTSTEP SEGSAPGTST EPSEGSAPGS PAGSPTSTEE GTSTEPSEGS APGTSESATP 600
ESGPGSEPAT SGSETPGTSE SATPESGPGS EPATSGSETP GTSESATPES GPGTSTEPSE 660
GSAPGTSESA TPESGPGSPA GSPTSTEEGS PAGSPTSTEE GSPAGSPTST EEGTSESATP 720
ESGPGTSTEP SEGSAPGTSE SATPESGPGS EPATSGSETP GTSESATPES GPGSEPATSG 780
SETPGTSESA TPESGPGTST EPSEGSAPGS PAGSPTSTEE GTSESATPES GPGSEPATSG 840
SETPGTSESA TPESGPGSPA GSPTSTEEGS PAGSPTSTEE GTSTEPSEGS APGTSESATP 900
ESGPGTSESA TPESGPGTSE SATPESGPGS EPATSGSETP GSEPATSGSE TPGSPAGSPT 960
STEEGTSTEP SEGSAPGTST EPSEGSAPGS EPATSGSETP GTSESATPES GPGTSTEPSE 1020
GSAPG                                                             1025

SEQ ID NO: 172           moltype = AA  length = 168
FEATURE                  Location/Qualifiers
source                   1..168
                         mol_type = protein
                         note = Synthetic polypeptide
                         organism = synthetic construct
SEQUENCE: 172
GSDLGKKLLE AARAGQDDEV RILMANGADV NAFDWMGWTP LHLAAHEGHL EIVEVLLKNG  60
ADVNATDVSG YTPLHLAAAD GHLEIVEVLL KHGADVNTKD NTGWTPLHLS ADLGHLEIVE 120
VLLKNGADVN AQDKFGKTAF DISIDNGNED LAEILQKAAG GGSGGGSC               168

SEQ ID NO: 173           moltype = AA  length = 135
FEATURE                  Location/Qualifiers
source                   1..135
                         mol_type = protein
                         note = Synthetic polypeptide
                         organism = synthetic construct
SEQUENCE: 173
GSDLDKKLLE AARAGQDDEV RILMANGADV NARDSTGWTP LHLAAPWGHP EIVEVLLKNG  60
ADVNAADFQG WTPLHLAAAV GHLEIVEVLL KYGADVNAQD KFGKTAFDIS IDNGNEDLAE 120
ILQKAAGGGS GGGSC                                                  135

SEQ ID NO: 174           moltype = AA  length = 540
FEATURE                  Location/Qualifiers
source                   1..540
                         mol_type = protein
                         note = Synthetic polypeptide
                         organism = synthetic construct
SEQUENCE: 174
GSDLGKKLLE AARAGQDDEV RILMANGADV NTADSTGWTP LHLAVPWGHL EIVEVLLKYG  60
ADVNAKDFQG WTPLHLAAAI GHQEIVEVLL KNGADVNAQD KFGKTAFDIS IDNGNEDLAE 120
ILQKAAGSGS ASPAAPAPAS PAAPAPSAPA ASPAAPAPAS PAAPAPSAPA ASPAAPAPAS 180
PAAPAPSAPA ASPAAPAPAS PAAPAPSAPA ASPAAPAPAS PAAPAPSAPA ASPAAPAPAS 240
PAAPAPSAPA ASPAAPAPAS PAAPAPSAPA ASPAAPAPAS PAAPAPSAPA ASPAAPAPAS 300
PAAPAPSAPA ASPAAPAPAS PAAPAPSAPA ASPAAPAPAS PAAPAPSAPA ASPAAPAPAS 360
PAAPAPSAPA ASPAAPAPAS PAAPAPSAPA ASPAAPAPAS PAAPAPSAPA ASPAAPAPAS 420
PAAPAPSAPA ASPAAPAPAS PAAPAPSAPA ASPAAPAPAS PAAPAPSAPA ASPAAPAPAS 480
PAAPAPSAPA ASPAAPAPAS PAAPAPSAPA ASPAAPAPAS PAAPAPSAPA ASPAAPAPAS 540
```

```
SEQ ID NO: 175          moltype = AA  length = 135
FEATURE                 Location/Qualifiers
source                  1..135
                        mol_type = protein
                        note = Synthetic polypeptide
                        organism = synthetic construct
SEQUENCE: 175
GSDLGKKLLE AARVGQDDEV RILMADGADV NASDFKGDTP LHLAASQGHL EIVEVLLKYG  60
ADVNAYDMLG WTPLHLAADL GHLEIVEVLL KYGADVNAQD RFGKTAFDIS IDNGNEDLAE  120
ILQKAAGSPS TADGC                                                  135

SEQ ID NO: 176          moltype = AA  length = 130
FEATURE                 Location/Qualifiers
source                  1..130
                        mol_type = protein
                        note = Synthetic polypeptide
                        organism = synthetic construct
SEQUENCE: 176
GSDLGKKLLE AVRAGQDDEV RILMTNGADV NAKDQFGFTP LQLAAYNGHL EIVEVLLKYG  60
ADVNAFDIFG WTPLHLAADL GHLEIVEVLL KNGADVNAQD KFGRTAFDIS IDNGNEDLAE  120
ILQKAASGSC                                                        130

SEQ ID NO: 177          moltype = AA  length = 168
FEATURE                 Location/Qualifiers
source                  1..168
                        mol_type = protein
                        note = Synthetic polypeptide
                        organism = synthetic construct
SEQUENCE: 177
GSDLGKKLLE AARAGQDDEV RILMANGADV NAVDYIGWTP LHLAAAYGHL EIVEVLLKYS  60
ADVNAEDFAG YTPLHLAASN GHLEIVEVLL KYGADVNTKD NTGWTPLHLS ADLGHLEIVE  120
VLLKYGADVN TQDKFGKTAF DISIDNGNED LAEILQKAAG SPSTADGC              168

SEQ ID NO: 178          moltype = AA  length = 33
FEATURE                 Location/Qualifiers
MOD_RES                 1
                        note = Any amino acid
MOD_RES                 3..4
                        note = Any amino acid
MOD_RES                 6
                        note = Any amino acid
MOD_RES                 14..15
                        note = Any amino acid
MOD_RES                 27
                        note = Any amino acid
source                  1..33
                        mol_type = protein
                        note = Synthetic polypeptide
                        organism = synthetic construct
SEQUENCE: 178
XDXXGXTPLH LAAXXGHLEI VEVLLKXGAD VNA                              33

SEQ ID NO: 179          moltype = AA  length = 33
FEATURE                 Location/Qualifiers
MOD_RES                 1
                        note = Any amino acid
MOD_RES                 3..4
                        note = Any amino acid
MOD_RES                 14..15
                        note = Any amino acid
MOD_RES                 27
                        note = Any amino acid
source                  1..33
                        mol_type = protein
                        note = Synthetic polypeptide
                        organism = synthetic construct
SEQUENCE: 179
XDXXGWTPLH LAAXXGHLEI VEVLLKXGAD VNA                              33

SEQ ID NO: 180          moltype = AA  length = 33
FEATURE                 Location/Qualifiers
MOD_RES                 1
                        note = Any amino acid
MOD_RES                 3..4
                        note = Any amino acid
MOD_RES                 6
                        note = Any amino acid
MOD_RES                 14..15
                        note = Any amino acid
```

```
MOD_RES                27
                       note = Any amino acid
MOD_RES                33
                       note = Any amino acid
source                 1..33
                       mol_type = protein
                       note = Synthetic polypeptide
                       organism = synthetic construct
SEQUENCE: 180
XDXXGXTPLH LAAXXGHLEI VEVLLKXGAD VNX                          33

SEQ ID NO: 181         moltype = AA  length = 33
FEATURE                Location/Qualifiers
MOD_RES                1
                       note = Any amino acid
MOD_RES                3..4
                       note = Any amino acid
MOD_RES                12
                       note = Any amino acid
MOD_RES                17
                       note = Any amino acid
MOD_RES                27
                       note = Any amino acid
MOD_RES                33
                       note = Any amino acid
source                 1..33
                       mol_type = protein
                       note = Synthetic polypeptide
                       organism = synthetic construct
SEQUENCE: 181
XDXXGWTPLH LXADLGXLEI VEVLLKXGAD VNX                          33

SEQ ID NO: 182         moltype = AA  length = 33
FEATURE                Location/Qualifiers
MOD_RES                1
                       note = Any amino acid
MOD_RES                3..4
                       note = Any amino acid
MOD_RES                6
                       note = Any amino acid
MOD_RES                14..15
                       note = Any amino acid
MOD_RES                18
                       note = Any amino acid
MOD_RES                27
                       note = Any amino acid
source                 1..33
                       mol_type = protein
                       note = Synthetic polypeptide
                       organism = synthetic construct
SEQUENCE: 182
XDXXGXTPLH LAAXXGHXEI VEVLLKXGAD VNA                          33

SEQ ID NO: 183         moltype = AA  length = 33
FEATURE                Location/Qualifiers
MOD_RES                1
                       note = Any amino acid
MOD_RES                3..4
                       note = Any amino acid
MOD_RES                6
                       note = Any amino acid
MOD_RES                14..15
                       note = Any amino acid
MOD_RES                27
                       note = Any amino acid
source                 1..33
                       mol_type = protein
                       note = Synthetic polypeptide
                       organism = synthetic construct
SEQUENCE: 183
XDXXGXTPLH LAAXXGHLEI VEVLLKXGAD VNA                          33

SEQ ID NO: 184         moltype = AA  length = 33
FEATURE                Location/Qualifiers
MOD_RES                1
                       note = Any amino acid
MOD_RES                3..4
                       note = Any amino acid
MOD_RES                14..15
```

```
                        note = Any amino acid
MOD_RES                 27
                        note = Any amino acid
source                  1..33
                        mol_type = protein
                        note = Synthetic polypeptide
                        organism = synthetic construct
SEQUENCE: 184
XDXXGWTPLH LAAXXGHLEI VEVLLKXGAD VNA                              33

SEQ ID NO: 185          moltype = AA  length = 33
FEATURE                 Location/Qualifiers
MOD_RES                 1
                        note = Any amino acid
MOD_RES                 3..4
                        note = Any amino acid
MOD_RES                 6
                        note = Any amino acid
MOD_RES                 14..15
                        note = Any amino acid
MOD_RES                 27
                        note = Any amino acid
MOD_RES                 33
                        note = Any amino acid
source                  1..33
                        mol_type = protein
                        note = Synthetic polypeptide
                        organism = synthetic construct
SEQUENCE: 185
XDXXGXTPLH LAAXXGHLEI VEVLLKXGAD VNX                              33

SEQ ID NO: 186          moltype = AA  length = 33
FEATURE                 Location/Qualifiers
MOD_RES                 1
                        note = Any amino acid
MOD_RES                 3..4
                        note = Any amino acid
MOD_RES                 6
                        note = Any amino acid
MOD_RES                 12
                        note = Any amino acid
MOD_RES                 14..15
                        note = Any amino acid
MOD_RES                 27
                        note = Any amino acid
source                  1..33
                        mol_type = protein
                        note = Synthetic polypeptide
                        organism = synthetic construct
SEQUENCE: 186
XDXXGXTPLH LXAXXGHLEI VEVLLKXGAD VNA                              33

SEQ ID NO: 187          moltype = AA  length = 33
FEATURE                 Location/Qualifiers
MOD_RES                 1
                        note = Any amino acid
MOD_RES                 5
                        note = Any amino acid
MOD_RES                 14..15
                        note = Any amino acid
MOD_RES                 18
                        note = Any amino acid
MOD_RES                 27
                        note = Any amino acid
source                  1..33
                        mol_type = protein
                        note = Synthetic polypeptide
                        organism = synthetic construct
SEQUENCE: 187
XDFKXDTPLH LAAXXGHXEI VEVLLKXGAD VNA                              33

SEQ ID NO: 188          moltype = AA  length = 33
FEATURE                 Location/Qualifiers
MOD_RES                 1
                        note = Any amino acid
MOD_RES                 3
                        note = Any amino acid
MOD_RES                 5..6
                        note = Any amino acid
```

```
MOD_RES               13..15
                      note = Any amino acid
MOD_RES               27
                      note = Any amino acid
source                1..33
                      mol_type = protein
                      note = Synthetic polypeptide
                      organism = synthetic construct
SEQUENCE: 188
XDXLXXTPLH LAXXXGHLEI VEVLLKXGAD VNA                           33

SEQ ID NO: 189        moltype = AA  length = 33
FEATURE               Location/Qualifiers
MOD_RES               1
                      note = Any amino acid
MOD_RES               3..4
                      note = Any amino acid
MOD_RES               6
                      note = Any amino acid
MOD_RES               10
                      note = Any amino acid
MOD_RES               14..15
                      note = Any amino acid
MOD_RES               27
                      note = Any amino acid
source                1..33
                      mol_type = protein
                      note = Synthetic polypeptide
                      organism = synthetic construct
SEQUENCE: 189
XDXXGXTPLX LAAXXGHLEI VEVLLKXGAD VNA                           33

SEQ ID NO: 190        moltype = AA  length = 33
FEATURE               Location/Qualifiers
MOD_RES               1
                      note = Any amino acid
MOD_RES               3..4
                      note = Any amino acid
MOD_RES               8
                      note = Any amino acid
MOD_RES               17
                      note = Any amino acid
MOD_RES               27
                      note = Any amino acid
source                1..33
                      mol_type = protein
                      note = Synthetic polypeptide
                      organism = synthetic construct
SEQUENCE: 190
XDXXGWTXLH LAADLGXLEI VEVLLKXGAD VNA                           33

SEQ ID NO: 191        moltype = AA  length = 159
FEATURE               Location/Qualifiers
source                1..159
                      mol_type = protein
                      note = Synthetic polypeptide
                      organism = synthetic construct
SEQUENCE: 191
GSDLGKKLLE AARAGQDDEV RILMANGADV NAFDWMGWTP LHLAAHEGHL EIVEVLLKNG  60
ADVNATDVSG YTPLHLAAAD GHLEIVEVLL KYGADVNTKD NTGWTPLHLS ADLGHLEIVE  120
VLLKYGADVN AQDKFGKTAF DISIDNGNED LAEILQKAA                     159

SEQ ID NO: 192        moltype = AA  length = 159
FEATURE               Location/Qualifiers
source                1..159
                      mol_type = protein
                      note = Synthetic polypeptide
                      organism = synthetic construct
SEQUENCE: 192
GSDLGKKLLE AARVGQDDEV RILMANGADV NAFDWMGWTP LHLAAHEGHL EIVEVLLKNG  60
ADVNATDVSG YTPLHLAAAD GHLEIVEVLL KYGADVNTKD NTGWTPLHLS ADLGHLEIVE  120
VLLKYGADVN AQDKFGKTAF DISIDNGNED LAEILQKAA                     159

SEQ ID NO: 193        moltype = AA  length = 159
FEATURE               Location/Qualifiers
source                1..159
                      mol_type = protein
                      note = Synthetic polypeptide
                      organism = synthetic construct
```

```
SEQUENCE: 193
GSDLGKKLLE AARAGQDDEV RILMANGADV NAFDWMGWTP LHLAAHEGHL EIVEVLLKNG  60
ADVNATDVSG YTPLHLAAAD GHLEIVEVLL KYGADVNTKD NTGWTPLHLS ADLGRLEIVE  120
VLLKYGADVN AQDKFGKTAF DISIDNGNED LAEILQKAA                         159

SEQ ID NO: 194         moltype = AA  length = 159
FEATURE                Location/Qualifiers
source                 1..159
                       mol_type = protein
                       note = Synthetic polypeptide
                       organism = synthetic construct
SEQUENCE: 194
GSDLGKKLLE AARAGQDDEV RILMANGADV NAFDWMGWTP LHLAAHEGHL EIVEVLLKNG  60
TDVNATDVSG YTPLHLAAAD GHLEIVEVLL KYGADVNTKD NTGWTPLHLS ADLGHLEIVE  120
VLLKHGADVN AQDKFGKTAF DISIDNGNED LAEILQKAA                         159

SEQ ID NO: 195         moltype = AA  length = 159
FEATURE                Location/Qualifiers
source                 1..159
                       mol_type = protein
                       note = Synthetic polypeptide
                       organism = synthetic construct
SEQUENCE: 195
GSDLGKKLLE AARAGQDDEV RILMANGADV NAFDWMGWTP LHLAAHEGHL EIVEVLLKNG  60
ADVNATDVSG YTPLHLAAAD GHLEIVEVLL KHGADVNTKD NTGWTPLHLS ADLGHLEIVE  120
VLLKNGADVN AQDKFGKTAF DISIDNGNED LAEILQKAA                         159

SEQ ID NO: 196         moltype = AA  length = 159
FEATURE                Location/Qualifiers
source                 1..159
                       mol_type = protein
                       note = Synthetic polypeptide
                       organism = synthetic construct
SEQUENCE: 196
GSDLGKKLLE AARAGQDDEV RILMANGADV NAFDWMGWTP LHLAAHEGHL EIVEVLLKNG  60
ADVNATDVSG YTPLHLAAAD GHLEIVEVLL KHGADVNTKD NTGWTPLHLS ADLGHLEIVE  120
VLLKNGADIN AQDKFGKTAF DISIDNGNED LAEILQKAA                         159

SEQ ID NO: 197         moltype = AA  length = 159
FEATURE                Location/Qualifiers
source                 1..159
                       mol_type = protein
                       note = Synthetic polypeptide
                       organism = synthetic construct
SEQUENCE: 197
GSDLGKKLLE AARAGQDDEV RILMANGADV NAFDWMGWTP LHLAAHEGHL EIVEVLLKNG  60
ADVNATDVSG YTPLHLAAAD GHLEIVEVLL KHGADVNTTD NTGWTPLHLS ADLGHLEIVE  120
VLLKYGADVN AQDKFGKTAF DISIDNGNED LAEILQKAA                         159

SEQ ID NO: 198         moltype = AA  length = 159
FEATURE                Location/Qualifiers
source                 1..159
                       mol_type = protein
                       note = Synthetic polypeptide
                       organism = synthetic construct
SEQUENCE: 198
GSDLGKKLLE AARAGQDDEV RILMANGADV NAFDYMGWTP LHLAAHNGHM EIVEVLLKYG  60
ADVNASDYSG YTPLHLAAAD GHLEIVEVLL KYGADVNTKD NTGWTPLHLS ADLGHLEIVE  120
VLLKYGADVN AQDKFGKTAF DISIDNGNED LAEILQKAA                         159

SEQ ID NO: 199         moltype = AA  length = 159
FEATURE                Location/Qualifiers
source                 1..159
                       mol_type = protein
                       note = Synthetic polypeptide
                       organism = synthetic construct
SEQUENCE: 199
GSDLGKKLLE AARAGQDDEV RILMANGADV NAVDYIGWTP LHLAAAYGHL EIVEVLLKYS  60
ADVNAEDFAG YTPLHLAASN GHLEIVEVLL KYGADVNTKD NTGWTPLHLS ADLGHLEIVE  120
VLLKYGADVN TQDKFGKTAF DISIDNGNED LAEILQKAA                         159

SEQ ID NO: 200         moltype = AA  length = 159
FEATURE                Location/Qualifiers
source                 1..159
                       mol_type = protein
                       note = Synthetic polypeptide
                       organism = synthetic construct
SEQUENCE: 200
GSDLGKKLLE AARTGQDDEV RILMANGADV NATDYMGWTP LHLAAKVGHL EIVEVLLKYG  60
```

```
ADVNAEDYNG YTPLHLAAAM GHLEIAEVLL KYGADVNTKD NTGWTPLHLS ADLGHLEIVE  120
VLLKNGADVN AQDKFGKTAF DISIDNGNED LAEILQKAA                         159

SEQ ID NO: 201          moltype = AA  length = 126
FEATURE                 Location/Qualifiers
source                  1..126
                        mol_type = protein
                        note = Synthetic polypeptide
                        organism = synthetic construct
SEQUENCE: 201
GSDLGKKLLE AARAGQDDEV RILMANGADV NARDSTGWTP LHLAAPWGHP EIVEVLLKNG  60
ADVNAADFQG WTPLHLAAAV GHLEIVEVLL KYGADVNAQD KFGKTAFDIS IDNGNEDLAE  120
ILQKAA                                                             126

SEQ ID NO: 202          moltype = AA  length = 126
FEATURE                 Location/Qualifiers
source                  1..126
                        mol_type = protein
                        note = Synthetic polypeptide
                        organism = synthetic construct
SEQUENCE: 202
GSDLGKKLLE AARAGQDDEV RILMANGADV NARDSTGWTP LHLAAPWGHP EIVEVLLKNG  60
ADVNAADFQG WTPLHLAAAV GHLEIVEVLL KHGADVNAQD KFGKTAFDIS IDNGNEDLAE  120
ILQKAA                                                             126

SEQ ID NO: 203          moltype = AA  length = 126
FEATURE                 Location/Qualifiers
source                  1..126
                        mol_type = protein
                        note = Synthetic polypeptide
                        organism = synthetic construct
SEQUENCE: 203
GSDLGKKLLE AARAGQDDEV RILMANGADV NTADSTGWTP LHLAAPWGHP EIVEVLLKNG  60
ADVNAHDYQG WTPLHLAATL GHLEIVEVLL KYGADVNAQD KFGKTAFDIS IDNGNEDLAE  120
ILQKAA                                                             126

SEQ ID NO: 204          moltype = AA  length = 126
FEATURE                 Location/Qualifiers
source                  1..126
                        mol_type = protein
                        note = Synthetic polypeptide
                        organism = synthetic construct
SEQUENCE: 204
GSDLGKKLLE AARAGQDDEV RILMANGADV NTADSTGWTP LHLVAPWGHP EIVEVLLKHG  60
ADVNTHDYQG WTPLHLAATL GHLEIVEVLL RYGADVNAQD KFGKTAFDIS IDNGNEDLAE  120
ILQKAA                                                             126

SEQ ID NO: 205          moltype = AA  length = 126
FEATURE                 Location/Qualifiers
source                  1..126
                        mol_type = protein
                        note = Synthetic polypeptide
                        organism = synthetic construct
SEQUENCE: 205
GSDLGKKLLE AARAGQDDEV RILMANGADV NTADSTGWTP MHLAAPWGHP EIVEVLLKHG  60
ADVNAQDFQG WTPLHLAAAI GHLEIVEVLL KYGADVNAQD KFGKTAFDIS IDNGNEDLAE  120
ILQKAA                                                             126

SEQ ID NO: 206          moltype = AA  length = 126
FEATURE                 Location/Qualifiers
source                  1..126
                        mol_type = protein
                        note = Synthetic polypeptide
                        organism = synthetic construct
SEQUENCE: 206
GSDLGKKLLE AARAGQDDEV RILMANGADV NTADSTGWTP LHLAVPWGHL EIVEVLLKYG  60
ADVNAKDFQG WTPLHLAAAI GHQEIVEVLL KNGADVNAQD KFGKTAFDIS IDNGNEDLAE  120
ILQKAA                                                             126

SEQ ID NO: 207          moltype = AA  length = 126
FEATURE                 Location/Qualifiers
source                  1..126
                        mol_type = protein
                        note = Synthetic polypeptide
                        organism = synthetic construct
SEQUENCE: 207
GSDLGKKLLE AARVGQDDEV RILMADGADV NASDFKGDTP LHLAASQGHL EIVEVLLKYG  60
ADVNAYDMLG WTPLHLAADL GHLEIVEVLL KYGADVNAQD RFGKTAFDIS IDNGNEDLAE  120
ILQKAA                                                             126
```

```
SEQ ID NO: 208          moltype = AA  length = 126
FEATURE                 Location/Qualifiers
source                  1..126
                        mol_type = protein
                        note = Synthetic polypeptide
                        organism = synthetic construct
SEQUENCE: 208
GSDLGKKLLE AARVGQDDEV RILMANGADV NASDFKGDTP LHLAASQGHL EIVEVLLKNS  60
ADVNAFDLLG WTPLHLAADL GHLEIVEVLL KYGADVNAQD KFGKTAFDIS IDNGNEDLAE  120
ILQKAA                                                             126

SEQ ID NO: 209          moltype = AA  length = 126
FEATURE                 Location/Qualifiers
source                  1..126
                        mol_type = protein
                        note = Synthetic polypeptide
                        organism = synthetic construct
SEQUENCE: 209
GSDLGKKLLE AARVGQDDEV RILMANGADV NALDFKGDTP LHLAAASGHL EIVEVLLKNG  60
ADVNAHDMLS WTPLHLAGDL GHLEIVEVLL KYGADVNAQD RFGKTAFDIS IDNGNEDLAE  120
ILQKAA                                                             126

SEQ ID NO: 210          moltype = AA  length = 126
FEATURE                 Location/Qualifiers
source                  1..126
                        mol_type = protein
                        note = Synthetic polypeptide
                        organism = synthetic construct
SEQUENCE: 210
GSDLGKKLLE AVRAGQDDEV RILMTNGADV NAKDQFGFTP LQLAAYNGHL EIVEVLLKYG  60
ADVNAFDIFG WTPLHLAADL GHLEIVEVLL KNGADVNAQD KFGRTAFDIS IDNGNEDLAE  120
ILQKAA                                                             126

SEQ ID NO: 211          moltype = AA  length = 127
FEATURE                 Location/Qualifiers
source                  1..127
                        mol_type = protein
                        note = Synthetic polypeptide
                        organism = synthetic construct
SEQUENCE: 211
GSDLGKKLLE AVRAGQDDEV RILMANGADV NASDNQGTTP LHLAASHGHL EIVEVLLKYG  60
ADVNDAHDDL GWTPLHLSAD LGHLEIVEVL LKYGADVNAQ DKFGKTAFDI SIDNGNEDLA  120
EILQKAA                                                            127

SEQ ID NO: 212          moltype = AA  length = 127
FEATURE                 Location/Qualifiers
source                  1..127
                        mol_type = protein
                        note = Synthetic polypeptide
                        organism = synthetic construct
SEQUENCE: 212
GSDLGKKLLE ATRAGQDDEV RILMANGADV NASDNQGTTP LHLAASHGHL EIVEVLLKYG  60
ADVNDAHDDL GWTPLHLAAD LGHLEIVEVL LKYGADVNAQ DKFGKTAFDI SIDNGNEDLA  120
EILQKAA                                                            127

SEQ ID NO: 213          moltype = AA  length = 126
FEATURE                 Location/Qualifiers
source                  1..126
                        mol_type = protein
                        note = Synthetic polypeptide
                        organism = synthetic construct
SEQUENCE: 213
GSDLGKKLLE AARVGQDDEV RILMADGADV NASDFKGDTP LHLAASQGHL EIVEVLLKYG  60
ADVNAYDMLG WTPLHLAADL GHLEIVEVLL KYGADVNAQD RFGKTAFDIS IDNGNEDLAE  120
ILQKAA                                                             126

SEQ ID NO: 214          moltype = AA  length = 126
FEATURE                 Location/Qualifiers
source                  1..126
                        mol_type = protein
                        note = Synthetic polypeptide
                        organism = synthetic construct
SEQUENCE: 214
GSDLGKKLLE AARVGQDDEV RILMANDADV NASDFKGDTP LHLAASQGHL EIVEVLLKYG  60
ADVNAYDMLG WTPLHLAADL GHLEIVEVLL KHGADVNAQD KFGKTAFDIS IDNGNEDLAE  120
ILQKAA                                                             126

SEQ ID NO: 215          moltype = AA  length = 126
```

-continued

```
FEATURE                 Location/Qualifiers
source                  1..126
                        mol_type = protein
                        note = Synthetic polypeptide
                        organism = synthetic construct
SEQUENCE: 215
GSDLGKKLLE AARAGQDDEV RILMANGADV NTLDFKSDTP LHLAAASGHL EIVEVLLKNG  60
ADVNAHDMLS WTPLHLAGDL GHLEIVEVLL KHGADVNAQD KFGKTAFDIS IDNGNEDLAE  120
ILQKAA                                                            126

SEQ ID NO: 216          moltype = AA  length = 159
FEATURE                 Location/Qualifiers
source                  1..159
                        mol_type = protein
                        note = Synthetic polypeptide
                        organism = synthetic construct
SEQUENCE: 216
GSDLGKKLLE AARAGQDDEV RILMANGADV NAKDIYGRTP LHLAALHGHP EIVEVLLKYG  60
ADVNANDYWG TTSLHLVAIW GHLEIVEVLL KYGADVNAVD DIGQTPLHLA AAWGHLEIVE  120
VLLKHGADVN AQDKFGKTAF DISIDNGNED LAEILQKAA                        159

SEQ ID NO: 217          moltype = AA  length = 158
FEATURE                 Location/Qualifiers
source                  1..158
                        mol_type = protein
                        note = Synthetic polypeptide
                        organism = synthetic construct
SEQUENCE: 217
GSDLGKKLLE AARAGQDDEV RILMANGADV NANDYDGMTP LHLAAMEGHL EIVEVLLKYG  60
ADVNANDHYG FTPLHLAWTG RLEIVEVLLK NGADVNAADV FGRTPLHLAA TSGHLEIVEV  120
LLKYGADVNA QDKFGKTAFD ISIDNGNEDL AEILQKAA                         158

SEQ ID NO: 218          moltype = AA  length = 490
FEATURE                 Location/Qualifiers
source                  1..490
                        mol_type = protein
                        note = Synthetic polypeptide
                        organism = synthetic construct
SEQUENCE: 218
MVSSAQFLGL LLLCFQGTRC DVVMTQSPSF LSASVGDRVT ITCKASQHVG TAVAWYQQRP  60
GKAPKLLIYW ASTRHTGVPS RFSGSGSGTE FTLTISSLQP EDFATYFCQQ YSSYPFTFGG  120
GTKLEIKRTV AAPSVFIFPP SDEQLKSGTA SVVCLLNNFY PREAKVQWKV DNALQSGNSQ  180
ESVTEQDSKD STYSLSSTLT LSKADYEKHK VYACEVTHQG LSSPVTKSFN RGECGGGGSE  240
IVMTQSPSTL SASVGDRVII TCQASEIIHS WLAWYQQKPG KAPKLLIYLA STLASGVPSR  300
FSGSGSGAEF TLTISSLQPD DFATYYCQNV YLASTNGANF GQGTKLTVLG GGGGSGGGGS  360
GGGGSGGGGS EVQLVESGGG LVQPGGSLRL SCTASGFSLT DYYYMTWVRQ APGKGLEWVG  420
FIDPDDDPYY ATWAKGRFTI SRDNSKNTLY LQMNSLRAED TAVYYCAGGD HNSGWGLDIW  480
GQGTLVTVSS                                                        490

SEQ ID NO: 219          moltype = AA  length = 444
FEATURE                 Location/Qualifiers
source                  1..444
                        mol_type = protein
                        note = Synthetic polypeptide
                        organism = synthetic construct
SEQUENCE: 219
MVSSAQFLGL LLLCFQGTRC DVVMTQSPSF LSASVGDRVT ITCKASQHVG TAVAWYQQRP  60
GKAPKLLIYW ASTRHTGVPS RFSGSGSGTE FTLTISSLQP EDFATYFCQQ YSSYPFTFGG  120
GTKLEIKRTV AAPSVFIFPP SDEQLKSGTA SVVCLLNNFY PREAKVQWKV DNALQSGNSQ  180
ESVTEQDSKD STYSLSSTLT LSKADYEKHK VYACEVTHQG LSSPVTKSFN RGECGGGGSS  240
DTGRPFVEMY SEIPEIIHMT EGRELVIPCR VTSPNITVTL KKFPLDTLIP DGKRIIWDSR  300
KGFIISNATY KEIGLLTCEA TVNGHLYKTN YLTHRQTNTI IDVVLSPSHG IELSVGEKLV  360
LNCTARTELN VGIDFNWEYP SSKHQHKKLV NRDLKTQSGS EMKKFLSTLT IDGVTRSDQG  420
LYTCAASSGL MTKKNSTFVR VHEK                                        444

SEQ ID NO: 220          moltype = AA  length = 330
FEATURE                 Location/Qualifiers
source                  1..330
                        mol_type = protein
                        organism = Homo sapiens
SEQUENCE: 220
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPGK                                  330

SEQ ID NO: 221          moltype = AA  length = 326
```

-continued

```
FEATURE                Location/Qualifiers
source                 1..326
                       mol_type = protein
                       organism = Homo sapiens
SEQUENCE: 221
ASTKGPSVFP LAPCSRSTSE STAALGCLVK DYFPEPVTVS WNSGALTSGV HTFPAVLQSS  60
GLYSLSSVVT VPSSNFGTQT YTCNVDHKPS NTKVDKTVER KCCVECPPCP APPVAGPSVF  120
LFPPKPKDTL MISRTPEVTC VVVDVSHEDP EVQFNWYVDG VEVHNAKTKP REEQFNSTFR  180
VVSVLTVVHQ DWLNGKEYKC KVSNKGLPAP IEKTISKTKG QPREPQVYTL PPSREEMTKN  240
QVSLTCLVKG FYPSDISVEW ESNGQPENNY KTTPPMLDSD GSFFLYSKLT VDKSRWQQGN  300
VFSCSVMHEA LHNHYTQKSL SLSPGK                                      326

SEQ ID NO: 222         moltype = AA  length = 377
FEATURE                Location/Qualifiers
source                 1..377
                       mol_type = protein
                       organism = Homo sapiens
SEQUENCE: 222
ASTKGPSVFP LAPCSRSTSG GTAALGCLVK DYFPEPVTVS WNSGALTSGV HTFPAVLQSS  60
GLYSLSSVVT VPSSSLGTQT YTCNVNHKPS NTKVDKRVEL KTPLGDTTHT CPRCPEPKSC  120
DTPPPCPRCP EPKSCDTPPP CPRCPEPKSC DTPPPCPRCP APELLGGPSV FLFPPKPKDT  180
LMISRTPEVT CVVVDVSHED PEVQFKWYVD GVEVHNAKTK PREEQYNSTF RVVSVLTVLH  240
QDWLNGKEYK CKVSNKALPA PIEKTISKTK GQPREPQVYT LPPSREEMTK NQVSLTCLVK  300
GFYPSDIAVE WESSGQPENN YNTTPPMLDS DGSFFLYSKL TVDKSRWQQG NIFSCSVMHE  360
ALHNRFTQKS LSLSPGK                                                377

SEQ ID NO: 223         moltype = AA  length = 428
FEATURE                Location/Qualifiers
source                 1..428
                       mol_type = protein
                       organism = Homo sapiens
SEQUENCE: 223
ASTQSPSVFP LTRCCKNIPS NATSVTLGCL ATGYFPEPVM VTWDTGSLNG TTMTLPATTL  60
TLSGHYATIS LLTVSGAWAK QMFTCRVAHT PSSTDWVDNK TFSVCSRDFT PPTVKILQSS  120
CDGGGHFPPT IQLLCLVSGY TPGTINITWL EDGQVMDVDL STASTTQEGE LASTQSELTL  180
SQKHWLSDRT YTCQVTYQGH TFEDSTKKCA DSNPRGVSAY LSRPSPFDLF IRKSPTITCL  240
VVDLAPSKGT VNLTWSRASG KPVNHSTRKE EKQRNGTLTV TSTLPVGTRD WIEGETYQCR  300
VTHPHLPRAL MRSTTKTSGP RAAPEVYAFA TPEWPGSRDK RTLACLIQNF MPEDISVQWL  360
HNEVQLPDAR HSTTQPRKTK GSGFFVFSRL EVTRAEWEQK DEFICRAVHE AASPSQTVQR  420
AVSVNPGK                                                          428

SEQ ID NO: 224         moltype = AA  length = 353
FEATURE                Location/Qualifiers
source                 1..353
                       mol_type = protein
                       organism = Homo sapiens
SEQUENCE: 224
ASPTSPKVFP LSLCSTQPDG NVVIACLVQG FFPQEPLSVT WSESGQGVTA RNFPPSQDAS  60
GDLYTTSSQL TLPATQCLAG KSVTCHVKHY TNPSQDVTVP CPVPSTPPTP SPSTPPTPSP  120
SCCHPRLSLH RPALEDLLLG SEANLTCTLT GLRDASGVTF TWTPSSGKSA VQGPPERDLC  180
GCYSVSSVLP GCAEPWNHGK TFTCTAAYPE SKTPLTATLS KSGNTFRPEV HLLPPPSEEL  240
ALNELVTLTC LARGFSPKDV LVRWLQGSQE LPREKYLTWA SRQEPSQGTT TFAVTSILRV  300
AAEDWKKGDT FSCMVGHEAL PLAFTQKTID RLAGKPTHVN VSVVMAEVDG TCY        353

SEQ ID NO: 225         moltype = AA  length = 340
FEATURE                Location/Qualifiers
source                 1..340
                       mol_type = protein
                       organism = Homo sapiens
SEQUENCE: 225
ASPTSPKVFP LSLDSTPQDG NVVVACLVQG FFPQEPLSVT WSESGQNVTA RNFPPSQDAS  60
GDLYTTSSQL TLPATQCPDG KSVTCHVKHY TNSSQDVTVP CRVPPPPPCC HPRLSLHRPA  120
LEDLLLGSEA NLTCTLTGLR DASGATFTWT PSSGKSAVQG PPERDLCGCY SVSSVLPGCA  180
QPWNHGETFT CTAAHPELKT PLTANITKSG NTFRPEVHLL PPPSEELALN ELVTLTCLAR  240
GFSPKDVLVR WLQGSQELPR EKYLTWASRQ EPSQGTTTYA VTSILRVAAE DWKKGETFSC  300
MVGHEALPLA FTQKTIDRMA GKPTHINVSV VMAEADGTCY                       340

SEQ ID NO: 226         moltype = AA  length = 453
FEATURE                Location/Qualifiers
source                 1..453
                       mol_type = protein
                       organism = Homo sapiens
SEQUENCE: 226
GSASAPTLFP LVSCENSPSD TSSVAVGCLA QDFLPDSITF SWKYKNNSDI SSTRGFPSVL  60
RGGKYAATSQ VLLPSKDVMQ GTDEHVVCKV QHPNGNKEKN VPLPVIAELP PKVSVFVPPR  120
DGFFGNPRKS KLICQATGFS PRQIQVSWLR EGKQVGSGVT TDQVQAEAKE SGPTTYKVTS  180
TLTIKESDWL GQSMFTCRVD HRGLTFQQNA SSMCVPDQDT AIRVFAIPPS FASIFLTKST  240
KLTCLVTDLT TYDSVTISWT RQNGEAVKTH TNISESHPNA TFSAVGEASI CEDDWNSGER  300
FTCTVTHTDL PSPLKQTISR PKGVALHRPD VYLLPPAREQ LNLRESATIT CLVTGFSPAD  360
```

```
VFVQWMQRGQ PLSPEKYVTS APMPEPQAPG RYFAHSILTV SEEEWNTGET YTCVVAHEAL  420
PNRVTERTVD KSTGKPTLYN VSLVMSDTAG TCY                               453

SEQ ID NO: 227         moltype = AA  length = 384
FEATURE                Location/Qualifiers
source                 1..384
                       mol_type = protein
                       organism = Homo sapiens
SEQUENCE: 227
APTKAPDVFP IISGCRHPKD NSPVVLACLI TGYHPTSVTV TWYMGTQSQP QRTFPEIQRR  60
DSYYMTSSQL STPLQQWRQG EYKCVVQHTA SKSKKEIFRW PESPKAQASS VPTAQPQAEG  120
SLAKATTAPA TTRNTGRGGE EKKKEKEKEE QEERETKTPE CPSHTQPLGV YLLTPAVQDL  180
WLRDKATFTC FVVGSDLKDA HLTWEVAGKV PTGGVEEGLL ERHSNGSQSQ HSRLTLPRSL  240
WNAGTSVTCT LNHPSLPPQR LMALREPAAQ APVKLSLNLL ASSDPPEAAS WLLCEVSGFS  300
PPNILLMWLE DQREVNTSGF APARPPPQPR STTFWAWSVL RVPAPPSPQP ATYTCVVSHE  360
DSRTLLNASR SLEVSYVTDH GPMK                                         384

SEQ ID NO: 228         moltype = AA  length = 106
FEATURE                Location/Qualifiers
source                 1..106
                       mol_type = protein
                       organism = Homo sapiens
SEQUENCE: 228
GQPKANPTVT LFPPSSEELQ ANKATLVCLI SDFYPGAVTV AWKADGSPVK AGVETTKPSK  60
QSNNKYAASS YLSLTPEQWK SHRSYSCQVT HEGSTVEKTV APTECS                 106

SEQ ID NO: 229         moltype = AA  length = 7
FEATURE                Location/Qualifiers
source                 1..7
                       mol_type = protein
                       note = Synthetic peptide
                       organism = synthetic construct
SEQUENCE: 229
HHHRHSF                                                            7

SEQ ID NO: 230         moltype = AA  length = 8
FEATURE                Location/Qualifiers
source                 1..8
                       mol_type = protein
                       note = Synthetic peptide
                       organism = synthetic construct
SEQUENCE: 230
CHHHRHSF                                                           8

SEQ ID NO: 231         moltype = AA  length = 596
FEATURE                Location/Qualifiers
source                 1..596
                       mol_type = protein
                       note = Synthetic polypeptide
                       organism = synthetic construct
SEQUENCE: 231
MGWTLVFLFL LSVTAGVHSE VQLVESGGGL VQPGGSLRLS CAASGFTFNA NAMNWVRQAP  60
GKGLEWVGRI RTKSNNYATY YAGSVKDRFT ISRDDSKNSL YLQMNSLKTE DTAVYYCVRD  120
YYGSSAWITY WGQGTLVTVS SASTKGPSVF PLAPCSRSTS ESTAALGCLV KDYFPEPVTV  180
SWNSGALTSG VHTFPAVLQS SGLYSLSSVV TVPSSSLGTK TYTCNVDHKP SNTKVDKRVE  240
SKYGPPCPPC PAPEFLGGPS VFLFPPKPKD TLMISRTPEV TCVVVDVSQE DPEVQFNWYV  300
DGVEVHNAKT KPREEQFNST YRVVSVLTVL HQDWLNGKEY KCKVSNKGLP SSIEKTISKA  360
KGQPREPQVY TLPPSQEEMT KNQVSLTCLV KGFYPSDIAV EWESNGQPEN NYKTTPPVLD  420
SDGSFFLYSR LTVDKSRWQE GNVFSCSVMH EALHNHYTQK SLSLSLGGGG GSDLDKKLLE  480
AARAGQDDEV RILMANGADV NARDSTGWTP LHLAAPWGHP EIVEVLLKNG ADVNAADFQG  540
WTPLHLAAAV GHLEIVEVLL KYGADVNAQD KFGKTAFDIS IDNGNEDLAE ILQKAA      596

SEQ ID NO: 232         moltype = AA  length = 363
FEATURE                Location/Qualifiers
source                 1..363
                       mol_type = protein
                       note = Synthetic polypeptide
                       organism = synthetic construct
SEQUENCE: 232
MVSSAQFLGL LLLCFQGTRC DVVMTQSPSF LSASVGDRVT ITCKASQHVG TAVAWYQQRP  60
GKAPKLLIYW ASTRHTGVPS RFSGSGSGTE FTLTISSLQP EDFATYFCQQ YSSYPFTFGG  120
GTKLEIKRTV AAPSVFIFPP SDEQLKSGTA SVVCLLNNFY PREAKVQWKV DNALQSGNSQ  180
ESVTEQDSKD STYSLSSTLT LSKADYEKHK VYACEVTHQG LSSPVTKSFN RGECGGGGSD  240
LDKKLLEAAR AGQDDEVRIL MANGADVNAR DSTGWTPLHL AAPWGHPEIV EVLLKNGADV  300
NAADFQGWTP LHLAAAVGHL EIVEVLLKYG ADVNAQDKFG KTAFDISIDN GNEDLAEILQ  360
KAA                                                                363

SEQ ID NO: 233         moltype = AA  length = 33
FEATURE                Location/Qualifiers
```

```
source                  1..33
                        mol_type = protein
                        note = Synthetic polypeptide
                        organism = synthetic construct
SEQUENCE: 233
DLDKKLLEAA RAGQDDEVRI LMANGADVNA RDS                                 33

SEQ ID NO: 234          moltype = AA  length = 33
FEATURE                 Location/Qualifiers
source                  1..33
                        mol_type = protein
                        note = Synthetic polypeptide
                        organism = synthetic construct
SEQUENCE: 234
TGWTPLHLAA PWGHPEIVEV LLKNGADVNA ADF                                 33

SEQ ID NO: 235          moltype = AA  length = 33
FEATURE                 Location/Qualifiers
source                  1..33
                        mol_type = protein
                        note = Synthetic polypeptide
                        organism = synthetic construct
SEQUENCE: 235
QGWTPLHLAA AVGHLEIVEV LLKYGADVNA QDK                                 33

SEQ ID NO: 236          moltype = AA  length = 22
FEATURE                 Location/Qualifiers
source                  1..22
                        mol_type = protein
                        note = Synthetic peptide
                        organism = synthetic construct
SEQUENCE: 236
FGKTAFDISI DNGNEDLAEI LQ                                             22

SEQ ID NO: 237          moltype = AA  length = 33
FEATURE                 Location/Qualifiers
MOD_RES                 1
                        note = K, T, or Y
MOD_RES                 3
                        note = N or M
MOD_RES                 4
                        note = T or F
MOD_RES                 12
                        note = S or A
MOD_RES                 17
                        note = H or R
MOD_RES                 27
                        note = A, Y, H, or N
MOD_RES                 33
                        note = A or T
source                  1..33
                        mol_type = protein
                        note = Synthetic polypeptide
                        organism = synthetic construct
SEQUENCE: 237
XDXXGWTPLH LXADLGXLEI VEVLLKXGAD VNX                                 33

SEQ ID NO: 238          moltype = AA  length = 33
FEATURE                 Location/Qualifiers
MOD_RES                 1
                        note = K, M, N, R, or V
MOD_RES                 3
                        note = Y, H, M, or V
MOD_RES                 4
                        note = F, L, M, or V
MOD_RES                 14
                        note = R, H, V, A, K, or N
MOD_RES                 15
                        note = F, D, H, T, Y, M, or K
MOD_RES                 27
                        note = A, H, N, or Y
source                  1..33
                        mol_type = protein
                        note = Synthetic polypeptide
                        organism = synthetic construct
SEQUENCE: 238
XDXXGWTPLH LAAXXGHLEI VEVLLKXGAD VNA                                 33

SEQ ID NO: 239          moltype = AA  length = 33
```

```
FEATURE                 Location/Qualifiers
MOD_RES                 1
                        note = L, S, or T
MOD_RES                 5
                        note = G, S, or C
MOD_RES                 14
                        note = S or A
MOD_RES                 15
                        note = Q, S, M, or N
MOD_RES                 18
                        note = L, M, or Q
MOD_RES                 27
                        note = A, H, N, Y, or D
source                  1..33
                        mol_type = protein
                        note = Synthetic polypeptide
                        organism = synthetic construct
SEQUENCE: 239
XDFKXDTPLH LAAXXGHXEI VEVLLKXGAD VNA                              33

SEQ ID NO: 240          moltype = AA  length = 33
FEATURE                 Location/Qualifiers
MOD_RES                 1
                        note = K, S, I, N, T, or V
MOD_RES                 3
                        note = K, N, W, A, H, M, Q, or S
MOD_RES                 4
                        note = F, Q, L, H, or V
MOD_RES                 6
                        note = F or T
MOD_RES                 10
                        note = Q or H
MOD_RES                 14
                        note = Y or S
MOD_RES                 15
                        note = N, H, Y, or M
MOD_RES                 27
                        note = A, H, N, or Y
source                  1..33
                        mol_type = protein
                        note = Synthetic polypeptide
                        organism = synthetic construct
SEQUENCE: 240
XDXXGXTPLX LAAXXGHLEI VEVLLKXGAD VNA                              33

SEQ ID NO: 241          moltype = AA  length = 33
FEATURE                 Location/Qualifiers
MOD_RES                 1
                        note = A, N, R, V, Y, E, H, I, K, L, Q, S, or T
MOD_RES                 3
                        note = S, A, N, R, D, F, L, P, T, or Y
MOD_RES                 4
                        note = T, V, S, A, L, or F
MOD_RES                 6
                        note = W, F, or H
MOD_RES                 14
                        note = P, I, A, L, S, T, V, or Y
MOD_RES                 15
                        note = W, F, I, L, T, or V
MOD_RES                 18
                        note = L or P
MOD_RES                 27
                        note = A, H, N, or Y
source                  1..33
                        mol_type = protein
                        note = Synthetic polypeptide
                        organism = synthetic construct
SEQUENCE: 241
XDXXGXTPLH LAAXXGHXEI VEVLLKXGAD VNA                              33

SEQ ID NO: 242          moltype = AA  length = 33
FEATURE                 Location/Qualifiers
MOD_RES                 1
                        note = H, Q, A, K, R, D, I, L, M, N, V, or Y
MOD_RES                 3
                        note = Y, F, or H
MOD_RES                 4
                        note = Q, F, or T
MOD_RES                 6
```

```
                        note = W, M, G, H, N, or T
MOD_RES                 14
                        note = T, A, M, L, or V
MOD_RES                 15
                        note = I, L, V, D, or T
MOD_RES                 27
                        note = A, H, N, or Y
source                  1..33
                        mol_type = protein
                        note = Synthetic polypeptide
                        organism = synthetic construct
SEQUENCE: 242
XDXXGXTPLH LAAXXGHLEI VEVLLKXGAD VNA                              33

SEQ ID NO: 243          moltype = AA  length = 484
FEATURE                 Location/Qualifiers
source                  1..484
                        mol_type = protein
                        note = Synthetic polypeptide
                        organism = synthetic construct
SEQUENCE: 243
MVSSAQFLGL LLLCFQGTRC DVVMTQSPSF LSASVGDRVT ITCKASQHVG TAVAWYQQRP  60
GKAPKLLIYW ASTRHTGVPS RFSGSGSGTE FTLTISSLQP EDFATYFCQQ YSSYPFTFGG  120
GTKLEIKRTV AAPSVFIFPP SDEQLKSGTA SVVCLLNNFY PREAKVQWKV DNALQSGNSQ  180
ESVTEQDSKD STYSLSSTLT LSKADYEKHK VYACEVTHQG LSSPVTKSFN RGECGGGGSE  240
VQLVESGGGL VQPGGSLRLS CAASGYDFTH YGMNWVRQAP GKGLEWVGWI NTYTGEPTYA  300
ADFKRRFTFS LDTSKSTAYL QMNSLRAEDT AVYYCAKYPY YYGTSHWYFD VWGQGTLVTV  360
SSGGGGSGGG GSGGGGSDIQ LTQSPSSLSA SVGDRVTITC SASQDISNYL NWYQQKPGKA  420
PKVLIYFTSS LHSGVPSRFS GSGSGTDFTL TISSLQPEDF ATYYCQQYST VPWTFGQGTK  480
VEIK                                                              484

SEQ ID NO: 244          moltype = AA  length = 124
FEATURE                 Location/Qualifiers
source                  1..124
                        mol_type = protein
                        note = Synthetic polypeptide
                        organism = synthetic construct
SEQUENCE: 244
DLDKKLLEAA RAGQDDEVRI LMANGADVNA RDSTGWTPLH LAAPWGHPEI VEVLLKNGAD  60
VNAADFQGWT PLHLAAAVGH LEIVEVLLKY GADVNAQDKF GKTAFDISID NGNEDLAEIL  120
QKAA                                                              124

SEQ ID NO: 245          moltype = AA  length = 467
FEATURE                 Location/Qualifiers
source                  1..467
                        mol_type = protein
                        note = Synthetic polypeptide
                        organism = synthetic construct
SEQUENCE: 245
MGWTLVFLFL LSVTAGVHSE VQLVESGGGL VQPGGSLRLS CAASGFTFNA NAMNWVRQAP  60
GKGLEWVGRI RTKSNNYATY YAGSVKDRFT ISRDDSKNSL YLQMNSLKTE DTAVYYCVRD  120
YYGSSAWITY WGQGTLVTVS SASTKGPSVF PLAPCSRSTS ESTAALGCLV KDYFPEPVTV  180
SWNSGALTSG VHTFPAVLQS SGLYSLSSVV TVPSSSLGTK TYTCNVDHKP SNTKVDKRVE  240
SKYGPPCPPC PAPEFLGGPS VFLFPPKPKD TLMISRTPEV TCVVVDVSQE DPEVQFNWYV  300
DGVEVHNAKT KPREEQFNST YRVVSVLTVL HQDWLNGKEY KCKVSNKGLP SSIEKTISKA  360
KGQPREPQVY TLPPSQEEMT KNQVSLTCLV KGFYPSDIAV EWESNGQPEN NYKTTPPVLD  420
SDGSFFLYSR LTVDKSRWQE GNVFSCSVMH EALHNHYTQK SLSLSLG               467

SEQ ID NO: 246          moltype = AA  length = 449
FEATURE                 Location/Qualifiers
source                  1..449
                        mol_type = protein
                        note = Synthetic polypeptide
                        organism = synthetic construct
SEQUENCE: 246
EVQLVESGGG LVQPGGSLKL SCAASGFTFN ANAMNWVRQA SGKGLEWVGR IRTKSNNYAT  60
YYAGSVKDRF TISRDDSKNT AYLQMNSLKT EDTAAYYCVR DYYGSSAWIT YWGQGTLVTV  120
SSASTKGPSV FPLAPCSRST SESTAALGCL VKDYFPEPVT VSWNSGALTS GVHTFPAVLQ  180
SSGLYSLSSV VTVPSSSLGT KTYTCNVDHK PSNTKVDKRV ESKYGPPCPP CPAPEFLGGP  240
SVFLFPPKPK DTLMISRTPE VTCVVVDVSQ EDPEVQFNWY VDGVEVHNAK TKPREEQFNS  300
TYRVVSVLTV LHQDWLNGKE YKCKVSNKGL PSSIEKTISK AKGQPREPQV YTLPPSQEEM  360
TKNQVSLTCL VKGFYPSDIA VEWESNGQPE NNYKTTPPVL DSDGSFFLYS RLTVDKSRWQ  420
EGNVFSCSVM HEALHNHYTQ KSLSLSLGK                                   449

SEQ ID NO: 247          moltype = AA  length = 449
FEATURE                 Location/Qualifiers
source                  1..449
                        mol_type = protein
                        note = Synthetic polypeptide
```

```
                         organism = synthetic construct
SEQUENCE: 247
EVQLVESGGG LVQPGGSLRL SCAASGFTFN ANAMNWVRQA PGKGLEWVGR IRTKSNNYAT  60
YYAGSVKDRF TISRDDSKNS LYLQMNSLKT EDTAVYYCVR DYYGSSAWIT YWGQGTLVTV  120
SSASTKGPSV FPLAPCSRST SESTAALGCL VKDYFPEPVT VSWNSGALTS GVHTFPAVLQ  180
SSGLYSLSSV VTVPSSSLGT KTYTCNVDHK PSNTKVDKRV ESKYGPPCPP CPAPEFLGGP  240
SVFLFPPKPK DTLMISRTPE VTCVVVDVSQ EDPEVQFNWY VDGVEVHNAK TKPREEQFNS  300
TYRVVSVLTV LHQDWLNGKE YKCKVSNKGL PSSIEKTISK AKGQPREPQV YTLPPSQEEM  360
TKNQVSLTCL VKGFYPSDIA VEWESNGQPE NNYKTTPPVL DSDGSFFLYS RLTVDKSRWQ  420
EGNVFSCSVM HEALHNHYTQ KSLSLSLGK                                   449

SEQ ID NO: 248           moltype = AA  length = 449
FEATURE                  Location/Qualifiers
source                   1..449
                         mol_type = protein
                         note = Synthetic polypeptide
                         organism = synthetic construct
SEQUENCE: 248
EVQLVESGGG LVQPGRSLRL SCTASGFTFN ANAMNWVRQA PGKGLEWVGR IRTKSNNYAT  60
YYAGSVKDRF TISRDDSKNI AYLQMNSLKT EDTAVYYCVR DYYGSSAWIT YWGQGTLVTV  120
SSASTKGPSV FPLAPCSRST SESTAALGCL VKDYFPEPVT VSWNSGALTS GVHTFPAVLQ  180
SSGLYSLSSV VTVPSSSLGT KTYTCNVDHK PSNTKVDKRV ESKYGPPCPP CPAPEFLGGP  240
SVFLFPPKPK DTLMISRTPE VTCVVVDVSQ EDPEVQFNWY VDGVEVHNAK TKPREEQFNS  300
TYRVVSVLTV LHQDWLNGKE YKCKVSNKGL PSSIEKTISK AKGQPREPQV YTLPPSQEEM  360
TKNQVSLTCL VKGFYPSDIA VEWESNGQPE NNYKTTPPVL DSDGSFFLYS RLTVDKSRWQ  420
EGNVFSCSVM HEALHNHYTQ KSLSLSLGK                                   449

SEQ ID NO: 249           moltype = AA  length = 449
FEATURE                  Location/Qualifiers
source                   1..449
                         mol_type = protein
                         note = Synthetic polypeptide
                         organism = synthetic construct
SEQUENCE: 249
LVQLVESGGG LVKPGGSLRL SCAASGFTFN ANAMNWIRQA PGKGLEWVSR IRTKSNNYAT  60
YYAGSVKDRF TISRDNAKNS LYLQMNSLRA EDTAVHYCVR DYYGSSAWIT YWGQGTLVTV  120
SSASTKGPSV FPLAPCSRST SESTAALGCL VKDYFPEPVT VSWNSGALTS GVHTFPAVLQ  180
SSGLYSLSSV VTVPSSSLGT KTYTCNVDHK PSNTKVDKRV ESKYGPPCPP CPAPEFLGGP  240
SVFLFPPKPK DTLMISRTPE VTCVVVDVSQ EDPEVQFNWY VDGVEVHNAK TKPREEQFNS  300
TYRVVSVLTV LHQDWLNGKE YKCKVSNKGL PSSIEKTISK AKGQPREPQV YTLPPSQEEM  360
TKNQVSLTCL VKGFYPSDIA VEWESNGQPE NNYKTTPPVL DSDGSFFLYS RLTVDKSRWQ  420
EGNVFSCSVM HEALHNHYTQ KSLSLSLGK                                   449

SEQ ID NO: 250           moltype = AA  length = 214
FEATURE                  Location/Qualifiers
source                   1..214
                         mol_type = protein
                         note = Synthetic polypeptide
                         organism = synthetic construct
SEQUENCE: 250
DVVMTQSPSF LSASVGDRVT ITCKASQHVG TAVAWYQQRP GKAPKLLIYW ASTRHTGVPS  60
RFSGSGSGTE FTLTISSLQP EDFATYFCQQ YSSYPFTFGG GTKLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 251           moltype = AA  length = 214
FEATURE                  Location/Qualifiers
source                   1..214
                         mol_type = protein
                         note = Synthetic polypeptide
                         organism = synthetic construct
SEQUENCE: 251
DIVMTQSPDS LAVSLGERAT INCKASQHVG TAVAWYQQKP GQPPKLLIYW ASTRHTGVPD  60
RFSGSGSGTD FTLTISSLQA EDVAVYYCQQ YSSYPFTFGQ GTKLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 252           moltype = AA  length = 214
FEATURE                  Location/Qualifiers
source                   1..214
                         mol_type = protein
                         note = Synthetic polypeptide
                         organism = synthetic construct
SEQUENCE: 252
DIQMTQSPFS LSASVGDRVT ITCKASQHVG TAVAWYQQKP GKAPKLLIYW ASTRHTGVPS  60
RFSGSGSGTD FTLTISSLQP EDFATYFCQQ YSSYPFTFGG GTKLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214
```

-continued

```
SEQ ID NO: 253          moltype = AA  length = 214
FEATURE                 Location/Qualifiers
source                  1..214
                        mol_type = protein
                        note = Synthetic polypeptide
                        organism = synthetic construct
SEQUENCE: 253
DIVMTQSPDS LAVSLGERAT INCKASQHVG TAVAWYQQKP EQPPKLLIYW ASTRHTGVPD  60
RFSGSGSGTD FTLTISSLQA EDVAVYYCQQ YSSYPFTFGG GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 254          moltype = AA  length = 659
FEATURE                 Location/Qualifiers
source                  1..659
                        mol_type = protein
                        note = Synthetic polypeptide
                        organism = synthetic construct
SEQUENCE: 254
EVQLVESGGG LVQPGGSLRL SCAASGFTFN ANAMNWVRQA PGKGLEWVGR IRTKSNNYAT  60
YYAGSVKDRF TISRDDSKNS LYLQMNSLKT EDTAVYYCVR DYYGSSAWIT YWGQGTLVTV  120
SSASTKGPSV FPLAPCSRST SESTAALGCL VKDYFPEPVT VSWNSGALTS GVHTFPAVLQ  180
SSGLYSLSSV VTVPSSSLGT KTYTCNVDHK PSNTKVDKRV ESKYGPPCPP CPAPEFLGGP  240
SVFLFPPKPK DTLMISRTPE VTCVVVDVSQ EDPEVQFNWY VDGVEVHNAK TKPREEQFNS  300
TYRVVSVLTV LHQDWLNGKE YKCKVSNKGL PSSIEKTISK AKGQPREPQV YTLPPSQEEM  360
TKNQVSLTCL VKGFYPSDIA VEWESNGQPE NNYKTTPPVL DSDGSFFLYS RLTVDKSRWQ  420
EGNVFSCSVM HEALHNHYTQ KSLSLSLGKG GGGSSDTGRP FVEMYSEIPE IIHMTEGREL  480
VIPCRVTSPN ITVTLKKFPL DTLIPDGKRI IWDSRKGFII SNATYKEIGL LTCEATVNGH  540
LYKTNYLTHR QTNTIIDVVL SPSHGIELSV GEKLVLNCTA RTELNVGIDF NWEYPSSKHQ  600
HKKLVNRDLK TQSGSEMKKF LSTLTIDGVT RSDQGLYTCA ASSGLMTKKN STFVRVHEK   659

SEQ ID NO: 255          moltype = AA  length = 705
FEATURE                 Location/Qualifiers
source                  1..705
                        mol_type = protein
                        note = Synthetic polypeptide
                        organism = synthetic construct
SEQUENCE: 255
EVQLVESGGG LVQPGGSLRL SCAASGFTFN ANAMNWVRQA PGKGLEWVGR IRTKSNNYAT  60
YYAGSVKDRF TISRDDSKNS LYLQMNSLKT EDTAVYYCVR DYYGSSAWIT YWGQGTLVTV  120
SSASTKGPSV FPLAPCSRST SESTAALGCL VKDYFPEPVT VSWNSGALTS GVHTFPAVLQ  180
SSGLYSLSSV VTVPSSSLGT KTYTCNVDHK PSNTKVDKRV ESKYGPPCPP CPAPEFLGGP  240
SVFLFPPKPK DTLMISRTPE VTCVVVDVSQ EDPEVQFNWY VDGVEVHNAK TKPREEQFNS  300
TYRVVSVLTV LHQDWLNGKE YKCKVSNKGL PSSIEKTISK AKGQPREPQV YTLPPSQEEM  360
TKNQVSLTCL VKGFYPSDIA VEWESNGQPE NNYKTTPPVL DSDGSFFLYS RLTVDKSRWQ  420
EGNVFSCSVM HEALHNHYTQ KSLSLSLGKG GGGSEIVMTQ SPSTLSASVG DRVIITCQAS  480
EIIHSWLAWY QQKPGKAPKL LIYLASTLAS GVPSRFSGSG SGAEFTLTIS SLQPDDFATY  540
YCQNVYLAST NGANFGQGTK LTVLGGGGGS GGGGSGGGGS GGGGSEVQLV ESGGGLVQPG  600
GSLRLSCTAS GFSLTDYYYM TWVRQAPGKG LEWVGFIDPD DDPYYATWAK GRFTISRDNS  660
KNTLYLQMNS LRAEDTAVYY CAGGDHNSGW GLDIWGQGTL VTVSS                  705

SEQ ID NO: 256          moltype = AA  length = 699
FEATURE                 Location/Qualifiers
source                  1..699
                        mol_type = protein
                        note = Synthetic polypeptide
                        organism = synthetic construct
SEQUENCE: 256
EVQLVESGGG LVQPGGSLRL SCAASGFTFN ANAMNWVRQA PGKGLEWVGR IRTKSNNYAT  60
YYAGSVKDRF TISRDDSKNS LYLQMNSLKT EDTAVYYCVR DYYGSSAWIT YWGQGTLVTV  120
SSASTKGPSV FPLAPCSRST SESTAALGCL VKDYFPEPVT VSWNSGALTS GVHTFPAVLQ  180
SSGLYSLSSV VTVPSSSLGT KTYTCNVDHK PSNTKVDKRV ESKYGPPCPP CPAPEFLGGP  240
SVFLFPPKPK DTLMISRTPE VTCVVVDVSQ EDPEVQFNWY VDGVEVHNAK TKPREEQFNS  300
TYRVVSVLTV LHQDWLNGKE YKCKVSNKGL PSSIEKTISK AKGQPREPQV YTLPPSQEEM  360
TKNQVSLTCL VKGFYPSDIA VEWESNGQPE NNYKTTPPVL DSDGSFFLYS RLTVDKSRWQ  420
EGNVFSCSVM HEALHNHYTQ KSLSLSLGKG GGGSEVQLVE SGGGLVQPGG SLRLSCAASG  480
YDFTHYGMNW VRQAPGKGLE WVGWINTYTG EPTYAADFKR RFTFSLDTSK STAYLQMNSL  540
RAEDTAVYYC AKYPYYYGTS HWYFDVWGQG TLVTVSSGGG GSGGGGSGGG GSDIQLTQSP  600
SSLSASVGDR VTITCSASQD ISNYLNWYQQ KPGKAPKVLI YFTSSLHSGV PSRFSGSGSG  660
TDFTLTISSL QPEDFATYYC QQYSTVPWTF GQGTKVEIK                         699

SEQ ID NO: 257          moltype = AA  length = 577
FEATURE                 Location/Qualifiers
source                  1..577
                        mol_type = protein
                        note = Synthetic polypeptide
                        organism = synthetic construct
SEQUENCE: 257
EVQLVESGGG LVQPGGSLRL SCAASGFTFN ANAMNWVRQA PGKGLEWVGR IRTKSNNYAT  60
```

-continued

```
YYAGSVKDRF TISRDDSKNS LYLQMNSLKT EDTAVYYCVR DYYGSSAWIT YWGQGTLVTV  120
SSASTKGPSV FPLAPCSRST SESTAALGCL VKDYFPEPVT VSWNSGALTS GVHTFPAVLQ  180
SSGLYSLSSV VTVPSSSLGT KTYTCNVDHK PSNTKVDKRV ESKYGPPCPP CPAPEFLGGP  240
SVFLFPPKPK DTLMISRTPE VTCVVVDVSQ EDPEVQFNWY VDGVEVHNAK TKPREEQFNS  300
TYRVVSVLTV LHQDWLNGKE YKCKVSNKGL PSSIEKTISK AKGQPREPQV YTLPPSQEEM  360
TKNQVSLTCL VKGFYPSDIA VEWESNGQPE NNYKTTPPVL DSDGSFFLYS RLTVDKSRWQ  420
EGNVFSCSVM HEALHNHYTQ KSLSLSLGGG GGSDLDKKLL EAARAGQDDE VRILMANGAD  480
VNARDSTGWT PLHLAAPWGH PEIVEVLLKN GADVNAADFQ GWTPLHLAAA VGHLEIVEVL  540
LKYGADVNAQ DKFGKTAFDI SIDNGNEDLA EILQKAA                           577

SEQ ID NO: 258          moltype = AA  length = 470
FEATURE                 Location/Qualifiers
source                  1..470
                        mol_type = protein
                        note = Synthetic polypeptide
                        organism = synthetic construct
SEQUENCE: 258
DVVMTQSPSF LSASVGDRVT ITCKASQHVG TAVAWYQQRP GKAPKLLIYW ASTRHTGVPS  60
RFSGSGSGTE FTLTISSLQP EDFATYFCQQ YSSYPFTFGG GTKLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGECGGGGSE IVMTQSPSTL SASVGDRVII  240
TCQASEIIHS WLAWYQQKPG KAPKLLIYLA STLASGVPSR FSGSGSGAEF TLTISSLQPD  300
DFATYYCQNV YLASTNGANF GQGTKLTVLG GGGGSGGGGS GGGGSGGGGS EVQLVESGGG  360
LVQPGGSLRL SCTASGFSLT DYYYMTWVRQ APGKGLEWVG FIDPDDDPYY ATWAKGRFTI  420
SRDNSKNTLY LQMNSLRAED TAVYYCAGGD HNSGWGLDIW GQGTLVTVSS             470

SEQ ID NO: 259          moltype = AA  length = 424
FEATURE                 Location/Qualifiers
source                  1..424
                        mol_type = protein
                        note = Synthetic polypeptide
                        organism = synthetic construct
SEQUENCE: 259
DVVMTQSPSF LSASVGDRVT ITCKASQHVG TAVAWYQQRP GKAPKLLIYW ASTRHTGVPS  60
RFSGSGSGTE FTLTISSLQP EDFATYFCQQ YSSYPFTFGG GTKLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGECGGGGSS DTGRPFVEMY SEIPEIIHMT  240
EGRELVIPCR VTSPNITVTL KKFPLDTLIP DGKRIIWDSR KGFIISNATY KEIGLLTCEA  300
TVNGHLYKTN YLTHRQTNTI IDVVLSPSHG IELSVGEKLV LNCTARTELN VGIDFNWEYP  360
SSKHQHKKLV NRDLKTQSGS EMKKFLSTLT IDGVTRSDQG LYTCAASSGL MTKKNSTFVR  420
VHEK                                                               424

SEQ ID NO: 260          moltype = AA  length = 464
FEATURE                 Location/Qualifiers
source                  1..464
                        mol_type = protein
                        note = Synthetic polypeptide
                        organism = synthetic construct
SEQUENCE: 260
DVVMTQSPSF LSASVGDRVT ITCKASQHVG TAVAWYQQRP GKAPKLLIYW ASTRHTGVPS  60
RFSGSGSGTE FTLTISSLQP EDFATYFCQQ YSSYPFTFGG GTKLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGECGGGGSE VQLVESGGGL VQPGGSLRLS  240
CAASGYDFTH YGMNWVRQAP GKGLEWVGWI NTYTGEPTYA ADFKRRFTFS LDTSKSTAYL  300
QMNSLRAEDT AVYYCAKYPY YYGTSHWYFD VWGQGTLVTV SSGGGGSGGG GSGGGGSDIQ  360
LTQSPSSLSA SVGDRVTITC SASQDISNYL NWYQQKPGKA PKVLIYFTSS LHSGVPSRFS  420
GSGSGTDFTL TISSLQPEDF ATYYCQQYST VPWTFGQGTK VEIK                   464

SEQ ID NO: 261          moltype = AA  length = 343
FEATURE                 Location/Qualifiers
source                  1..343
                        mol_type = protein
                        note = Synthetic polypeptide
                        organism = synthetic construct
SEQUENCE: 261
DVVMTQSPSF LSASVGDRVT ITCKASQHVG TAVAWYQQRP GKAPKLLIYW ASTRHTGVPS  60
RFSGSGSGTE FTLTISSLQP EDFATYFCQQ YSSYPFTFGG GTKLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGECGGGGSD LDKKLLEAAR AGQDDEVRIL  240
MANGADVNAR DSTGWTPLHL AAPWGHPEIV EVLLKNGADV NAADFQGWTP LHLAAAVGHL  300
EIVEVLLKYG ADVNAQDKFG KTAFDISIDN GNEDLAEILQ KAA                    343

SEQ ID NO: 262          moltype = AA  length = 448
FEATURE                 Location/Qualifiers
source                  1..448
                        mol_type = protein
                        note = Synthetic polypeptide
                        organism = synthetic construct
SEQUENCE: 262
```

-continued

```
EVQLVESGGG LVQPGGSLRL SCAASGFTFN ANAMNWVRQA PGKGLEWVGR IRTKSNNYAT  60
YYAGSVKDRF TISRDDSKNS LYLQMNSLKT EDTAVYYCVR DYYGSSAWIT YWGQGTLVTV  120
SSASTKGPSV FPLAPCSRST SESTAALGCL VKDYFPEPVT VSWNSGALTS GVHTFPAVLQ  180
SSGLYSLSSV VTVPSSSLGT KTYTCNVDHK PSNTKVDKRV ESKYGPPCPP CPAPEFLGGP  240
SVFLFPPKPK DTLMISRTPE VTCVVVDVSQ EDPEVQFNWY VDGVEVHNAK TKPREEQFNS  300
TYRVVSVLTV LHQDWLNGKE YKCKVSNKGL PSSIEKTISK AKGQPREPQV YTLPPSQEEM  360
TKNQVSLTCL VKGFYPSDIA VEWESNGQPE NNYKTTPPVL DSDGSFFLYS RLTVDKSRWQ  420
EGNVFSCSVM HEALHNHYTQ KSLSLSLG                                    448
```